(12) United States Patent
Piazza et al.

(10) Patent No.: US 11,130,744 B2
(45) Date of Patent: Sep. 28, 2021

(54) INDENYL COMPOUNDS, PHARMACEUTICAL COMPOSITIONS, AND MEDICAL USES THEREOF

(71) Applicant: ADT Pharmaceuticals, LLC, Orange Beach, AL (US)

(72) Inventors: Gary A. Piazza, Daphne, AL (US); Xi Chen, Hoover, AL (US); Adam B. Keeton, Gardendale, AL (US); Michael R. Boyd, Orange Beach, AL (US)

(73) Assignee: ADT Pharmaceuticals, LLC, Orange Beach, AL (US)

( * ) Notice: Subject to any disclaimer, the term of this patent is extended or adjusted under 35 U.S.C. 154(b) by 0 days.

(21) Appl. No.: 16/834,348

(22) Filed: Mar. 30, 2020

(65) Prior Publication Data

US 2020/0223816 A1    Jul. 16, 2020

Related U.S. Application Data

(63) Continuation of application No. 16/593,776, filed on Oct. 4, 2019, now Pat. No. 10,975,054, which is a
(Continued)

(51) Int. Cl.
| | | |
|---|---|---|
| *A61K 31/341* | (2006.01) | |
| *A61K 31/36* | (2006.01) | |
| *A61K 31/40* | (2006.01) | |
| *A61K 31/401* | (2006.01) | |
| *A61K 31/44* | (2006.01) | |
| *A61K 31/445* | (2006.01) | |
| *A61K 45/06* | (2006.01) | |
| *C07C 233/58* | (2006.01) | |
| *C07C 235/32* | (2006.01) | |
| *C07C 237/20* | (2006.01) | |
| *C07D 207/14* | (2006.01) | |
| *C07D 207/337* | (2006.01) | |
| *C07D 211/56* | (2006.01) | |
| *C07D 213/24* | (2006.01) | |
| *C07D 213/75* | (2006.01) | |
| *C07D 235/30* | (2006.01) | |

(Continued)

(52) U.S. Cl.
CPC .......... *C07D 317/64* (2013.01); *A61K 31/341* (2013.01); *A61K 31/36* (2013.01); *A61K 31/40* (2013.01); *A61K 31/401* (2013.01); *A61K 31/44* (2013.01); *A61K 31/445* (2013.01); *A61K 45/06* (2013.01); *C07C 233/58* (2013.01); *C07C 235/32* (2013.01); *C07C 237/20* (2013.01); *C07D 207/14* (2013.01); *C07D 207/337* (2013.01); *C07D 211/56* (2013.01); *C07D 213/24* (2013.01); *C07D 213/75* (2013.01); *C07D 235/30* (2013.01); *C07D 307/38* (2013.01); *C07D 307/52* (2013.01); *C07D 307/54* (2013.01); *C07D 405/12* (2013.01); *A61K 2300/00* (2013.01); *C07C 2601/02* (2017.05); *C07C 2602/08* (2017.05)

(58) Field of Classification Search
CPC .. C07D 317/64; C07D 235/30; C07D 405/12; C07D 213/24; C07D 307/38; C07D 307/52; C07D 211/56; C07D 213/75; C07D 207/14; C07D 207/337; C07D 307/54; C07C 235/32; C07C 237/20; C07C 233/58; C07C 2601/02; C07C 2602/08; A61K 45/06; A61K 31/445; A61K 31/44; A61K 31/40; A61K 31/401; A61K 31/36; A61K 31/341; A61K 2300/00; A61P 43/00; A61P 35/02; A61P 35/00
See application file for complete search history.

(56) References Cited

U.S. PATENT DOCUMENTS

| | | |
|---|---|---|
| 3,642,785 A | 2/1972 | Shen et al. |
| 3,888,902 A | 6/1975 | Shen et al. |

(Continued)

FOREIGN PATENT DOCUMENTS

| | | |
|---|---|---|
| AU | 2013/206215 A1 | 6/2013 |
| AU | 2013/206218 A1 | 6/2013 |

(Continued)

OTHER PUBLICATIONS

U.S. Appl. No. 15/863,285, filed Jan. 5, 2018.
(Continued)

*Primary Examiner* — Amanda L. Aguirre
(74) *Attorney, Agent, or Firm* — Leydig, Voit & Mayer, Ltd.

(57) ABSTRACT

Disclosed are compounds, for example, compounds of formula I,

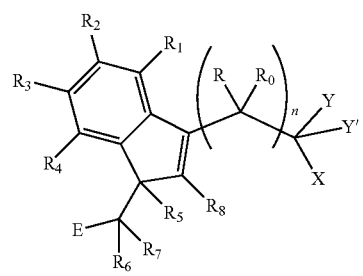

wherein R, $R_0$, $R_1$-$R_8$, n, X, Y, Y', and E are as described herein, pharmaceutical compositions containing such compounds, and methods of treating or preventing a disease or condition, for example, cancer.

15 Claims, 18 Drawing Sheets

Related U.S. Application Data continuation of application No. 15/537,292, filed as application No. PCT/US2015/066146 on Dec. 16, 2015, now Pat. No. 10,526,307, which is a continuation-in-part of application No. 14/571,647, filed on Dec. 16, 2014, now Pat. No. 9,862,698.

(51) Int. Cl.
*C07D 307/38* (2006.01)
*C07D 307/52* (2006.01)
*C07D 307/54* (2006.01)
*C07D 317/64* (2006.01)
*C07D 405/12* (2006.01)

(56) References Cited

U.S. PATENT DOCUMENTS

| | | | |
|---|---|---|---|
| 5,093,356 A | 3/1992 | Girard | |
| 5,401,774 A | 3/1995 | Pamukcu et al. | |
| 5,965,582 A | 10/1999 | Lebaut | |
| 5,965,619 A | 10/1999 | Pamukcu et al. | |
| 6,028,116 A | 2/2000 | Sperl et al. | |
| 6,063,818 A * | 5/2000 | Sperl | A61K 31/4402 |
| | | | 514/622 |
| 6,071,934 A | 6/2000 | Sperl et al. | |
| 6,121,321 A | 9/2000 | Sperl et al. | |
| 6,166,053 A * | 12/2000 | Sperl | C07D 241/12 |
| | | | 514/357 |
| 6,403,831 B1 | 6/2002 | Sperl et al. | |
| 6,538,029 B1 | 3/2003 | Thompson et al. | |
| 6,649,629 B2 | 11/2003 | Bandarage et al. | |
| 7,166,618 B2 | 1/2007 | Bandarage et al. | |
| 7,211,598 B2 | 5/2007 | Ranatunge et al. | |
| 7,432,285 B2 | 10/2008 | Bandarage et al. | |
| 7,491,744 B2 | 2/2009 | Marnett et al. | |
| 8,044,048 B2 | 10/2011 | Piazza et al. | |
| 9,862,698 B2 | 1/2018 | Piazza et al. | |
| 9,931,315 B2 | 4/2018 | Piazza et al. | |
| 10,526,307 B2 | 1/2020 | Piazza et al. | |
| 2003/0009033 A1 | 1/2003 | Sperl et al. | |
| 2003/0176316 A1 | 9/2003 | Whitehead et al. | |
| 2003/0194750 A1 | 10/2003 | Li et al. | |
| 2007/0155734 A1 | 7/2007 | Ranatunge et al. | |
| 2009/0099139 A1 | 4/2009 | Bandarage et al. | |
| 2009/0221703 A1 | 9/2009 | Yu et al. | |
| 2016/0168108 A1 | 6/2016 | Piazza et al. | |
| 2016/0168113 A1 | 6/2016 | Piazza et al. | |
| 2016/0175275 A1 | 6/2016 | Piazza et al. | |
| 2017/0342021 A1 | 11/2017 | Piazza et al. | |
| 2018/0208573 A1 | 7/2018 | Piazza et al. | |
| 2018/0251443 A9 | 9/2018 | Piazza et al. | |
| 2020/0031795 A1 | 1/2020 | Piazza et al. | |
| 2020/0048217 A1 | 2/2020 | Piazza et al. | |
| 2020/0223815 A1 | 7/2020 | Piazza et al. | |
| 2020/0223817 A1 | 7/2020 | Piazza et al. | |

FOREIGN PATENT DOCUMENTS

| | | |
|---|---|---|
| AU | 2013/231152 A1 | 10/2013 |
| AU | 2014/201024 A1 | 3/2014 |
| AU | 2016/219617 A1 | 9/2016 |
| CN | 101031289 A | 9/2007 |
| CN | 103491772 A | 1/2014 |
| DE | 2020762 A1 | 11/1970 |
| DE | 10163426 A1 | 7/2003 |
| EP | 0 132 690 A1 | 2/1985 |
| EP | 0142801 A2 | 5/1985 |
| EP | 1044187 B1 | 1/2004 |
| GB | 1370028 | 10/1974 |
| HU | 9903620 A2 | 2/2000 |
| JP | 2000-514417 A | 10/2000 |
| JP | 2002-508358 A | 3/2002 |
| JP | 2004-510762 A | 3/2004 |
| JP | 2004-510762 A | 4/2004 |
| JP | 2007-534702 A | 11/2007 |
| JP | 2009-522364 A | 6/2009 |
| JP | 2013-518060 A | 5/2013 |
| WO | WO 97/47303 A1 | 12/1997 |
| WO | WO 2001/045703 A1 | 6/2001 |
| WO | WO 2001/047939 A1 | 7/2001 |
| WO | WO 2004/002420 A2 | 1/2004 |
| WO | WO 2005/112921 A2 | 12/2005 |
| WO | WO 2006/124874 A2 | 11/2006 |
| WO | WO 2007/065924 A1 | 6/2007 |
| WO | WO 2007/081694 A2 | 7/2007 |
| WO | WO 2008/007171 A1 | 1/2008 |
| WO | WO 2008/010025 A1 | 1/2008 |
| WO | WO 2008/012602 A1 | 1/2008 |
| WO | WO 2008/012603 A1 | 1/2008 |
| WO | WO 2008/012605 A1 | 1/2008 |
| WO | WO 2008/017903 A1 | 2/2008 |
| WO | WO 2008/019357 A2 | 2/2008 |
| WO | WO 2008/020270 A1 | 2/2008 |
| WO | WO 2008/029199 A1 | 3/2008 |
| WO | WO 2008/029200 A1 | 3/2008 |
| WO | WO 2008/044095 A1 | 4/2008 |
| WO | WO 2008/149181 A1 | 12/2008 |
| WO | WO 2011/091417 A1 | 7/2011 |
| WO | WO 2012/135650 A1 | 10/2012 |
| WO | WO 2014/047592 A2 | 3/2014 |
| WO | WO 2014/169080 A1 | 10/2014 |
| WO | WO 2015/126462 A1 | 8/2015 |
| WO | WO 2016/099452 A1 | 6/2016 |
| WO | WO 2016/100542 A1 | 6/2016 |
| WO | WO 2016/100546 A1 | 6/2016 |
| WO | WO 2017/106520 A1 | 6/2017 |
| WO | WO 2019/210223 A1 | 10/2019 |

OTHER PUBLICATIONS

Mexico Institute of the Industrial Property, Second Substantive Examination requirement issued in Mexican Application No. MX/a/2017/007840 (dated Nov. 17, 2020).

Chabner, Bruce A.,"Clinical Strategies for Cancer Treatment: The Role of Drugs", Chapter 1 of *Cancer Chemotherapy and Biotherapy: Principles and Practice*, Lippincott Williams & Wilkins, a Wolters Kluwer business, Philadelphia, PA, pp. 3-14 (2011).

Decker et al., "Target Identification and Drug Discovery", Chapter 2 of *Cancer Chemotherapy and Biotherapy: Principles and Practice*, Lippincott Williams & Wilkins, a Wolters Kluwer business, Philadelphia, PA, pp. 15-27 (2011).

Roberts, Thomas G. Jr., "Clinical Drug Development and Marketing Approval", Chapter 3 of *Cancer Chemotherapy and Biotherapy: Principles and Practice*, Lippincott Williams & Wilkins, a Wolters Kluwer business, Philadelphia, PA, pp. 28-49 (2011).

Collins et al., "Principles of Pharmacokinetics", Chapter 4 of *Cancer Chemotherapy and Biotherapv: Principles and Practice*, Lippincott Williams & Wilkins, a Wolters Kluwer business, Philadelphia, PA, pp. 50-61 (2011).

Clark, Jeffrey W., "Molecular Targeted Drugs", Chapter 29 of *Cancer Chemotherapy and Biotherapy: Principles and Practice*, Lippincott Williams & Wilkins, a Wolters Kluwer business, Philadelphia, PA, pp. 526-546 (2011).

Alcalde et al., "Indene-based scaffolds. Design and synthesis of novel serotonin 5-HT$_6$receptor ligands", *Org. Biomol. Chem.*, vol. 6, 3795-3810 (2008).

Murata et al., "An Efficient Catalyst System for Palladium-Catalyzed Borylation of Aryl Halides with Pinacolborane", *Synlett*, pp. 1867-1870 (2006).

Pekol et al., "Human Metabolism of the Proteasome Inhibitor Bortezomib: Identification of Circulating Metabolites", *Drug Metab. Dispos.*, vol. 33, pp. 771-777 (2005).

Pettit et. al., "Antineoplastic Agents. 291. Isolation and Synthesis of Combretastatins A-4, A-5, and A-6", *J. Med. Chem.*, vol. 38, pp. 1666-1672 (1995).

Pettit et al., "Antineoplastic agents 322. Synthesis of combretastatin A-4 prodrugs", *Anticancer Drug Des.*, vol. 10, pp. 299-309 (1995).

Schacter, Lee, "Etoposide phosphate: What, Why, Where, and How?", *Semin. Oncol.*, vol. 23: (6 Suppl. 13): 1-7, (1996).

(56) References Cited

OTHER PUBLICATIONS

Snyder et al., "Reductive Coupling and Polymerization of Unsaturated Amides. II. Effect of Substituents", *J. Am. Chem. Soc.*, vol. 76, pp. 1893-1898 (1954).
Yamaguchi et al., "Efficient Heterogeneous Aerobic Oxidation of Amines by a Supported Ruthenium Catalyst", *Angew. Chem. Int. Ed.*, vol. 42, pp. 1480-1483 (2003).
European Patent Office, second Examination Report issued in European Application No. 15823453.4 (dated Oct. 13, 2020).
IP Australian, Notice of Acceptance for Patent Application issued in Australian Patent Application No. 2015364696 (dated Oct. 1, 2020).
"All RAS Mutation Panel", *TrimGen Genetic Diagnostics*, 2 pp. (Retrieved Jan. 28, 2017).
Al-Saeed, "Gastrointestinal and Cardiovascular Risk of Nonsteroidal Anti-inflammatory Drugs", *Oman Medical Journal*, 26(6), pp. 385-391 (2011).
Antman et al., "Use of Nonsteroidal Antiinflammatory Drugs: An Update for Clinicians—A Scientific Statement From the American Heart Association", *Circulation*, vol. 115, pp. 1634-1642 (2007).
Aparoy et al., "Pharmacophore modeling and virtual screening for designing potential 5-Lipoxygenase inhibitors," *Bioorganic and Medicinal Chemistry Letter*, 20: 1013-1018 (2010).
Arber, Nadir, et al., "A K-ras Oncogene Increases Resistance to Sulindac-Induced Apoptosis in Rat Enterocytes," *Gastroenterology*, vol. 113, pp. 1892-1900 (1997).
Arisawa, Mitsuhiro, et al., "Design and Synthesis of Indomethacin Analogues That Inhibit P-Glycoprotein and/or Multidrug Resistant Protein without Cox Inhibitory Activity," *Journal of Medicinal Chemistry*, vol. 55, pp. 8152-8163 (2012).
"ASCO Updates Guideline to Include Testing for New RAS Mutations", *Gastrointestinal Cancers Symposium*, 3 pp. (2016).
Baldwin et al., "Structural requirements for the binding of non-steroidal anti-inflammatory drugs to the 78 kDa gastrin binding protein," *Biochimica et Biophysica Acta (BBA)*, 1428 (1): 68-76 (1999) Abstract only.
Bittker, Joshua a., et al., "Screen for RAS-Selective Lethal Compounds and VDAC Ligands," Probe Reports from NIH Molecular Libraries Program, Bethesda, ML210, Dec. 12, 2011 update, http://www.ncbi.nlm.nih.gov/books/NBK98919/.
Chen, Xi, et al., "A novel series of substituted indene derivatives that potently and selectively inhibit growth of tumor cells harboring mutant Ras," *American Association for Cancer Research—Special Conference on Ras Oncogenes: From Biology to Therapy*, Disney Yacht Club Resort, Lake Buena Vista, Florida (Feb. 24-27, 2014).
Chennamaneni, Snigdha, et al., "COX inhibitors Indomethacin and Sulindac derivatives as antiproliferative agents: Synthesis, biological evaluation, and mechanism investigation," *European Journal of Medicinal Chemistry*, vol. 56, pp. 17-29 (2012).
"Cobas KRAS Mutation Test—P140023", www.fda.gov, 2 pp. (Retrieved Jan. 28, 2017).
Cox et al., "Drugging the undruggable RAS: Mission Possible?", *Nature Reviews*, vol. 13, pp. 828-840 (2014).
De Jong, Tanya A., et al., "Inhibition of rat colon tumors by sulindac and sulindac sulfone is independent of K-ras (codon 12) mutation," *American Journal of Physiology—Gastrointestinal and Liver Physiology*, vol. 278, pp. G266-G272 (2000).
Dolma, Sonam, et al., "Identification of genotype-selective antitumor agents using synthetic lethal chemical screening in engineered human tumor cells," *Cancer Cell*, vol. 3, pp. 285-296 (Mar. 2003).
Downward, Julian, "Targeting RAS Signalling Pathways in Cancer Therapy," *Nature Reviews—Cancer*, vol. 3, pp. 11-22 (Jan. 2003).
Gala, Manish, et al., "Inhibition of cell transformation in sulindac sulfide is confined to specific oncogenic pathways," *Cancer Letters*, vol. 175, pp. 89-94 (2002).
Goldstein et al., "Overexpression of protein kinase β1 in the SW480 colon cancer cell line causes growth suppression", *Carcinogenesis*, 16(5), pp. 1121-1126 (1995).
Guo, Wei, et al., "Identification of a Small Molecule with Synthetic Lethality for K-Ras and Protein Kinase C Iota," *Cancer Research*, vol. 68, No. 18, pp. 7403-7408 (Sep. 15, 2008).

Guo, Wei, et al., "Antitumor Activity of a Novel Oncrasin Analogue Is Mediated by JNK Activation and STAT3 Inhibition," *PLoS One*, vol. 6, No. 12, pp. 1-10 (Dec. 2011).
Gurpinar, Evrim, et al., "A Novel Sulindac Derivative Inhibits Lung Adenocarcinoma Cell Growth through Suppression of Akt/mTOR Signaling and Induction of Autophagy," *Molecular Cancer Therapeutics*, vol. 12, No. 5, pp. 663-674 (Feb. 26, 2013).
Gurpinar et al., "NSAIDs Inhibit Tumorigenesis, but How?", *Clinical Cancer Research*, 20(5), pp. 1104-1113 (2014).
Gysin, Stephan, et al., "Therapeutic Strategies for Targeting Ras Proteins," *Genes & Cancer*, vol. 2, no. 3, pp. 359-372 (2011).
Herrmann, Christian, et al., "Sulindac sulfide inhibits Ras signaling," *Oncogene*, vol. 17, pp. 1769-1776 (1998).
Jemal, Ahmedin, et al., "Cancer Statistics, 2008," *CA: A Cancer Journal for Clinicians*, vol. 58, pp. 71-96 (2008).
Karaguni, Ioanna-Maria, et al., "New Indene-Derivatives with Anti-Proliferative Properties," *Bioorganic & Medicinal Chemistry Letters*, vol. 12, pp. 709-713 (2002).
Kaufman, Dwight C., et al., "Clinical Strategies for Cancer Treatment: The Role of Drugs," *Cancer Chemotherapy and Biotherapy: Principles and Practice*, Chapter 1, Lippincott, Williams and Wilkins, pp. 1-16 (2011).
Keeton et al., "Search for Inhibitors of Ras-Driven Cancers", *Conquering RAS, 1st Edition. From Biology to Cancer Therapy*, Ch. 8, pp. 135-154 (2016).
"KRAS Mutation Testing", www.trovagene.com, 5 pp. (Retrieved Jan. 28, 2017).
Lawson, Kathryn R., et al., "Influence of K-ras Activation on the Survival Responses of Caco-2 Cells to the Chemopreventive Agents Sulindac and Difluoromethylornithine," *Cancer Epidemiology, Biomarkers & Prevention*, vol. 9, pp. 1155-1162 (Nov. 2000).
Ledford, "The RAS Renaissance", *Nature*, vol. 520, pp. 278-280 (2015).
Lee et al., "Effect of Simbastatin on Cetuximab Resistance in Human Colorectal Cancer With KRAS Mutations", *JNCI*, 103(8), pp. 674-688 (2011).
Liedtke et al., "Cyclooxygenase-1-Selective Inhibitors Based on the ( E )-2'-Des-methyl-sulindac Sulfide Scaffold," *Journal of Medicinal Chemistry*, 55(5): 2287-2300 (2012).
Lim, Jin T.E., et al., "Sulindac Derivatives Inhibit Growth and Induce Apoptosis in Human Prostate Cancer Cell Lines," *Biochemical Pharmacology*, 58(7): 1097-1107 (1999).
Lim, Jin T.E., et al., "Exisulind and Related Compounds Inhibit Expression and Function of the Androgen Receptor in Human Prostate Cancer Cells," *Clinical Cancer Research*, vol. 9, pp. 4972-4982 (Oct. 15, 2003).
Magar et al., "Synthesis of Diverse Indene Derivatives from 1-Diazonaphthalen-2(1H)-ones via Thermal Cascade Reactions," *Organic Letters*, (2013) 4 pages.
McGettigan et al., "Cardiovascular Risk and Inhibition of Cyclooxygenase: A Systematic Review of the Observational Studies of Selective and Nonselective Inhibitors of Cyclooxygenase 2", *Journal of American Medical Association*, 296(13), pp. E1-E12 (2006—Reprinted).
Mielgo et al., "A MEK-independent role for CRAF in mitosis and tumor progression", *Nature Medicine*, 17(12), pp. 1641-1646 (2011).
Moon et al., "Benzylamide Sulindac Analogues Induce Changes in Cell Shape, Loss of Microtubules and $G_2$-M Arrest in a Chronic Lymphocytic Leukemia (CLL) Cell Line and Apoptosis in Primary CLL Cells 1," *Cancer Research*, 5711-5719 (2002).
Mulcahy et al., "Anti-EGFR Agents Detrimental in Colorectal Cancer Patients With KRAS Mutation", *Medscape Medical News*, 3 pp. (2009).
Müller et al., "Identification of Potent Ras Signaling Inhibitors by Pathway-Selective Phenotype-Based Screening," *Angewandte Chemie International Edition*, Wiley, 43(4): 450-454 (2004).
Ostrem, Jonathan M., et al., "K-Ras(G12C) inhibitors allosterically control GTP affinity and effector interactions," *Nature*, vol. 503, pp. 548-551 (Nov. 28, 2013).
Pan, Mei-Ran, et al., "Non-steroidal anti-inflammatory drugs suppress the ERK signaling pathway via block of Ras/c-Raf interaction and activation of MAP kinase phosphatases," *Cellular Signalling*, vol. 20, pp. 1134-1141 (2008).

(56) References Cited

OTHER PUBLICATIONS

Piazza et al., "A Novel Sulindac Derivative That Does Not Inhibit Cyclooxygenases but Potently Inhibits Colon Tumor Cell Growth and Induces Apoptosis with Antitumor Activity", *Cancer Prevention Research*, 2(6), pp. 572-580 (2009).
Qiagen Manchester Ltd., "TheraScreen: K-RAS Mutation Kit: For the Detection of 7 Mutations in the K-RAS Gene", $D_xS$ *Diagnostic Innovations*, pp. 124 (2012).
Rickles et al., "Adenosine A2A receptor agonists and PDE inhibitors: a synergistic multitarget mechanism discovered through systematic combination screening in B-cell malignancies," *Blood*, 116: 593-602 (2010).
Romeiro, Nelilma C., et al., "Synthesis, pharmacological evaluation and docking studies of new sulindac analogues," *European Journal of Medicinal Chemistry*, vol. 44, pp. 1959-1971 (2009).
Schramm et al., "Activated K-ras is Involved in Regulation of Integrin Expression in Human Colon Carcinoma Cells," *In. J. Cancer*, 87: 155-164 (2000).
Scudellari, "Mix and Match: Doctors face a maze of drug options and genetic markers to find the right treatment for people with advanced colorectal cancer", *Nature*, vol. 521, pp. 512-514 (2015).
Shaw, Alice T., et al., "Selective killing of K-ras mutant cancer cells by small molecule inducers of oxidative stress," *Proceedings of the National Academy of Sciences of the United States of America*, vol. 108, No. 21, pp. 8773-8778 (May 24, 2011).
Sheridan, "The Most Common Chemical Replacements in Drug-Like Compounds," *J. Chem. Inf. Comput. Sci.*, 42: 103-108 (2002).
Shigaki et al., "KRAS and BRAF Mutations in 203 Esophageal Squamous Cell Carcinomas: Pyrosequencing Technology and Literature Review", *Annals of Surgical Oncology*, 8 pp. (2012).
Shirasawa, Senji, et al., "Altered Growth of Human Colon Cancer Cell Lines Disrupted at Activated Ki-ras," *Science*, vol. 260, pp. 85-88 (Apr. 2, 1993).
Spiegel, Jochen, et al., "Small-molecule modulation of Ras signaling," *Nature Chemical Biology*, vol. 10, pp. 613-622 (Aug. 2014).
Stephen, Andrew G., et al., "Dragging Ras Back in the Ring," *Cancer Cell*, vol. 25, pp. 272-281 (Mar. 17, 2014).
Stoneman, V, et al., "Induction of intercellular adhesion molecule I and class II histocompatibility antigens in colorectal tumour cells expressing activated ras oncogene," *Journal of Clinical Pathology—Molecular Pathology*, vol. 48, pp. M326-M332 (1995).
Takashima, Asami, et al., "Targeting the RAS oncogene," *Expert Opinion on Therapeutic Targets*, vol. 17, No. 5, pp. 507-531 (May 2013).
Teicher, Beverly A., et al., *Anticancer Drug Development Guide: Preclinical Screening, Clinical Trials, and Approval*, Second Edition, Humana Press, Inc., Totowa, NJ, pp. 1-450 (2004).
"Therascreen KRAS RGQ PCR Kit—P110027", www.fda.gov, 2 pp. (Retrieved Jan. 28, 2017).
Thompson, Henry J., et al., "Sulfone Metabolite of Sulindac Inhibits Mammary Carcinogenesis," *Cancer Research*, vol. 57, pp. 267-271 (Jan. 15, 1997).
Thompson, W. Joseph, et al., "Exisulind Induction of Apoptosis Involves Guanosine 3', 5'-Cyclic Monophosphate Phosphodiesterase Inhibition, Protein Kinase G Activation, and Attenuated β-Catenin," *Cancer Research*, vol. 60, pp. 3338-3342 (2000).
Thompson, "US National Cancer Institute's new Ras project targets an old foe", *Nature Medicine*, 19(8), pp. 949-950 (2013).
Tidyman, William E., et al., "The RASopathies: Developmental syndromes of Ras/MAPK pathway dysregulation," *Current Opinion in Genetics & Development*, vol. 19, No. 3, pp. 230-236 (Jun. 2009).
Waldmann, Herbert, et al., "Sulindac-Derived Ras Pathway Inhibitors Target the Ras-Raf Interaction and Downstream Effectors in the Ras Pathway," *Angewandte Chemie International Edition*, vol. 43, pp. 454-458 (2004).
Wu, Shuhong, et al., "Prodrug oncrasin-266 improves the stability, pharmacokinetics, and safety of NSC-743380," *Bioorganic & Medicinal Chemistry*, vol. 22, pp. 5234-5240 (2014).
Xiao, Danhua, et al., "The sulindac derivatives OSI-461, OSIP486823, and OSIP487703 arrest colon cancer cells in mitosis by causing microtubule depolymerization," *Molecular Cancer Therapeutics*, vol. 5, No. 1, pp. 60-67 (Jan. 2006).
Yang, Wan Seok, et al., "Synthetic Lethal Screening Identifies Compounds Activating Iron-Dependent, Nonapoptotic Cell Death in Oncogenic-RAS-Harboring Cancer Cells," *Chemistry & Biology*, vol. 15, pp. 234-245 (Mar. 2008).
Yoon, Jung-Taek, et al., "CP248, a Derivative of Exisulind, Causes Growth Inhibition, Mitotic Arrest, and Abnormalities in Microtubule Polymerization in Glioma Cells," *Molecular Cancer Therapeutics*, vol. 1, pp. 393-404 (Apr. 2002).
Zimmermann, Gunther, et al., "Structure Guided Design and Kinetic Analysis of Highly Potent Benzimidazole Inhibitors Targeting the PDEδ Prenyl Binding Site," *Journal of Medicinal Chemistry*, vol. 57, pp. 5435-5448 (2014).
International Bureau of WIPO, International Search Report and Written Opinion issued in PCT Application No. PCT/US2015/066146 (dated Feb. 25, 2016).
International Bureau of WIPO, International Preliminary Report on Patentability issued in PCT Application No. PCT/US2015/066146 (dated Apr. 6, 2017).
International Searching Authority, "International Search Report in International Application No. PCT/US2019/029430", European Patent Office, dated Oct. 4, 2019, pp. 8.
International Searching Authority, "Written Opinion in International Application No. PCT/US2019/029430", European Patent Office, dated Oct. 4, 2019, pp. 10.
European Patent Office, International Search Report and Written Opinion issued in International Application No. PCT/US2015/066154 (dated Apr. 26, 2016).
European Patent Office, International Preliminary Report on Patentability issued in International Application No. PCT/US2015/066154 (dated Dec. 6, 2016).
European Patent Office, Examination Report issued in European Application No. 15821218.3 (dated Jul. 19, 2018).
European Patent Office, Examination Report issued in European Application No. 15823453.4 (dated Mar. 20, 2019).
Intellectual Property of India, First Examination Report issued in Indian Patent Application No. 201717021093 (dated Nov. 8, 2019).
IP Australian, Examination Report No. 1 issued in Australian Patent Application No. 2015364696 (dated Nov. 1, 2019).
IP Australian, Examination Report No. 2 issued in Australian Patent Application No. 2015364696 (dated Mar. 6, 2020).
Japan Patent Office, Notice of Reasons for Rejection issued in Japanese Application No. 2017-533501 (dated Sep. 11, 2019) 7 pp.
Japan Patent Office, Notice of Reasons for Rejection issued in Japanese Patent Application No. 2017-533501 (dated Jan. 9, 2020).
Mexico Patent Divisional, First Office Action issued in Mexican Application No. MX/a/2017/007840 (dated Feb. 25, 2020).
Republic of Colombia Superintendence of Industry and Commerce, Office Action issued in Colombian Application No. NC2017/0007076 (dated Aug. 2, 2017).
State Intellectual Property Office of the People's Republic of China, Office Action issued in Chinese Application No. 201580076108.1 (dated Feb. 2, 2019).
State Intellectual Property Office of the People's Republic of China, Office Action issued in Chinese Application No. 201580076108.1 (dated Jul. 18, 2019).
State Intellectual Property Office of the People's Republic of China, Third Office Action issued in Chinese Patent Application No. 201580076108.1 (dated Dec. 31, 2019).
Vietnamese National Office of Intellectual Property, Office Action issued in Vietnamese Application No. 1-2017-02611 (dated Feb. 12, 2018).
U.S. Appl. No. 14/571,690, filed Dec. 16, 2014.
U.S. Appl. No. 15/056,202, filed Feb. 29, 2016.
U.S. Appl. No. 15/537,283, filed Jun. 16, 2017.
U.S. Appl. No. 15/900,213, filed Feb. 20, 2018.
U.S. Appl. No. 16/593,806, filed Oct. 4, 2019.
U.S. Appl. No. 16/834,267, filed Mar. 30, 2020.
U.S. Appl. No. 16/837,757, filed Apr. 1, 2020.
U.S. Appl. No. 14/571,647, filed Dec. 16, 2014.
U.S. Appl. No. 15/537,292, filed Jun. 16, 2017.
U.S. Appl. No. 16/593,776, filed Oct. 4, 2019.

(56) References Cited

OTHER PUBLICATIONS

Andreyev et al., "Antisense treatment directed against mutated Ki-ras in human colorectal adenocarcinoma", *Gut.*, vol. 48, pp. 230-237 (2001).
Nagase et al., "Abstract 2602: KRAS G12D and G12V specific alkylating agent (KR12) inhibits growth of colon cancer with those KRAS mutations in vitro as well as in vivo", Proceedings: AACR Annual Meeting 2014, *Cancer Research*, vol. 74, No. 19 (2014).
O'Bryant et al., "A dose-ranging study of pharmacokinetics and pharmacodynamics of the selective apoptotic antineoplastic drug (SAAND), OSI-461, in patients with advanced cancer, in the fasted and fed state", *Cancer Chemotherapy and Pharmacology*, 63(3): 477-489 (May 29, 2008).
European Patent Office, Extended European Search Report issued in European Application No. 19197686.9 (dated May 14, 2020).
IP Australian, Examination Report No. 3 issued in Australian Patent Application No. 2015364696 (dated Apr. 28, 2020).
China National Intellectual Property Administration, The First Office Action issued in Chinese Application No. 201580076204.6 (dated Dec. 11, 2019) 8 pp.
Japan Patent Office, Notice of Reasons for Rejection issued in Japanese Application No. 2017-533502 (dated Aug. 21, 2019) 9 pp.
Japan Patent Office, Notice of Final Rejection issued in Japanese Application No. 2017-533502 (dated Feb. 5, 2020) 11 pp.
U.S. Appl. No. 17/047,787, filed Oct. 15, 2020.
China National Intellectual Property Administration, The Second Office Action issued in Chinese Application No. 201580076204.6 (dated Jul. 21, 2020) 6 pp.
International Searching Authority, "Written Opinion of the International Preliminary Examining Authority in Application No. PCT/US2019/029430," European Patent Office, dated Mar. 20, 2020, pp. 7.
U.S. Appl. No. 15/537,222, filed Jun. 16, 2017.
International Searching Authority, International Search Report in International Application No. PCT/US2014/070511 (dated Apr. 20, 2015) pp. 5.
International Searching Authority, Written Opinion in International Application No. PCT/US2014/070511 (dated Apr. 20, 2015) pp. 4.
International Preliminary Examining Authority, "International Preliminary Report on Patentability Chapter II with Annexes in International Application No. PCT/US2014/070511" (dated Jun. 21, 2017).
International Searching Authority, International Search Report in International Application No. PCT/US2016/066962 (dated Apr. 4, 2017) pp. 6.
International Searching Authority, Written Opinion in International Application No. PCT/US2016/066962 (dated Apr. 4, 2017) pp. 7.
The International Bureau of WIPO, "International Preliminary Report on Patentability in International Application No. PCT/US2016/066962" (dated Jun. 28, 2018) pp. 9.
Pubchem, Compound Summary for CID 70682824, Create Date: Feb. 4, 2013, [retrieved on Apr. 2, 2015]. Retrieved from the Internet, <URL: https://pubchem.ncbi.nlm.nih.gov/compund/70682824.?from=summary>. entire document.
Database Chemcats [Online], May 16, 2014 (May 16, 2014), "TimeTec Stock Building Blocks and Screening Compounds", XP002767898, Database accession No. 1287187215 abstract.

National Institute of Industrial Property, Brazilian Office Action issued in Brazilian Application No. BR112017013012-2 (dated Oct. 13, 2020).
Japan Patent Office, Notice of Reasons for Refusal issued in Japanese Application No. 2020-005245 (dated Nov. 12, 2020) pp. 3.
Alcalde et al., "Indene-based scaffolds. Design and synthesis of novel serotonin 5-$HT_6$receptor ligands", (Abstract only), *Org. Biomol. Chem.*, vol. 6, 3795-3810 (2008).
Berge et al., "Pharmaceutical Salts," *Journal of Pharmaceutical Sciences*, vol. 66 No. 1 pp. 2-19 (1977).
Jemal et al. "Cancer Statistics, 2003", *CA Cancer J Clin*, vol. 53, pp. 5-26 (2003).
Murata et al., "An Efficient Catalyst System for Palladium-Catalyzed Borylation of Aryl Halides with Pinacolborane", (Abstract only), *Synlett*, pp. 1867-1870 (2006).
Okedula et. al., "K-ras Gene Mutation Enhances Motility of Immortalized Airway Cells and Lung Adenocarcinoma Cells via Akt Activation", *Am. J. Pathol.*, vol. 164, No. 1 pp. 91-100 (2004).
Pekol et al., "Human Metabolism of the Proteasome Inhibitor Bortezomib: Identification of Circulating Metabolites", (Abstract only), *Drug Metab. Dispos.*, vol. 33, pp. 771-777 (2005).
Pettit et. al., "Antineoplastic Agents. 291. Isolation and Synthesis of Combretastatins A-4, A-5, and A-6", (Abstract only), *J. Med. Chem.*, vol. 38, pp. 1666-1672 (1995).
Pettit et al., "Antineoplastic agents 322. synthesis of combretastatin A-4 prodrugs", (Abstract only), *Anticancer Drug Des.*, vol. 10, pp. 299-309 (1995).
*Remington's Pharmaceutical Sciences*, Mack Publishing Company, Easton, Pennsylvania, $18^{th}$ edition, pp. 1445 (1990).
Schacter, L., "Etoposide phosphate: what, why, where, and how?", (Abstract only), *Semin. Oncol.*, vol. 23: (6 Suppl. 13): 1-7, (1996).
Slatter et al., "Pharmacokinetics, Metabolism, and Excretion of Irinotecan (CPT-11) Following I.V. Infusion of [$^{14}$C]CPT-11 in Cancer Patients", *Drug Metab. Dispos.*, 28(4): 423-433 (2000).
Snyder et al., "Reductive Coupling and Polymerization of Unsaturated Amides. II. Effect of Substituents", (Abstract only), *J. Am. Chem. Soc.*, vol. 76, pp. 1893 (1954).
Yamaguchi et al., "Efficient Heterogeneous Aerobic Oxidation of Amines by a Supported Ruthenium Catalyst", (Abstract only) *Angew. Chem. Int. Ed.*, vol. 42, pp. 1480-1483 (2003).
International Bureau of WIPO, International Preliminary Report on Patentability issued in PCT Application No. PCT/US2019/029430 (dated Aug. 28, 2020).
Brink et al., "K-ras oncogene mutations in sporadic colorectal cancer in The Netherlands Cohort Study," *Carcinogenesis*, 24(4): 703-710 (2003.
Greig et al., "Tumorigenic and metastatic properties of "normal" and ras-transfected NIH/3T3 cells", *Proc. Natl. Acad. Sci. USA*, 82: 3698-3701 (1985).
Igarashi et al., "Synthesis and Evaluation of Carbamate Prodrugs of a Phenolic Compound", *Chem. Pharm. Bull.*, 55(2): 328-333 (2007).
Ito et al., "A medium-term rat liver bioassay for rapid in vivo detection of carcinogenic potential of chemicals", *Cancer Sol.*, 94(1): 3-8 (2003).
Satta et al., "Establishment of drug resistance in human gastric and colon carcinoma xenograft lines.", *Jpn. J. Cancer Res.*, 82(5): 593-598 (1991) Abstract only.
Suhasani et al., "Cyclic-GMP-Dependent Protein Kinase Inhibits the Ras/Mitogen-Activated Protein Kinase Pathway", *Molecular and Cellular Biology*, 18(12): 6983-6994 (1998).

* cited by examiner

INDENYL COMPOUNDS, PHARMACEUTICAL COMPOSITIONS, AND MEDICAL USES THEREOF

CROSS-REFERENCE TO RELATED APPLICATIONS

This application is a continuation of co-pending U.S. patent application Ser. No. 16/593,776, filed Oct. 4, 2019, which is a continuation of U.S. patent application Ser. No. 15/537,292, filed Jun. 16, 2017, now U.S. Pat. No. 10,526,307, as the U.S. national phase of PCT/US2015/066146, filed Dec. 16, 2015, claiming the benefit of U.S. patent application Ser. No. 14/571,647, filed Dec. 16, 2014, now U.S. Pat. No. 9,862,698, the disclosures of all of which are incorporated herein by reference in their entireties for all purposes.

STATEMENT REGARDING FEDERALLY SPONSORED RESEARCH AND DEVELOPMENT

This invention was made with partial support under NIH/NCI Grant Numbers CA 155638 and CA 148817. Therefore, the U.S. Government has certain rights in this invention.

BACKGROUND OF THE INVENTION

Cancer is a leading cause of death in the developed world, with over one million people diagnosed and more than 500,000 deaths per year in the United States alone. Overall it is estimated that at least one in three people will develop some form of cancer during their lifetime. There are more than 200 different histopathological types of cancer, four of which (breast, lung, colorectal, and prostate) account for over half of all new cases in the U.S. (Jemal et al., Cancer J. Clin., 53, 5-26 (2003)).

Many of these tumors arise from mutations that activate Ras proteins, which control critically important cellular signaling pathways that regulate growth and other processes associated with tumorigenesis. The name "Ras" is an abbreviation of "Rat sarcoma" reflecting the way the first members of the Ras protein family were discovered. The name "ras" also is used to refer to the family of genes encoding these proteins.

Ras-driven cancers have remained the most intractable diseases to any available treatment. New therapeutic and preventative strategies are urgently needed for such cancers (Stephen et al., Cancer Cell, 25, 272-281 (2014)). Drug discovery programs worldwide have sought Ras-selective drugs for many years, but heretofore no avail (Spiegel, et al., Nature Chem. Biol., 10, 613-622 (2014)). New drugs that selectively target abnormal or mutant Ras and/or Ras-mediated pathological processes in patients' tumors will enable highly efficacious treatments of such patients while minimizing toxicity to cells and tissues with normal Ras functions (Stephen et al., supra; Spiegel et al., supra).

Ras proteins are key regulators of several aspects of normal cell growth and malignant transformation, including cellular proliferation, survival and invasiveness, tumor angiogenesis and metastasis (Downward, Nature Rev. Cancer, 3, 11-22 (2003)). Ras proteins are abnormally active in most human tumors due to mutations in the ras genes themselves, or in upstream or downstream Ras pathway components, or other alterations in Ras signaling. Targeted therapies that inhibit Ras-mediated pathways therefore are expected to inhibit the growth, proliferation, survival and spread of tumor cells having activated or mutant Ras. Some such new experimental therapeutic agents have shown promising activity in preclinical studies, albeit with only modest activity in human clinical trials.

Genetic mutations in ras genes were first identified in human cancer over 3 decades ago. Such mutations result in the activation of one or more of three major Ras protein isoforms, including H-Ras, N-Ras, or K-Ras, that turn on signaling pathways leading to uncontrolled cell growth and tumor development. Activating ras gene mutations occur de novo in approximately one third of all human cancers and are especially prevalent in pancreatic, colorectal, and lung tumors. Ras mutations also develop in tumors that become resistant to chemotherapy and/or radiation, as well as to targeted therapies, such as receptor tyrosine kinase inhibitors (Gysin et al., Genes Cancer, 2, 359-372 (2011)). While ras mutations are relatively infrequent in other tumor types, for example, breast cancer, Ras can be pathologically activated by certain growth factor receptors that signal through Ras.

Although ras gene mutations have been known for many years, there currently are no available cancer therapeutics approved by the U.S. Food and Drug Administration that are known to selectively suppress the growth of tumors driven by activated Ras. In fact, Ras has been described as "undruggable" because of the relative abundance in cells and high affinity for its substrate, GTP (Takashima and Faller, Expert Opin. Ther. Targets, 17, 507-531 (2013)).

In addition to its role in cancer, activated Ras is important in a variety of other diseases, collectively referred to as "rasopathies." One such disease, neurofibromatosis type 1 (NF1), a very prevalent autosomal dominant heritable disease, is caused by a mutation in neurofibromin, a Ras GAP (inactivating protein), which results in Ras hyperactivation in the relatively common event of loss of the second NF1 allele. Such mutations reportedly affect 1:3000 live births. The most dire symptoms associated with NF1 include numerous benign tumors (neurofibromas) arising from precursor nerve cells and Schwann cells of the peripheral nervous system. These tumors can cause severe problems depending on their location within the body, such as hearing or vision loss, as well as disfiguring masses on visible areas. Less common but extremely serious complications may arise when central nervous system gliomas develop or plexiform neurofibromas become transformed, resulting in the development of metastatic peripheral nerve sheath tumors (Tidyman and Rauen, Curr. Opin. Genet. Dev., 19, 230-236 (2009)). Another rare developmental disease which is attributable to hyperactive H-Ras is Costello syndrome. This condition causes a range of developmental abnormalities as well as predisposing patients to a variety of benign and malignant neoplasms (Tidyman and Rauen, supra).

Several approaches to treat diseases that arise from activating ras mutations have been undertaken. Because full maturation of the Ras protein requires lipid modification, attempts have been made to target this enzymatic process with inhibitors of farnesyl transferase and geranylgeranyltransferase, but with limited success and significant toxicity. Targeting of downstream components of Ras signaling with inhibitors of Raf/Mek/Erk kinase components of the cascading pathway has been an extremely active area of pharmaceutical research, but also fraught with difficulties and paradoxes arising from complex feedback systems within the pathways (Takashima and Faller, supra).

Inhibitors targeting components within the PI3K/Akt pathway also have not been successful as single agents, but presumably might synergize with Raf/Mek/Erk pathway inhibitors to block Ras-dependent tumor growth and survival. Similarly, several other molecular targets have been identified from RNAi screening, which might provide new opportunities to inhibit the growth of Ras-driven tumors; such other potential targets include CDK4, Cyclin D1, Tiam1, Myc, STK33, and TBK, as well as several genes involved in mitosis (Takashima and Faller, supra).

The nonsteroidal anti-inflammatory drug, sulindac (FIG. 1) has been reported to selectively inhibit proliferation of cultured tumor cells having ras mutations (Herrmann et al., Oncogene, 17, 1769-1776 (1998)). Extensive chemical modifications of sulindac and the related NSAID, indomethacin, have been aimed at removing cyclooxygenase-inhibitory activity, while improving anticancer activity (Gurpinar et al., Mol. Cancer Ther., 12, 663-674 (2013); Romeiro et al., Eur. J. Med. Chem., 44, 1959-1971 (2009); Chennamaneni et al., Eur. J. Med. Chem., 56, 17-29 (2012)). An example of a highly potent antiproliferative derivative is a hydroxy-substituted indene derivative of sulindac, OSIP-487703 (FIG. 1), that was reported to arrest colon cancer cells in mitosis by causing microtubule depolymerization (Xiao et al., Mol. Cancer Ther., 5, 60-67 (2006)). OSIP-487703 also was reported to inhibit the growth and induce apoptosis of human SW480 colon cancer cells. These properties of mitotic arrest and microtubule disruption were shared by several additional related compounds, including a pyridine (CP461) and trimethoxy (CP248) substituted variants (FIG. 1) (Lim et al., Clin. Cancer Res, 9, 4972-4982 (2003); Yoon, et al., Mol. Cancer Ther., 1, 393-404 (2002)). However, there was no reported association of antitumor properties of these compounds (FIG. 1) with Ras function, but rather such properties were attributed to direct binding to the microtubule subunit, tubulin, thereby causing mitotic arrest and blocking cell division. Still other reports describe their ability to induce apoptosis by inhibition of cGMP phosphodiesterase (Thompson et al., Cancer Research, 60, 3338-3342 (2000)).

Other investigators reported that sulindac sulfide (FIG. 1) can inhibit Ras-induced malignant transformation, possibly by decreasing the effects of activated Ras on its main effector, the c-Raf-1kinase, due to direct binding to the ras gene product p21 in a non-covalent manner (Herrmann et al., supra). Sulindac sulfide also can inhibit focus formation, a marker of malignant transformation, by rat or mouse fibroblasts by forced Ras expression, but not by other transformation pathways (Gala et al., Cancer Lett., 175, 89-94 (2002); Herrmann et al., supra). Sulindac sulfide was reported also to bind Ras directly and interfere with nucleotide exchange. Several groups additionally reported that sulindac interferes with Ras binding to the downstream signaling kinase c-Raf, and blocks activation of downstream signaling or transcription (Herrmann et al., supra; Pan et al., Cell Signal., 20, 1134-1141 (2008)).

The aforementioned findings led to efforts to improve the Ras inhibitory activity of sulindac sulfide through chemical modifications (Karaguni et al., Bioorg. Med. Chem. Lett., 12, 709-713 (2002)). Several derivatives were identified that were more potent inhibitors of tumor cell proliferation, and four related compounds (FIG. 2) exhibited selectivity towards a Ras-transfected MDCK cell line compared to the parental cell line. Three of these compounds also potently disrupted the Ras-Raf interaction. However, none of the four were more potent toward the mutant K-Ras-bearing SW-480 cell line, although they did inhibit Erk phosphorylation and bound weakly to the G-domain of H-Ras (Waldmann et al., Angew. Chem. Int. Ed. Engl., 43, 454-458 (2004)).

In addition to sulindac sulfide, the non-COX inhibitory sulfone metabolite of sulindac has been reported to have selective effects on tumor cells with mutant Ras. For example, transfection of Caco-2 colon tumor cells with the activated K-Ras oncogene caused cells treated with either sulindac sulfide or sulfone to undergo apoptosis earlier than non-transfected cells. (Lawson et al., Cancer Epidemiol. Biomarkers Prev., 9, 1155-62 (2000)). Other investigators have reported that sulindac sulfone can inhibit mammary tumorigenesis in rats and that the effect was greater on tumors with the mutant H-Ras genotype (Thompson et al., Cancer Research 57, 267-271 (1997)). However, other investigators report that the inhibition of colon tumorigenesis in rats by either sulindac or sulindac sulfone occurs independently of K-Ras mutations (de Jong et al., Amer. J. Physio. Gastro and Liver Phys. 278, 266-272 (2000)). Yet other investigators report that the K-Ras oncogene increases resistance to sulindac-induced apoptosis in rat enterocytes (Arber et al., Gastroenterology, 113, 1892-1900 (1997)). As such, the influence of Ras mutations on the anticancer activity of sulindac and its metabolites is controversial and unresolved, and has not been exploited to improve anticancer potency or selectivity.

Certain other compounds have been described with selective toxicity toward cells expressing activated Ras. A high-throughput phenotypic screen of over 300,000 compounds was conducted within NIH Molecular Libraries Screening Center program to identify compounds which were synthetically lethal to cells expressing oncogenic H-Ras. A lead compound, ML210 (FIG. 3), inhibited growth of cells expressing mutant Ras with an IC50 of 71 nM, and was 4-fold selective versus cells lacking oncogenic Ras. Though the specific molecular target of ML210 is unknown, the compound was chemically optimized to eliminate reactive groups and improve pharmacologic properties (ML210, Dec. 12, 2011 update, Probe Reports from NIH Molecular Libraries Program, Bethesda, http://www.ncbi.nlm.nih.gov/books/NBK98919/).

A separate high-throughput screen identified two compounds, RSL3 and RSL5 (FIG. 3) which induce non-apoptotic, Mek-dependent, oxidative cell death (Yang and Stockwell, Chem. Biol., 15, 234-245 (2008). RSL5, like a previously identified Ras synthetic lethal compound, erastin (FIG. 3), binds the voltage-dependent anion channel (VDAC) (Dolma et al., Cancer Cell, 3, 285-296 (2003)). Yet another small-molecule screen identified oncrasin, a compound selectively active against K-Ras mutant cell lines (Guo et al., Cancer Res., 68, 7403-7408 (2008)). One analog, NSC-743380 (FIG. 3), is highly potent and has shown anti-tumor activity in a preclinical model of K-Ras driven renal cancer (Guo et al., PLoS One, 6, e28487 (2011)). A prodrug approach has recently been described for oncrasin derivatives, to improve stability, pharmacokinetics, and safety (Wu et al., Bioorg. Med. Chem., 22, 5234-5240 (2014)). A synthetic lethal screen using embryonic fibroblasts derived from mice expressing the oncogenic K-Ras (G12D) identified a compound, lanperisone (FIG. 3), that induced non-apoptotic cell death via a mechanism involving oxidative stress (Shaw et al., Proc. Natl. Acad. Sci. USA, 108, 8773-8778 (2011)). In contrast to the synthetic lethal approach, a fragment-based screening approach paired with crystallographic studies has been used to identify compounds which irreversibly bind to and inhibit K-Ras in lung tumor cells having the relatively rare G12C ras gene mutation (Ostrem et al., Nature, 503, 548-551 (2013)). While compounds of this series potently inhibit Ras through a covalent interaction, the low frequency of this mutation may limit the utility of such compounds. Finally, a new investigational strategy for targeting oncogenic Ras has been described (Zimmerman et al., J. Med. Chem., 57, 5435-5448 (2014)) which involves structure guided design and kinetic analysis of benzimidazole inhibitors targeting the PDEδ prenyl binding site.

WO 97/47303 and WO 2014/047592, U.S. Patent Application Publication Nos. 2003/0009033 and 2003/0194750, U.S. Pat. Nos. 6,063,818; 6,071,934, 5,965,619; 5,401,774; 6,538,029, 6,121,321, and UK Patent No. GB 1370028 disclose certain anticancer compounds; however, these documents do not disclose that the compounds have any Ras-specific activity, nor any basis for a selective Ras-directed method of use.

The foregoing shows that there exists an unmet need for compounds that are suitable for treating or preventing cancers. There further exists an unmet need for compounds that inhibit Ras-dependent diseases or undesirable conditions.

BRIEF SUMMARY OF THE INVENTION

The invention provides a compound of formula I:

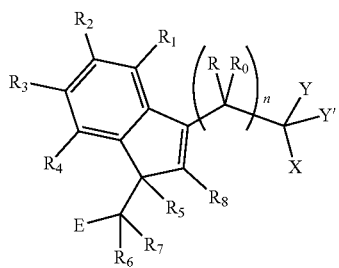

wherein:

R and $R_0$ are independently selected from hydrogen, hydroxyl, alkyl, cycloalkyl, cycloalkylalkyl, heterocyclyl, heterocyclylalkyl, alkenyl, alkenylalkyl, alkynyl, alkynylalkyl, cyano, cyanoalkyl, halogen, azido, alkoxy, haloalkyl and a substituted or unsubstituted group selected from aminocarbonyl, aminocarbonylalkyl, aminosulfonyl, aminosulfonylalkyl, alkylcarbonyl, alkylcarbonylalkyl, amino, alkylamino, dialkylamino, aminocarbonylalkylamino, and carbocyclylamino, carbocyclylalkylamino, heterocyclylamino and heterocyclylalkylamino wherein the ring structures are saturated or unsaturated; or R and $R_0$ together is double-bonded oxygen or double-bonded sulfur, or R and $R_0$ together is a double-bonded nitrogen bonded to one of hydrogen, hydroxyl, alkyl, or haloalkyl, or R and $R_0$ together is a double-bonded carbon bonded to two substituents independently selected from hydrogen, hydroxyl, alkyl and haloalkyl, or $R_0$ is nitrogen which is part of a substituted or unsubstituted, saturated or unsaturated, 3-, 4-, 5-, 6- or 7-membered heterocyclic ring; or R and $R_0$ together is a substituted or unsubstituted, saturated or unsaturated 3-, 4-, 5-, 6- or 7-membered heterocyclic ring;

n is 0, 1 or 2;

$R_1$, $R_2$, $R_3$, and $R_4$ are independently selected from hydrogen, halogen, alkyl, cycloalkyl, haloalkyl, hydroxyl, carboxyl, alkoxy, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, and sulfonamido, or any two of $R_1$, $R_2$, $R_3$, and $R_4$ form an alkylenedioxy group;

$R_5$, $R_6$, $R_7$, and $R_8$ are independently selected from hydrogen, alkyl, haloalkyl, and alkoxy; or $R_5$ and $R_6$ together form a carbon-carbon bond;

Y is hydrogen, alkyl, or haloalkyl, and Y' is hydrogen, alkyl, haloalkyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or haloalkyl;

X is selected from hydrogen, alkyl, haloalkyl, alkoxy, alkylmercapto, and hydroxyl with the proviso that X is not hydroxyl when Y and Y' together is oxygen in a compound of formula I wherein $R_5$ and $R_6$ together is a carbon-carbon bond, or X is NR'R", where R' and R" are independently selected from the group consisting of hydrogen, hydroxyl, alkyl, aryloxy, cyanoalkyl, haloalkyl, alkoxy, alkenyl, alkynyl, hydroxyalkyl, polyhydroxyalkyl, alkylaminoalkyl, dialkylaminoalkyl, aminoalkyl, alkylamino, aryl, arylalkyl, arylalkenyl, arylcycloalkyl, arylcycloalkenyl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one, two or three double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, sulfonamido and $COR_{11}$, wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen and optionally oxygen or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and E is a substituted or unsubstituted, saturated or unsaturated, 7-membered, 6-membered, 5-membered, 4-membered or 3-membered carbocyclic or heterocyclic ring; or a pharmaceutically acceptable salt thereof or a prodrug thereof;

with the proviso that when E is a substituted aryl or heteroaryl, then no substituent on the aryl or heteroaryl ring can be alkylsulfinyl or alkylsulfonyl, and no substituent on the aryl ring can be alkylmercapto, nor p-halo when R' is dialkylaminoalkyl;

or, when $R_5$ and $R_6$ together is a carbon-carbon bond, R" is hydrogen and R' is a substituted arylalkyl, then E cannot be a substituted or unsubstituted heterocyclic ring selected from the group consisting of pyridinyl, pyrimidinyl, pyrazinyl, imidazolyl, triazinyl, thiophenyl, furanyl, thiazolyl, pyrazolyl, quinolinyl, isoquinolinyl, indolyl, benzimidazolyl, azinyl, tratrazolyl, pyridazinyl, and pyrrolyl;

or, when n is 1 or 2, $R_5$ and $R_6$ together form a carbon-carbon bond, Y and Y' are hydrogens or Y and Y' together is oxygen, and E is a substituted phenyl, then X cannot be hydrogen, alkyl, haloalkyl, alkylmercapto or NR'R" wherein R' is hydrogen, hydroxyl or alkyl, and R" is hydrogen, alkyl or haloalkyl;

or, when $R_5$ and $R_6$ are independently selected from hydrogen or alkyl or $R_5$ and $R_6$ together form a carbon-carbon bond, E is a substituted aryl or heteroaryl, and X is NR'R" wherein R' is hydrogen or hydroxyl and R" is $COR_{11}$, then $R_{11}$ cannot be alkyl, alkoxy or amino;

or, when $R_5$, $R_6$, $R_7$ and $R_8$ are independently selected from hydrogen, alkyl and alkoxy, or $R_5$ and $R_6$ form a carbon-carbon bond, $R_7$ is hydrogen, $R_8$ is hydrogen, alkoxy or alkyl, E is phenyl substituted with at least two hydroxyl groups or at least two alkoxy groups, and Y and Y' together is double-bonded oxygen, then X cannot be substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocycoalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl;

or, when R and $R_0$ are hydrogens, at least one of $R_1$, $R_2$, $R_3$, and $R_4$ is halogen, Y and Y' together is double-bonded oxygen, and X is NR'R", wherein R' is furanylalkyl and R" is selected from hydrogen and $COR_{11}$, wherein $R_{11}$ is selected from hydrogen, amino, alkyl, haloalkyl, alkoxy, alkylmercapto, and aryl, then E cannot be 3,4,5-trimethoxyphenyl;

or, when R' is halophenylalkyl and R" is hydrogen, then E cannot be halophenyl;

or, when n=0 and Y and Y' together is double-bonded oxygen, then X cannot be alkoxy, aryloxy, arylalkyloxy, or NR'R" wherein R" is hydrogen and R' is alkyl, aryl, or arylalkyl.

In an embodiment, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is a substituted aryl, then E cannot be a substituted aryl. For example, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, R' is an aryl substituted with any of halo, alkoxy, amino, alkylamino, dialkylamino and sulfonamido, then E cannot be a substituted aryl wherein two substituents are identically selected from hydroxyl and alkoxy.

The invention additionally provides a compound of formula I:

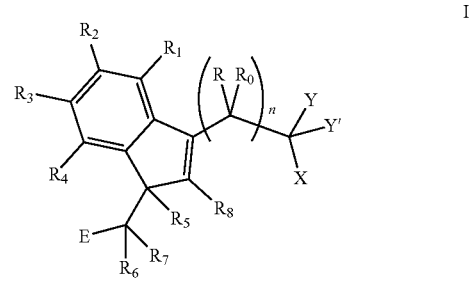

wherein:

R and $R_0$ are independently selected from hydrogen, hydroxyl, alkyl, cycloalkyl, cycloalkylalkyl, heterocyclyl, heterocyclylalkyl, alkenyl, alkenylalkyl, alkynyl, alkynylalkyl, cyano, cyanoalkyl, halogen, azido, alkoxy, haloalkyl and a substituted or unsubstituted group selected from aminocarbonyl, aminocarbonylalkyl, aminosulfonyl, aminosulfonylalkyl, alkylcarbonyl, alkylcarbonylalkyl, amino, alkylamino, dialkylamino, aminocarbonylalkylamino, and carbocyclylamino, carbocyclylalkylamino, heterocyclylamino and heterocyclylalkylamino wherein the ring structures are saturated or unsaturated; or R and $R_0$ together is double-bonded oxygen or double-bonded sulfur, or R and $R_0$ together is a double-bonded nitrogen bonded to one of hydrogen, hydroxyl, alkyl, or haloalkyl, or R and $R_0$ together is a double-bonded carbon bonded to two substituents independently selected from hydrogen, hydroxyl, alkyl and haloalkyl, or $R_0$ is nitrogen which is part of a substituted or unsubstituted, saturated or unsaturated, 3-, 4-, 5-, 6- or 7-membered heterocyclic ring; or R and $R_0$ together is a substituted or unsubstituted, saturated or unsaturated 3-, 4-, 5-, 6- or 7-membered heterocyclic ring;

n is 0, 1 or 2;

$R_1$, $R_2$, $R_3$, and $R_4$ are independently selected from hydrogen, halogen, alkyl, haloalkyl, hydroxyl, carboxyl, alkoxy, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylcarbonyloxy, alkylcarbonyloxyalkyloxy, alkylsulfinyloxy, alkylsulfonyloxy, carbamate, carbamido, alkoxycarbonyl, alkylaminocarbonyl, aminocarbonyl, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy and sulfamido, or any two of $R_1$, $R_2$, $R_3$ and $R_4$ form an alkylenedioxy group;

$R_5$, $R_6$, $R_7$ and $R_8$ are independently selected from hydrogen, alkyl and alkoxy, or $R_5$ and $R_6$ form a carbon-carbon bond, $R_7$ is hydrogen, $R_8$ is hydrogen, alkoxy or alkyl, E is phenyl substituted with at least two hydroxyl groups or at least two alkoxy groups, and at least one substituted or unsubstituted group selected from phosphonooxy, phosphonoalkyloxy, formyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy;

Y and Y' together is double-bonded oxygen;

X is substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocyclylalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl;

or a pharmaceutically acceptable salt thereof.

The invention further provides a compound of formula (II):

wherein:

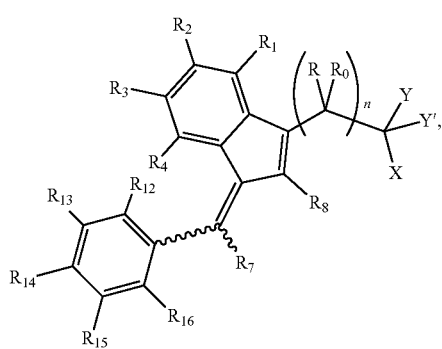

R and $R_0$ are independently selected from hydrogen, hydroxyl, alkyl, cycloalkyl, cycloalkylalkyl, heterocyclyl, heterocyclylalkyl, alkenyl, alkenylalkyl, alkynyl, alkynylalkyl, cyano, cyanoalkyl, halogen, azido, alkoxy, haloalkyl and a substituted or unsubstituted group selected from aminocarbonyl, aminocarbonylalkyl, aminosulfonyl, aminosulfonylalkyl, alkylcarbonyl, alkylcarbonylalkyl, amino, alkylamino, dialkylamino, aminocarbonylalkylamino, and carbocyclylamino, carbocyclylalkylamino, heterocyclylamino and heterocyclylalkylamino wherein the ring structures are saturated or unsaturated; or R and $R_0$ together is double-bonded oxygen or double-bonded sulfur, or R and $R_0$ together is a double-bonded nitrogen bonded to one of hydrogen, hydroxyl, alkyl, or haloalkyl, or R and $R_0$ together is a double-bonded carbon bonded to two substituents independently selected from hydrogen, hydroxyl, alkyl and haloalkyl, or $R_0$ is nitrogen which is part of a substituted or unsubstituted, saturated or unsaturated, 3-, 4-, 5-, 6- or 7-membered heterocyclic ring; or R and $R_0$ together is a substituted or unsubstituted, saturated or unsaturated 3-, 4-, 5-, 6- or 7-membered heterocyclic ring;

n is 0, 1 or 2;

Y is hydrogen, alkyl, or haloalkyl, and Y' is hydrogen, alkyl, cycloalkyl, haloalkyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or haloalkyl;

$R_1$, $R_2$, $R_3$, $R_4$, $R_{12}$, $R_{13}$, $R_{14}$, $R_{15}$, and $R_{16}$ are independently selected from hydrogen, halogen, alkyl, cycloalkyl, haloalkyl, hydroxyl, carboxyl, alkoxy, formyloxy, alkylcarbonyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy and sulfonamido, or any two of $R_1$, $R_2$, $R_3$, and $R_4$ or any two of $R_{12}$, $R_{13}$, $R_{14}$, $R_{15}$ and $R_{16}$ form an alkylenedioxy group;

$R_7$ and $R_8$ are independently selected from hydrogen, alkyl, haloalkyl, and alkoxy;

X is selected from hydrogen, alkyl, haloalkyl, alkoxy, alkylmercapto, and hydroxyl with the proviso that X is not hydroxyl when Y and Y' together is oxygen, or X is NR'R", where R' is selected from the group consisting of hydrogen, hydroxyl, alkyl, aryloxy, cyanoalkyl, haloalkyl, alkoxy, alkenyl, alkynyl, hydroxyalkyl, polyhydroxyalkyl, alkylaminoalkyl, dialkylaminoalkyl, aminoalkyl, alkylamino, arylalkyl, arylalkenyl, arylcycloalkyl, arylcycloalkenyl, aryl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one, two, or three double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, alkoxy, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; or a pharmaceutically acceptable salt thereof or a prodrug thereof;

with the proviso that when n is 1 or 2, Y and Y' are hydrogens or Y and Y' together is double-bonded oxygen, and at least one of $R_{12}$, $R_{13}$, $R_{14}$, $R_{15}$ and $R_{16}$ is not hydrogen, then X cannot be hydrogen, alkyl, haloalkyl, alkylmercapto or NR'R" wherein R' is hydrogen, hydroxyl or alkyl, and R" is hydrogen, alkyl or haloalkyl;

or, when X is NR'R" wherein R' is phenylalkyl and R" is hydrogen, then two of $R_{12}$ to $R_{16}$ cannot be identically selected from hydroxyl or alkoxy;

or, when X is NR'R" wherein R' is hydrogen or hydroxyl, and R" is $COR_{11}$, then $R_{11}$ cannot be alkyl, alkoxy or amino;

or, when R and $R_0$ are hydrogens, at least one of $R_1$, $R_2$, $R_3$, and $R_4$ is halogen, Y and Y' together is double-bonded oxygen and X is NR'R" wherein R' is furanylalkyl and R" is selected from hydrogen and $COR_{11}$, wherein $R_{11}$ is selected from hydrogen, amino, alkyl, haloalkyl, alkoxy, alkylmercapto, and aryl, then $R_{13}$, $R_{14}$, and $R_{15}$ cannot each be methoxy;

or, when R and $R_0$ together is double-bonded oxygen and n is 1, then the heterocycle of the heterocyclyl or heterocyclylalkyl is furanyl or pyrrolyl;

or, when R' is halophenylalkyl and R" is hydrogen, then none of $R_{12}$, $R_{13}$, $R_{14}$, $R_{15}$ or $R_{16}$ can be halogen;

or, when n=0 and Y and Y' together is double bonded oxyen, then X cannot be alkoxy, aryloxy, arylalkyloxy, or NR'R" wherein R" is hydrogen and R' is alkyl, aryl or arylalkyl.

In an embodiment, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is a substituted aryl, then each of $R_{12}$, $R_{13}$, $R_{14}$, $R_{15}$ and $R_{16}$ must be hydrogen. For example, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is an aryl substituted with any of halo, alkoxy, amino, alkylamino, dialkylamino, and sulfonamido, then no two of $R_{12}$, $R_{13}$, $R_{14}$, $R_{15}$ and $R_{16}$ can be identically selected from hydroxyl and alkoxy;

or, when $R_7$ is hydrogen, $R_8$ is hydrogen, alkoxy, or alkyl, least two of $R_{12}$, $R_{13}$, $R_{14}$, $R_{15}$ and $R_{16}$ are identically selected from hydroxyl or alkoxy, and Y and Y' together is double-bonded oxygen, then X cannot be substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocycoalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl. For example, when $R_7$ is hydrogen and $R_8$ is selected from hydrogen, alkyl and alkoxy, at least two of $R_{12}$, $R_{13}$, $R_{14}$, $R_{15}$ and $R_{16}$ are identically selected from hydroxyl or alkyl, Y and Y' together is oxygen and R" is hydrogen, then R' cannot be phenylalkyl.

The invention also provides a compound of formula (II): wherein:

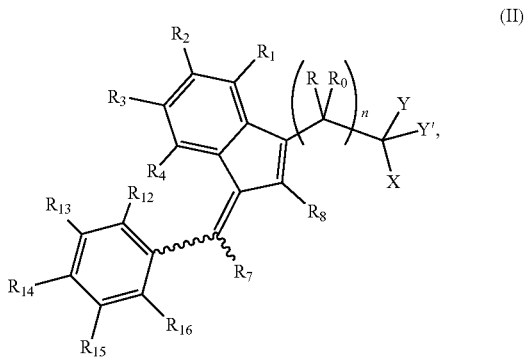

(II)

R and $R_0$ are independently selected from hydrogen, hydroxyl, alkyl, cycloalkyl, cycloalkylalkyl, heterocyclyl, heterocyclylalkyl, alkenyl, alkenylalkyl, alkynyl, alkynylalkyl, cyano, cyanoalkyl, halogen, azido, alkoxy, haloalkyl and a substituted or unsubstituted group selected from aminocarbonyl, aminocarbonylalkyl, aminosulfonyl, aminosulfonylalkyl, alkylcarbonyl, alkylcarbonylalkyl, amino, alkylamino, dialkylamino, aminocarbonylalkylamino, and carbocyclylamino, carbocyclylalkylamino, heterocyclylamino and heterocyclylalkylamino wherein the ring structures are saturated or unsaturated; or R and $R_0$ together is double-bonded oxygen or double-bonded sulfur, or R and $R_0$ together is a double-bonded nitrogen bonded to one of hydrogen, hydroxyl, alkyl, or haloalkyl, or R and $R_0$ together is a double-bonded carbon bonded to two substituents independently selected from hydrogen, hydroxyl, alkyl and haloalkyl, or $R_0$ is nitrogen which is part of a substituted or unsubstituted, saturated or unsaturated, 3-, 4-, 5-, 6- or 7-membered heterocyclic ring; or R and $R_0$ together is a substituted or unsubstituted, saturated or unsaturated 3-, 4-, 5-, 6- or 7-membered heterocyclic ring;

n is 0, 1 or 2;

Y is hydrogen, alkyl, or haloalkyl, and Y' is hydrogen, alkyl, haloalkyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or haloalkyl;

$R_1$, $R_2$, $R_3$, $R_4$, $R_{12}$, $R_{13}$, $R_{14}$, $R_{15}$ and $R_{16}$ are independently selected from hydrogen, halogen, alkyl, cycloalkyl, haloalkyl, hydroxyl, carboxyl, alkoxy, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, and sulfonamido, or any two of $R_1$, $R_2$, $R_3$ and $R_4$ or any two of $R_{12}$, $R_{13}$, $R_{14}$, $R_{15}$ and $R_{16}$ form an alkylenedioxy group;

$R_7$ and $R_8$ are independently selected from hydrogen, alkyl, haloalkyl, and alkoxy;

X is selected from hydrogen, alkyl, haloalkyl, alkoxy, alkylmercapto, and hydroxyl with the proviso that X is not hydroxyl when Y and Y' together is oxygen, or X is NR'R", where R' is selected from the group consisting of hydrogen, hydroxyl, alkyl, aryloxy, cyanoalkyl, haloalkyl, alkoxy, alkenyl, alkynyl, hydroxyalkyl, polyhydroxyalkyl, alkylaminoalkyl, dialkylaminoalkyl, aminoalkyl, alkylamino, arylalkyl, arylalkenyl, arylcycloalkyl, arylcycloalkenyl, aryl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one, two or three double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; or a pharmaceutically acceptable salt thereof or a prodrug thereof;

with the proviso that when n is 1 or 2, Y and Y' are hydrogens or Y and Y' together is double-bonded oxygen, and at least one of $R_{12}$, $R_{13}$, $R_{14}$, $R_{15}$ and $R_{16}$ is not hydrogen, then X cannot be hydrogen, alkyl, haloalkyl, alkylmercapto or NR'R" wherein R' is hydrogen, hydroxyl or alkyl, and R" is hydrogen, alkyl or haloalkyl;

or, when X is NR'R" wherein R' is phenylalkyl and R" is hydrogen, then two of $R_{12}$ to $R_{16}$ cannot be identically selected from hydroxyl or alkoxy;

or, when X is NR'R" wherein R' is hydrogen or hydroxyl, and R" is $COR_{11}$, then $R_{11}$ cannot be alkyl, alkoxy or amino;

or, when R and $R_0$ are hydrogens, at least one of $R_1$, $R_2$, $R_3$ and $R_4$ is halogen, Y and Y' together is double-bonded oxygen and X is NR'R" wherein R' is furanylalkyl and R" is selected from hydrogen and $COR_{11}$, wherein $R_{11}$ is selected from hydrogen, amino, alkyl, haloalkyl, alkoxy, alkylmercapto and aryl, then $R_{13}$, $R_{14}$ and $R_{15}$ cannot each be methoxy;

or, when R' is halophenylalkyl and R" is hydrogen, then none of $R_{12}$, $R_{13}$, $R_{14}$, $R_{15}$ or $R_{16}$ can be halogen;

or, when n=0 and Y and Y' together is double-bonded oxygen, then X cannot be alkoxy, aryloxy, arylalkyloxy, or NR'R" wherein R" is hydrogen and R' is alkyl, aryl or arylalkyl;

or, when the heterocycle of the heterocyclyl and heterocyclylalkyl of R' is selected from 7-membered heterocyclic rings, 6-membered heterocyclic rings, and 5-membered heterocyclic rings, and Y and Y' together is double-bonded oxygen, then $R_7$ and $R_8$ are independently selected from hydrogen, alkyl, haloalkyl, and alkoxy;

or, when the heterocycle of the heterocyclyl and heterocyclylalkyl of R' is selected from azepanyl, oxazepanyl, thiazepanyl, azepinyl, oxepinyl, thiepanyl, homopiperazinyl, diazepinyl, thiazepinyl, oxanyl, thianyl, pyranyl, thiopyranyl, thiomorpholinyl, dioxanyl, dithianyl, diazinyl, oxazinyl, thiazinyl, dioxinyl, dithiinyl, trioxanyl, trithianyl, triazinyl, tetrazinyl, tetrahydrofuranyl, tetrahydrothiophenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl, and tetrazolyl, then $R_7$ and $R_8$ are independently selected from hydrogen, alkyl, haloalkyl and alkoxy.

In an embodiment, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is a substituted aryl, then each of $R_{12}$, $R_{13}$, $R_{14}$, $R_{15}$ and $R_{16}$ must be hydrogen. For example, when R and Ro are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is an aryl substituted with any of halo, alkoxy, amino, alkylamino, dialkylamino and sulfonamido, then no two of $R_{12}$, $R_{13}$, $R_{14}$, $R_{15}$ and $R_{16}$ can be identically selected from hydroxyl and alkoxy;

or, when $R_7$ is hydrogen, $R_8$ is hydrogen, alkoxy or alkyl, least two of $R_{12}$, $R_{13}$, $R_{14}$, $R_{15}$ and $R_{16}$ are identically selected from hydroxyl or alkoxy, and Y and Y' together is double-bonded oxygen, then X cannot be substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocycoalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl. For example, when $R_7$ is hydrogen and $R_8$ is selected from hydrogen, alkyl and alkoxy, at least two of $R_{12}$, $R_{13}$, $R_{14}$, $R_{15}$ and $R_{16}$ are identically selected from hydroxyl or alkyl, Y and Y' together is oxygen and R" is hydrogen, then R' cannot be phenylalkyl.

The compounds of the invention are suitable for treating or preventing cancer.

The present invention further provides a pharmaceutical composition comprising a compound described above and a pharmaceutically acceptable carrier.

The present invention further provides a method of therapeutically or prophylactically treating a human or nonhuman mammalian patient with cancer comprising administering to said patient an anticancer effective amount of at least one compound of formula I or II, a pharmaceutically acceptable salt or prodrug thereof, either alone or in combination with at least one therapeutic agent which is not a compound of the present invention, or a pharmaceutically acceptable salt or prodrug thereof, for example, an anticancer drug or radiation.

In an embodiment, the present invention provides a method of therapeutically or prophylactically treating a human or nonhuman mammalian patient with a disease or condition treatable by the inhibition of one or more neoplastic or cancerous process, which method comprises administering to a patient in need thereof a therapeutically or prophylactically effective amount of at least one neoplastic or cancerous inhibitory compound of formula I or II, as described above, or a pharmaceutically acceptable salt or prodrug thereof, either alone or in combination with at least one therapeutic agent which is not a compound of formula I or II as described above, or a pharmaceutically acceptable salt or prodrug thereof, for example an anticancer drug or radiation.

BRIEF DESCRIPTION OF THE SEVERAL VIEWS OF THE DRAWING(S)

Figure 5A:
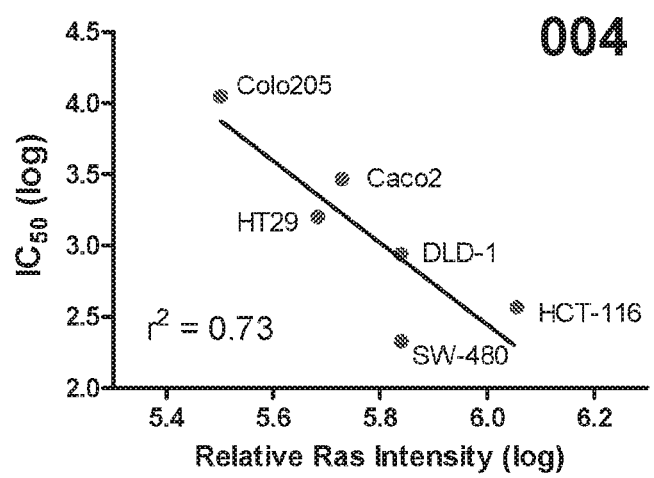

FIG. 5A reveals a correlation between sensitivity of tumor cells to compound 004 and Ras activation status of the cells as determined by Western blot analysis.

Figure 5B:
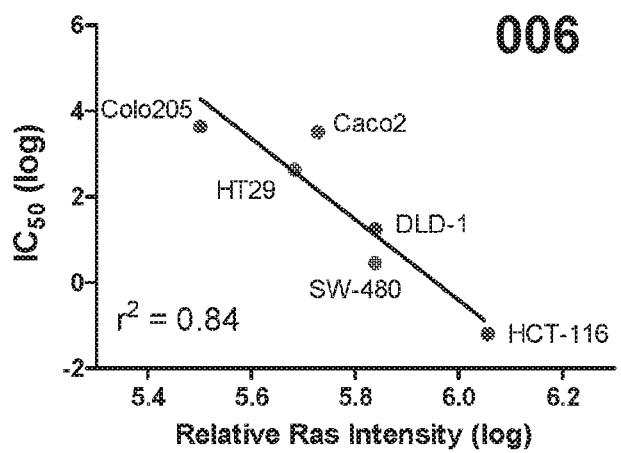

FIG. 5B reveals a correlation between sensitivity of tumor cells to compound 006 and Ras activation status of the cells as determined by Western blot analysis.

Figure 5C:
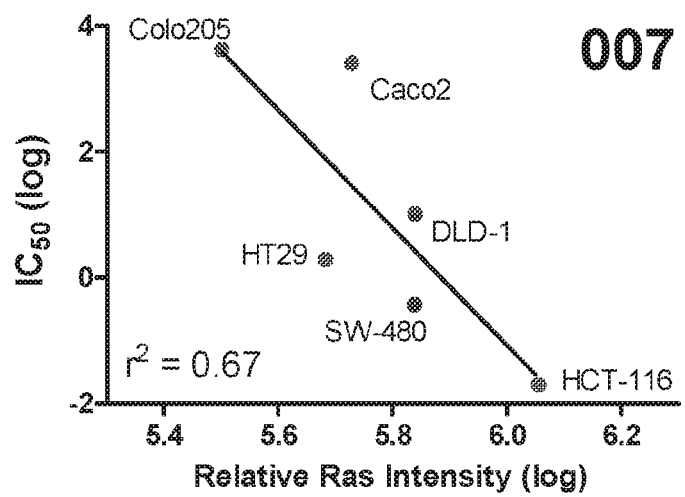

FIG. 5C reveals a correlation between sensitivity of tumor cells to compound 007 and Ras activation status of the cells as determined by Western blot analysis.

Figure 5D:
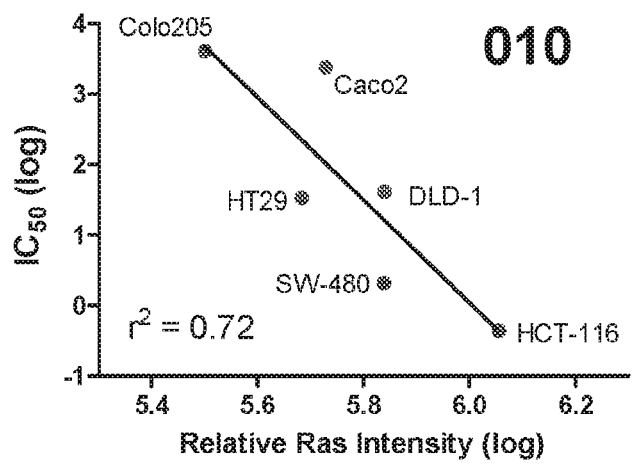
Figure 6A:
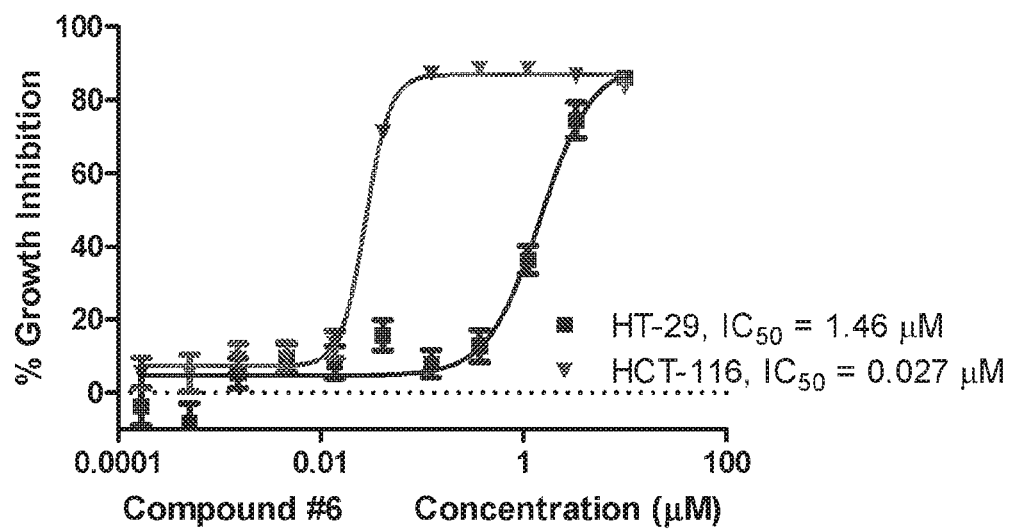
Figure 6B:
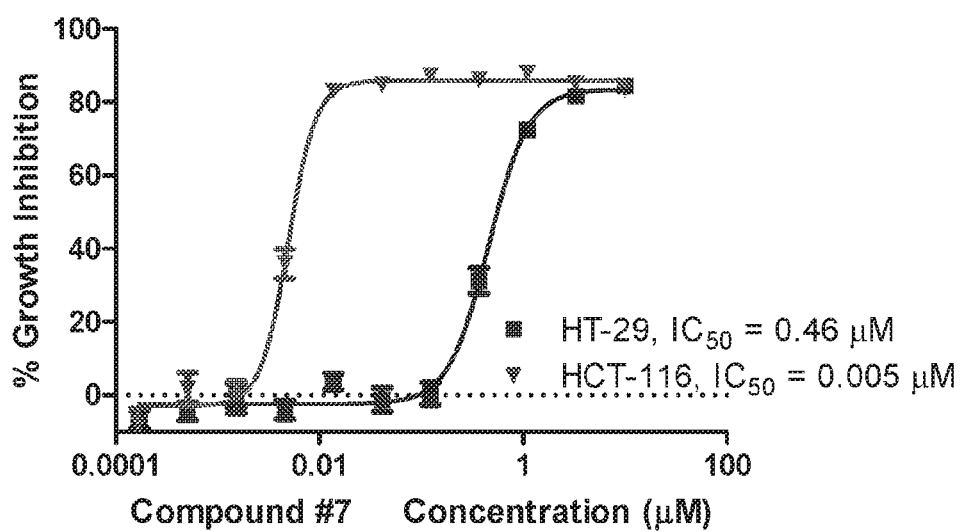
Figure 6C:
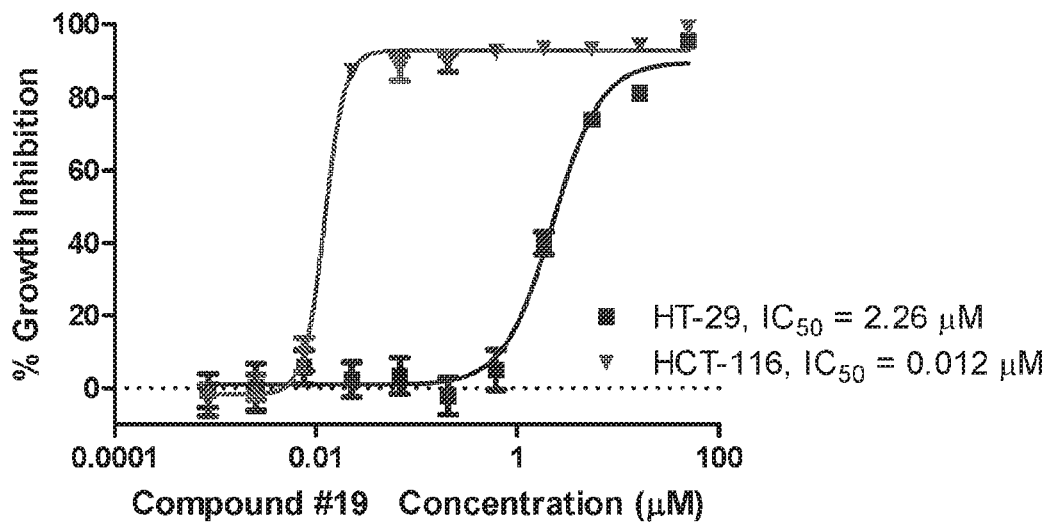
Figure 6D:
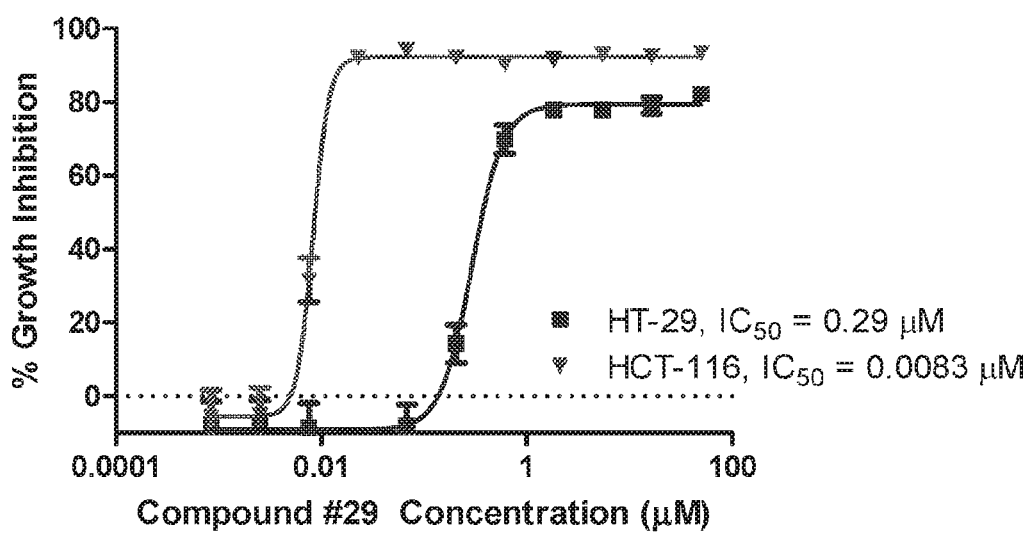
Figure 6E:
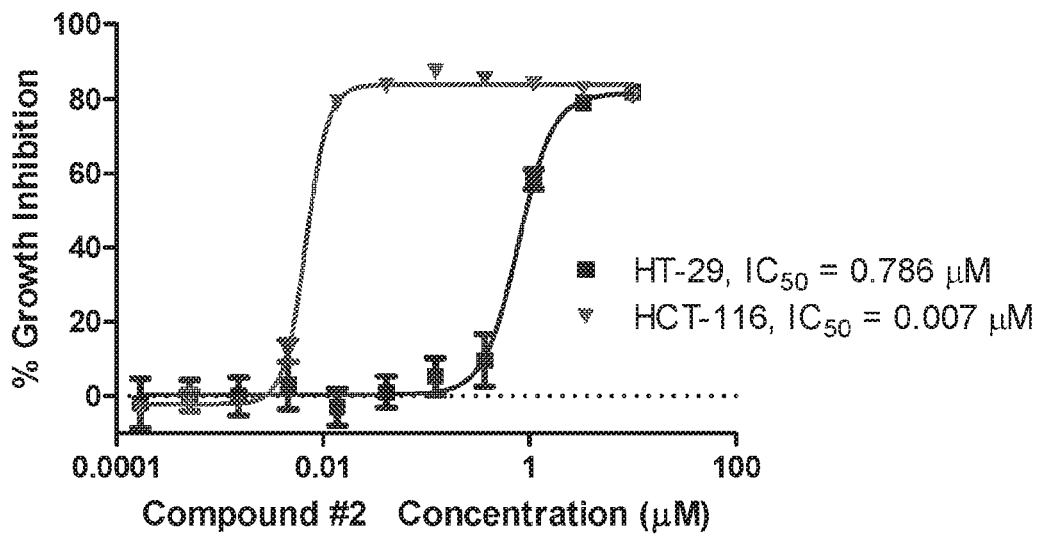
Figure 6F:
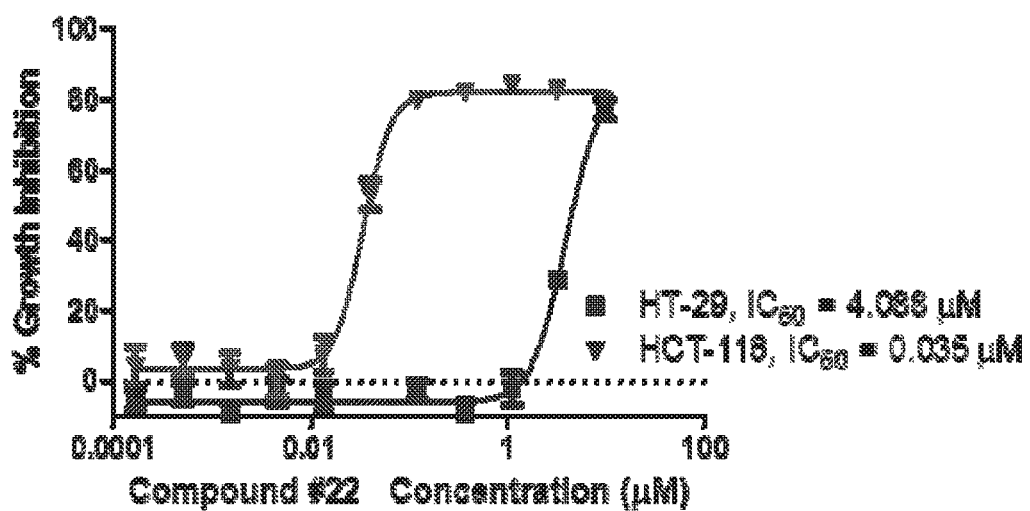
Figure 6G:
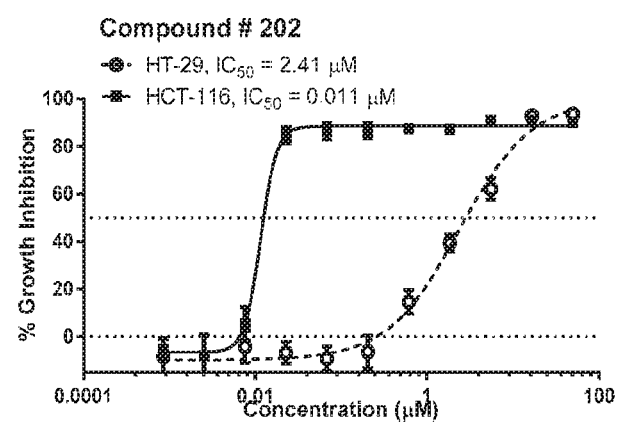
Figure 6H:
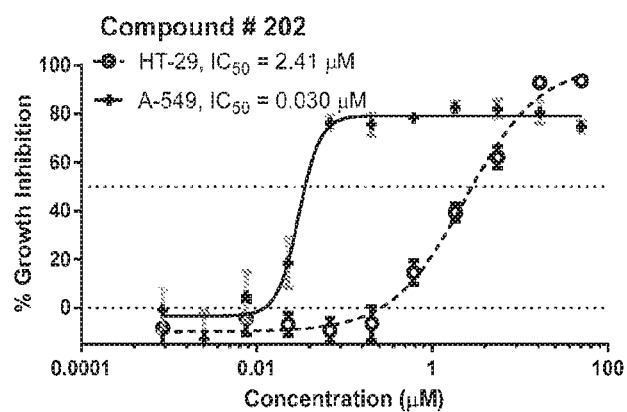
Figure 6I:
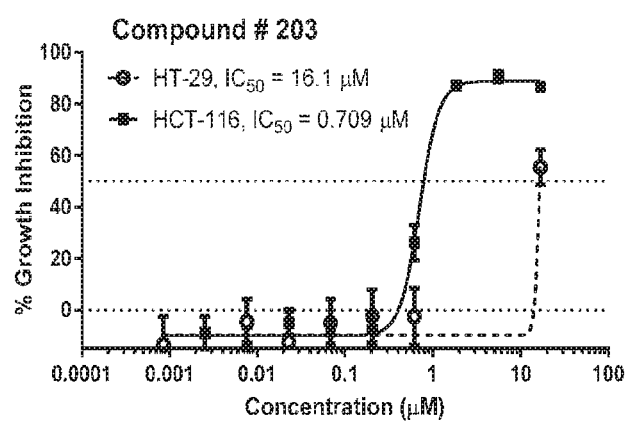
Figure 6J:
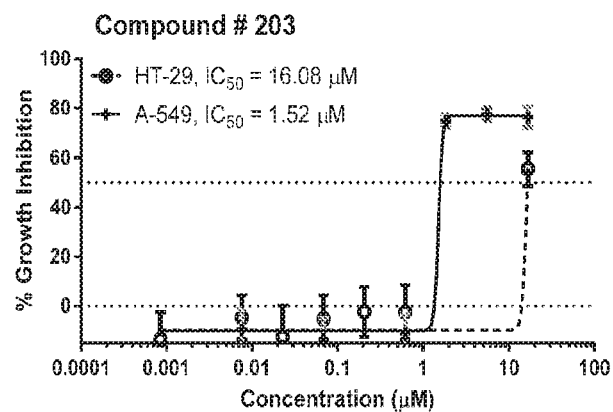

FIG. 5D reveals a correlation between sensitivity of tumor cells to compound 010 and Ras activation status of the cells as determined by Western blot analysis.

FIG. 6A-6F show Ras-selective tumor cell growth-inhibiting activity of exemplary Ras-inhibitory compounds 006 (FIG. 6A), 007 (FIG. 6B), 019 (FIG. 6C), 029 (FIG. 6D), 002 (FIG. 6E), and 022 (FIG. 6F) against human HCT-116 colon tumor cells expressing mutant Ras, compared to human HT-29 colon tumor cells expressing wild-type Ras. FIG. 6G-6J show similar effects of compounds 202 and 203 on HCT-116 and A549 cells as compared to HT-29 cells, as labeled in the Figures accordingly.

Figure 7A:
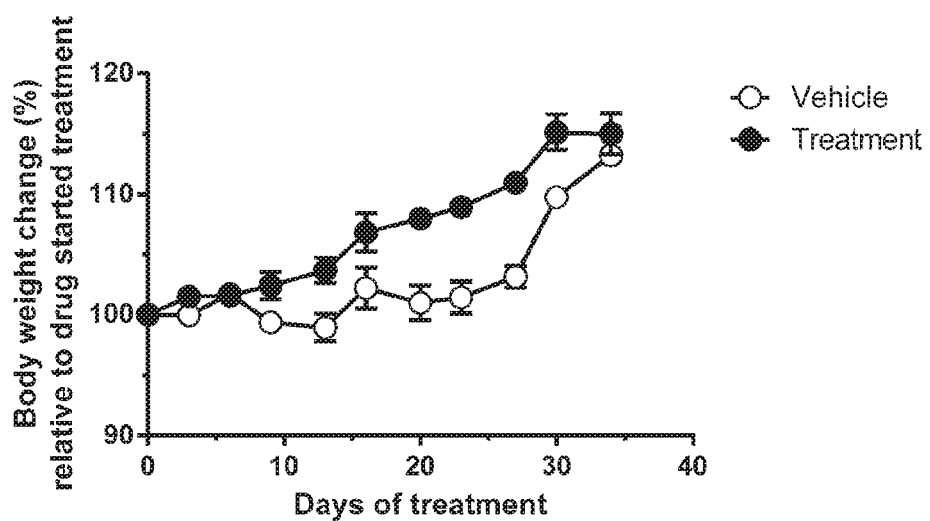
Figure 7B:
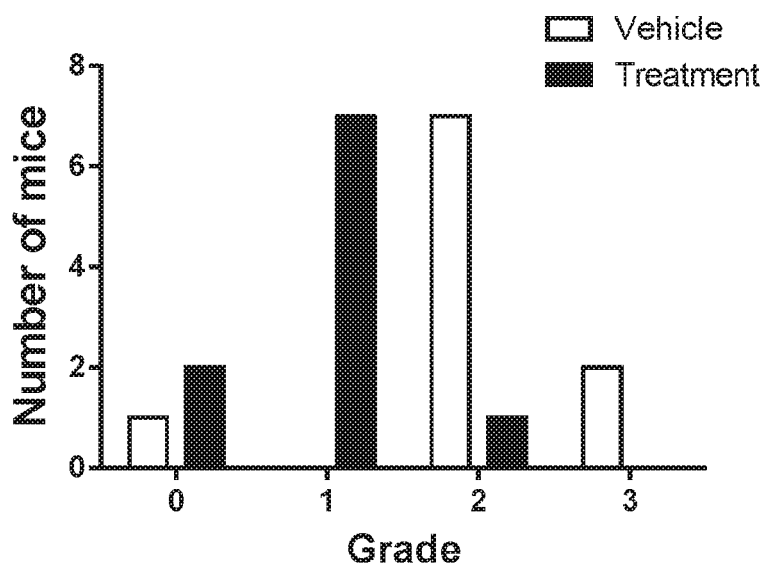
Figure 7C:
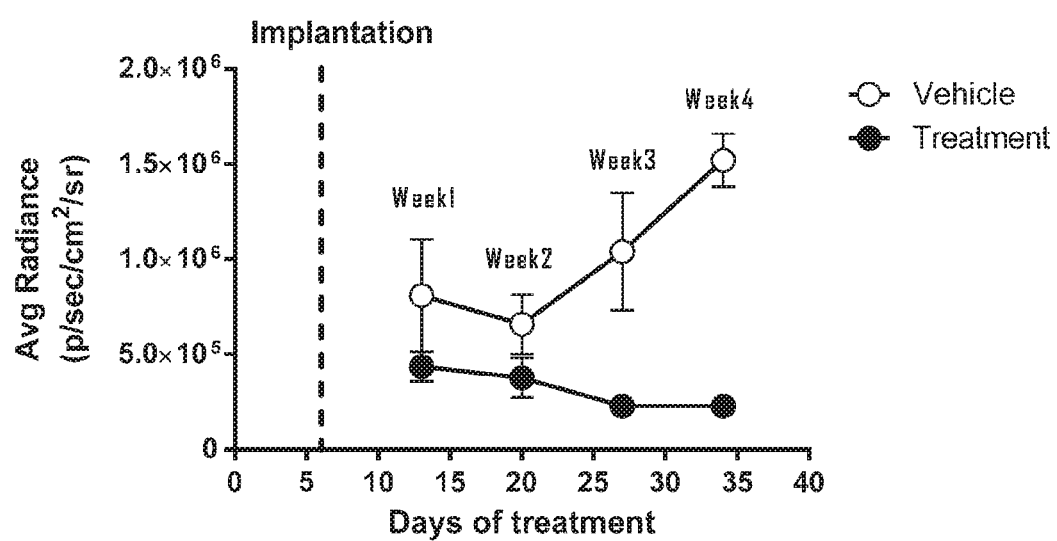

FIG. 7A-7C illustrate treatment of a mammalian patient with a compound of the present invention. FIG. 7A shows the effect of compound 030 (100 mg/kg) on body weight for the duration of the experiment; data points are means±SE, n=9 (vehicle), n=10 (treatment). FIG. 7B shows the results of the aforementioned experiment, with tumor grading at necropsy; grade assignments are as follows: 0=no tumors on chest or lungs, 1=tumors present on chest cavity but not lung, 2=tumors on lung and chest cavity, 3=pleural effusions in addition to tumors on lung and chest cavity. FIG. 7C shows the effect of the treatment with 030 (100 mg/kg) on tumor growth in live mice over the duration of the experiment as measured by luminescence; data points are means±SE, n=5.

Figure 8A:
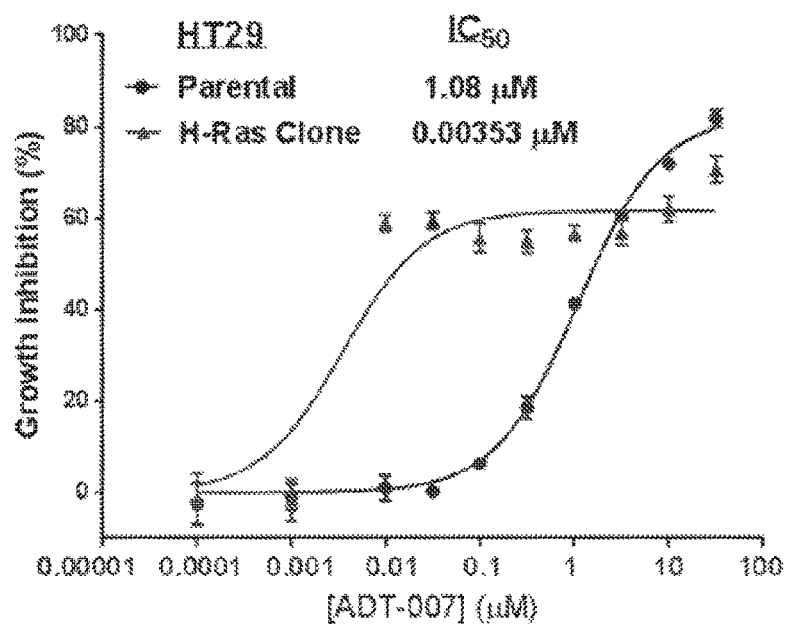
Figure 8A:
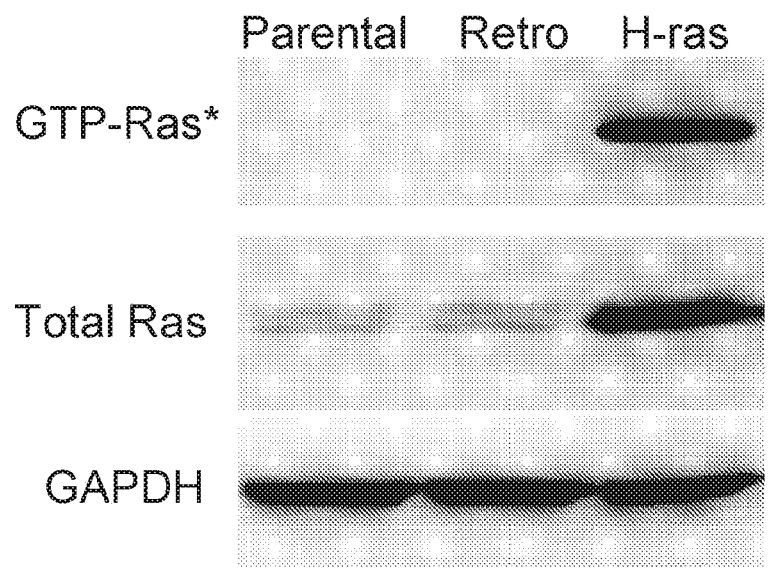

FIG. 8A demonstrates that the HT-29 cells transfected with activated Ras were hypersensitive to the test drug (007) relative to the respective control cells.

Figure 8B:
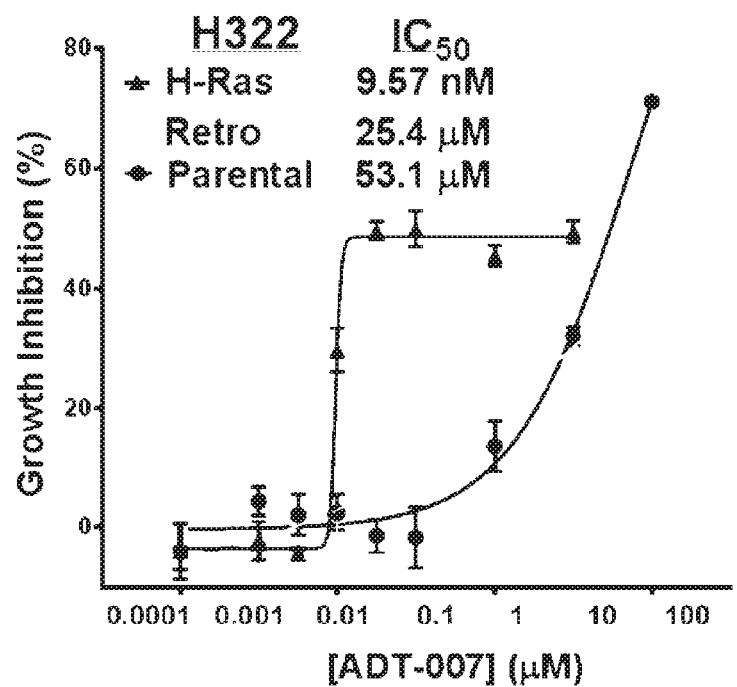
Figure 8B:
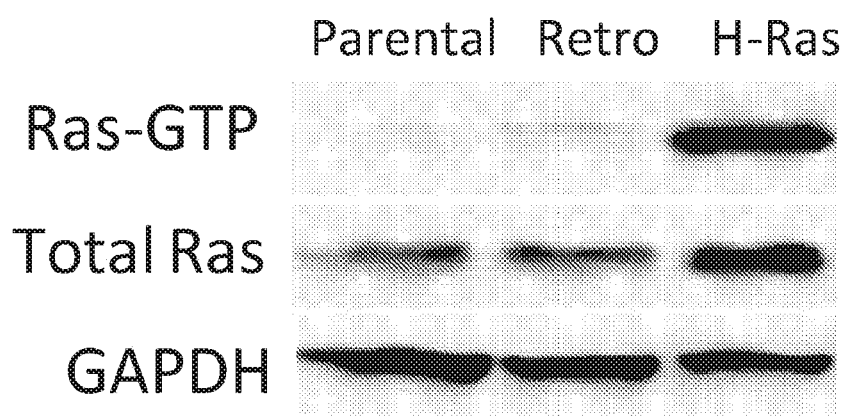

FIG. 8B demonstrates that the H322 cells transfected with activated Ras were hypersensitive to the test drug (007) relative to the respective control cells.

Figure 9:
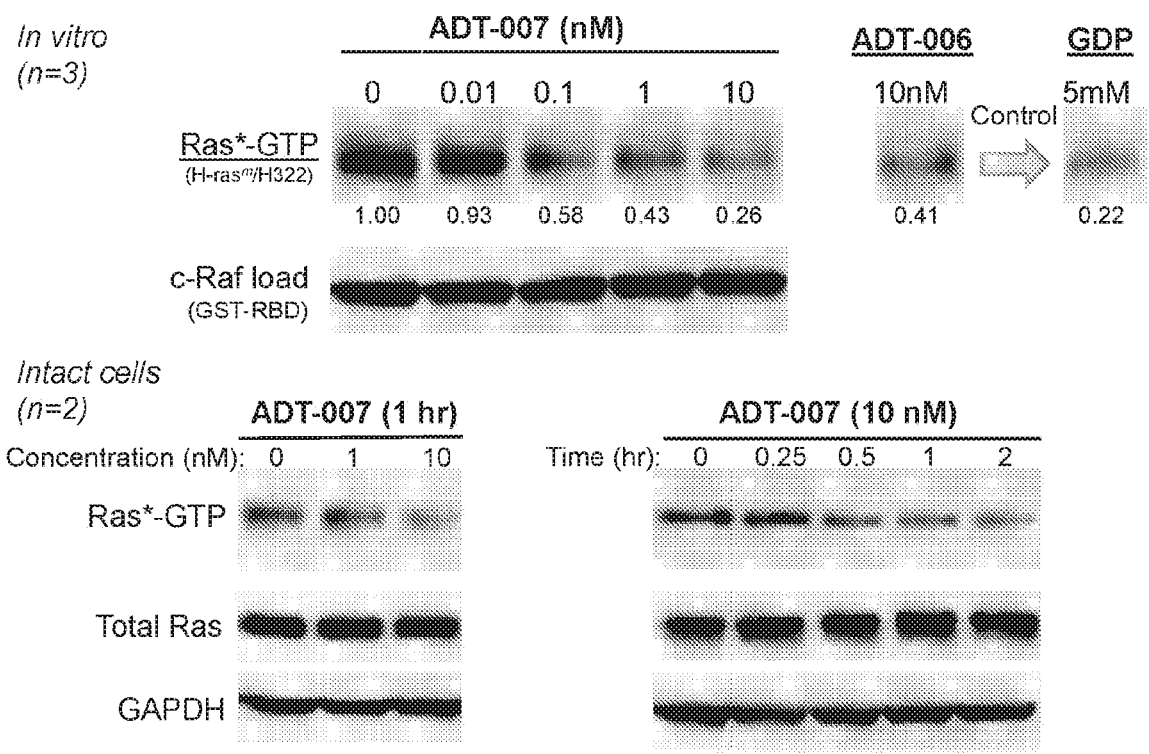

FIG. 9 illustrates that representative Ras-inhibitory compounds (006 and 007) used in the methods of the present invention interact with high affinity directly with activated Ras to disrupt Ras interactions with its normal binding partner, Raf.

Figure 10:
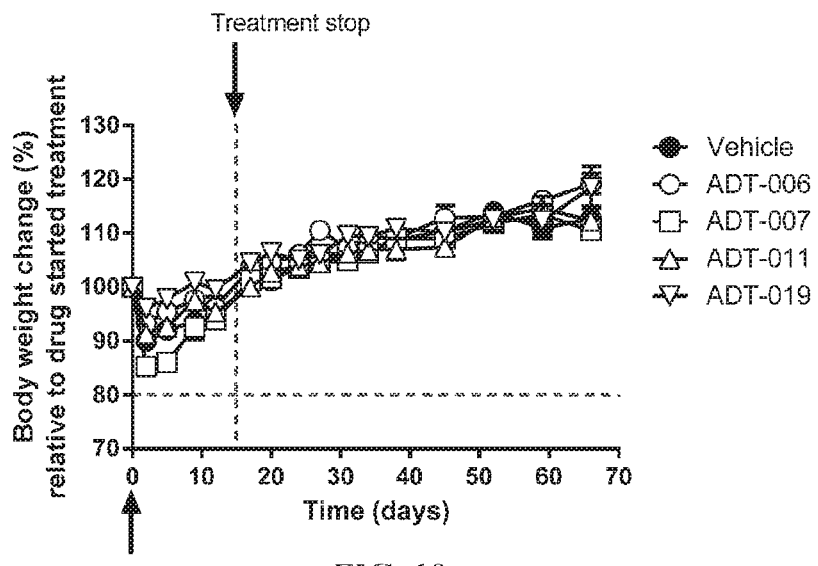
Figure 11A:
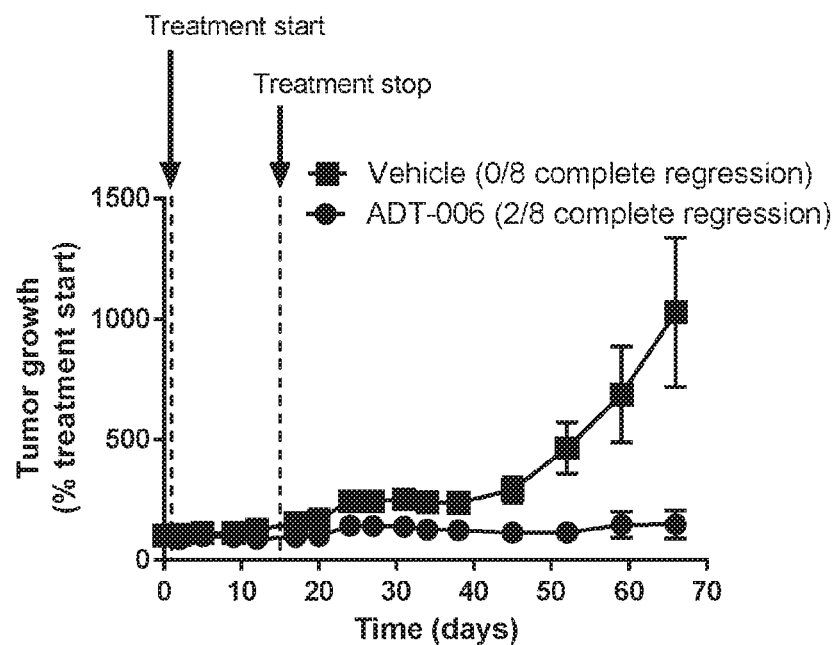
Figure 11B:
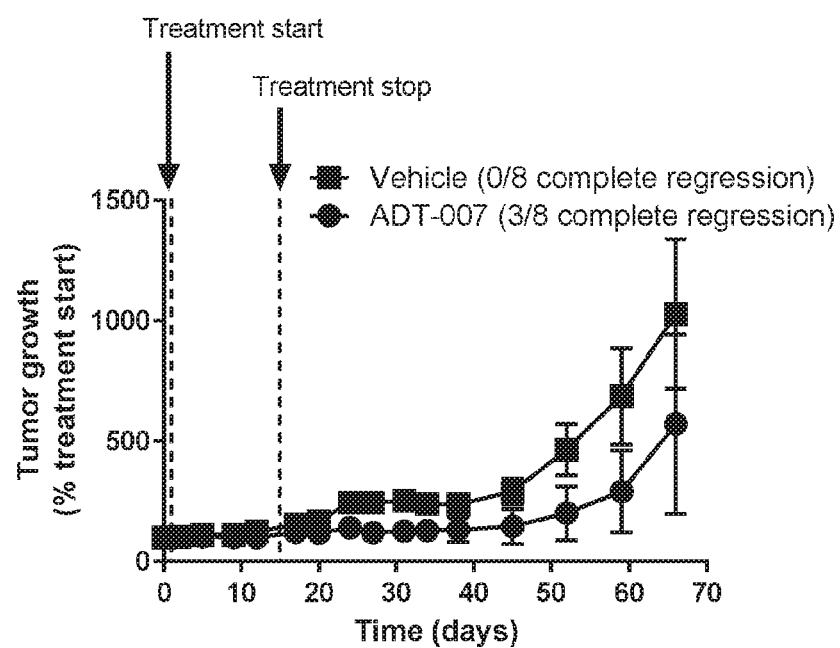
Figure 11C:
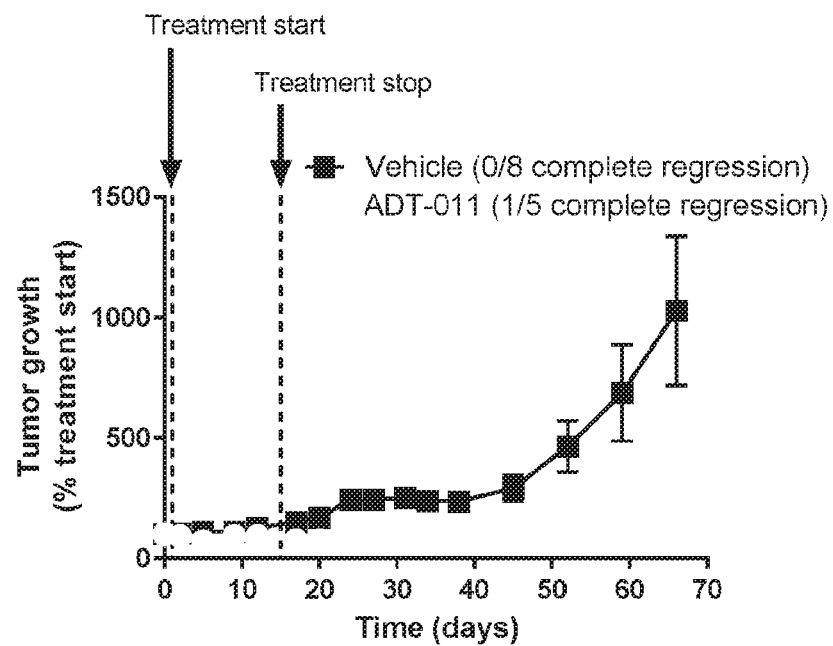
Figure 11D:
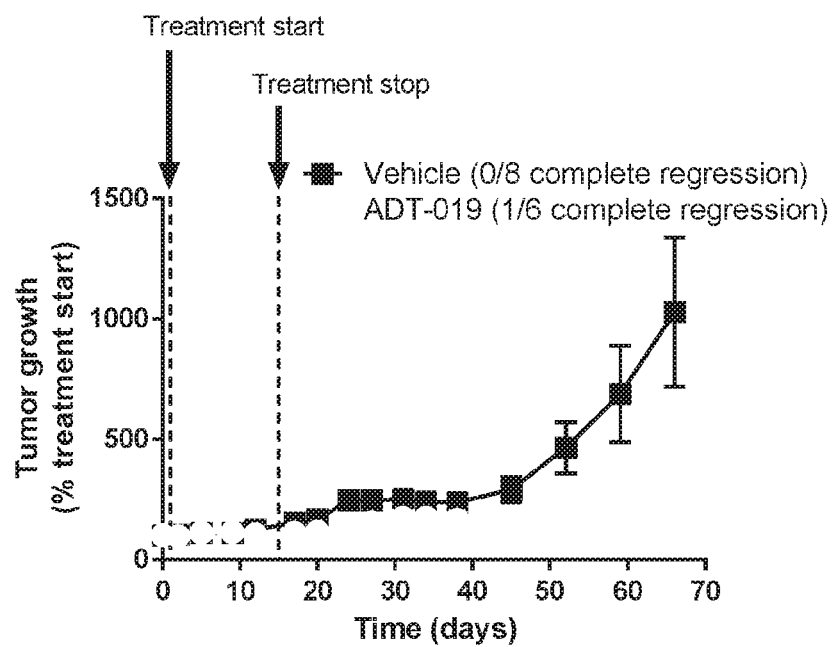
Figure 11E:
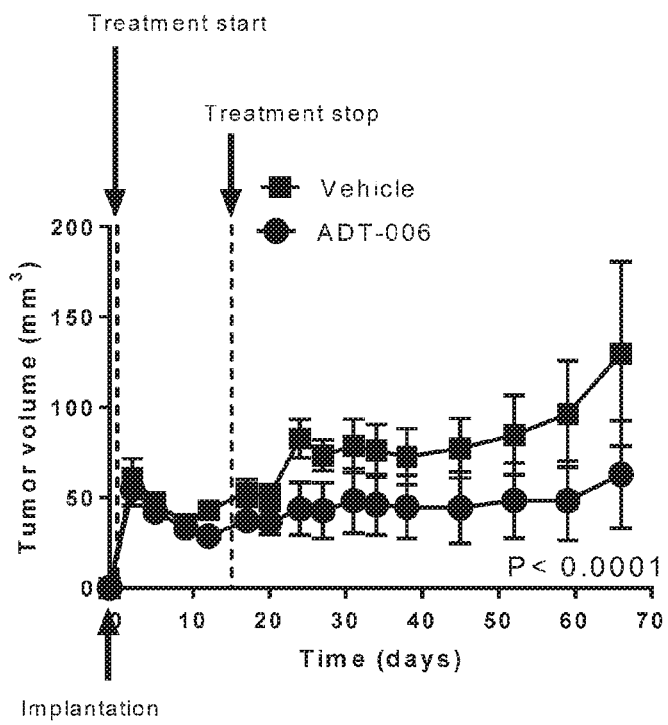
Figure 11F:
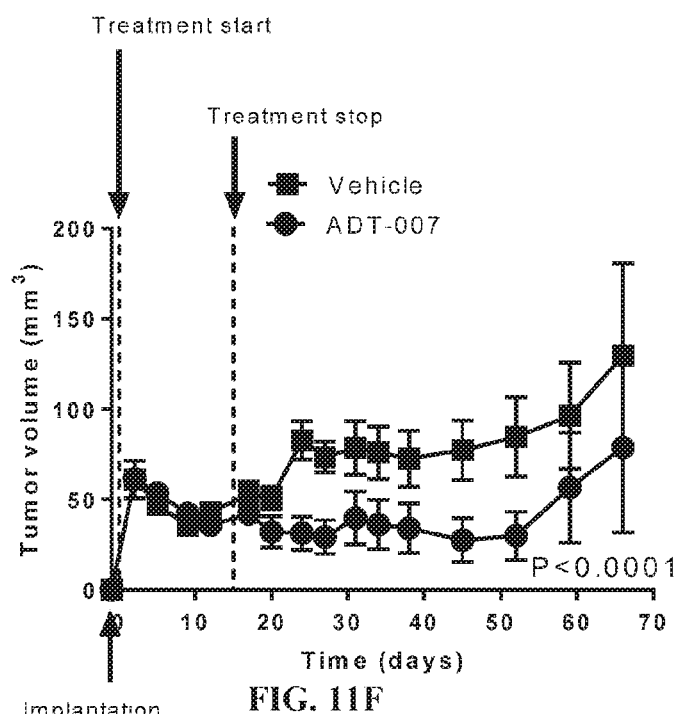
Figure 11G:
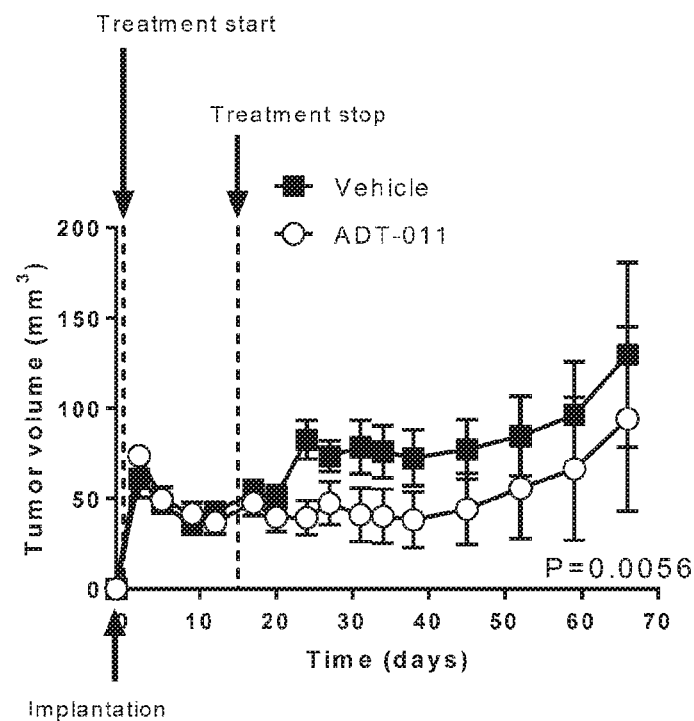
Figure 11H:
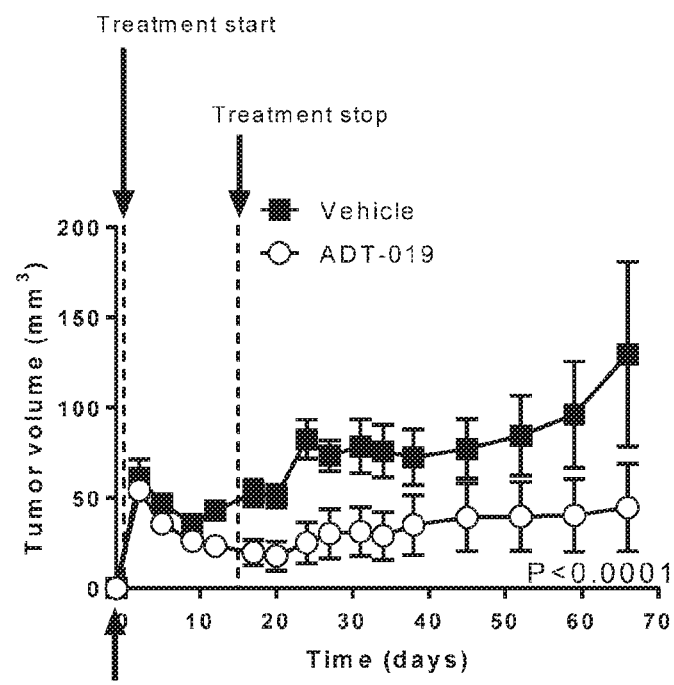

FIG. 10 shows that administration of antitumor therapeutic or preventative doses of representative compounds (006, 007, and 019) as used in the present invention produced no evidence of in vivo animal toxicity as assessed by animal weight gains over time. Compound 011 is a comparative compound.

FIG. 11A-11H illustrate that efficacious therapeutic (FIG. 11A-11D) or preventive (FIG. 11E-11H) antitumor treatments of a representative Ras-driven tumor (HCT-116 human colon tumor xenografts) in vivo with exemplary Ras-inhibitory compounds 006, 007, 011 and 019 (named in FIGS. 11A and 11E as ADT-006, in FIGS. 11B and 11F as ADT-007, in FIGS. 11C and 11G as ADT-011 and in FIGS. 11D and 11H as ADT-019, respectively) employed in the present invention.

DETAILED DESCRIPTION OF THE INVENTION

In accordance with an embodiment, the invention provides a compound of formula I:

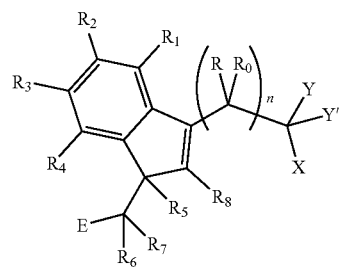

wherein:

R and $R_0$ are independently selected from hydrogen, hydroxyl, alkyl, cycloalkyl, cycloalkylalkyl, heterocyclyl, heterocyclylalkyl, alkenyl, alkenylalkyl, alkynyl, alkynylalkyl, cyano, cyanoalkyl, halogen, azido, alkoxy, haloalkyl and a substituted or unsubstituted group selected from aminocarbonyl, aminocarbonylalkyl, aminosulfonyl, aminosulfonylalkyl, alkylcarbonyl, alkylcarbonylalkyl, amino, alkylamino, dialkylamino, aminocarbonylalkylamino, and carbocyclylamino, carbocyclylalkylamino, heterocyclylamino and heterocyclylalkylamino wherein the ring structures are saturated or unsaturated; or R and $R_0$ together is double-bonded oxygen or double-bonded sulfur, or R and $R_0$ together is a double-bonded nitrogen bonded to one of hydrogen, hydroxyl, alkyl, or haloalkyl, or R and $R_0$ together is a double-bonded carbon bonded to two substituents independently selected from hydrogen, hydroxyl, alkyl and haloalkyl, or $R_0$ is nitrogen which is part of a substituted or unsubstituted, saturated or unsaturated, 3-, 4-, 5-, 6- or 7-membered heterocyclic ring; or R and $R_0$ together is a substituted or unsubstituted, saturated or unsaturated 3-, 4-, 5-, 6- or 7-membered heterocyclic ring;

n is 0, 1 or 2;

$R_1$, $R_2$, $R_3$, and $R_4$ are independently selected from hydrogen, halogen, alkyl, haloalkyl, hydroxyl, carboxyl, alkoxy, formyloxy, alkylcarbonyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy and sulfonamido, or any two of $R_1$, $R_2$, $R_3$, and $R_4$ form an alkylenedioxy group;

$R_5$, $R_6$, $R_7$, and $R_8$ are independently selected from hydrogen, alkyl, haloalkyl, and alkoxy; or $R_5$ and $R_6$ together form a carbon-carbon bond;

Y is hydrogen, alkyl, or haloalkyl, and Y' is hydrogen, alkyl, haloalkyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or haloalkyl;

X is selected from hydrogen, alkyl, haloalkyl, alkoxy, alkylmercapto, and hydroxyl with the proviso that X is not hydroxyl when Y and Y' together is oxygen in a compound of formula I wherein $R_5$ and $R_6$ together is a carbon-carbon bond, or X is NR'R", where R' and R" are independently selected from the group consisting of hydrogen, hydroxyl, alkyl, aryloxy, cyanoalkyl, haloalkyl, alkoxy, alkenyl, alkynyl, hydroxyalkyl, polyhydroxyalkyl, alkylaminoalkyl, dialkylaminoalkyl, aminoalkyl, alkylamino, aryl, arylalkyl, arylalkenyl, arylcycloalkyl, arylcycloalkenyl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one, two or three double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, sulfonamido and $COR_{11}$, wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen and optionally oxygen or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and E is a substituted or unsubstituted, saturated or unsaturated, 7-membered, 6-membered, 5-membered, 4-membered or 3-membered carbocyclic or heterocyclic ring; or a pharmaceutically acceptable salt thereof or a prodrug thereof;

with the proviso that when E is a substituted aryl or heteroaryl, then no substituent on the aryl or heteroaryl ring can be alkylsulfinyl or alkylsulfonyl, and no substituent on the aryl ring can be alkylmercapto, nor p-halo when R' is dialkylaminoalkyl;

or, when $R_5$ and $R_6$ together is a carbon-carbon bond, R" is hydrogen and R' is a substituted arylalkyl, then E cannot be a substituted or unsubstituted heterocyclic ring selected from the group consisting of pyridinyl, pyrimidinyl, pyrazinyl, imidazolyl, triazinyl, thiophenyl, furanyl, thiazolyl, pyrazolyl, quinolinyl, isoquinolinyl, indolyl, benzimidazolyl, azinyl, tratrazolyl, pyridazinyl, and pyrrolyl;

or, when n is 1 or 2, $R_5$ and $R_6$ together form a carbon-carbon bond, Y and Y' are hydrogens or Y and Y' together is oxygen, and E is a substituted phenyl, then X cannot be hydrogen, alkyl, haloalkyl, alkylmercapto or NR'R" wherein R' is hydrogen, hydroxyl or alkyl, and R" is hydrogen, alkyl or haloalkyl;

or, when $R_5$ and $R_6$ are independently selected from hydrogen or alkyl or $R_5$ and $R_6$ together form a carbon-carbon bond, E is a substituted aryl or heteroaryl, and X is NR'R" wherein R' is hydrogen or hydroxyl and R" is $COR_{11}$, then $R_{11}$ cannot be alkyl, alkoxy or amino;

or, when $R_5$, $R_6$, $R_7$ and $R_8$ are independently selected from hydrogen, alkyl and alkoxy, or $R_5$ and $R_6$ form a carbon-carbon bond, $R_7$ is hydrogen, $R_8$ is hydrogen, alkoxy or alkyl, E is phenyl substituted with at least two hydroxyl groups or at least two alkoxy groups, and Y and Y' together is double-bonded oxygen, then X cannot be substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocyclylalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl;

or, when R and $R_0$ are hydrogens, at least one of $R_1$, $R_2$, $R_3$, and $R_4$ is halogen, Y and Y' together is double-bonded oxygen, and X is NR'R", wherein R' is furanylalkyl and R" is selected from hydrogen and $COR_{11}$, wherein $R_{11}$ is selected from hydrogen, amino, alkyl, haloalkyl, alkoxy, alkylmercapto, and aryl, then E cannot be 3,4,5-trimethoxyphenyl;

or, when R' is halophenylalkyl and R" is hydrogen, then E cannot be halophenyl;

or, when n=0 and Y and Y' together is double-bonded oxygen, then X cannot be alkoxy, aryloxy, arylalyloxy, or NR'R" wherein R" is hydrogen and R' is alkyl, aryl or arylalkyl.

In an embodiment of formula I, R and $R_0$ are independently selected from hydrogen, hydroxyl, alkyl, haloalkyl, amino, alkoxy and alkylamino, or R and $R_0$ together is oxygen or sulfur, or R and $R_0$ together is a double-bonded nitrogen bonded to hydrogen, hydroxyl, alkyl, or haloalkyl;

n is 0, 1 or 2;

$R_1$, $R_2$, $R_3$, and $R_4$ are independently selected from hydrogen, hydroxyl, halogen, alkyl, haloalkyl, alkoxy, and alkylmercapto;

$R_5$, $R_6$, $R_7$, $R_8$ are independently selected from hydrogen, alkyl, haloalkyl and alkoxy; or $R_5$ and $R_6$ together form a carbon-carbon bond;

Y is hydrogen, alkyl, or haloalkyl, and Y' is hydrogen, alkyl, haloalkyl, amino, alkylamino, or alkoxy, or Y and Y' together is oxygen or sulfur, or Y and Y' together is a double-bonded nitrogen bonded to hydrogen, hydroxyl, alkyl, or haloalkyl;

X is selected from hydrogen, alkyl, haloalkyl, alkoxy, alkylmercapto, and hydroxyl with the proviso that X is not hydroxyl when Y and Y' together is oxygen in a compound of formula I wherein $R_5$ and $R_6$ together is a carbon-carbon bond, or X is NR'R", where R' is selected from the group consisting of hydrogen, hydroxyl, alkyl, haloalkyl, alkoxy, alkenyl, alkynyl, hydroxyalkyl, polyhydroxyalkyl, alkylaminoalkyl, dialkylaminoalkyl, aminoalkyl, alkylamino, aryl, arylalkyl, arylalkenyl, arylcycloalkyl, arylcycloalkenyl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one or two double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and E is a substituted or unsubstituted, saturated or unsaturated, 7-membered, 6-membered, 5-membered, 4-membered or 3-membered carbocyclic or heterocyclic ring; or a pharmaceutically acceptable salt thereof or a prodrug thereof;

with the proviso that when E is a substituted aryl or heteroaryl, then no substituent on the aryl or heteroaryl ring can be alkylsulfinyl or alkylsulfonyl, and no substituent on the aryl ring can be alkylmercapto, nor p-halo when R' is dialkylaminoalkyl;

or, when $R_5$ and $R_6$ together is a carbon-carbon bond, R" is hydrogen and R' is a substituted arylalkyl, then E cannot be a substituted or unsubstituted heterocyclic ring selected from the group consisting of pyridinyl, pyrimidinyl, pyrazinyl, imidazolyl, triazinyl, thiophenyl, furanyl, thiazolyl, pyrazolyl, quinolinyl, isoquinolinyl, indolyl, benzimidazolyl, azinyl, tratrazolyl, pyridazinyl, and pyrrolyl;

or, when n is 1 or 2, $R_5$ and $R_6$ together form a carbon-carbon bond, Y and Y' are hydrogens or Y and Y' together is double-bonded oxygen, and E is a substituted phenyl, then X cannot be hydrogen, alkyl, haloalkyl, alkylmercapto or NR'R" wherein R' is hydrogen, hydroxyl or alkyl, and R" is hydrogen, alkyl or haloalkyl;

or, when $R_5$ and $R_6$ are independently selected from hydrogen or alkyl or $R_5$ and $R_6$ together form a carbon-carbon bond, E is a substituted aryl or heteroaryl, and X is NR'R" wherein R' is hydrogen or hydroxyl and R" is $COR_{11}$, then $R_{11}$ cannot be alkyl, alkoxy or amino;

or, when $R_5$, $R_6$, $R_7$ and $R_8$ are independently selected from hydrogen, alkyl and alkoxy, or $R_5$ and $R_6$ form a carbon-carbon bond, $R_7$ is hydrogen, $R_8$ is hydrogen, alkoxy or alkyl, E is phenyl substituted with at least two hydroxyl groups or at least two alkoxy groups, and Y and Y' together is double-bonded oxygen, then X cannot be substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocyclylalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl;

or, when R and $R_0$ are hydrogens, at least one of $R_1$, $R_2$, $R_3$, and $R_4$ is halogen, Y and Y' together is double-bonded oxygen, and X is NR'R", wherein R' is furanylalkyl and R" is selected from hydrogen and $COR_{11}$, wherein $R_{11}$ is selected from hydrogen, amino, alkyl, haloalkyl, alkoxy, alkylmercapto, and aryl, then E cannot be 3,4,5-trimethoxyphenyl;

or, when R' is halophenylalkyl and R" is hydrogen, then E cannot be halophenyl;

or, when n=0 and Y and Y' together is double-bonded oxygen, then X cannot be alkoxy, aryloxy, arylalkyloxy, or NR'R" wherein R" is hydrogen and R' is alkyl, aryl, or arylalkyl.

In an embodiment, in R', the 7-membered heterocyclic ring is selected from azepanyl, oxazepanyl, thiazepanyl, azepinyl, oxepinyl, thiepanyl, homopiperazinyl, diazepinyl and thiazepinyl, the 6-membered heterocyclic ring is selected from piperidinyl, oxanyl, thianyl, pyridinyl, pyranyl, thiopyranyl, piperazinyl, morpholinyl, thiomorpholinyl, dioxanyl, dithianyl, diazinyl, oxazinyl, thiazinyl, dioxinyl, dithiinyl, trioxanyl, trithianyl, triazinyl and tetrazinyl, and the 5-membered heterocyclic ring is selected from pyrrolidinyl, tetrahydrofuranyl, tetrahydrothiophenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl.

In an embodiment, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is double-bonded oxygen, X is NR'R" wherein R" is hydrogen, and R' is a substituted aryl, then each of $R_{12}$, $R_{13}$, $R_{14}$, $R_{15}$ and $R_{16}$ must be hydrogen. For example, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is double-bonded oxygen, X is NR'R" wherein R" is hydrogen, and R' is an aryl substituted with any of halo, alkoxy, amino, alkylamino, dialkylamino and sulfonamido, then no two of $R_{12}$, $R_{13}$, $R_{14}$, $R_{15}$ and $R_{16}$ can be identically selected from hydroxyl and alkoxy.

In another embodiment, E is a carbocyclic or heterocyclic ring, optionally substituted with one or more substituents selected from hydroxyl, carboxyl, halogen, alkyl, haloalkyl, cyano, cyanoalkyl, nitro, oxo, alkoxy, formyloxy, amino, alkylamino, dialkylamino, aminoalkyl, alkylaminoalkyl, hydroxyalkyl, aldehydo, mercapto, alkylmercapto, azido, and substituted or unsubstituted groups selected from alkylsulfonyl, alkylsulfinyl, alkylsulfinyloxy, alkylsulfonyloxy, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, carbamate, carbamido, alkoxycarbonyl, alkylaminocarbonyl, aminocarbonyl, sulfonamido, and alkylenedioxy spanning two substituent positions.

In yet another embodiment, E is selected from cycloheptanyl, cycloheptenyl, cycloheptadienyl, cycloheptatrienyl, cyclohexanyl, cyclohexenyl, cyclohexadienyl, phenyl, cyclopentanyl, cyclopentenyl, cyclopentadienyl, cyclopropanyl, cyclobutanyl, azepanyl, oxazepanyl, thiazepanyl, azepinyl, oxepinyl, thiepanyl, homopiperazinyl, diazepinyl, thiazepinyl, piperidinyl, oxanyl, thianyl, pyridinyl, pyranyl, thiopyranyl, piperazinyl, morpholinyl, thiomorpholinyl, dioxanyl, dithianyl, diazinyl, oxazinyl, thiazinyl, dioxinyl, dithiinyl, trioxanyl, trithianyl, triazinyl, tetrazinyl, pyrrolidinyl, tetrahydrofuranyl, tetrahydrothiophenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl, and tetrazolyl, each of which is substituted or unsubstituted.

For example, the compound of formula (I), prodrug, or salt have E as:

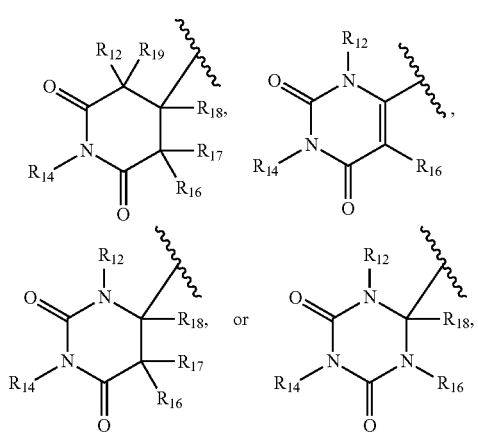

wherein $R_{12}$, $R_{14}$, $R_{16}$, $R_{17}$, $R_{18}$ and $R_{19}$ are independently selected from hydrogen, hydroxyl, carboxyl, halogen, alkyl, haloalkyl, alkoxy, amino, alkylamino, dialkylamino, aminoalkyl, alkylamino, alkylaminoalkyl, hydroxyalkyl, aldehydo, mercapto, alkylmercapto, azido, cyano, cyanoalkyl, nitro, and substituted or unsubstituted groups selected from alkylsulfonyl, alkylsulfinyl, alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, and sulfonamido.

In another embodiment, a prodrug of a compound of formula I has the formula I wherein any one of $R_1$, $R_2$, $R_3$, $R_4$, R', R", or any substituent on E is of the formula Q-U-wherein U is selected from the group consisting of oxygen, sulfur, nitrogen, $OCH_2$, $SCH_2$ and $NHCH_2$; and Q is selected from the group consisting of hydrogen, alkyl, PEG-CO, HCO, acetyl, amino acid, substituted benzoic acid, and phosphoric acid; or, wherein Q-U- together is selected from phosphonooxy, phosphonoalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy.

In a further embodiment, the invention provides a compound of formula I:

wherein:

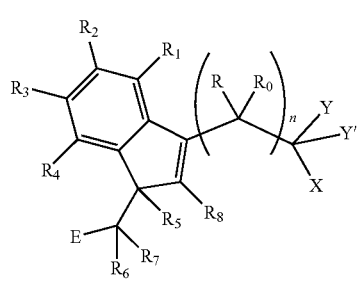

R and $R_0$ are independently selected from hydrogen, hydroxyl, alkyl, cycloalkyl, cycloalkylalkyl, heterocyclyl, heterocyclylalkyl, alkenyl, alkenylalkyl, alkynyl, alkynylalkyl, cyano, cyanoalkyl, halogen, azido, alkoxy, haloalkyl and a substituted or unsubstituted group selected from aminocarbonyl, aminocarbonylalkyl, aminosulfonyl, aminosulfonylalkyl, alkylcarbonyl, alkylcarbonylalkyl, amino, alkylamino, dialkylamino, aminocarbonylalkylamino, and carbocyclylamino, carbocyclylalkylamino, heterocyclylamino and heterocyclylalkylamino wherein the ring structures are saturated or unsaturated; or R and $R_0$ together is double-bonded oxygen or double-bonded sulfur, or R and $R_0$ together is a double-bonded nitrogen bonded to one of hydrogen, hydroxyl, alkyl, or haloalkyl, or R and $R_0$ together is a double-bonded carbon bonded to two substituents independently selected from hydrogen, hydroxyl, alkyl and haloalkyl, or $R_0$ is nitrogen which is part of a substituted or unsubstituted, saturated or unsaturated, 3-, 4-, 5-, 6- or 7-membered heterocyclic ring; or R and $R_0$ together is a substituted or unsubstituted, saturated or unsaturated 3-, 4-, 5-, 6- or 7-membered heterocyclic ring;

n is 0, 1 or 2;

$R_1$, $R_2$, $R_3$, and $R_4$ are independently selected from hydrogen, halogen, alkyl, haloalkyl, hydroxyl, carboxyl, alkoxy, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylcarbonyloxy, alkylcarbonyloxyalkyloxy, alkylsulfinyloxy, alkylsulfonyloxy, carbamate, carbamido, alkoxycarbonyl, alkylaminocarbonyl, aminocarbonyl, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy and sulfamido, or any two of $R_1$, $R_2$, $R_3$ and $R_4$ form an alkylenedioxy group;

$R_5$, $R_6$, $R_7$ and $R_8$ are independently selected from hydrogen, alkyl and alkoxy, or $R_5$ and $R_6$ form a carbon-carbon bond, $R_7$ is hydrogen, $R_8$ is hydrogen, alkoxy or alkyl, E is phenyl substituted with at least two hydroxyl groups or at least two alkoxy groups, and at least one substituted or unsubstituted group selected from phosphonooxy, phosphonoalkyloxy, formyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy;

Y and Y' together is double-bonded oxygen;

X is substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocycoalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl;

or, a pharmaceutically acceptable salt thereof.

In another embodiment of the compound of formula I, the invention provides a compound of formula I wherein R and $R_0$ are independently selected from hydrogen, hydroxyl, alkyl, alkoxy, alkylamino and amino;

at least one of $R_1$, $R_2$, $R_3$ and $R_4$ is hydrogen and three of $R_1$, $R_2$, $R_3$ and $R_4$ are independently selected from hydrogen, hydroxyl, halogen, alkoxy, alkyl and alkylmercapto; n is 0, 1 or 2;

$R_5$ and $R_6$ together form a carbon-carbon bond, $R_7$ is hydrogen and $R_8$ is selected from hydrogen, alkyl and alkoxy;

E is phenyl substituted with at least two hydroxyl groups or at least two alkoxy groups, and at least one substituted or unsubstituted group selected from phosphonooxy, phosphonoalkyloxy, formyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy;

Y and Y' together is double-bonded oxygen;

X is substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocycoalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl;

or, a pharmaceutically acceptable salt thereof.

In another embodiment, the invention provides a compound of formula I, wherein R and $R_0$ are independently selected from hydrogen, hydroxyl, alkyl, alkoxy, alkylamino and amino;

at least one of $R_1$, $R_2$, $R_3$ and $R_4$ is hydrogen and three of $R_1$, $R_2$, $R_3$ and $R_4$ are independently selected from hydrogen, hydroxyl, halogen, alkoxy, alkyl and alkylmercapto; n is 0, 1 or 2;

$R_5$ and $R_6$ together form a carbon-carbon bond, $R_7$ is hydrogen and $R_8$ is selected from hydrogen, alkyl and alkoxy;

E is phenyl substituted with at least two hydroxyl groups or at least two alkoxy groups, and at least one substituted or unsubstituted group selected from phosphonooxy, phosphonoalkyloxy, formyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy;

Y and Y' together is a double-bonded oxygen;

X is substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocycoalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl;

or a pharmaceutically acceptable salt thereof.

In a further embodiment, the invention provides a compound of formula (II):

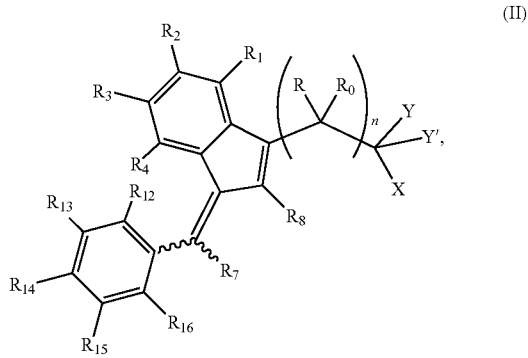

wherein:

R and $R_0$ are independently selected from hydrogen, hydroxyl, alkyl, cycloalkyl, cycloalkylalkyl, heterocyclyl, heterocyclylalkyl, alkenyl, alkenylalkyl, alkynyl, alkynylalkyl, cyano, cyanoalkyl, halogen, azido, alkoxy, haloalkyl and a substituted or unsubstituted group selected from aminocarbonyl, aminocarbonylalkyl, aminosulfonyl, aminosulfonylalkyl, alkylcarbonyl, alkylcarbonylalkyl, amino, alkylamino, dialkylamino, aminocarbonylalkylamino, and carbocyclylamino, carbocyclylalkylamino, heterocyclylamino and heterocyclylalkylamino wherein the ring structures are saturated or unsaturated; or R and $R_0$ together is double-bonded oxygen or double-bonded sulfur, or R and $R_0$ together is a double-bonded nitrogen bonded to one of hydrogen, hydroxyl, alkyl, or haloalkyl, or R and $R_0$ together is a double-bonded carbon bonded to two substituents independently selected from hydrogen, hydroxyl, alkyl and haloalkyl, or $R_0$ is nitrogen which is part of a substituted or unsubstituted, saturated or unsaturated, 3-, 4-, 5-, 6- or 7-membered heterocyclic ring; or R and $R_0$ together is a substituted or unsubstituted, saturated or unsaturated 3-, 4-, 5-, 6- or 7-membered heterocyclic ring;

n is 0, 1 or 2;

Y is hydrogen, alkyl, or haloalkyl, and Y' is hydrogen, alkyl, haloalkyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or haloalkyl;

$R_1$, $R_2$, $R_3$, $R_4$, $R_{12}$, $R_{13}$, $R_{14}$, $R_{15}$, and $R_{16}$ are independently selected from hydrogen, halogen, alkyl, cycloalkyl, haloalkyl, hydroxyl, carboxyl, alkoxy, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy and sulfonamido, or any two of $R_1$, $R_2$, $R_3$, and $R_4$ or any two of $R_{12}$, $R_{13}$, $R_{14}$, $R_{15}$ and $R_{16}$ form an alkylenedioxy group;

$R_7$ and $R_8$ are independently selected from hydrogen, alkyl, haloalkyl, and alkoxy;

X is selected from hydrogen, alkyl, haloalkyl, alkoxy, alkylmercapto, and hydroxyl with the proviso that X is not hydroxyl when Y and Y' together is oxygen, or X is NR'R", where R' is selected from the group consisting of hydrogen, hydroxyl, alkyl, aryloxy, cyanoalkyl, haloalkyl, alkoxy, alkenyl, alkynyl, hydroxyalkyl, polyhydroxyalkyl, alkylaminoalkyl, dialkylaminoalkyl, aminoalkyl, alkylamino, arylalkyl, arylalkenyl, arylcycloalkyl, arylcycloalkenyl, aryl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one, two, or three double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, alkoxy, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; or a pharmaceutically acceptable salt thereof or a prodrug thereof.

In a preferred embodiment of the above, when n is 1 or 2, Y and Y' are hydrogens or Y and Y' together is double-bonded oxygen, and at least one of $R_{12}$, $R_{13}$, $R_{14}$, $R_{15}$ and $R_{16}$ is not hydrogen, then X cannot be hydrogen, alkyl, haloalkyl, alkylmercapto or NR'R" wherein R' is hydrogen, hydroxyl or alkyl, and R" is hydrogen, alkyl or haloalkyl;

or, when X is NR'R" wherein R' is phenylalkyl and R" is hydrogen, then two of $R_{12}$ to $R_{16}$ cannot be identically selected from hydroxyl or alkoxy;

or, when X is NR'R" wherein R' is hydrogen or hydroxyl, and R" is $COR_{11}$, then $R_{11}$ cannot be alkyl, alkoxy or amino;

or, when R and $R_0$ are hydrogens, at least one of $R_1$, $R_2$, $R_3$, and $R_4$ is halogen, Y and Y' together is double-bonded oxygen and X is NR'R" wherein R' is furanylalkyl and R" is selected from hydrogen and $COR_{11}$, wherein $R_{11}$ is selected from hydrogen, amino, alkyl, haloalkyl, alkoxy, alkylmercapto, and aryl, then $R_{13}$, $R_{14}$, and $R_{15}$ cannot each be methoxy;

or, when R' is halophenylalkyl and R" is hydrogen, then none of $R_{12}$, $R_{13}$, $R_{14}$, $R_{15}$ or $R_{16}$ can be halogen;

or, when n=0 and Y and Y' together is double bonded oxyen, then X cannot be alkoxy, aryloxy, arylalkyloxy, or NR'R" wherein R" is hydrogen and R' is alkyl, aryl, or arylalkyl;

or, when R and $R_0$ together is double-bonded oxygen and n is 1, then the heterocycle of the heterocyclyl or heterocyclylalkyl is furanyl or pyrrolyl.

In an embodiment, a prodrug of a compound of formula II is a compound of formula II wherein any one of $R_1$, $R_2$, $R_3$, $R_4$, $R_{12}$, $R_{13}$, $R_{14}$, $R_{15}$, $R_{16}$, R', or R" is of the formula Q-U- wherein U is selected from the group consisting of oxygen, sulfur, nitrogen, $OCH_2$, $SCH_2$ and $NHCH_2$, and Q is selected from the group consisting of hydrogen, alkyl, PEG-CO, HCO, acetyl, amino acid, substituted benzoic acid and phosphoric acid; or, wherein Q-U together is selected from phosphonooxy, phosphonoalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy.

In an embodiment, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is a substituted aryl, then each of $R_{12}$, $R_{13}$, $R_{14}$, $R_{15}$ and $R_{16}$ must be hydrogen. For example, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is an aryl substituted with any of halo, alkoxy, amino, alkylamino, dialkylamino and sulfonamido, then no two of $R_{12}$, $R_{13}$, $R_{14}$, $R_{15}$ and $R_{16}$ can be identically selected from hydroxyl and alkoxy;

or, when $R_7$ is hydrogen, $R_8$ is hydrogen, alkoxy or alkyl, least two of $R_{12}$, $R_{13}$, $R_{14}$, $R_{15}$ and $R_{16}$ are identically selected from hydroxyl or alkoxy, and Y and Y' together is double-bonded oxygen, then X cannot be substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocycoalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl. For example, when $R_7$ is hydrogen and $R_8$ is selected from hydrogen, alkyl and alkoxy, at least two of $R_{12}$, $R_{13}$, $R_{14}$, $R_{15}$ and $R_{16}$ are identically selected from hydroxyl or alkyl, Y and Y' together is oxygen and R" is hydrogen, then R' cannot be phenylalkyl.

In another embodiment, the invention provides a compound of formula (II):
wherein:

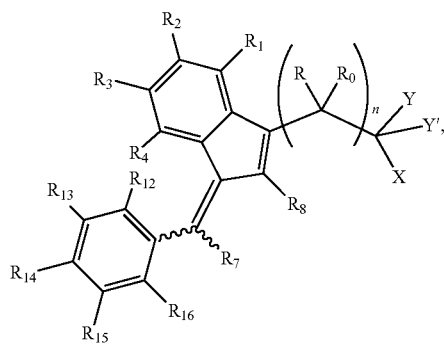

(II)

R and $R_0$ are independently selected from hydrogen, hydroxyl, alkyl, cycloalkyl, cycloalkylalkyl, heterocyclyl, heterocyclylalkyl, alkenyl, alkenylalkyl, alkynyl, alkynylalkyl, cyano, cyanoalkyl, halogen, azido, alkoxy, haloalkyl and a substituted or unsubstituted group selected from aminocarbonyl, aminocarbonylalkyl, aminosulfonyl, aminosulfonylalkyl, alkylcarbonyl, alkylcarbonylalkyl, amino, alkylamino, dialkylamino, aminocarbonylalkylamino, and carbocyclylamino, carbocyclylalkylamino, heterocyclylamino and heterocyclylalkylamino wherein the ring structures are saturated or unsaturated; or R and $R_0$ together is double-bonded oxygen or double-bonded sulfur, or R and $R_0$ together is a double-bonded nitrogen bonded to one of hydrogen, hydroxyl, alkyl, or haloalkyl, or R and $R_0$ together is a double-bonded carbon bonded to two substituents independently selected from hydrogen, hydroxyl, alkyl and haloalkyl, or $R_0$ is nitrogen which is part of a substituted or unsubstituted, saturated or unsaturated, 3-, 4-, 5-, 6- or 7-membered heterocyclic ring; or R and $R_0$ together is a substituted or unsubstituted, saturated or unsaturated 3-, 4-, 5-, 6- or 7-membered heterocyclic ring;

n is 0, 1 or 2;

Y is hydrogen, alkyl, or haloalkyl, and Y' is hydrogen, alkyl, haloalkyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or haloalkyl;

$R_1$, $R_2$, $R_3$, $R_4$, $R_{12}$, $R_{13}$, $R_{14}$, $R_{15}$ and $R_{16}$ are independently selected from hydrogen, halogen, alkyl, cycloalkyl, haloalkyl, hydroxyl, carboxyl, alkoxy, formyloxy, hydroxyalkyl, aldehydo, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy and sulfonamido, or any two of $R_1$, $R_2$, $R_3$ and $R_4$ or any two of $R_{12}$, $R_{13}$, $R_{14}$, $R_{15}$ and $R_{16}$ form an alkylenedioxy group;

$R_7$ and $R_8$ are independently selected from hydrogen, alkyl, haloalkyl, and alkoxy;

X is selected from hydrogen, alkyl, aryloxy, cyanoalkyl, haloalkyl, alkoxy, alkylmercapto, and hydroxyl with the proviso that X is not hydroxyl when Y and Y' together is oxygen, or X is NR'R", where R' is selected from the group consisting of hydrogen, hydroxyl, alkyl, haloalkyl, alkoxy, alkenyl, alkynyl, hydroxyalkyl, polyhydroxyalkyl, alkylaminoalkyl, dialkylaminoalkyl, aminoalkyl, alkylamino, arylalkyl, arylalkenyl, arylcycloalkyl, arylcycloalkenyl, aryl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one, two or three double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; or a pharmaceutically acceptable salt thereof or a prodrug thereof.

In a preferred embodiment of the above, when n is 1 or 2, Y and Y' are hydrogens or Y and Y' together is double-bonded oxygen, and at least one of $R_{12}$, $R_{13}$, $R_{14}$, $R_{15}$ and $R_{16}$ is not hydrogen, then X cannot be hydrogen, alkyl, haloalkyl, alkylmercapto or NR'R" wherein R' is hydrogen, hydroxyl or alkyl, and R" is hydrogen, alkyl or haloalkyl;

or, when X is NR'R" wherein R' is phenylalkyl and R" is hydrogen, then two of $R_{12}$ to $R_{16}$ cannot be identically selected from hydroxyl or alkoxy;

or, when X is NR'R" wherein R' is hydrogen or hydroxyl, and R" is $COR_{11}$, then $R_{11}$ cannot be alkyl, alkoxy or amino;

or, when R and $R_0$ are hydrogens, at least one of $R_1$, $R_2$, $R_3$ and $R_4$ is halogen, Y and Y' together is double-bonded oxygen and X is NR'R" wherein R' is furanylalkyl and R" is selected from hydrogen and $COR_{11}$, wherein $R_{11}$ is selected from hydrogen, amino, alkyl, haloalkyl, alkoxy, alkylmercapto and aryl, then $R_{13}$, $R_{14}$ and $R_{15}$ cannot each be methoxy;

or, when R' is halophenylalkyl and R" is hydrogen, then none of $R_{12}$, $R_{13}$, $R_{14}$, $R_{15}$ or $R_{16}$ can be halogen;

or, when n=0 and Y and Y' together is double bonded oxyen, then X cannot be alkoxy, aryloxy, arylalkyloxy, or NR'R" wherein R" is hydrogen and R' is alkyl, aryl, or arylalkyl;

or, when the heterocycle of the heterocyclyl and heterocyclylalkyl of R' is selected from 7-membered heterocyclic rings, 6-membered heterocyclic rings, and 5-membered heterocyclic rings, and Y and Y' together is oxygen, then $R_7$ and $R_8$ are independently selected from hydrogen, alkyl, haloalkyl and alkoxy;

or, with the proviso that when the heterocycle of the heterocyclyl and heterocyclylalkyl of R' is selected from azepanyl, oxazepanyl, thiazepanyl, azepinyl, oxepinyl, thiepanyl, homopiperazinyl, diazepinyl, thiazepinyl, oxanyl, thianyl, pyranyl, thiopyranyl, thiomorpholinyl, dioxanyl, dithianyl, diazinyl, oxazinyl, thiazinyl, dioxinyl, dithiinyl, trioxanyl, trithianyl, triazinyl, tetrazinyl, tetrahydrofuranyl, tetrahydrothiophenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl, and tetrazolyl, then $R_7$ and $R_8$ are independently selected from hydrogen, alkyl, haloalkyl and alkoxy.

In an embodiment, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is a substituted aryl, then each of $R_{12}$, $R_{13}$, $R_{14}$, $R_{15}$ and $R_{16}$ must be hydrogen. For example, when R and $R_0$ are hydrogen, n is 1, three of $R_1$, $R_2$, $R_3$, and $R_4$ are hydrogens and one is halogen, alkyl, or alkoxy or two of $R_1$, $R_2$, $R_3$ and $R_4$ are hydrogens and two are alkoxy, $R_5$ and $R_6$ together form a carbon-carbon bond, $R_7$ is hydrogen, $R_8$ is alkyl, Y and Y' together is oxygen, X is NR'R" wherein R" is hydrogen, and R' is an aryl substituted with any of halo, alkoxy, amino, alkylamino, dialkylamino and sulfonamido, then no two of $R_{12}$, $R_{13}$, $R_{14}$, $R_{15}$ and $R_{16}$ can be identically selected from hydroxyl and alkoxy;

or, when $R_7$ is hydrogen, $R_8$ is hydrogen, alkoxy or alkyl, least two of $R_{12}$, $R_{13}$, $R_{14}$, $R_{15}$ and $R_{16}$ are identically selected from hydroxyl or alkoxy, and Y and Y' together is double-bonded oxygen, then X cannot be substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, carbocycoalkyl wherein the carbocycle is 3-membered, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, haloalkyl, alkoxy, hydroxy, amino, alkylamino, dialkylamino, and sulfonamido; and R" is selected from hydrogen, alkyl, alkylamino, cyanoalkyl, haloalkyl, hydroxyalkyl, dialkylaminoalkyl, alkylcarbonylalkylcarbonyloxy, and pyridinyl. For example, when $R_7$ is hydrogen and $R_8$ is selected from hydrogen, alkyl and alkoxy, at least two of $R_{12}$, $R_{13}$, $R_{14}$, $R_{15}$ and $R_{16}$ are identically selected from hydroxyl or alkyl, Y and Y' together is oxygen and R" is hydrogen, then R' cannot be phenylalkyl.

In the above embodiment of formula (II), in particular, X is NR'R" where R' is selected from alkyl, haloalkyl, alkenyl, alkynyl, hydroxyalkyl, alkylaminoalkyl, dialkylaminoalkyl, arylalkyl selected from the group consisting of phenylalkyl, indanyl, heterocyclyl, and heterocyclylalkyl, where the heterocycle is selected from furanyl, pyrrolyl, thiophenyl, and imidazolyl, and the cyclic structure of heterocyclyl and heterocyclylalkyl is optionally substituted with one or more of halo, alkyl, haloalkyl, hydroxy, alkoxy, amino, alkylamino, dialkylamino, mercapto, alkylmercapto, and carboxamido; R" is selected from hydrogen, alkyl, haloalkyl, cyanoalkyl, and dialkylaminoalkyl, or R' and R" together form a 5, 6, or 7-member heterocyclic ring, saturated or unsaturated, substituted or unsubstituted, that contains at least one nitrogen and optionally oxygen.

In the above embodiment, preferably X is NR'R" where R' is selected from alkylaminoalkyl, dialkylaminoalkyl, arylalkyl, heterocyclyl, and heterocyclylalkyl where the heterocycle is selected from furanyl, pyrrolyl, and thiophenyl, and the cyclic structure of heterocyclyl and heterocyclylalkyl is optionally substituted with one or more of halo, alkyl, haloalkyl, hydroxy, alkoxy, amino, alkylamino, and dialkylamino; R" is selected from hydrogen, alkyl, haloalkyl or dialkylaminoalkyl, or R' and R" together form a 5, 6, or 7-member heterocyclic ring, saturated or unsaturated, substituted or unsubstituted, that contains at least one nitrogen and optionally oxygen.

In the above embodiment, more preferably X is NR'R" where R' is selected from dialkylaminoalkyl, arylalkyl, heterocyclyl, and heterocyclylalkyl where the heterocycle is selected from furanyl and pyrrolyl, and the cyclic structure is optionally substituted with one or more of halo, alkyl, haloalkyl, alkoxy, alkylamino and dialkylamino; and R" is selected from hydrogen, alkyl, haloalkyl or dialkylaminoalkyl.

In the above embodiment, it is further preferred that X is NR'R" where R' is benzyl, or a heterocyclyl or heterocyclylalkyl selected from 2-furfuryl, 2-pyrrolylmethyl, and (1-methyl-1H-pyrrol-2-yl)methyl; and R" is hydrogen.

In the above embodiment, it is more preferred that X is NR'R" where R' is heterocyclyl or heterocyclylalkyl selected from 2-furfuryl, (1H-pyrrol-2-yl)methyl, and (1-methyl-1H-pyrrol-2-yl)methyl; and R" is hydrogen.

In any of the embodiments of the compounds of formula (II) above, R and $R_0$ are independently selected from hydrogen and hydroxyl, and $R_1$, $R_2$, $R_3$ and $R_4$ are independently selected from halogen, alkoxy, alkyl and haloalkyl; n is 1; $R_{12}$, $R_{13}$, $R_{14}$, $R_{15}$ and $R_{16}$ are independently selected from hydrogen, halogen, alkyl, haloalkyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, and sulfonamido, or any two of $R_{12}$, $R_{13}$, $R_{14}$, $R_{15}$ and $R_{16}$ form an alkylenedioxy group.

In any of the embodiments of the compounds of formula (II) above, $R_1$, $R_2$, $R_3$ and $R_4$ are independently selected from halogen, alkoxy, alkyl and haloalkyl; three of $R_{12}$, $R_{13}$, $R_{14}$, $R_{15}$ and $R_{16}$ are independently selected from hydrogen, halogen, alkyl, haloalkyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, and sulfonamido, and one of $R_{12}$, $R_{13}$, $R_{14}$, $R_{15}$ and $R_{16}$ is independently selected from hydroxyl, hydroxyalkyl, amino, alkylamino, dialkylamino, and mercapto.

In any of the embodiments of the compounds of formula (II) above, three of $R_{12}$, $R_{13}$, $R_{14}$, $R_{15}$ and $R_{16}$ are independently selected from hydrogen, halogen, alkyl, haloalkyl, alkoxy, amino, alkylamino, aminoalkyl, alkylaminoalkyl, dialkylamino, and mercapto, and one of $R_{12}$, $R_{13}$, $R_{14}$, $R_{15}$ and $R_{16}$ is independently selected from hydroxyl, hydroxyalkyl, aldehydo, amino and alkylamino, dialkylamino, and mercapto; and $R_8$ is methyl.

In the embodiments of the compounds of formula (II) above, $R_2$ is selected from halogen, alkoxy and alkylmercapto, $R_1$ and $R_3$ are hydrogen; and three of $R_{12}$, $R_{13}$, $R_{14}$, $R_{15}$ and $R_{16}$ are independently selected from hydrogen, halogen, alkyl, haloalkyl, alkoxy, alkylamino, alkylaminoalkyl, and dialkylamino, and one of $R_{12}$, $R_{13}$, $R_{14}$, $R_{15}$ and $R_{16}$ is independently selected from hydroxyl, hydroxyalkyl, amino, alkylamino, dialkylamino, and mercapto.

In a particular embodiment of the above compound, $R_2$ is selected from halogen and alkoxy, and $R_1$ and $R_3$ are hydrogen.

In the above embodiment, preferably $R_2$ is selected from fluoro and methoxy.

In the prodrug of any of embodiments of formula (II), any of $R_{12}$, $R_{13}$, $R_{14}$, $R_{15}$ and $R_{16}$ is selected from phosphonooxy, phosphonoalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy.

Examples of compounds of the invention include:

(Z)—N-(furan-2-ylmethyl)-2-(1-(4-hydroxy-3,5-dimethylbenzylidene)-5-methoxy-2-methyl-1H-inden-3-yl)acetamide (001), (Z)-2-(5-fluoro-1-(4-formoxy-3,5-dimethoxybenzylidene)-2-methyl-1H-inden-3-yl)-N-(furan-2-ylmethyl)acetamide (002), (Z)—N-(furan-2-ylmethyl)-2-(1-(4-hydroxy-3,5-dimethoxybenzylidene)-5-methoxy-2-methyl-1H-inden-3-yl)acetamide (006), (Z)-2-(5-fluoro-1-(4-hydroxy-3,5-dimethoxybenzylidene)-2-methyl-1H-inden-3-yl)-N-(furan-2-ylmethyl)acetamide (007), (Z)—N-(furan-2-ylmethyl)-2-(1-(4-hydroxy-3,5-dimethoxybenzylidene)-5,6-dimethoxy-2-methyl-1H-inden-3-yl)acetamide (008), (Z)—N-(furan-2-ylmethyl)-2-(1-(4-hydroxy-3-methoxybenzylidene)-5-methoxy-2-methyl-1H-inden-3-yl)acetamide (012), (Z)-2-(1-(3-bromo-4-hydroxy-5-methoxybenzylidene)-5-methoxy-2-methyl-1H-inden-3-yl)-N-(furan-2-ylmethyl)acetamide (013), (Z)-2-(1-(3-chloro-4-hydroxy-5-methoxybenzylidene)-5-methoxy-2-methyl-1H-inden-3-yl)-N-(furan-2-ylmethyl)acetamide (014), (Z)-2-(1-(3-fluoro-4-hydroxy-5-methoxybenzylidene)-5-methoxy-2-methyl-1H-inden-3-yl)-N-(furan-2-ylmethyl)acetamide (016), (Z)-2-(5-fluoro-1-((7-hydroxybenzo[d][1,3]dioxol-5-yl)methylene)-2-methyl-1H-inden-3-yl)-N-(furan-2-ylmethyl)acetamide (017), (Z)—N-((1H-pyrrol-2-yl)methyl)-2-(5-fluoro-1-(4-hydroxy-3,5-dimethoxybenzylidene)-2-methyl-1H-inden-3-yl)acetamide (018), (Z)-2-(5-fluoro-1-(4-hydroxy-3,5-dimethoxybenzylidene)-2-methyl-1H-inden-3-yl)-N-((1-methyl-1H-pyrrol-2-yl)methyl)acetamide (019), (Z)—N-(furan-2-ylmethyl)-2-(1-(3-hydroxy-4-methoxybenzylidene)-5-methoxy-2-methyl-1H-inden-3-yl)acetamide (020), (Z)-2-(5-fluoro-1-(4-(hydroxymethyl)-3,5-dimethoxybenzylidene)-2-methyl-1H-inden-3-yl)-N-(furan-2-ylmethyl)acetamide (021), (Z)—N-((1H-pyrrol-2-yl)methyl)-2-(1-(4-hydroxy-3,5-dimethoxybenzylidene)-5-methoxy-2-methyl-1H-inden-3-yl)acetamide (022), (Z)—N-(2-(dimethylamino)ethyl)-2-(5-fluoro-1-(furan-2-ylmethylene)-2-methyl-1H-inden-3-yl)acetamide (026), (Z)-2-(5-fluoro-1-(4-mesyloxy-3,5-dimethoxybenzylidene)-2-methyl-1H-inden-3-yl)-N-(furan-2-ylmethyl)acetamide (029), (Z)-2-(5-methoxy-2-methyl-1-(3,4,5-trimethoxybenzylidene)-1H-inden-3-yl)-N-(1-methylpyrrolidin-3-yl)acetamide (030), (Z)-2-(5-fluoro-2-methyl-1-(3,4,5-trimethoxybenzylidene)-1H-inden-3-yl)-N-(1-methylpyrrolidin-3-yl)acetamide (031), (Z)-2-(5-methoxy-2-methyl-1-(3,4,5-trimethoxybenzylidene)-1H-inden-3-yl)-N-(1-methylpiperidin-3-yl)acetamide (032), (Z)-2-(5-fluoro-2-methyl-1-(3,4,5-trimethoxybenzylidene)-1H-inden-3-yl)-N-(1-methylpiperidin-3-yl)acetamide (033), (Z)-2-(5-methoxy-2-methyl-1-(3,4,5-trimethoxybenzylidene)-1H-inden-3-yl)-N-(5-methylpyridin-3-yl)acetamide (063), (Z)-2-(1-(4-aminocarbonyl-3,5-dimethoxybenzylidene)-5-fluoro-2-methyl-1H-inden-3-yl)-N-((1-methyl-1H-pyrrol-2-yl)methyl)acetamide (065), (Z)-methyl 2,6-dimethoxy-4-((5-methoxy-2-methyl-3-(2-((1-methylpyrrolidin-3-yl)amino)-2-oxoethyl)-1H-inden-1-ylidene)methyl)benzoate (066), (Z)-2-(1-(3,5-dimethoxy-4-sulfamoylbenzylidene)-5-methoxy-2-methyl-1H-inden-3-yl)-N-(1-methylpyrrolidin-3-yl)acetamide (067), (Z)-2-(1-(3,5-dimethoxy-4-ureidobenzylidene)-5-fluoro-2-methyl-1H-inden-3-yl)-N-((4-methylpyridin-3-yl)methyl)acetamide (069), (Z)—N-(furan-2-ylmethyl)-2-(1-(4-ethoxycarbonyl-3,5-dimethoxybenzylidene)-5-methoxy-2-methyl-1H-inden-3-yl)acetamide (095), (Z)-2-(5-methoxy-2-methyl-1-(3,4,5-trimethoxybenzylidene)-1H-inden-3-yl)-N-((1-methyl-1H-pyrrol-2-yl)methyl)acetamide (096), (Z)—N-((1H-pyrrol-2-yl)methyl)-2-(5-methoxy-2-methyl-1-(3,4,5-trimethoxybenzylidene)-1H-inden-3-yl)acetamide (097), (Z)-2-(1-(3,5-dimethoxy-4-sulfamoylbenzylidene)-5-fluoro-2-methyl-1H-inden-3-yl)-N-((6-methylpyridin-2-yl)methyl)acetamide (098), (Z)-4-((5-fluoro-3-(2-((furan-2-ylmethyl)amino)-2-oxoethyl)-2-methyl-1H-inden-1-ylidene)methyl)-2,6-dimethoxyphenyl (2-(dimethylamino)ethyl)carbamate (099), (Z)-2-(5-fluoro-1-(4-mercapto-3,5-dimethoxybenzylidene)-2-methyl-1H-inden-3-yl)-N-((1-methyl-1H-pyrrol-2-yl)methyl)acetamide (100), (Z)-2-(1-((6-(dimethylamino)pyridin-3-yl)methylene)-5-methoxy-2-methyl-1H-inden-3-yl)-N-(furan-2-ylmethyl)acetamide (130), (Z)-2-(1-((2-(dimethylamino)pyrimidin-5-yl)methylene)-5-methoxy-2-methyl-1H-inden-3-yl)-N-(furan-2-ylmethyl)acetamide (131), (Z)—N-(2-(dimethylamino)ethyl)-2-(5-fluoro-1-(furan-2-ylmethylene)-2-methyl-1H-inden-3-yl)acetamide (132), (Z)—N-(2-(dimethylamino)ethyl)-2-(5-methoxy-2-methyl-1-(pyridin-4-ylmethylene)-1H-inden-3-yl)acetamide (133), (Z)—N-(2-(dimethylamino)ethyl)-2-(1-((2-(dimethylamino)pyrimidin-5-yl)methylene)-5-methoxy-2-methyl-1H-inden-3-yl)acetamide (134), (Z)—N-(furan-2-ylmethyl)-2-(5-methoxy-2-methyl-1-(3,4,5-trimethoxybenzylidene)-1H-inden-3-yl)-N-methylacetamide (135), (Z)-2-(1-(4-(dimethylamino)benzylidene)-5-methoxy-2-methyl-1H-inden-3-yl)-N-(2-(dimethylamino)ethyl)-N-methylacetamide (138), (R,Z)-1-(3-(dimethylamino)pyrrolidin-1-yl)-2-(5-methoxy-2-methyl-1-(3,4,5-trimethoxybenzylidene)-1H-inden-3-yl)ethanone hydrochloride (139), (S,Z)-1-(3-(dimethylamino)pyrrolidin-1-yl)-2-(5-methoxy-2-methyl-1-(3,4,5-trimethoxybenzylidene)-1H-inden-3-yl)ethanone hydrochloride (141), (Z)-2-(5-methoxy-2-methyl-1-(3,4,5-trimethoxybenzylidene)-1H-inden-3-yl)-1-(4-methylpiperazin-1-yl)ethanone hydrochloride (143), (R,Z)-2-(2,5-dimethyl-1-(3,4,5-trimethoxybenzylidene)-1H-inden-3-yl)-1-(3-(dimethylamino)pyrrolidin-1-yl)ethanone hydrochloride (144), (S,Z)-2-(5,6-dimethoxy-2-methyl-1-(3,4,5-trimethoxybenzylidene)-1H-inden-3-yl)-N-(1-methylpyrrolidin-3-yl)acetamide hydrochloride (145), (Z)-2-(5-fluoro-1-(4-hydroxy-3,5-dimethoxybenzylidene)-2-methyl-1H-inden-3-yl)-N-phenoxyacetamide (151), (Z)-2-(5-fluoro-1-(4-hydroxy-3,5-dimethoxybenzylidene)-2-methyl-1H-inden-3-yl)-N-(furan-2-ylmethyl)-N-(trifluoromethyl)acetamide (152), (Z)-2-(5-cyano-1-(4-hydroxy-3,5-dimethoxybenzylidene)-2-methyl-1H-inden-3-yl)-N-(furan-2-ylmethyl)acetamide (154), (Z)—N-(furan-2-ylmethyl)-2-(1-(4-hydroxy-3,5-dimethoxybenzylidene)-2-methyl-5-(trifluoromethyl)-1H-inden-3-yl)acetamide (155), or the corresponding Z- or E-isomer thereof, prodrug, or salt thereof.

Preferred examples of the compounds include:

(Z)-2-(5-fluoro-1-(4-formoxy-3,5-dimethoxybenzylidene)-2-methyl-1H-inden-3-yl)-N-(furan-2-ylmethyl)acetamide (002), (Z)—N-(furan-2-ylmethyl)-2-(1-(4-hydroxy-3,5-dimethoxybenzylidene)-5-methoxy-2-methyl-1H-inden-3-yl)acetamide (006), (Z)-2-(5-fluoro-1-(4-hydroxy-3,5-dimethoxybenzylidene)-2-methyl-1H-inden-3-yl)-N-(furan-2-ylmethyl)acetamide (007), (Z)—N-((1H-pyrrol-2-yl)methyl)-2-(5-fluoro-1-(4-hydroxy-3,5-dimethoxybenzylidene)-2-methyl-1H-inden-3-yl)acetamide (018), (Z)-2-(5-fluoro-1-(4-hydroxy-3,5-dimethoxybenzylidene)-2-methyl-1H-inden-3-yl)-N-((1-methyl-1H-pyrrol-2-yl)methyl)acetamide (019), (Z)—N-((1H-pyrrol-2-yl)methyl)-2-(1-(4-hydroxy-3,5-dimethoxybenzylidene)-5-methoxy-2-methyl-1H-inden-3-yl)acetamide (022), (Z)-2-(5-fluoro-1-(4-mesyloxy-3,5-dimethoxybenzylidene)-2-methyl-1H-inden-3-yl)-N-(furan-2-ylmethyl)acetamide (029), and (Z)-2-(5-methoxy-2-methyl-1-(3,4,5-trimethoxybenzylidene)-1H-inden-3-yl)-N-(1-methylpyrrolidin-3-yl)acetamide (030), or the corresponding Z- or E-isomer thereof, prodrug, or salt thereof.

The structural formulas of the above compounds are as follows:

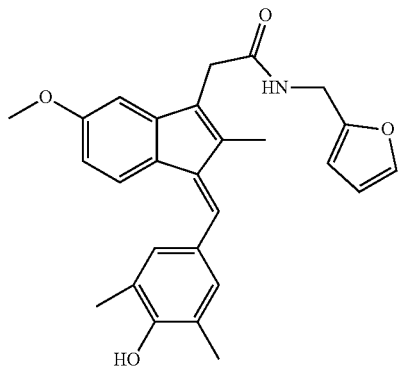

001

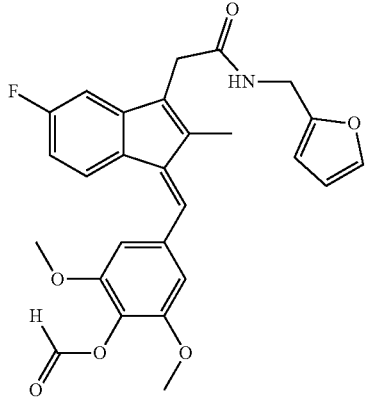

002

006
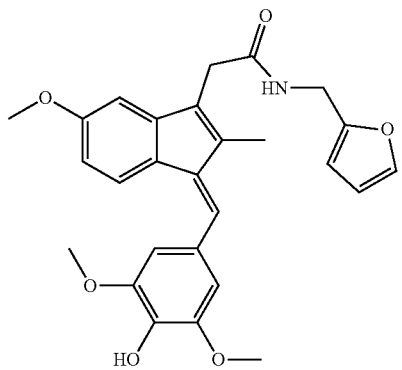
007
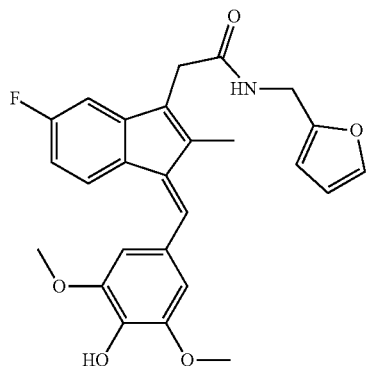
008
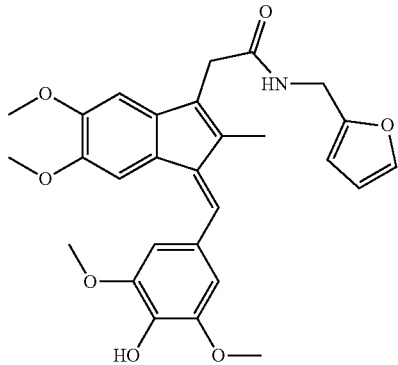
012
013
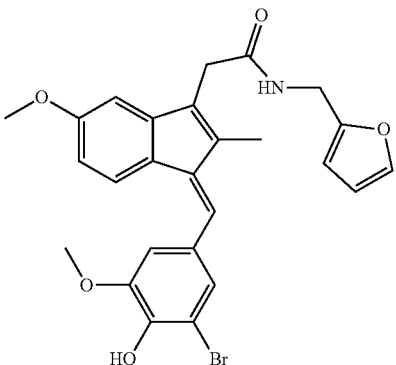
014
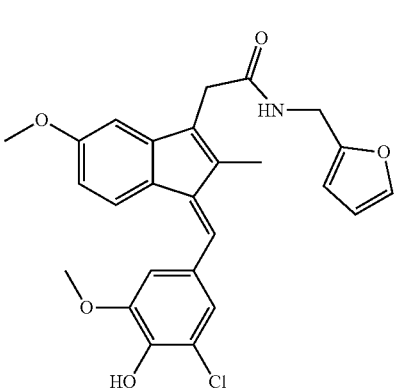
016
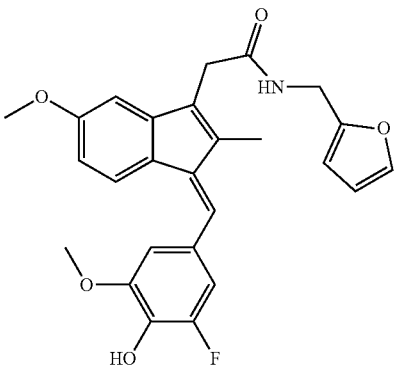
017
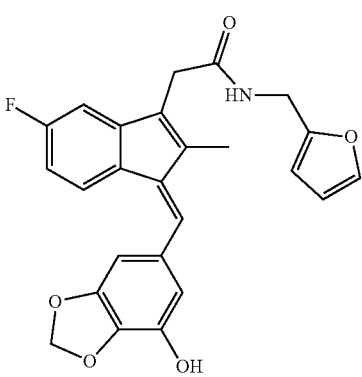

018
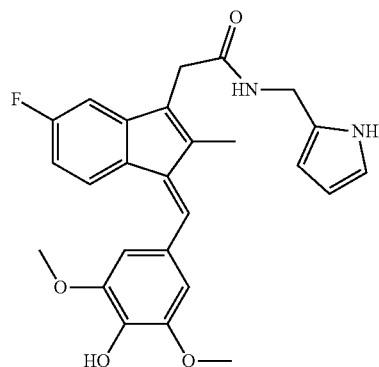
019
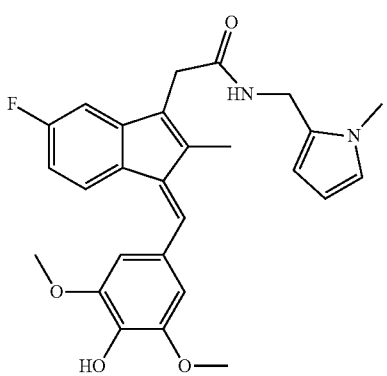
020
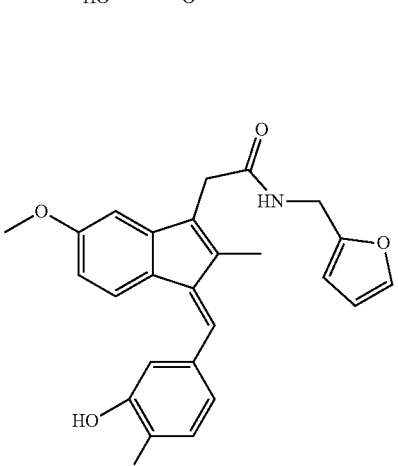
021
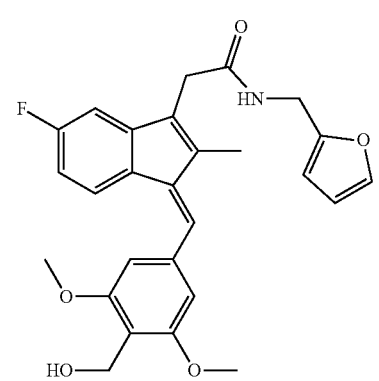
022
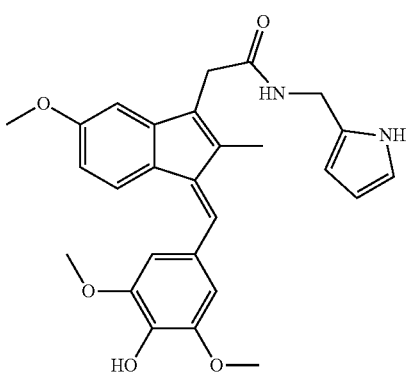
026
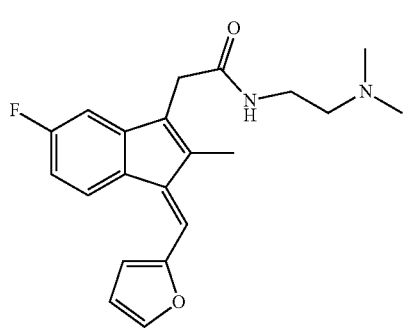
029
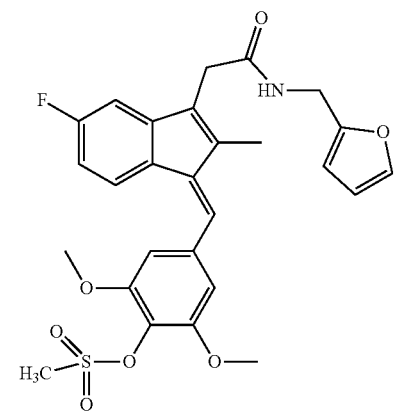
030
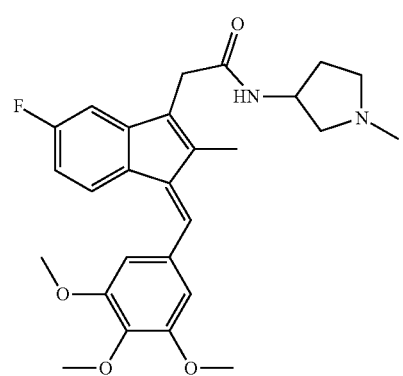

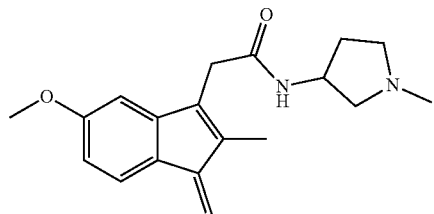
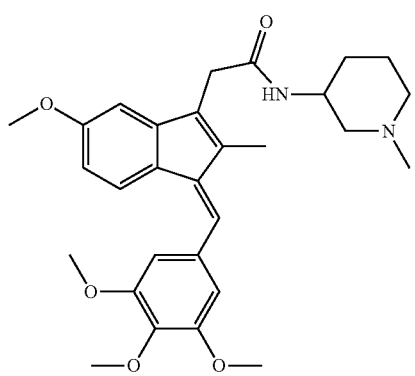
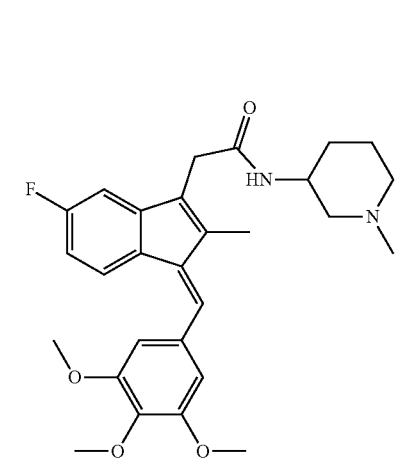
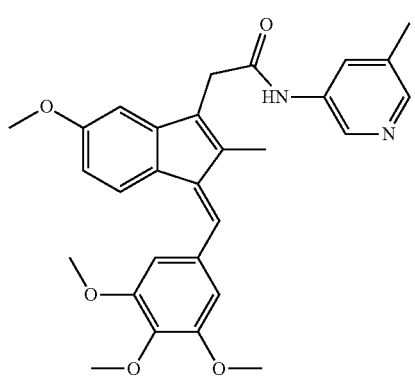
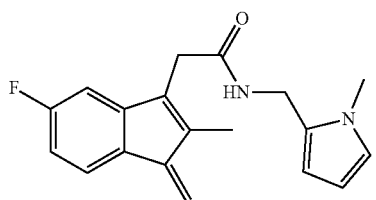
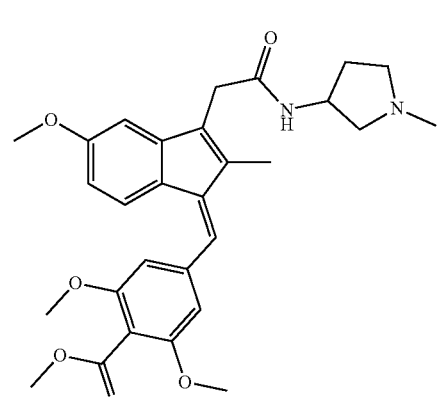
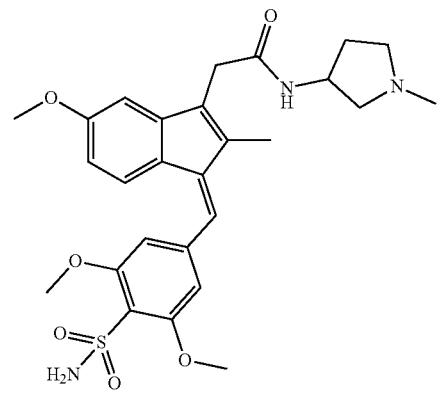
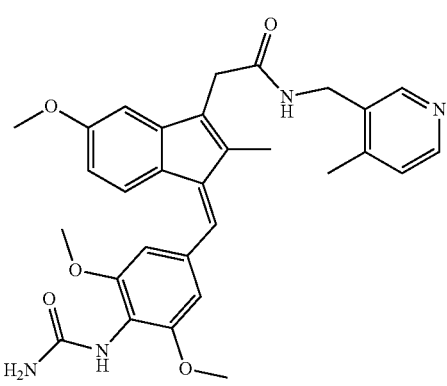

095
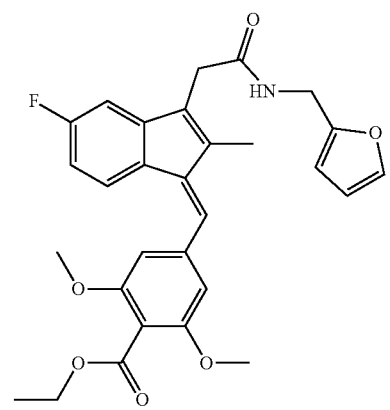
096
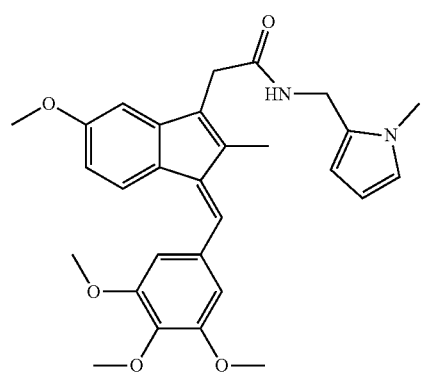
097
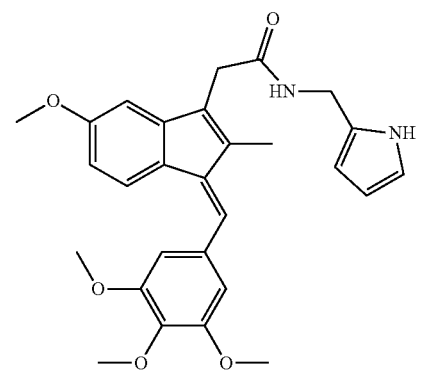
098
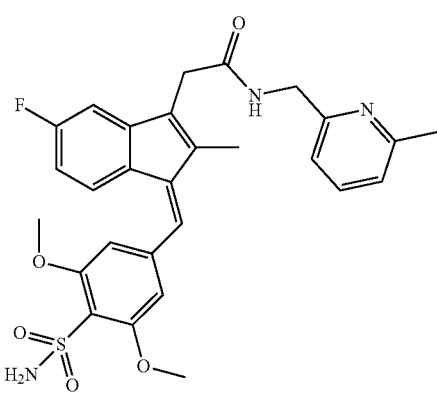
099
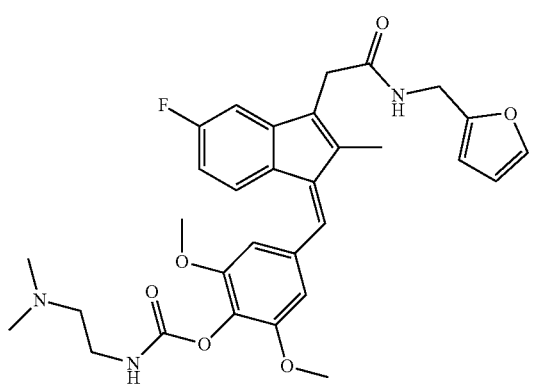
100
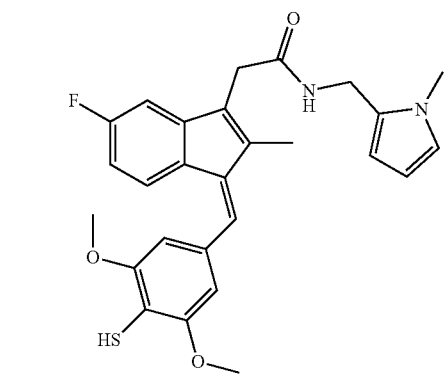
130
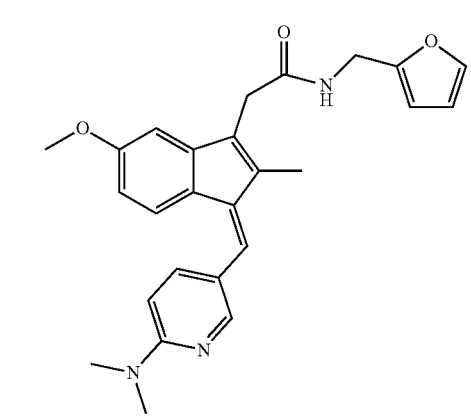
131
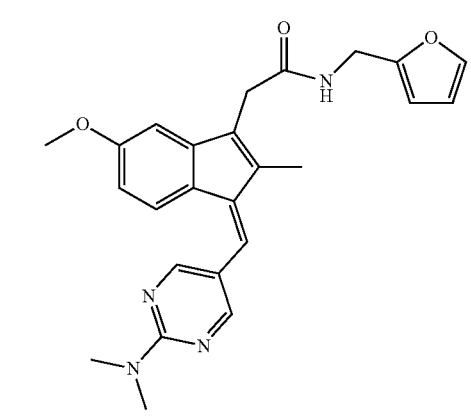

132 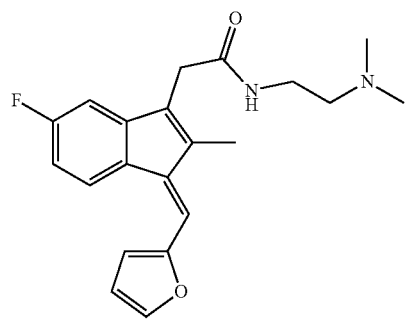
133 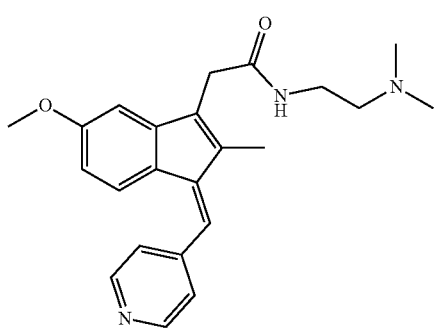
134 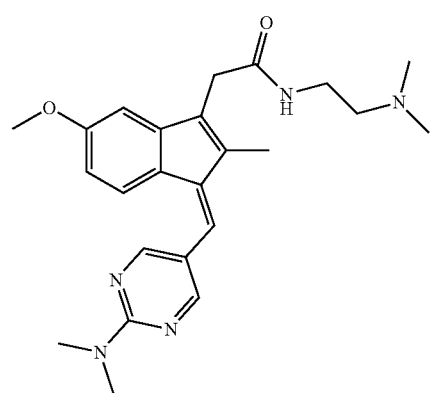
135 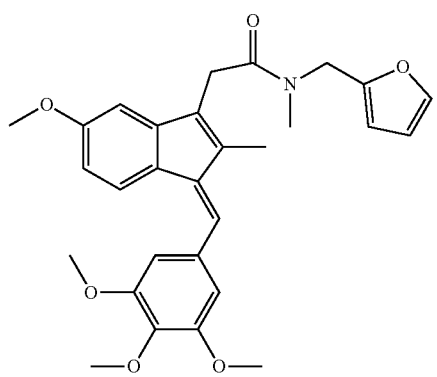
138 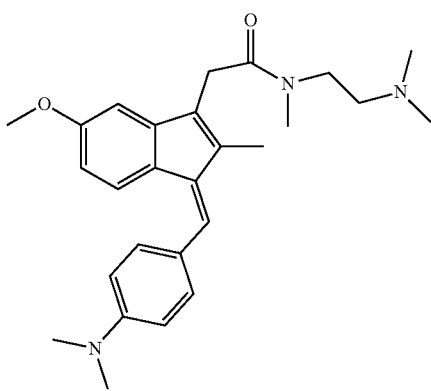
139 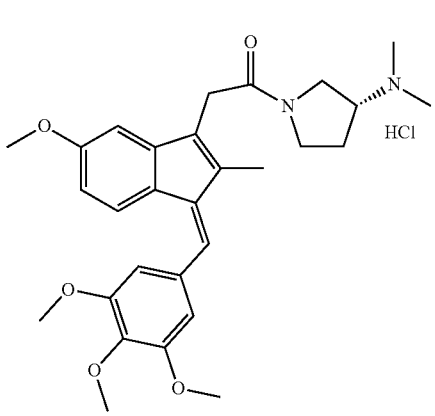
141 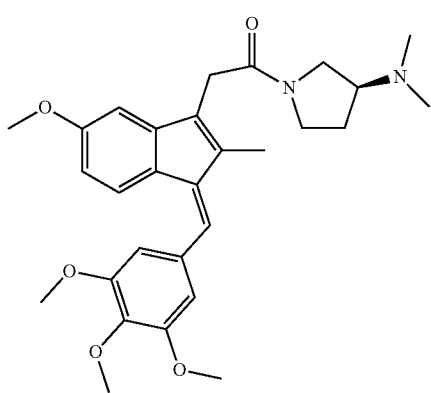
143 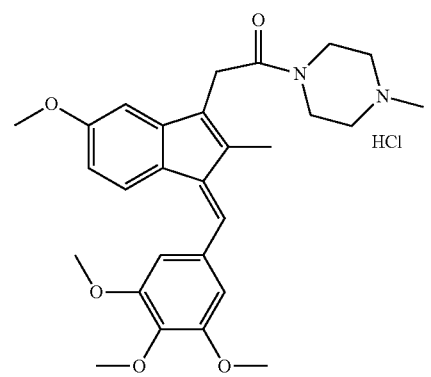

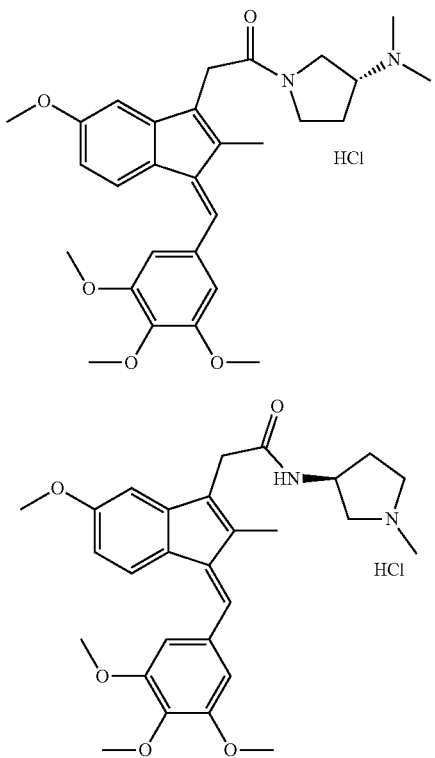

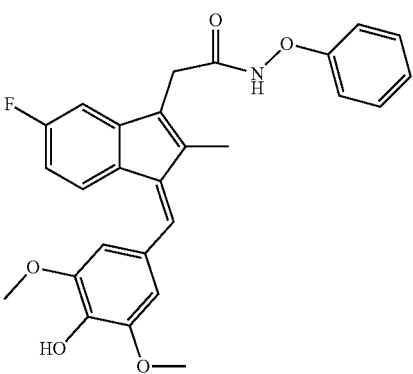

144

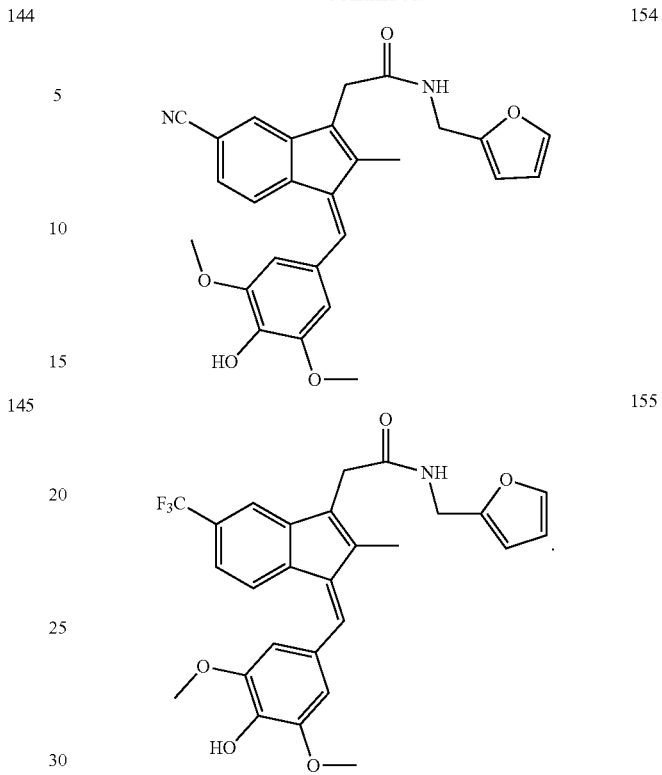

145

151

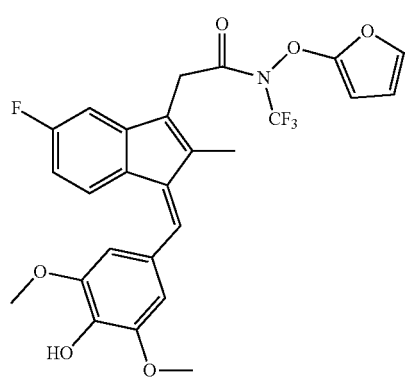

152

Examples of additional compounds of the invention, wherein R or R₀ is not hydrogen are as follows:

(Z)-2-(benzylamino)-2-(5-fluoro-1-(4-hydroxy-3,5-dimethoxybenzylidene)-2-methyl-1H-inden-3-yl)-N-(furan-2-ylmethyl)acetamide (202), (Z)-2-(5-fluoro-1-(4-hydroxy-3,5-dimethoxybenzylidene)-2-methyl-1H-inden-3-yl)-N-(furan-2-ylmethyl)-2-((pyridin-4-ylmethyl)amino)acetamide (203), (Z)—N-(furan-2-ylmethyl)-2-(1-(4-hydroxy-3,5-dimethoxybenzylidene)-5-methoxy-2-methyl-1H-inden-3-yl)-2-(1H-imidazol-1-yl)acetamide (401), (Z)-2-(5-fluoro-1-(4-hydroxy-3,5-dimethoxybenzylidene)-2-methyl-1H-inden-3-yl)-2-((furan-2-ylmethyl)amino)acetamide (404), (Z)-2-(cyclopropylamino)-2-(5-fluoro-1-(4-hydroxy-3,5-dimethoxybenzylidene)-2-methyl-1H-inden-3-yl)-N-(furan-2-ylmethyl)acetamide (410), (Z)-2-(5-fluoro-1-(4-hydroxy-3,5-dimethoxybenzylidene)-2-methyl-1H-inden-3-yl)-N-((1-methyl-1H-pyrrol-2-yl)methyl)-2-(pyrrolidin-1-yl)acetamide (412), (Z)-2-(5-fluoro-1-(4-hydroxy-3,5-dimethoxybenzylidene)-2-methyl-1H-inden-3-yl)-N-((1-methyl-1H-pyrrol-2-yl)methyl)-2-((pyridin-3-ylmethyl)amino)acetamide (413), (Z)-2-(dimethylamino)-2-(1-(4-hydroxy-3,5-dimethoxybenzylidene)-5-methoxy-2-methyl-1H-inden-3-yl)-N-phenylacetamide (415), (Z)-2-azido-2-(1-(4-hydroxy-3,5-dimethoxybenzylidene)-5-methoxy-2-methyl-1H-inden-3-yl)-N-phenylacetamide (416), (Z)-2-(ethylamino)-2-(1-(4-hydroxy-3,5-dimethoxybenzylidene)-5-methoxy-2-methyl-1H-inden-3-yl)-N-(1-methylpyrrolidin-3-yl)acetamide (420), (Z)-2-(((1H-imidazol-2-yl)methyl)amino)-2-(5-fluoro-1-(4-hydroxy-3,5-dimethoxybenzylidene)-2-methyl-1H-inden-3-yl)-N-(pyridin-3-ylmethyl)acetamide (423), (Z)-2-(5-fluoro-1-(4-hydroxy-3,5-dimethoxyben-zylidene)-2-methyl-1H-inden-3-yl)-2-((1-methylpyrrolidin-3-yl)amino)-N-(pyridin-3-ylmethyl)acetamide (425), (Z)—N-benzyl-2-(5-fluoro-1-(4-hydroxy-3,5-dimethoxy-benzylidene)-2-methyl-1H-inden-3-yl)-2-((oxazol-2-ylm-ethyl)amino)acetamide (426), (Z)—N-benzyl-2-(cyclopropylamino)-2-(5-fluoro-1-(4-hydroxy-3,5-dimethoxybenzylidene)-2-methyl-1H-inden-3-yl)acetamide (427), (Z)—N-benzyl-2-(5-fluoro-1-(4-hydroxy-3,5-dimethoxy-benzylidene)-2-methyl-1H-inden-3-yl)-2-((pyridin-3-ylm-ethyl)amino)acetamide (428), (Z)-2-(5-fluoro-1-(4-hydroxy-3,5-dimethoxyben-zylidene)-2-methyl-1H-inden-3-yl)-N-(furan-2-ylmethyl)-2-((1-methylpyrrolidin-3-yl)amino)acetamide (430), (Z)-2-(5-fluoro-1-(4-hydroxy-3,5-dimethoxyben-zylidene)-2-methyl-1H-inden-3-yl)-N-(furan-2-ylmethyl)-2-((oxazol-2-ylmethyl)amino)acetamide (431), (Z)-2-(5-fluoro-1-(4-hydroxy-3,5-dimethoxyben-zylidene)-2-methyl-1H-inden-3-yl)-2-((1-methylpiperidin-4-yl)amino)-N-(pyridin-2-ylmethyl)acetamide (433), (Z)-2-(5-fluoro-1-(4-hydroxy-3,5-dimethoxyben-zylidene)-2-methyl-1H-inden-3-yl)-N-(pyridin-2-ylm-ethyl)-2-((pyridin-3-ylmethyl)amino)acetamide (434), and (Z)-2-cyano-2-(5-fluoro-1-(4-hydroxy-3,5-dimethoxy-benzylidene)-2-methyl-1H-inden-3-yl)-N-((1-methyl-1H-pyrrol-2-yl)methyl)acetamide (436), or the corresponding Z- or E-isomer thereof, prodrug, or salt thereof.

The structural formulas of the above compounds are as follows:

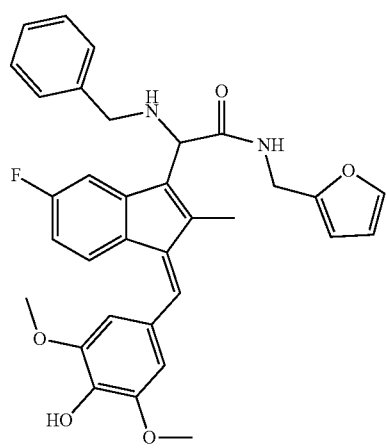

202

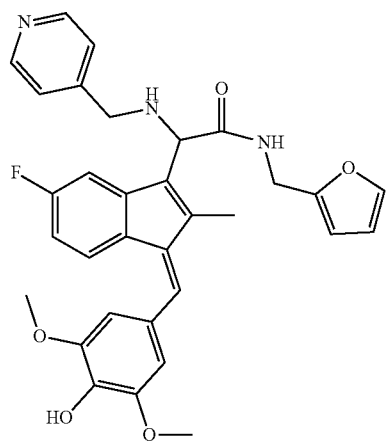

203

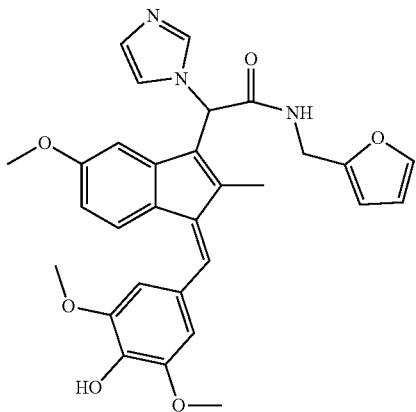

401

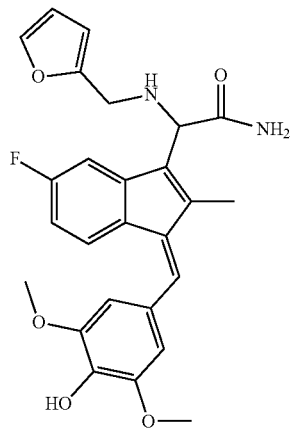

404

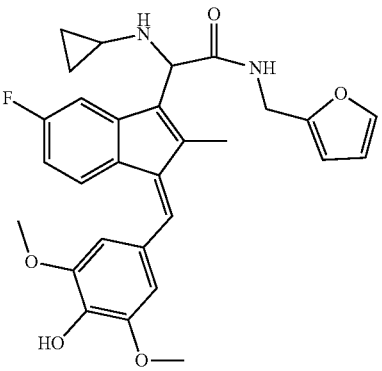

410

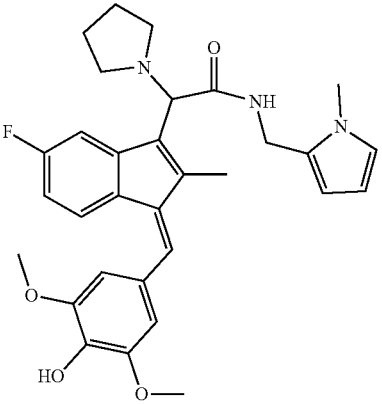

412

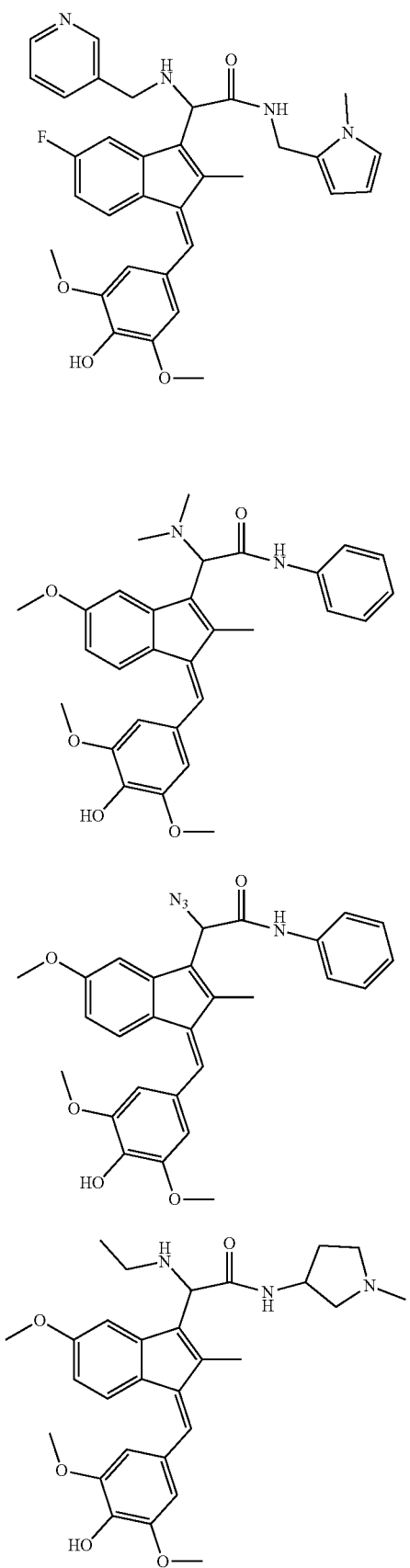
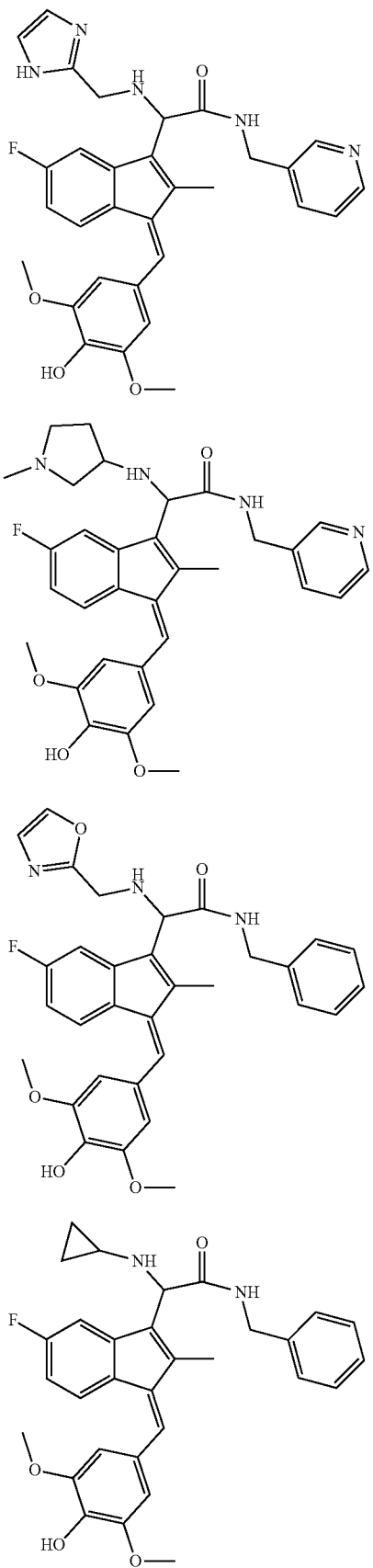

-continued

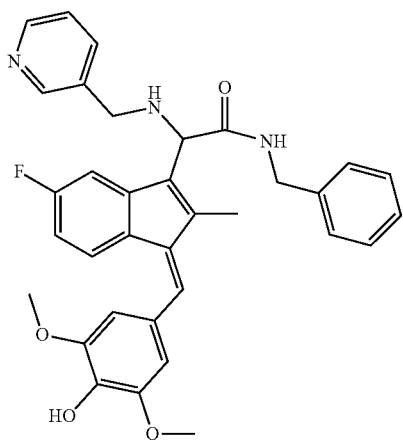

428

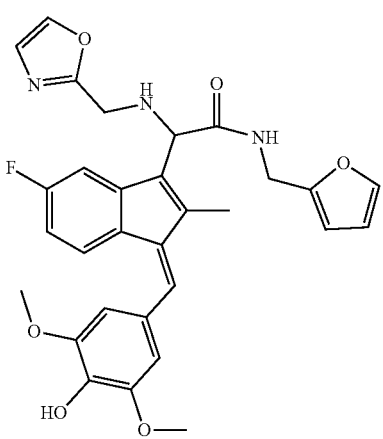

430

431

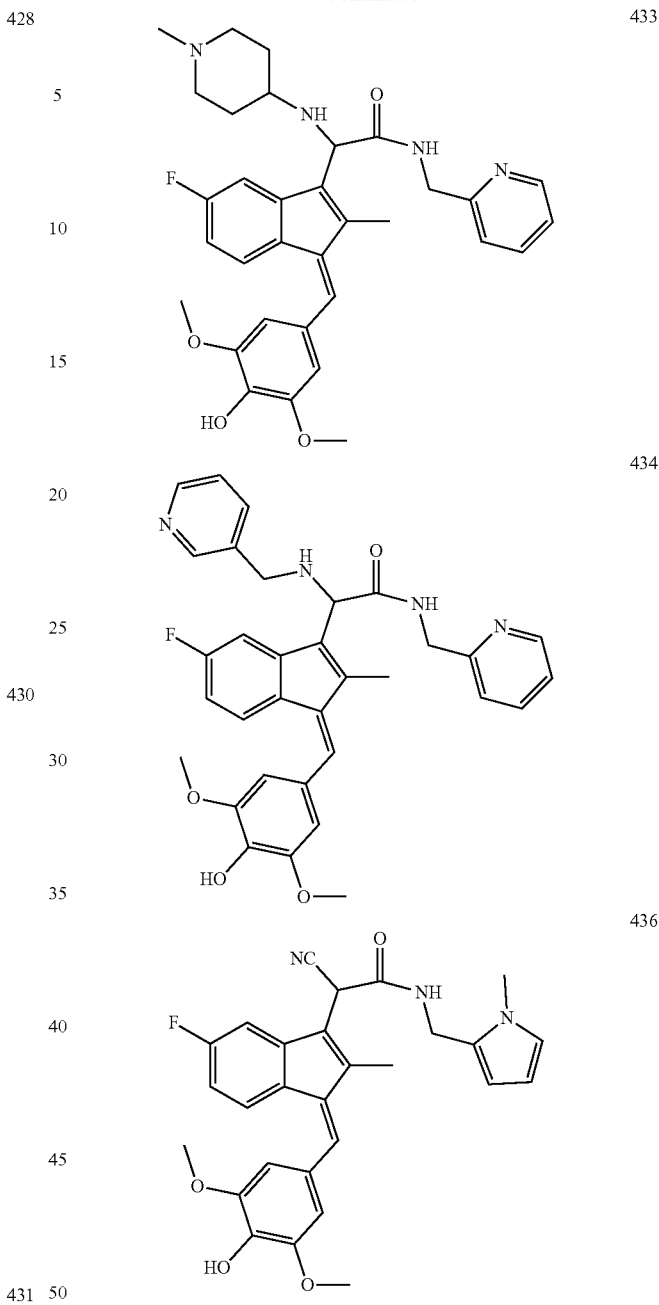

Examples of the prodrugs of the invention include:
(Z)-4-((5-fluoro-3-(2-((furan-2-ylmethyl)amino)-2-oxo-ethyl)-2-methyl-1H-inden-1-ylidene)methyl)-2,6-dimethoxyphenyl benzoate (214);
(Z)-4-((3-(2-((furan-2-ylmethyl)amino)-2-oxoethyl)-5-methoxy-2-methyl-1H-inden-1-ylidene)methyl)-2,6-dimethoxyphenyl (4-nitrophenyl) carbonate (300);
(Z)-4-((3-(2-((furan-2-ylmethyl)amino)-2-oxoethyl)-5-methoxy-2-methyl-1H-inden-1-ylidene)methyl)-2,6-dimethoxyphenyl benzoate (301);
(Z)-4-((3-(2-((furan-2-ylmethyl)amino)-2-oxoethyl)-5-methoxy-2-methyl-1H-inden-1-ylidene)methyl)-2,6-dimethoxyphenyl nicotinate (302);
(Z)-4-((3-(2-((furan-2-ylmethyl)amino)-2-oxoethyl)-5-methoxy-2-methyl-1H-inden-1-ylidene)methyl)-2,6-dimethoxyphenyl (2-(dimethylamino)ethyl)carbamate (303);

(Z)-4-((3-(2-((furan-2-ylmethyl)amino)-2-oxoethyl)-5-methoxy-2-methyl-1H-inden-1-ylidene)methyl)-2,6-dimethoxyphenyl morpholine-4-carboxylate (304);

(Z)-4-((3-(2-((furan-2-ylmethyl)amino)-2-oxoethyl)-5-methoxy-2-methyl-1H-inden-1-ylidene)methyl)-2,6-dimethoxyphenyl (1-methylpiperidin-4-yl)carbamate (305);

(Z)-4-((3-(2-((furan-2-ylmethyl)amino)-2-oxoethyl)-5-methoxy-2-methyl-1H-inden-1-ylidene)methyl)-2,6-dimethoxyphenyl 4-methylpiperazine-1-carboxylate (306);

(Z)-4-((3-(2-((furan-2-ylmethyl)amino)-2-oxoethyl)-5-methoxy-2-methyl-1H-inden-1-ylidene)methyl)-2,6-dimethoxyphenyl 4-(1-methylpiperidin-4-yl)piperazine-1-carboxylate (307);

(Z)-4-((3-(2-((furan-2-ylmethyl)amino)-2-oxoethyl)-5-methoxy-2-methyl-1H-inden-1-ylidene)methyl)-2,6-dimethoxyphenyl dihydrogen phosphate (308);

(Z)-(4-((3-(2-((furan-2-ylmethyl)amino)-2-oxoethyl)-5-methoxy-2-methyl-1H-inden-1-ylidene)methyl)-2,6-dimethoxyphenoxy)methyl dihydrogen phosphate (309);

(Z)-4-((5-fluoro-3-(2-((furan-2-ylmethyl)amino)-2-oxoethyl)-2-methyl-1H-inden-1-ylidene)methyl)-2,6-dimethoxyphenyl nicotinate (311);

(Z)-4-((5-fluoro-3-(2-((furan-2-ylmethyl)amino)-2-oxoethyl)-2-methyl-1H-inden-1-ylidene)methyl)-2,6-dimethoxyphenyl (4-nitrophenyl) carbonate (312);

(Z)-4-((5-fluoro-3-(2-((furan-2-ylmethyl)amino)-2-oxoethyl)-2-methyl-1H-inden-1-ylidene)methyl)-2,6-dimethoxyphenyl (2-(dimethylamino)ethyl)carbamate (313);

(Z)-4-((5-fluoro-3-(2-((furan-2-ylmethyl)amino)-2-oxoethyl)-2-methyl-1H-inden-1-ylidene)methyl)-2,6-dimethoxyphenyl morpholine-4-carboxylate (314);

(Z)-4-((5-fluoro-3-(2-((furan-2-ylmethyl)amino)-2-oxoethyl)-2-methyl-1H-inden-1-ylidene)methyl)-2,6-dimethoxyphenyl (1-methylpiperidin-4-yl)carbamate (315);

(Z)-4-((5-fluoro-3-(2-((furan-2-ylmethyl)amino)-2-oxoethyl)-2-methyl-1H-inden-1-ylidene)methyl)-2,6-dimethoxyphenyl 4-methylpiperazine-1-carboxylate (316);

(Z)-4-((5-fluoro-3-(2-((furan-2-ylmethyl)amino)-2-oxoethyl)-2-methyl-1H-inden-1-ylidene)methyl)-2,6-dimethoxyphenyl 4-(1-methylpiperidin-4-yl)piperazine-1-carboxylate (317);

(Z)-4-((5-fluoro-3-(2-((furan-2-ylmethyl)amino)-2-oxoethyl)-2-methyl-1H-inden-1-ylidene)methyl)-2,6-dimethoxyphenyl dihydrogen phosphate (318);

(Z)-(4-((5-fluoro-3-(2-((furan-2-ylmethyl)amino)-2-oxoethyl)-2-methyl-1H-inden-1-ylidene)methyl)-2,6-dimethoxyphenoxy)methyl dihydrogen phosphate (319);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl benzoate (320);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl nicotinate (321);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl (4-nitrophenyl) carbonate (322);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl (2-(dimethylamino)ethyl)carbamate (323);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl morpholine-4-carboxylate (324);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl (1-methylpiperidin-4-yl)carbamate (325);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl 4-methylpiperazine-1-carboxylate (326);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl 4-(1-methylpiperidin-4-yl)piperazine-1-carboxylate (327);

(Z)-4-((5-fluoro-2-methyl-3-(2-oxo-2-((pyridin-3-ylmethyl)amino)ethyl)-1H-inden-1-ylidene)methyl)-2,6-dimethoxyphenyl dihydrogen phosphate (328);

(Z)-(4-((5-fluoro-2-methyl-3-(2-oxo-2-((pyridin-3-ylmethyl)amino)ethyl)-1H-inden-1-ylidene)methyl)-2,6-dimethoxyphenoxy)methyl dihydrogen phosphate (329);

(Z)-4-((3-(2-(benzylamino)-2-oxoethyl)-5-fluoro-2-methyl-1H-inden-1-ylidene)methyl)-2,6-dimethoxyphenyl benzoate (330);

(Z)-4-((3-(2-(benzylamino)-2-oxoethyl)-5-fluoro-2-methyl-1H-inden-1-ylidene)methyl)-2,6-dimethoxyphenyl nicotinate (331);

(Z)-4-((3-(2-(benzylamino)-2-oxoethyl)-5-fluoro-2-methyl-1H-inden-1-ylidene)methyl)-2,6-dimethoxyphenyl (4-nitrophenyl) carbonate (332);

(Z)-4-((3-(2-(benzylamino)-2-oxoethyl)-5-fluoro-2-methyl-1H-inden-1-ylidene)methyl)-2,6-dimethoxyphenyl (2-(dimethylamino)ethyl)carbamate (333);

(Z)-4-((3-(2-(benzylamino)-2-oxoethyl)-5-fluoro-2-methyl-1H-inden-1-ylidene)methyl)-2,6-dimethoxyphenyl morpholine-4-carboxylate (334);

(Z)-4-((3-(2-(benzylamino)-2-oxoethyl)-5-fluoro-2-methyl-1H-inden-1-ylidene)methyl)-2,6-dimethoxyphenyl (1-methylpiperidin-4-yl)carbamate (335);

(Z)-4-((3-(2-(benzylamino)-2-oxoethyl)-5-fluoro-2-methyl-1H-inden-1-ylidene)methyl)-2,6-dimethoxyphenyl 4-methylpiperazine-1-carboxylate (336);

(Z)-4-((3-(2-(benzylamino)-2-oxoethyl)-5-fluoro-2-methyl-1H-inden-1-ylidene)methyl)-2,6-dimethoxyphenyl dihydrogen phosphate (338);

(Z)-(4-((3-(2-(benzylamino)-2-oxoethyl)-5-fluoro-2-methyl-1H-inden-1-ylidene)methyl)-2,6-dimethoxyphenoxy)methyl dihydrogen phosphate (339);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl benzoate (340);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl nicotinate (341);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl (4-nitrophenyl) carbonate (342);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl (2-(dimethylamino)ethyl)carbamate (343);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl morpholine-4-carboxylate (344);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl (1-methylpiperidin-4-yl)carbamate (345);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl 4-methylpiperazine-1-carboxylate (346);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl 4-(1-methylpiperidin-4-yl)piperazine-1-carboxylate (347);

(Z)-4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenyl dihydrogen phosphate (348);

(Z)-(4-((5-fluoro-2-methyl-3-(2-(((1-methyl-1H-pyrrol-2-yl)methyl)amino)-2-oxoethyl)-1H-inden-1-ylidene)methyl)-2,6-dimethoxyphenoxy)methyl dihydrogen phosphate (349);

(Z)-4-((5-fluoro-2-methyl-3-(2-oxo-2-(phenylamino)ethyl)-1H-inden-1-ylidene)methyl)-2,6-dimethoxyphenyl (4-nitrophenyl) carbonate (350);

(Z)-4-((5-fluoro-2-methyl-3-(2-oxo-2-(phenylamino)ethyl)-1H-inden-1-ylidene)methyl)-2,6-dimethoxyphenyl 4-methylpiperazine-1-carboxylate (351);

(Z)-4-((5-fluoro-3-(2-((3-methoxyphenyl)amino)-2-oxoethyl)-2-methyl-1H-inden-1-ylidene)methyl)-2,6-dimethoxyphenyl (4-nitrophenyl) carbonate (352);

(Z)-4-((5-fluoro-3-(2-((3-methoxyphenyl)amino)-2-oxoethyl)-2-methyl-1H-inden-1-ylidene)methyl)-2,6-dimethoxyphenyl 4-methylpiperazine-1-carboxylate (353);

(Z)-4-((5-fluoro-2-methyl-3-(2-oxo-2-((pyridin-2-ylmethyl)amino)ethyl)-1H-inden-1-ylidene)methyl)-2,6-dimethoxyphenyl (4-nitrophenyl) carbonate (354);

(Z)-4-((5-fluoro-2-methyl-3-(2-oxo-2-((pyridin-2-ylmethyl)amino)ethyl)-1H-inden-1-ylidene)methyl)-2,6-dimethoxyphenyl 4-methylpiperazine-1-carboxylate (355);

or the corresponding Z- or E-isomer thereof, or pharmaceutically acceptable salts thereof.

The structural formulas of the above prodrugs are as follows.

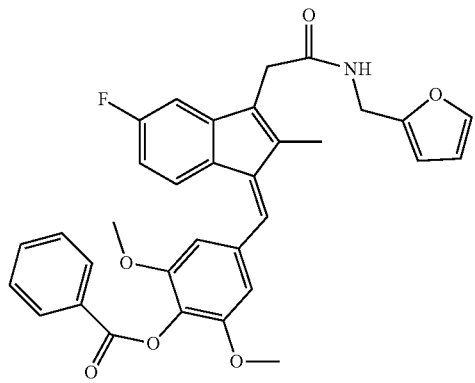

214

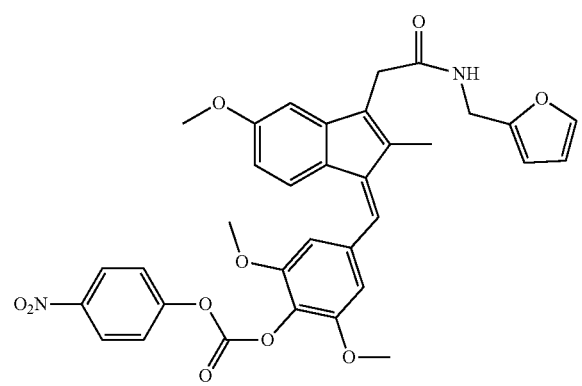

300

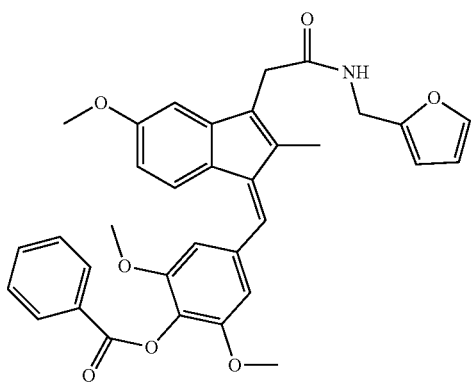

301

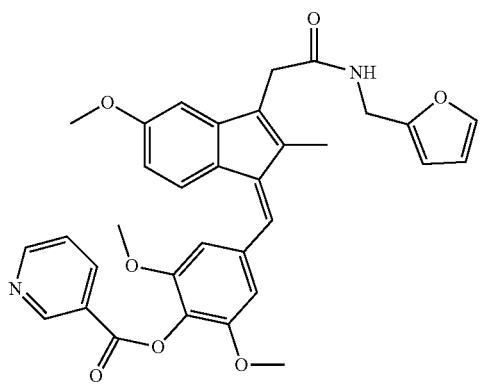

302

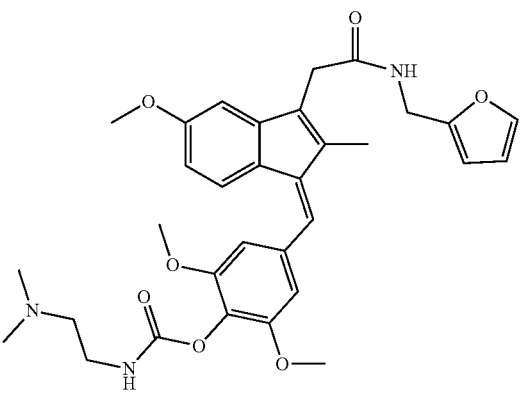

303

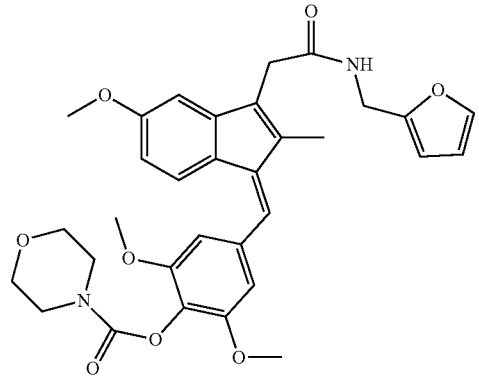

304

305
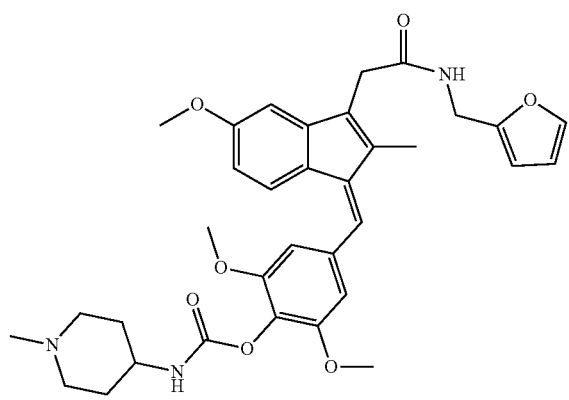
306
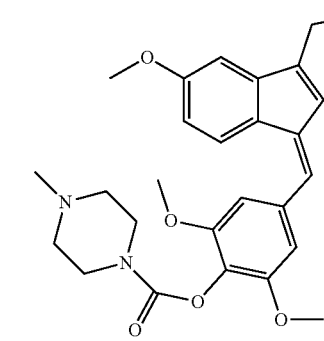
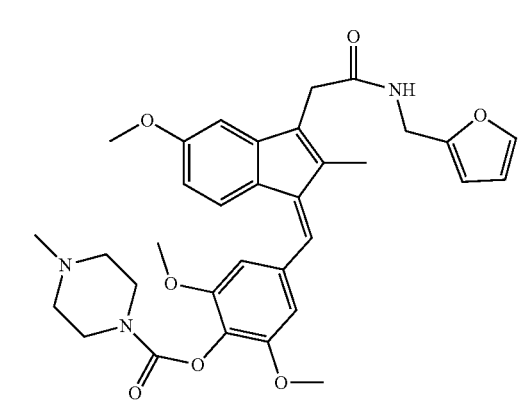
307
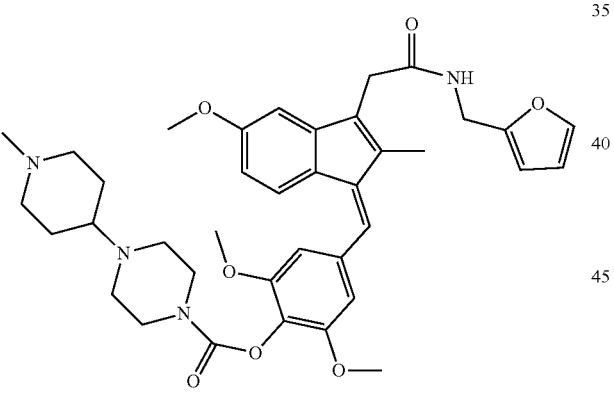
308
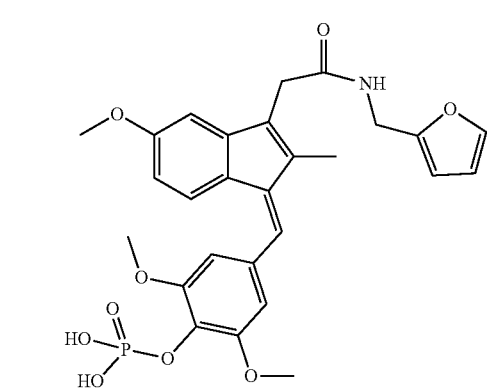
309
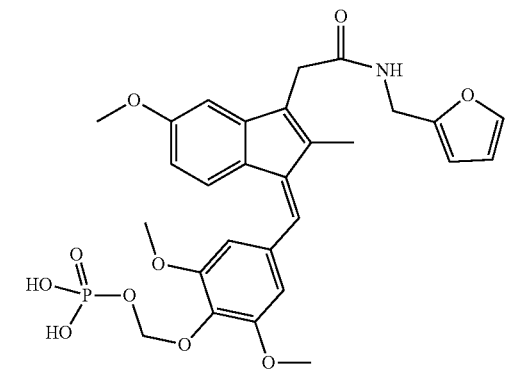
311
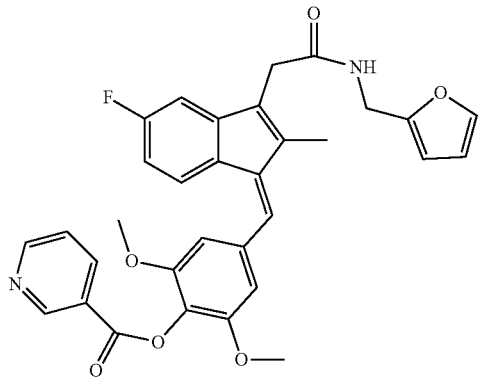
312
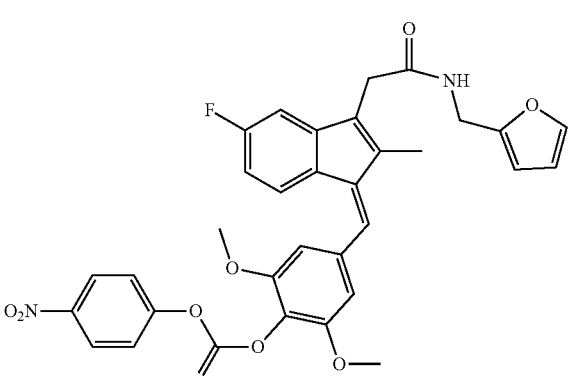
313
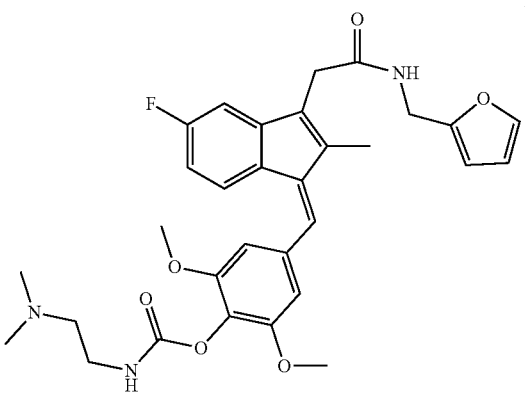

314
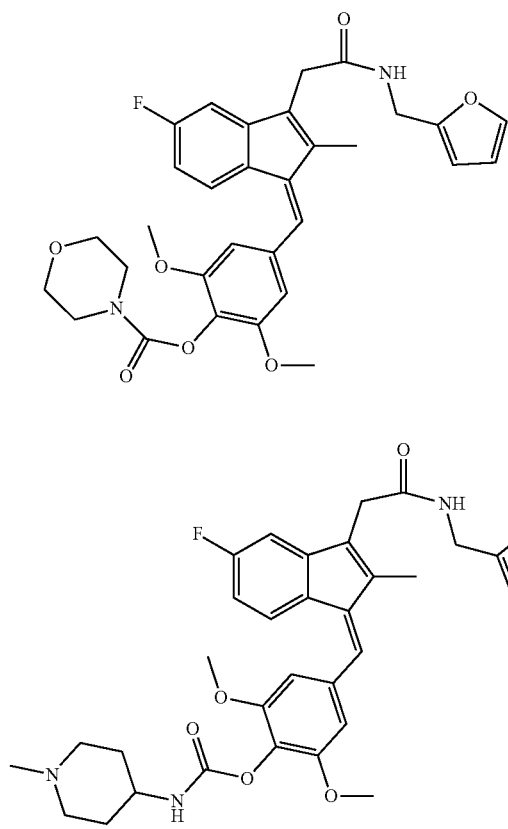
315
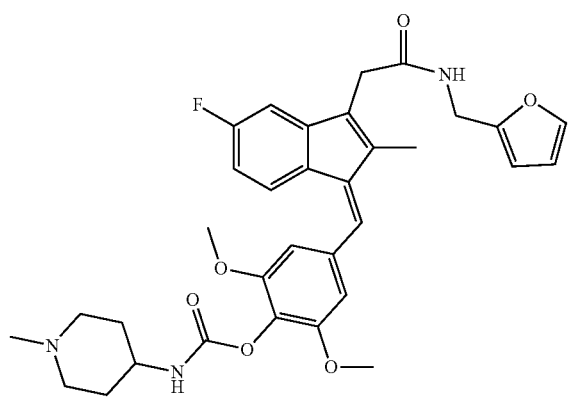
316
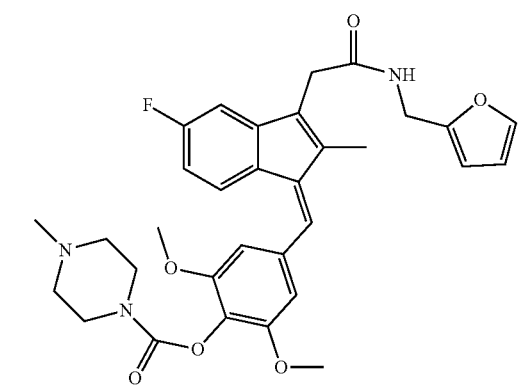
317
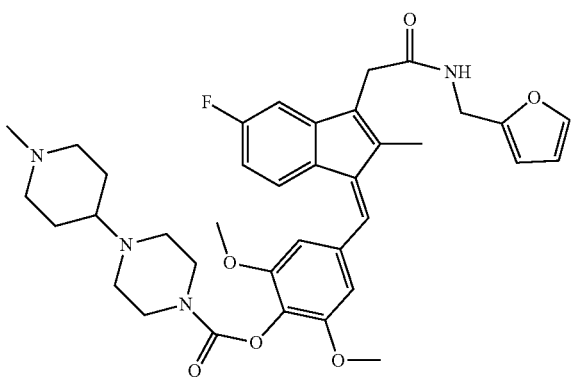
318
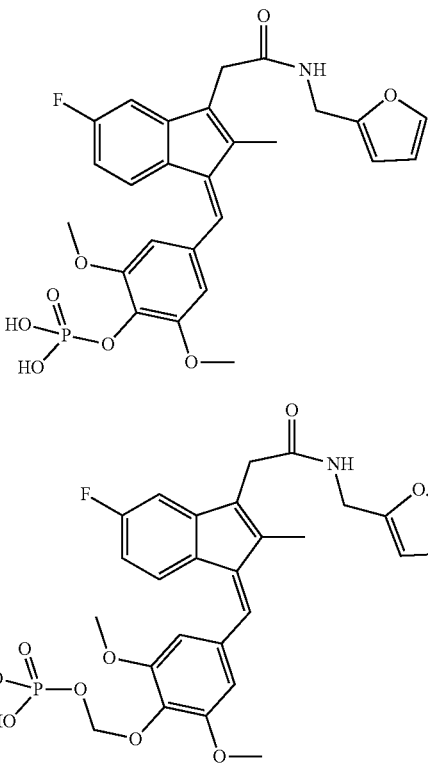
319
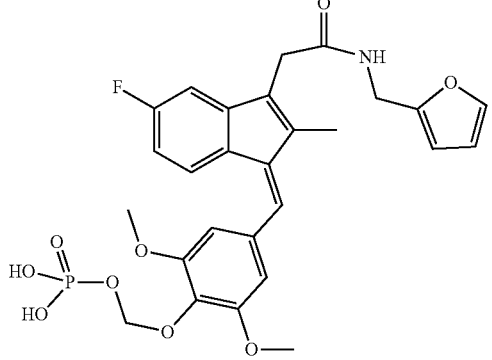
320
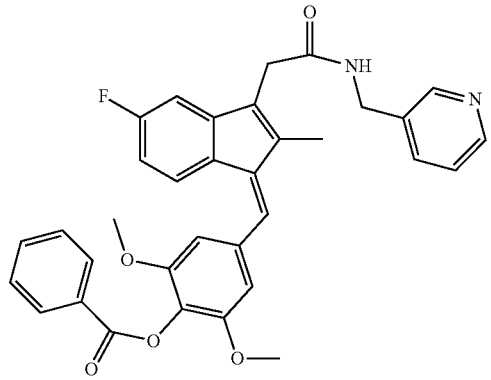
321
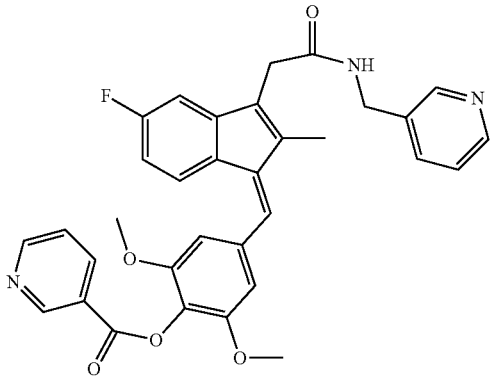

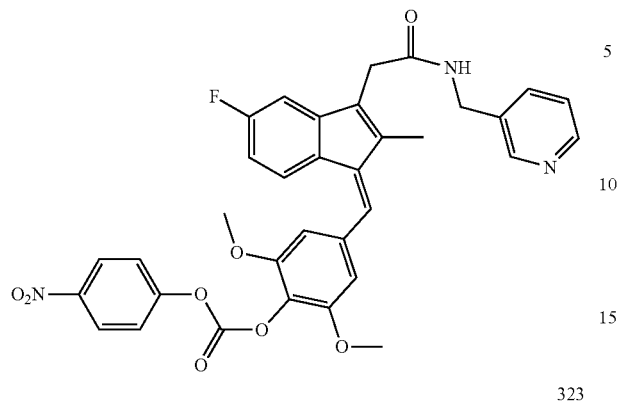
322
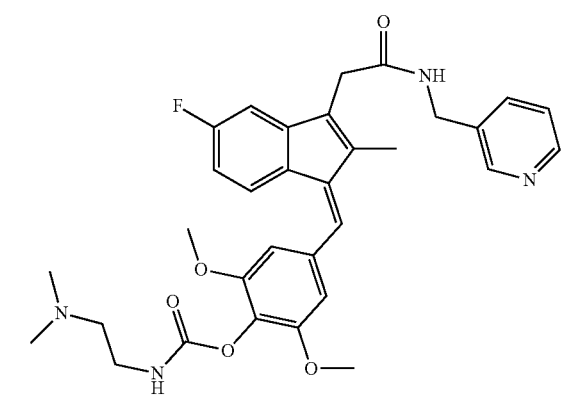
323
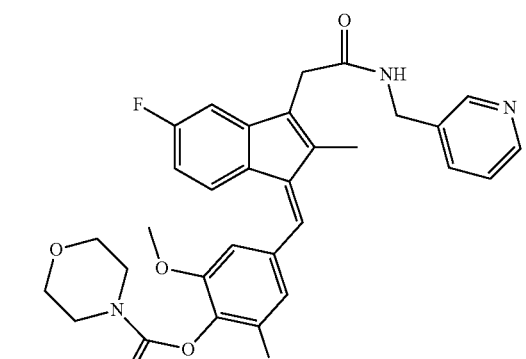
324
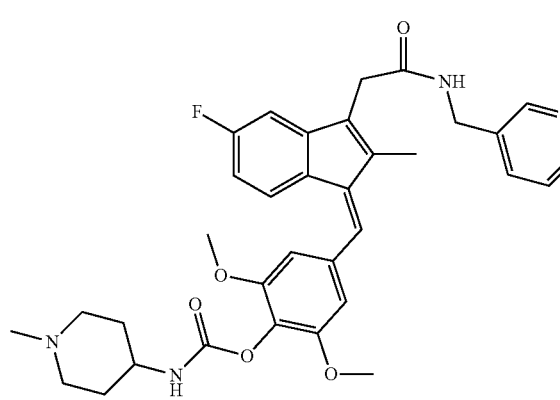
325
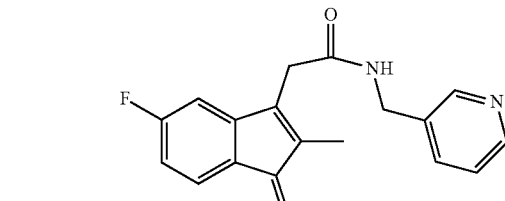
326
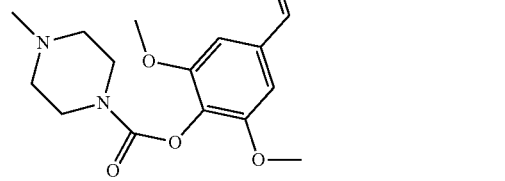
327
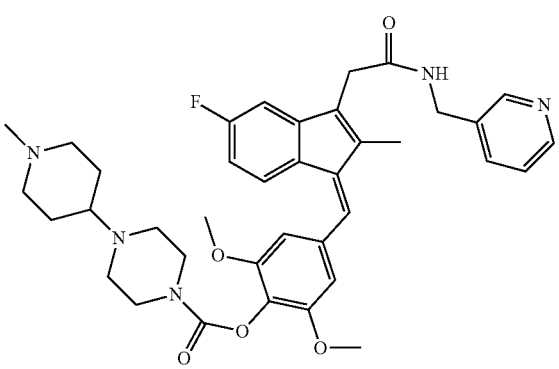
328
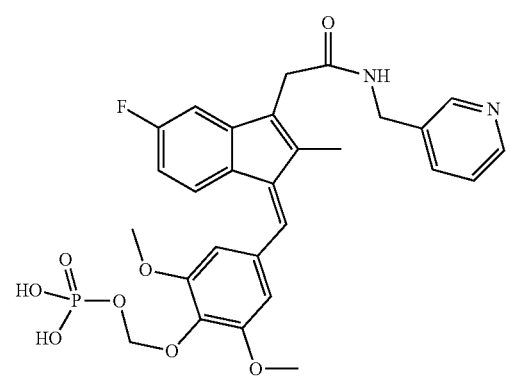
329

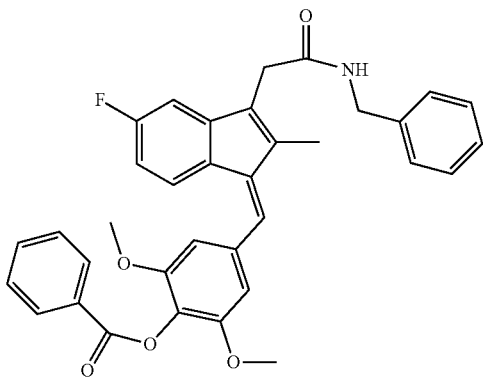
330
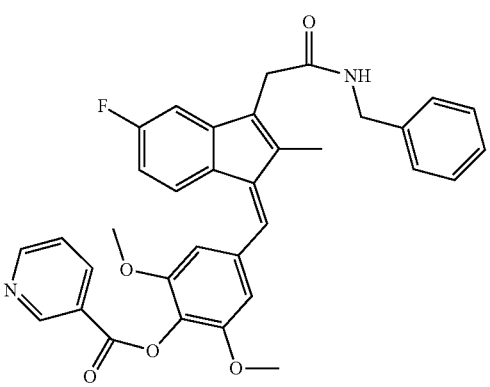
331
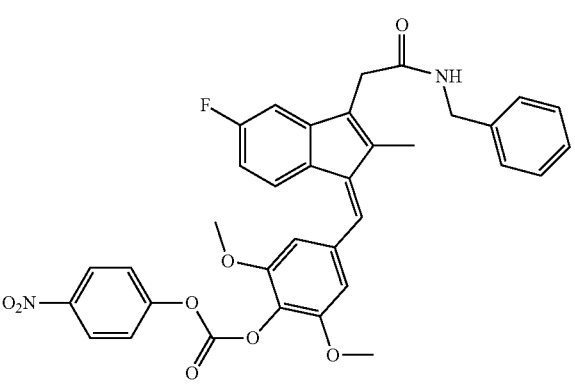
332
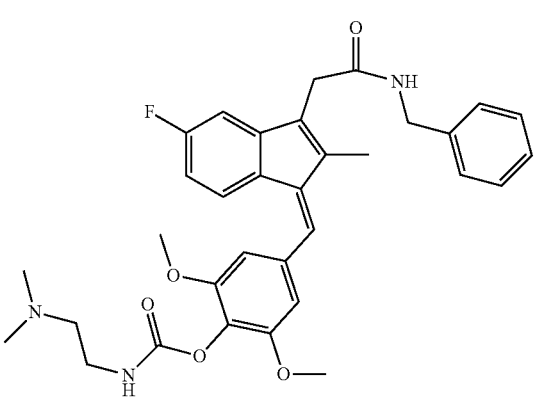
333
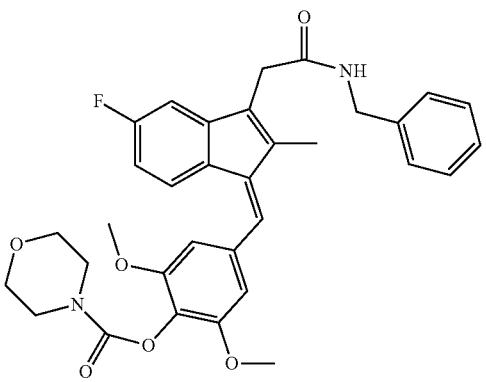
334
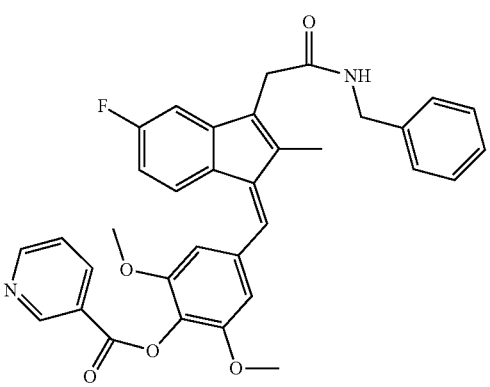
335
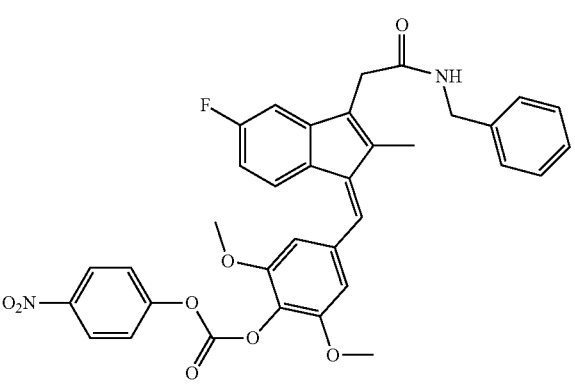
336
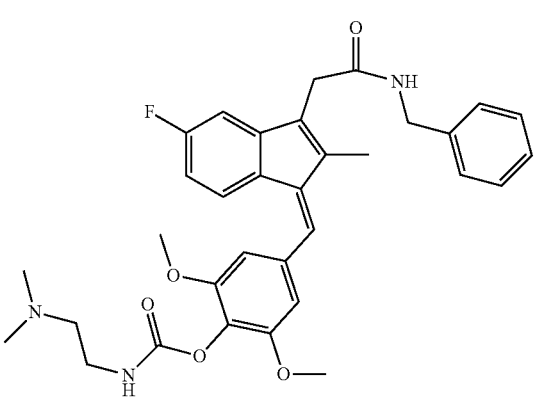
338
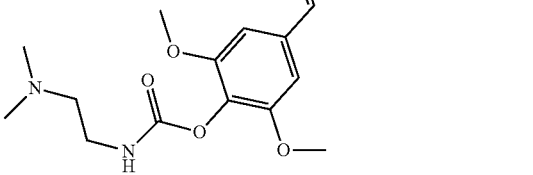

339
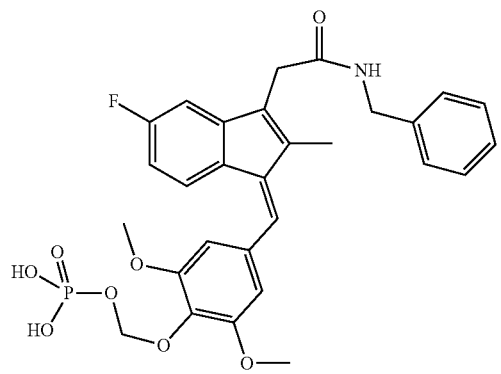
340
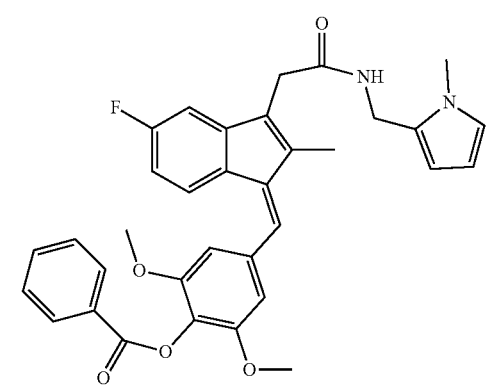
341
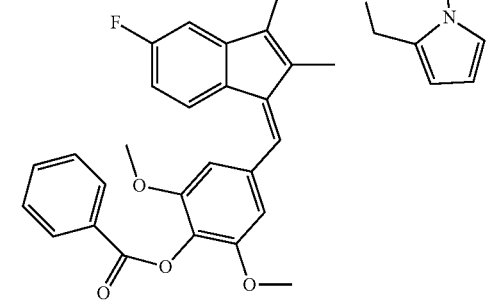
342
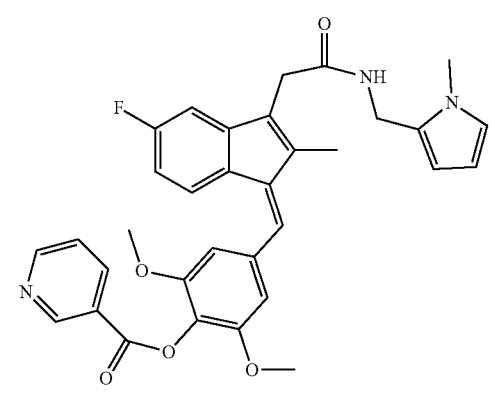
343
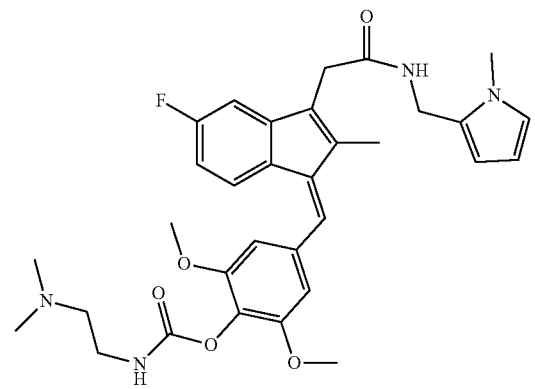
344
345
346
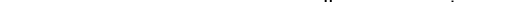

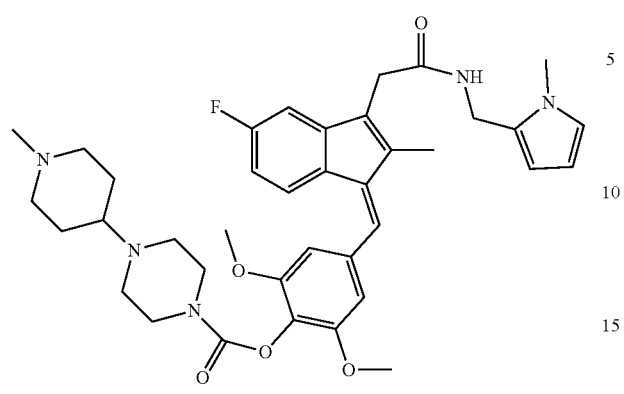
347
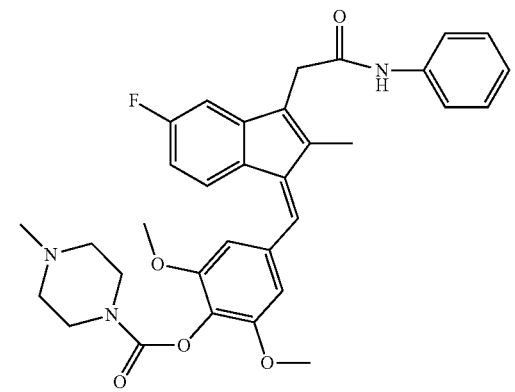
351
348
352
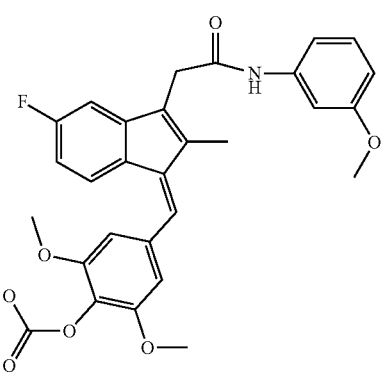
349
353
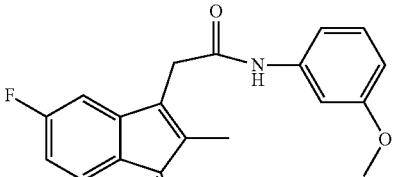
350
355
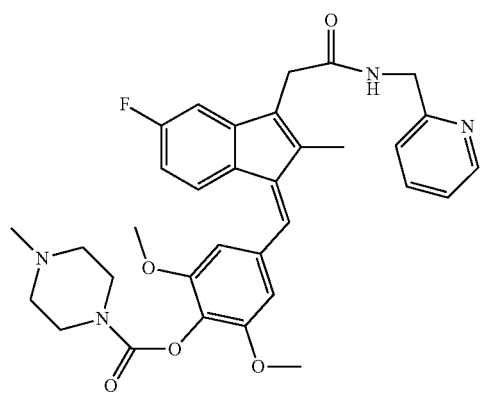
The present invention further provdes a method of therapeutically or prophylactically treating a human or nonhuman mammalian patient with a disease or condition treatable by the inhibition of one or more neoplastic or cancerous process, which method comprises administering to a patient in need thereof a therapeutically or prophylactically effective amount of at least one neoplastic or cancerous inhibitory compound of formula (I) or (II) or a compound selected from (001), (002), (006)-(008), (012)-(014), (016)-(022), (026), (029)-(033), (063), (065)-(067), (069), (095)-(100), (130)-(135), (138), (139), (141), (143), (144), (145), (151), (152), (154), (155), (214), (300)-(309), (311)-(336), (338)-(353), (355), (202), (203), (401), (404), (410), (412), (413), (415), (416), (420), (423), (425)-(428), (430), (431), (433), (434), and (436), or a pharmaceutically acceptable salt or prodrug thereof, either alone or in combination with at least one therapeutic agent other than a compound of formula (I) or (II) or a compound selected from (001), (002), (006)-(008), (012)-(014), (016)-(022), (026), (029)-(033), (063), (065)-(067), (069), (095)-(100), (130)-(135), (138), (139), (141), (143), (144), (145), (151), (152), (154), (155) (214), (300)-(309), (311)-(336), (338)-(353), (355), (202), (203), (401), (404), (410), (412), (413), (415), (416), (420), (423), (425)-(428), (430), (431), (433), (434), and (436), or a pharmaceutically acceptable salt or prodrug thereof, for example, an anticancer drug or radiation.

In an embodiment, the neoplastic or cancerous process is selected from growth, proliferation, survival, metastasis, drug resistance and radiation resistance of a tumor cell.

The present invention provides compounds as described above, pharmaceutically acceptable salts or prodrugs thereof, or the pharmaceutical composition, for use in the treatment or prophylaxis of a human or nonhuman mammalian patient with cancer.

In an embodiment, the cancer is selected from pancreatic cancer, lung cancer, colorectal cancer, melanoma, ovarian cancer, renal cancer, prostate cancer, head and neck cancer, endocrine cancer, uterine cancer, breast cancer, sarcoma cancer, gastric cancer, hepatic cancer, esophageal cancer, central nervous system cancer, brain cancer, hepatic cancer, germline cancer, lymphoma, and leukemia, particularly pancreatic cancer, colorectal cancer, and lung cancer.

In an embodiment of the above treatment or use, the cancer is drug-resistant or radiation-resistant.

In an embodiment, prodrugs of the compounds of formula (II) include those wherein any of $R_{12}$, $R_{13}$, $R_{14}$, $R_{15}$ and $R_{16}$ is selected from phosphonooxy, phosphonoalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy.

The present invention also includes the following aspects:
1. A compound of formula I:
wherein:

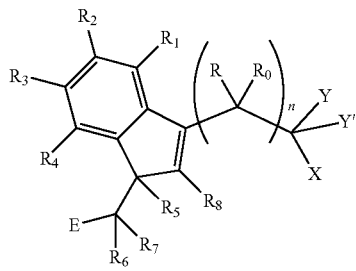

I

R and $R_0$ are independently selected from hydrogen, hydroxyl, alkyl, trifluoromethyl, amino, alkoxy and alkylamino, or R and $R_0$ together is oxygen or sulfur, or R and $R_0$ together is a single-bonded or a double-bonded nitrogen bonded to one or more of hydrogen, hydroxyl, alkyl, and trifluoromethyl; n is 0, 1 or 2;

$R_1$, $R_2$, $R_3$, and $R_4$ are independently selected from hydrogen, hydroxyl, halogen, alkyl, trifluoromethyl, alkoxy, and alkylmercapto;

$R_5$, $R_6$, $R_7$, $R_8$ are independently selected from hydrogen, alkyl, trifluoromethyl and alkoxy; or $R_5$ and $R_6$ together form a carbon-carbon bond;

Y is hydrogen, alkyl, or trifluoromethyl, and Y' is hydrogen, alkyl, trifluoromethyl, amino, alkylamino, or alkoxy, or Y and Y' together is oxygen or sulfur, or Y and Y' together is a single-bonded or a double-bonded nitrogen bonded to one or more of hydrogen, hydroxyl, alkyl, and trifluoromethyl;

X is selected from hydrogen, alkyl, trifluoromethyl, alkoxy, alkylmercapto, and hydroxyl with the proviso that X is not hydroxyl when Y and Y' together is oxygen in a compound of formula I wherein $R_5$ and $R_6$ together is a carbon-carbon bond, or X is NR'R", where R' is selected from the group consisting of hydrogen, hydroxyl, alkyl, trifluoromethyl, alkoxy, alkenyl, alkynyl, hydroxyalkyl, polyhydroxyalkyl, alkylaminoalkyl, dialkylaminoalkyl, aminoalkyl, aryl, arylalkyl, arylalkenyl, arylcycloalkyl, arylcycloalkenyl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one or two double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, trifluoromethyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; and E is a substituted or unsubstituted, saturated or unsaturated, 7-membered, 6-membered, 5-membered, 4-membered or 3-membered carbocyclic or heterocyclic ring; or
a pharmaceutically acceptable salt thereof or a prodrug thereof;

with the proviso that when E is a substituted aryl or heteroaryl, then no substituent on the aryl or heteroaryl ring can be alkylsulfinyl or alkylsulfonyl, and no substituent on the aryl ring can be alkylmercapto, nor p-halo when R' is dialkylaminoalkyl;

or, when $R_5$ and $R_6$ together is a carbon-carbon bond, R" is hydrogen and R' is a substituted arylalkyl, then E cannot be a substituted or unsubstituted heterocyclic ring selected from the group consisting of pyridinyl, pyrimidinyl, pyrazinyl, imidazolyl, triazinyl, thiophenyl, furanyl, thiazolyl, pyrazolyl and pyrrolyl;

or, when n is 1 or 2, $R_5$ and $R_6$ together form a carbon-carbon bond, Y and Y' are hydrogens or Y and Y' together is oxygen, and E is a substituted phenyl, then X cannot be hydrogen, alkyl, trifluoromethyl, alkylmercapto or NR'R" wherein R' is hydrogen hydroxyl or alkyl, and R" is hydrogen, alkyl or haloalkyl;

or, when $R_5$ and $R_6$ are independently selected from hydrogen or alkyl or $R_5$ and $R_6$ together form a carbon-carbon bond, E is a substituted aryl or heteroaryl, and X is NR'R" wherein R' is hydrogen or hydroxyl and R" is $COR_{11}$, then $R_{11}$ cannot be alkyl, alkoxy or amino;

or, when $R_5$, $R_6$, $R_7$ and $R_8$ are independently selected from hydrogen, alkyl and alkoxy, or $R_5$ and $R_6$ form a carbon-carbon bond, $R_7$ is hydrogen, $R_8$ is hydrogen, alkoxy or alkyl, E is phenyl substituted with at least two hydroxyl groups or at least two alkoxy groups, and Y and Y' together is oxygen, then X cannot be substituted alkoxy or NR'R", where R' is selected from hydrogen, alkyl, alkoxy, alkenyl, alkynyl, hydroxyalkyl, polyhydroxyalkyl, dialkylaminoalkyl, aminoalkyl, arylalkyl, phenyl, indanyl, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, alkoxy, hydroxy, amino, alkylamino, dialkylamino, and sulfonamido; and R" is selected from hydrogen, alkyl, alkylamino, cyanoalkyl, haloalkyl, dialkylaminoalkyl, alkylcarbonylalkylcarbonyloxy, and pyridinyl.

2. The compound, salt, or prodrug of aspect 1, wherein in R', the 7-membered heterocyclic ring is selected from azepanyl, oxazepanyl, thiazepanyl, azepinyl, oxepinyl, thiepanyl, homopiperazinyl, diazepinyl and thiazepinyl, the 6-membered heterocyclic ring is selected from piperidinyl, oxanyl, thianyl, pyridinyl, pyranyl, thiopyranyl, piperazinyl, morpholinyl, thiomorpholinyl, dioxanyl, dithianyl, diazinyl, oxazinyl, thiazinyl, dioxinyl, dithiinyl, trioxanyl, trithianyl, triazinyl and tetrazinyl, and the 5-membered heterocyclic ring is selected from pyrrolidinyl, tetrahydrofuranyl, tetrahydrothiophenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl.

3. The compound, salt, prodrug of aspect 1 or 2, wherein E is a carbocyclic or heterocyclic ring, optionally substituted with one or more substituents selected from hydroxyl, halogen, alkyl, haloalkyl, cyano, cyanoalkyl, nitro, oxo, alkoxy, formyloxy, amino, alkylamino, dialkylamino, aminoalkyl, alkylaminoalkyl, hydroxyalkyl, aldehydo, mercapto, and alkylmercapto, azido, and substituted or unsubstituted groups selected from alkylsulfonyl, alkylsulfinyl, alkylsulfinyloxy, alkylsulfonyloxy, alkylcarbonyloxy, carbamate, carbamido, alkoxycarbonyl, alkylaminocarbonyl, aminocarbonyl, sulfonamido, and alkylenedioxy spanning two substituent positions.

4. The compound of any one of aspects 1-3, prodrug, or a salt thereof, wherein E is selected from cycloheptanyl, cycloheptenyl, cycloheptadienyl, cycloheptatrienyl, cyclohexanyl, cyclohexenyl, cyclohexadienyl, phenyl, cyclopentanyl, cyclopentenyl, cyclopentadienyl, cyclopropanyl, cyclobutanyl, azepanyl, oxazepanyl, thiazepanyl, azepinyl, oxepinyl, thiepanyl, homopiperazinyl, diazepinyl, thiazepinyl, piperidinyl, oxanyl, thianyl, pyridinyl, pyranyl, thiopyranyl, piperazinyl, morpholinyl, thiomorpholinyl, dioxanyl, dithianyl, diazinyl, oxazinyl, thiazinyl, dioxinyl, dithiinyl, trioxanyl, trithianyl, triazinyl, tetrazinyl, pyrrolidinyl, tetrahydrofuranyl, tetrahydrothiophenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl, and tetrazolyl, each of which is substituted or unsubstituted.

5. The compound, prodrug, or salt of aspect 4, wherein E is:

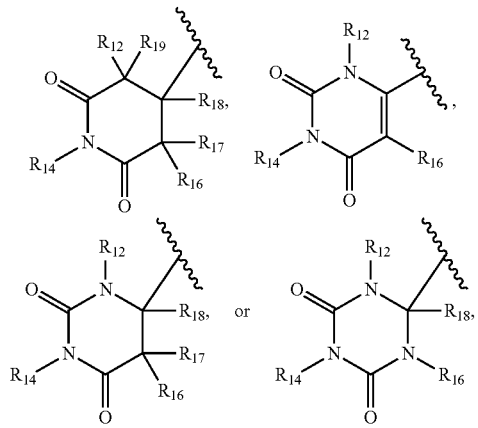

wherein $R_{12}$, $R_{14}$, $R_{16}$, $R_{17}$, $R_{18}$ and $R_{19}$ are independently selected from hydrogen, hydroxyl, halogen, alkyl, trifluoromethyl, alkoxy, amino, alkylamino, dialkylamino, aminoalkyl, alkylaminoalkyl, hydroxyalkyl, aldehydo, mercapto, alkylmercapto, azido, and substituted or unsubstituted groups selected from alkylsulfonyl, alkylsulfinyl, alkylsulfinyloxy, alkylsulfonyloxy, carbamate, carbamido, alkoxycarbonyl, alkylaminocarbonyl, aminocarbonyl, and sulfonamido.

6. A compound of the formula (II):

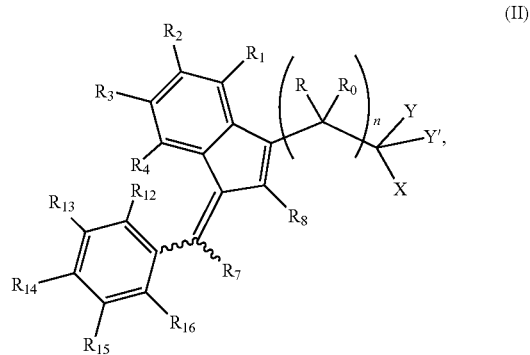

(II)

wherein:

R and R₀ are independently selected from hydrogen, hydroxyl, alkyl, trifluoromethyl, amino, alkoxy and alkylamino, or R and R₀ together is oxygen or sulfur, or R and R₀ together is a single-bonded or a double-bonded nitrogen bonded to one or more of hydrogen, hydroxyl, alkyl, and trifluoromethyl; n is 0, 1 or 2;

Y is hydrogen, alkyl, or trifluoromethyl, and Y' is hydrogen, alkyl, trifluoromethyl, amino, alkylamino, or alkoxy, or Y and Y' together is oxygen or sulfur, or Y and Y' together is a single-bonded or a double-bonded nitrogen bonded to one or more of hydrogen, hydroxyl, alkyl, and trifluoromethyl;

$R_1$, $R_2$, $R_3$ and $R_4$ are independently selected from hydrogen, hydroxyl, halogen, alkyl, trifluoromethyl, alkoxy, and alkylmercapto;

$R_7$ and $R_8$ are independently selected from hydrogen, alkyl, trifluoromethyl and alkoxy;

$R_{12}$, $R_{13}$, $R_{14}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, alkoxycarbonyl, alkylaminocarbonyl, aminocarbonyl, and sulfonamido, or any two of $R_{12}$, $R_{13}$, $R_{14}$, $R_{15}$ and $R_{16}$ form an alkylenedioxy group;

X is selected from hydrogen, alkyl, trifluoromethyl, alkoxy, alkylmercapto, and hydroxyl with the proviso that X is not hydroxyl when Y and Y' together is oxygen, or X is NR'R", where R' is selected from the group consisting of hydrogen, hydroxyl, alkyl, trifluoromethyl, alkoxy, alkenyl, alkynyl, hydroxyalkyl, polyhydroxyalkyl, alkylaminoalkyl, dialkylaminoalkyl, aminoalkyl, arylalkyl, arylalkenyl, arylcycloalkyl, arylcycloalkenyl, aryl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one or two double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, trifluoromethyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; or a pharmaceutically acceptable salt thereof or a prodrug thereof;

with the proviso that when n is 1 or 2, Y and Y' are hydrogens or Y and Y' together is oxygen, and at least one of $R_{12}$, $R_{13}$, $R_{14}$, $R_{15}$ and $R_{16}$ is not hydrogen, then X cannot be hydrogen, alkyl, trifluoromethyl, alkylmercapto or NR'R" wherein R' is hydrogen hydroxyl or alkyl, and R" is hydrogen, alkyl or haloalkyl;

or, when at least one of $R_{12}$, $R_{13}$, $R_{14}$, $R_{15}$ and $R_{16}$ is not hydrogen, and X is NR'R" wherein R' is hydrogen or hydroxyl, and R" is $COR_{11}$, then $R_{11}$ cannot be alkyl, alkoxy or amino;

or when R and R₀ together is oxygen and n is 1, then the heterocycle of the heterocyclyl or heterocyclylalkyl is furanyl or pyrrolyl.

7. A compound of formula (II):

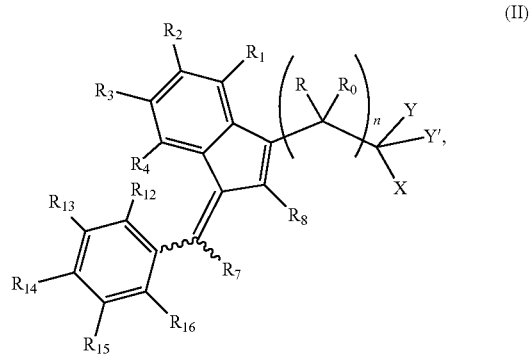

(II)

wherein:

R and R₀ are independently selected from hydrogen, hydroxyl, alkyl, trifluoromethyl, amino, alkoxy and alkylamino, or R and R₀ together is oxygen or sulfur, or R and R₀ together is a single-bonded or a double-bonded nitrogen bonded to one or more of hydrogen, hydroxyl, alkyl, and trifluoromethyl; n is 0, 1 or 2;

Y is hydrogen, alkyl, or trifluoromethyl, and Y' is hydrogen, alkyl, trifluoromethyl, amino, alkylamino, or alkoxy, or Y and Y' together is oxygen or sulfur, or Y and Y' together is a single-bonded or a double-bonded nitrogen bonded to one or more of hydrogen, hydroxyl, alkyl, and trifluoromethyl;

$R_1$, $R_2$, $R_3$ and $R_4$ are independently selected from hydrogen, hydroxyl, halogen, alkyl, trifluoromethyl, alkoxy, and alkylmercapto;

$R_7$ and $R_8$ are independently selected from hydrogen, alkyl, trifluoromethyl and alkoxy;

$R_{12}$, $R_{13}$, $R_{14}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, alkoxycarbonyl, alkylaminocarbonyl, aminocarbonyl, and sulfonamido, or any two of $R_{12}$, $R_{13}$, $R_{14}$, $R_{15}$ and $R_{16}$ form an alkylenedioxy group;

X is selected from hydrogen, alkyl, trifluoromethyl, alkoxy, alkylmercapto, and hydroxyl with the proviso that X is not hydroxyl when Y and Y' together is oxygen, or X is NR'R", where R' is selected from the group consisting of hydrogen, hydroxyl, alkyl, trifluoromethyl, alkoxy, alkenyl, alkynyl, hydroxyalkyl, polyhydroxyalkyl, alkylaminoalkyl, dialkylaminoalkyl, aminoalkyl, arylalkyl, arylalkenyl, arylcycloalkyl, arylcycloalkenyl, aryl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one or two double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, trifluoromethyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; or a pharmaceutically acceptable salt thereof or a prodrug thereof;

with the proviso that when n is 1 or 2, Y and Y' are hydrogens or Y and Y' together is oxygen, and at least one of $R_{12}$, $R_{13}$, $R_{14}$, $R_{15}$ and $R_{16}$ is not hydrogen, then X cannot be hydrogen, alkyl, trifluoromethyl, alkylmercapto or NR'R" wherein R' is hydrogen, hydroxyl or alkyl, and R" is hydrogen, alkyl or haloalkyl;

or, when at least one of $R_{12}$, $R_{13}$, $R_{14}$, $R_{15}$ and $R_{16}$ is not hydrogen, and X is NR'R" wherein R' is hydrogen or hydroxyl, and R" is $COR_{11}$, then $R_{11}$ cannot be alkyl, alkoxy or amino;

or, when the heterocycle of the heterocyclyl and heterocyclylalkyl of R' is selected from 7-membered heterocyclic rings, 6-membered heterocyclic rings, and 5-membered heterocyclic rings, and Y and Y' together is oxygen, then $R_7$ and $R_8$ are independently selected from trifluoromethyl and alkoxy; and with the proviso that when the heterocycle of the heterocyclyl and heterocyclylalkyl of R' is selected from azepanyl, oxazepanyl, thiazepanyl, azepinyl, oxepinyl, thiepanyl, homopiperazinyl, diazepinyl, thiazepinyl, oxanyl, thianyl, pyranyl, thiopyranyl, thiomorpholinyl, dioxanyl, dithianyl, diazinyl, oxazinyl, thiazinyl, dioxinyl, dithiinyl, trioxanyl, trithianyl, triazinyl, tetrazinyl, tetrahydrofuranyl, tetrahydrothiophenyl, pyrrolyl, furanyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl, and tetrazolyl, then $R_7$ and $R_8$ are independently selected from hydrogen, alkyl, trifluoromethyl and alkoxy.

8. The compound, prodrug, or salt of aspect 7, wherein X is NR'R" where R' is selected from alkyl, trifluoromethyl, alkenyl, alkynyl, hydroxyalkyl, alkylaminoalkyl, dialkylaminoalkyl, arylalkyl selected from the group consisting of benzyl, phenylalkyl, indanyl, heterocyclyl, and heterocyclylalkyl, where the heterocycle is selected from furanyl, pyrrolyl, thiophenyl, and imidazolyl, and the cyclic structure of heterocyclyl and heterocyclylalkyl is optionally substituted with one or more of halo, alkyl, trifluoromethyl, hydroxy, alkoxy, amino, alkylamino, dialkylamino, mercapto, alkylmercapto, and carboxamido; R" is selected from hydrogen, alkyl, cyanoalkyl, and dialkylaminoalkyl, or R' and R" together form a 5, 6, or 7-member heterocyclic ring, saturated or unsaturated, substituted or unsubstituted, that contains at least one nitrogen and optionally oxygen.

9. The compound, prodrug, or salt of aspect 8, wherein X is NR'R" where R' is selected from alkylaminoalkyl, dialkylaminoalkyl, arylalkyl, benzyl, heterocyclyl, and heterocyclylalkyl where the heterocycle is selected from furanyl, pyrrolyl, and thiophenyl, and the cyclic structure of heterocyclyl and heterocyclylalkyl is optionally substituted with one or more of halo, alkyl, trifluoromethyl, hydroxy, alkoxy, amino, alkylamino, and dialkylamino; R" is selected from hydrogen, alkyl, and dialkylaminoalkyl, or R' and R" together form a 5, 6, or 7-member heterocyclic ring, saturated or unsaturated, substituted or unsubstituted, that contains at least one nitrogen and optionally oxygen.

10. The compound, prodrug, or salt of aspect 9, wherein X is NR'R" where R' is selected from dialkylaminoalkyl, arylalkyl, benzyl, heterocyclyl, and heterocyclylalkyl where the heterocycle is selected from furanyl and pyrrolyl, and the cyclic structure is optionally substituted with one or more of halo, alkyl, trifluoromethyl, alkoxy, alkylamino and dialkylamino; and R" is selected from hydrogen, alkyl, trifluoromethyl or dialkylaminoalkyl.

11. The compound, prodrug, or salt of aspect 10, wherein X is NR'R" where R' is benzyl, or a heterocyclyl or heterocyclylalkyl selected from 2-furfuryl, 2-pyrrolylmethyl, and (1-methyl-1H-pyrrol-2-yl)methyl; and R" is hydrogen.

12. The compound, prodrug, or salt of aspect 11, wherein X is NR'R" where R' is heterocyclyl or heterocyclylalkyl selected 2-furfuryl, (1H-pyrrol-2-yl)methyl, and (1-methyl-1H-pyrrol-2-yl)methyl; and R" is hydrogen.

13. The compound, prodrug, or salt of any one of aspects 6-12, wherein R and $R_0$ are independently selected from hydrogen and hydroxyl, and $R_1$, $R_2$, $R_3$ and $R_4$ are independently selected from halogen, alkoxy, alkyl and trifluoromethyl; n is 1; $R_{12}$, $R_{13}$, $R_{14}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, and sulfonamido, or any two of $R_{12}$, $R_{13}$, $R_{14}$, $R_{15}$ and $R_{16}$ form an alkylenedioxy group.

14. The compound, prodrug, or salt of aspect 13, wherein $R_1$, $R_2$, $R_3$ and $R_4$ are independently selected from halogen, alkoxy, alkyl and trifluoromethyl; three of $R_{12}$, $R_{13}$, $R_{14}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, and sulfonamido, and one of $R_{12}$, $R_{13}$, $R_{14}$, $R_{15}$ and $R_{16}$ is independently selected from hydroxyl, hydroxyalkyl, amino, alkylamino, dialkylamino, and mercapto.

15. The compound, prodrug, or salt of aspect 14, wherein three of $R_{12}$, $R_{13}$, $R_{14}$, $R_{15}$ and $R_{16}$ are independently selected from halogen, alkyl, trifluoromethyl, alkoxy, amino, alkylamino, aminoalkyl, alkylaminoalkyl, dialkylamino, and mercapto, and one of $R_{12}$, $R_{13}$, $R_{14}$, $R_{15}$ and $R_{16}$ is independently selected from hydroxyl, hydroxyalkyl, aldehydo, amino, alkylamino, dialkylamino, and mercapto; and $R_8$ is methyl.

16. The compound, prodrug, or salt of aspect 6, wherein $R_2$ is selected from halogen, alkoxy and alkylmercapto, $R_1$ and $R_3$ are hydrogen; and three of $R_{12}$, $R_{13}$, $R_{14}$, $R_{15}$ and $R_{16}$ are independently selected from hydrogen, halogen, alkyl, trifluoromethyl, alkoxy, alkylamino, alkylaminoalkyl, and dialkylamino, and one of $R_{12}$, $R_{13}$, $R_{14}$, $R_{15}$ and $R_{16}$ is independently selected from hydroxyl, hydroxyalkyl, amino, alkylamino, dialkylamino, and mercapto.

17. The compound, prodrug, or salt of aspect 16, wherein $R_2$ is selected from halogen and alkoxy, and $R_1$ and $R_3$ are hydrogen.

18. The compound, prodrug, or salt of aspect 17, wherein $R_2$ is selected from fluoro and methoxy.

19. A compound selected from:

(Z)—N-(furan-2-ylmethyl)-2-(1-(4-hydroxy-3,5-dimethylbenzylidene)-5-methoxy-2-methyl-1H-inden-3-yl)acetamide (001), (Z)-2-(5-fluoro-1-(4-formoxy-3,5-dimethoxybenzylidene)-2-methyl-1H-inden-3-yl)-N-(furan-2-ylmethyl)acetamide (002), (Z)—N-(furan-2-ylmethyl)-2-(1-(4-hydroxy-3,5-dimethoxybenzylidene)-5-methoxy-2-methyl-1H-inden-3-yl)acetamide (006), (Z)-2-(5-fluoro-1-(4-hydroxy-3,5-dimethoxybenzylidene)-2-methyl-1H-inden-3-yl)-N-(furan-2-ylmethyl)acetamide (007), (Z)—N-(furan-2-ylmethyl)-2-(1-(4-hydroxy-3,5-dimethoxybenzylidene)-5,6-dimethoxy-2-methyl-1H-inden-3-yl)acetamide (008), (Z)—N-(furan-2-ylmethyl)-2-(1-(4-hydroxy-3-methoxybenzylidene)-5-methoxy-2-methyl-1H-inden-3-yl)acetamide (012), (Z)-2-(1-(3-bromo-4-hydroxy-5-methoxybenzylidene)-5-methoxy-2-methyl-1H-inden-3-yl)-N-(furan-2-ylmethyl)acetamide (013), (Z)-2-(1-(3-chloro-4-hydroxy-5-methoxybenzylidene)-5-methoxy-2-methyl-1H-inden-3-yl)-N-(furan-2-ylmethyl)acetamide (014), (Z)-2-(1-(3-fluoro-4-hydroxy-5-methoxybenzylidene)-5-methoxy-2-methyl-1H-inden-3-yl)-N-(furan-2-ylmethyl)acetamide (016), (Z)-2-(5-fluoro-1-((7-hydroxybenzo[d][1,3]dioxol-5-yl)methylene)-2-methyl-1H-inden-3-yl)-N-(furan-2-ylmethyl)acetamide (017), (Z)—N-((1H-pyrrol-2-yl)methyl)-2-(5-fluoro-1-(4-hydroxy-3,5-dimethoxybenzylidene)-2-methyl-1H-inden-3-yl)acetamide (018), (Z)-2-(5-fluoro-1-(4-hydroxy-3,5-dimethoxybenzylidene)-2-methyl-1H-inden-3-yl)-N-((1-methyl-1H-pyrrol-2-yl)methyl)acetamide (019), (Z)—N-(furan-2-ylmethyl)-2-(1-(3-hydroxy-4-methoxybenzylidene)-5-methoxy-2-methyl-1H-inden-3-yl)acetamide (020), (Z)-2-(5-fluoro-1-(4-(hydroxymethyl)-3,5-dimethoxybenzylidene)-2-methyl-1H-inden-3-yl)-N-(furan-2-ylmethyl)acetamide (021), (Z)—N-((1H-pyrrol-2-yl)methyl)-2-(1-(4-hydroxy-3,5-dimethoxybenzylidene)-5-methoxy-2-methyl-1H-inden-3-yl)acetamide (022), (Z)—N-(2-(dimethylamino)ethyl)-2-(5-fluoro-1-(furan-2-ylmethylene)-2-methyl-1H-inden-3-yl)acetamide (026), (Z)-2-(5-fluoro-1-(4-mesyloxy-3,5-dimethoxybenzylidene)-2-methyl-1H-inden-3-yl)-N-(furan-2-ylmethyl)acetamide (029), (Z)-2-(5-methoxy-2-methyl-1-(3,4,5-trimethoxybenzylidene)-1H-inden-3-yl)-N-(1-methylpyrrolidin-3-yl)acetamide (030), (Z)-2-(5-fluoro-2-methyl-1-(3,4,5-trimethoxybenzylidene)-1H-inden-3-yl)-N-(1-methylpyrrolidin-3-yl)acetamide (031), (Z)-2-(5-methoxy-2-methyl-1-(3,4,5-trimethoxybenzylidene)-1H-inden-3-yl)-N-(1-methylpiperidin-3-yl)acetamide (032), and (Z)-2-(5-fluoro-2-methyl-1-(3,4,5-trimethoxybenzylidene)-1H-inden-3-yl)-N-(1-methylpiperidin-3-yl)acetamide (033), (Z)-2-(5-methoxy-2-methyl-1-(3,4,5-trimethoxybenzylidene)-1H-inden-3-yl)-N-(5-methylpyridin-3-yl)acetamide (063), (Z)-2-(1-(4-aminocarbonyl-3,5-dimethoxybenzylidene)-5-fluoro-2-methyl-1H-inden-3-yl)-N-((1-methyl-1H-pyrrol-2-yl)methyl)acetamide (065), (Z)-methyl 2,6-dimethoxy-4-((5-methoxy-2-methyl-3-(2-((1-methylpyrrolidin-3-yl)amino)-2-oxoethyl)-1H-inden-1-ylidene)methyl)benzoate (066), (Z)-2-(1-(3,5-dimethoxy-4-sulfamoylbenzylidene)-5-methoxy-2-methyl-1H-inden-3-yl)-N-(1-methylpyrrolidin-3-yl)acetamide (067), (Z)-2-(1-(3,5-dimethoxy-4-ureidobenzylidene)-5-fluoro-2-methyl-1H-inden-3-yl)-N-((4-methylpyridin-3-yl)methyl)acetamide (069), (Z)—N-(furan-2-ylmethyl)-2-(1-(4-ethoxycarbonyl-3,5-dimethoxybenzylidene)-5-methoxy-2-methyl-1H-inden-3-yl)acetamide (095), (Z)-2-(5-methoxy-2-methyl-1-(3,4,5-trimethoxybenzylidene)-1H-inden-3-yl)-N-((1-methyl-1H-pyrrol-2-yl)methyl)acetamide (096), (Z)—N-((1H-pyrrol-2-yl)methyl)-2-(5-methoxy-2-methyl-1-(3,4,5-trimethoxybenzylidene)-1H-inden-3-yl)acetamide (097), (Z)-2-(1-(3,5-dimethoxy-4-sulfamoylbenzylidene)-5-fluoro-2-methyl-1H-inden-3-yl)-N-((6-methylpyridin-2-yl)methyl)acetamide (098), (Z)-4-((5-fluoro-3-(2-((furan-2-ylmethyl)amino)-2-oxoethyl)-2-methyl-1H-inden-1-ylidene)methyl)-2,6-dimethoxyphenyl (2-(dimethylamino)ethyl)carbamate (099), (Z)-2-(5-fluoro-1-(4-mercapto-3,5-dimethoxybenzylidene)-2-methyl-1H-inden-3-yl)-N-((1-methyl-1H-pyrrol-2-yl)methyl)acetamide (100), or the corresponding Z- or E-isomer thereof, prodrug, or salt thereof.

20. The compound, Z- or E-isomer prodrug, or salt of aspect 19, wherein the compound is selected from:

(Z)-2-(5-fluoro-1-(4-formoxy-3,5-dimethoxybenzylidene)-2-methyl-1H-inden-3-yl)-N-(furan-2-ylmethyl)acetamide (002), (Z)—N-(furan-2-ylmethyl)-2-(1-(4-hydroxy-3,5-dimethoxybenzylidene)-5-methoxy-2-methyl-1H-inden-3-yl)acetamide (006), (Z)-2-(5-fluoro-1-(4-hydroxy-3,5-dimethoxybenzylidene)-2-methyl-1H-inden-3-yl)-N-(furan-2-ylmethyl)acetamide (007), (Z)—N-((1H-pyrrol-2-yl)methyl)-2-(5-fluoro-1-(4-hydroxy-3,5-dimethoxybenzylidene)-2-methyl-1H-inden-3-yl)acetamide (018), (Z)-2-(5-fluoro-1-(4-hydroxy-3,5-dimethoxybenzylidene)-2-methyl-1H-inden-3-yl)-N-((1-methyl-1H-pyrrol-2-yl)methyl)acetamide (019), (Z)—N-((1H-pyrrol-2-yl)methyl)-2-(1-(4-hydroxy-3,5-dimethoxybenzylidene)-5-methoxy-2-methyl-1H-inden-3-yl)acetamide (022), (Z)-2-(5-fluoro-1-(4-mesyloxy-3,5-dimethoxybenzylidene)-2-methyl-1H-inden-3-yl)-N-(furan-2-ylmethyl)acetamide (029), and (Z)-2-(5-methoxy-2-methyl-1-(3,4,5-trimethoxybenzylidene)-1H-inden-3-yl)-N-(1-methylpyrrolidin-3-yl)acetamide (030).

21. A pharmaceutical composition comprising a compound of any one of aspects 1-20, a pharmaceutically acceptable salt or prodrug thereof, and a pharmaceutically acceptable carrier.

22. The pharmaceutical composition of aspect 21, further including at least one additional therapeutic agent other than a compound of formulas I and II, a pharmaceutically acceptable salt or prodrug thereof.

23. A method of therapeutically or prophylactically treating a human or nonhuman mammalian patient with cancer comprising administering to said patient an anticancer effective amount of at least one compound of any one of aspects 1-20, a pharmaceutically acceptable salt or prodrug thereof.

24. The method of aspect 23, wherein the cancer is selected from pancreatic cancer, lung cancer, colorectal cancer, melanoma, ovarian cancer, renal cancer, prostate cancer, head and neck cancer, endocrine cancer, uterine cancer, breast cancer, sarcoma cancer, gastric cancer, hepatic cancer, esophageal cancer, central nervous system cancer, brain cancer, hepatic cancer, germline cancer, lymphoma, and leukemia.

25. The method of aspect 24, wherein the cancer is selected from pancreatic cancer, colorectal cancer, and lung cancer.

26. The method of any one of aspects 23-25, wherein the cancer is drug-resistant or radiation-resistant.

27. A method of therapeutically or prophylactically treating a human or nonhuman mammalian patient with a disease or condition treatable by the inhibition of one or more neoplastic or cancerous process, which method comprises administering to a patient in need thereof a therapeutically or prophylactically effective amount of at least one neoplastic or cancerous inhibitory compound of any one of aspects 1-20 or a compound selected from (001), (002), (006)-(008), (012)-(014), (016)-(022), (026), (029)-(033), (063), (065)-(067), (069), and (095)-(100) or a pharmaceutically acceptable salt or prodrug thereof, either alone or in combination with one other therapeutic agent other than a compound of any one of aspects 1-20 or a compound selected from (001), (002), (006)-(008), (012)-(014), (016)-(022), (026), (029)-(033), (063), (065)-(067), (069), and (095)-(100) or a pharmaceutically acceptable salt or prodrug thereof.

28. The method of aspect 27, wherein the neoplastic or cancerous process is selected from growth, proliferation, survival, metastasis, drug resistance and radiation resistance of a tumor cell.

The present invention further provides the following preferred aspects:

1. A compound of formula I:

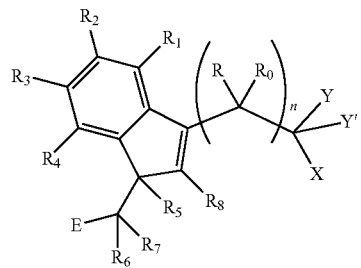

I wherein:
$R$ and $R_0$ are independently selected from hydrogen, hydroxyl, alkyl, trifluoromethyl, amino, alkoxy and alkylamino, or $R$ and $R_0$ together is double-bonded oxygen or double-bonded sulfur, or $R$ and $R_0$ together is a double-bonded nitrogen bonded to hydrogen, hydroxyl, alkyl, or trifluoromethyl;

n is 1 or 2;

$R_1$, $R_2$, $R_3$, and $R_4$ are independently selected from hydrogen, hydroxyl, halogen, alkyl, trifluoromethyl, alkoxy, and alkylmercapto;

$R_5$, $R_6$, $R_7$, $R_8$ are independently selected from hydrogen, alkyl, trifluoromethyl and alkoxy; or $R_5$ and $R_6$ together form a carbon-carbon bond;

Y is hydrogen, alkyl, or trifluoromethyl, and Y' is hydrogen, alkyl, trifluoromethyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or trifluoromethyl;

X is selected from hydrogen, alkyl, trifluoromethyl, alkoxy, alkylmercapto, and hydroxyl with the proviso that X is not hydroxyl when Y and Y' together is double-bonded oxygen in a compound of formula I wherein $R_5$ and $R_6$ together is a carbon-carbon bond, or X is NR'R", where R' is selected from the group consisting of hydrogen, hydroxyl, alkyl, trifluoromethyl, alkoxy, alkenyl, alkynyl, hydroxyalkyl, polyhydroxyalkyl, alkylaminoalkyl, dialkylaminoalkyl, aminoalkyl, aryl, arylalkenyl, arylcycloalkyl, arylcycloalkenyl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one or two double bonds, 5-membered carbocyclic rings containing no double bond, or one or two double bonds, 4-membered carbocyclic rings containing no double bond or one double bond, heterocyclyl, and heterocyclylalkyl, where the heterocycle of the heterocyclyl and heterocyclylalkyl is selected from azepanyl, oxazepanyl, thiazepanyl, azepinyl, oxepinyl, thiepanyl, homopiperazinyl, diazepinyl, thiazepinyl, piperidinyl, oxanyl, thianyl, pyridinyl, pyranyl, thiopyranyl, piperazinyl, morpholinyl, thiomorpholinyl, dioxanyl, dithianyl, diazinyl, oxazinyl, thiazinyl, dioxinyl, dithiinyl, trioxanyl, trithianyl, triazinyl, tetrazinyl, pyrrolidinyl, tetrahydrofuranyl, tetrahydrothiophenyl, pyrrolyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl, and the aryl of the aryl, arylalkylenyl, arylcycloalkyl, or arylcycloalkenyl structure or the carbocyclic or heterocyclic structure is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, trifluoromethyl, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; and E is a substituted or unsubstituted phenyl or substituted or unsubstituted furanyl ring;

or a pharmaceutically acceptable salt thereof or a prodrug thereof;

with the proviso that no substituent on the phenyl ring of E can be alkylsulfinyl or alkylsulfonyl, and no substituent on the phenyl ring of E can be alkylmercapto, nor p-halo when R' is dialkylaminoalkyl;

or, when $R_5$ and $R_6$ together form a carbon-carbon bond, Y and Y' are hydrogens or Y and Y' together is double-bonded oxygen, then X cannot be hydrogen, alkyl, trifluoromethyl, alkylmercapto or NR'R" wherein R' is hydrogen, hydroxyl or alkyl, and R" is hydrogen, alkyl or haloalkyl;

or, when $R_5$ and $R_6$ are independently selected from hydrogen or alkyl or $R_5$ and $R_6$ together form a carbon-carbon bond, E is a substituted or unsubstituted phenyl or substituted or unsubstituted furanyl, and X is NR'R" wherein R' is hydrogen or hydroxyl and R" is $COR_{11}$, then $R_{11}$ cannot be alkyl, alkoxy or amino;

or, when $R_5$, $R_6$, $R_7$ and $R_8$ are independently selected from hydrogen, alkyl and alkoxy, or $R_5$ and $R_6$ form a carbon-carbon bond, $R_7$ is hydrogen, $R_8$ is hydrogen, alkoxy or alkyl, E is phenyl substituted with at least two hydroxyl groups or at least two alkoxy groups, and Y and Y' together is double-bonded oxygen, then X cannot be alkoxy or NR'R", where R' is selected from hydrogen, alkyl, alkoxy, alkenyl, alkynyl, hydroxyalkyl, polyhydroxyalkyl, dialkylaminoalkyl, aminoalkyl, phenyl, indanyl, heterocyclyl, and heterocyclylalkyl, where the heterocycle of the heterocyclyl and the heterocyclylalkyl is selected from pyridinyl, piperidinyl, piperazinyl, pyrrolidinyl, and N-morpholino, and wherein any of the cyclic structures of the R' is unsubstituted or substituted with one or more of halo, trifluoromethyl, alkoxy, hydroxy, amino, alkylamino, dialkylamino, and sulfonamido; and R" is selected from hydrogen, alkyl, cyanoalkyl, haloalkyl, dialkylaminoalkyl, alkylcarbonylalkylcarbonyloxy, and pyridyl;

or, when R and $R_0$ are hydrogens, at least one of $R_1$, $R_2$, $R_3$, and $R_4$ is halogen, Y and Y' together is double-bonded oxygen, and X is NR'R", wherein R' is furanylalkyl and R" is selected from hydrogen, alkyl, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, trifluoromethyl, alkoxy, alkylmercapto, and aryl, then E cannot be 3,4,5-trimethoxyphenyl.

2. The compound, salt, prodrug of preferred aspect 1, wherein E is a phenyl ring, substituted with one or more substituents selected from hydroxyl, halogen, alkyl, haloalkyl, cyano, cyanoalkyl, nitro, oxo, alkoxy, formyloxy, amino, alkylamino, dialkylamino, aminoalkyl, alkylaminoalkyl, hydroxyalkyl, aldehydo, mercapto, alkylmercapto, azido, and substituted or unsubstituted groups selected from alkylsulfinyloxy, alkylsulfonyloxy, alkylcarbonyloxy, carbamate, carbamido, alkoxycarbonyl, alkylaminocarbonyl, aminocarbonyl, sulfonamido, and alkylenedioxy spanning two substituent positions.

3. A compound of the formula (II):

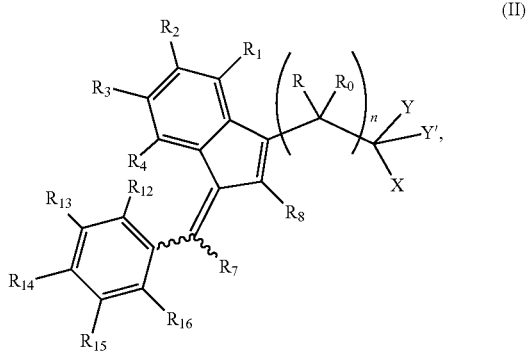

wherein:

R and $R_0$ are independently selected from hydrogen, hydroxyl, alkyl, trifluoromethyl, amino, alkoxy and alkylamino, or R and $R_0$ together is double-bonded oxygen or double-bonded sulfur, or R and $R_0$ together is a double-bonded nitrogen bonded to hydrogen, hydroxyl, alkyl, or trifluoromethyl;

n is 0, 1 or 2;

Y is hydrogen, alkyl, or trifluoromethyl, and Y' is hydrogen, alkyl, trifluoromethyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or trifluoromethyl;

$R_1$, $R_2$, $R_3$ and $R_4$ are independently selected from hydrogen, hydroxyl, halogen, alkyl, trifluoromethyl, alkoxy, and alkylmercapto;

$R_7$ and $R_8$ are independently selected from hydrogen, alkyl, trifluoromethyl and alkoxy;

$R_{14}$ is independently selected from hydrogen, halogen, alkyl, trifluoromethyl, hydroxyl, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, alkoxycarbonyl, alkylaminocarbonyl, aminocarbonyl, and sulfonamido, or any two of $R_{12}$, $R_{13}$, $R_{14}$, $R_{15}$ and $R_{16}$ form an alkylenedioxy group;

$R_{12}$, $R_{13}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, alkoxycarbonyl, alkylaminocarbonyl, aminocarbonyl, and sulfonamido, or any two of $R_{12}$, $R_{13}$, $R_{14}$, $R_{15}$ and $R_{16}$ form an alkylenedioxy group;

X is NR'R", where R' is furanyl or furanylalkyl wherein the furanyl of the furanyl or furanylalkyl_is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, trifluoromethyl, alkylmercapto, and aryl;

or a pharmaceutically acceptable salt thereof or a prodrug thereof with the proviso that when n is 1 or 2, Y and Y' are hydrogens or Y and Y' together is double-bonded oxygen, and at least one of $R_{12}$, $R_{13}$, $R_{14}$, $R_{15}$ and $R_{16}$ is not hydrogen, then X cannot be hydrogen, alkyl, trifluoromethyl, alkylmercapto or NR'R" wherein R' is hydrogen, hydroxyl or alkyl, and X is NR'R" wherein R' is is hydrogen, alkyl or haloalkyl;

or, when X is NR'R" wherein R' is hydrogen or hydroxyl, and R" is $COR_{11}$, then $R_{11}$ cannot be alkyl, alkoxy or amino;

or, when X is NR'R" wherein R' is phenylalkyl and R" is hydrogen, then two of $R_{12}$ to $R_{16}$ cannot be identically selected from hydroxyl or alkoxy;

or, when R and $R_0$ together is double-bonded oxygen and n is 1, then the heterocycle of the heterocyclyl or heterocyclylalkyl is furanyl or pyrrolyl;

or, when R and $R_0$ are hydrogens, at least one of $R_1$, $R_2$, $R_3$, and $R_4$ is halogen, Y and Y' together is double-bonded oxygen, and X is NR'R" wherein R' is furanylalkyl and R" is selected from hydrogen, alkyl, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, trifluoromethyl, alkoxy, alkylmercapto, and aryl, then $R_{13}$, $R_{14}$, and $R_{15}$ cannot each be methoxy.

4. The compound of preferred aspect 1, which is of the formula (II):

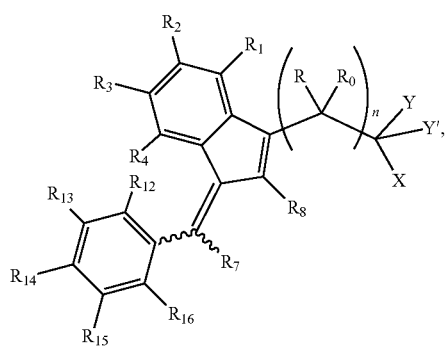

(II)

wherein:

R and $R_0$ are independently selected from hydrogen, hydroxyl, alkyl, trifluoromethyl, amino, alkoxy and alkylamino, or R and $R_0$ together is double-bonded oxygen or double-bonded sulfur, or R and $R_0$ together is a double-bonded nitrogen bonded to hydrogen, hydroxyl, alkyl, or trifluoromethyl;

n is 1 or 2;

Y is hydrogen, alkyl, or trifluoromethyl, and Y' is hydrogen, alkyl, trifluoromethyl, amino, alkylamino, or alkoxy, or Y and Y' together is double-bonded oxygen or double-bonded sulfur, or Y and Y' together is a double-bonded nitrogen bonded to hydrogen, hydroxyl, alkyl, or trifluoromethyl;

$R_1$, $R_2$, $R_3$ and $R_4$ are independently selected from hydrogen, hydroxyl, halogen, alkyl, trifluoromethyl, alkoxy, and alkylmercapto;

$R_7$ and $R_8$ are independently selected from hydrogen, alkyl, trifluoromethyl and alkoxy;

$R_{12}$, $R_{13}$, $R_{14}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, alkoxycarbonyl, alkylaminocarbonyl, aminocarbonyl, and sulfonamido, or any two of $R_{12}$, $R_{13}$, $R_{14}$, $R_{15}$ and $R_{16}$ form an alkylenedioxy group;

X is selected from hydrogen, alkyl, trifluoromethyl, alkoxy, alkylmercapto, and hydroxyl with the proviso that X is not hydroxyl when Y and Y' together is double-bonded oxygen, or X is NR'R", where R' is selected from the group consisting of hydrogen, hydroxyl, alkyl, trifluoromethyl, alkoxy, alkenyl, alkynyl, hydroxyalkyl, polyhydroxyalkyl, alkylaminoalkyl, dialkylaminoalkyl, aminoalkyl, arylalkenyl, arylcycloalkyl, arylcycloalkenyl, aryl, heterocyclyl, and heterocyclylalkyl, where the heterocycle of the heterocyclyl and heterocyclylalkyl is selected from azepanyl, oxazepanyl, thiazepanyl, azepinyl, oxepinyl, thiepanyl, homopiperazinyl, diazepinyl, thiazepinyl, oxanyl, thianyl, pyranyl, thiopyranyl, thiomorpholinyl, dioxanyl, dithianyl, diazinyl, oxazinyl, thiazinyl, dioxinyl, dithiinyl, trioxanyl, trithianyl, triazinyl, tetrazinyl, tetrahydrofuranyl, tetrahydrothiophenyl, pyrrolyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl, and tetrazolyl, and the aryl of the aryl, arylalkenyl, arylcycloalkyl, or arylcycloalkenyl or the heterocycle of the heterocyclyl or heterocyclylalkyl is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, trifluoromethyl, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido; or a pharmaceutically acceptable salt thereof or a prodrug thereof;

with the proviso that when Y and Y' are hydrogens or Y and Y' together is double-bonded oxygen, then X cannot be hydrogen, alkyl, trifluoromethyl, alkylmercapto or NR'R" wherein R' is hydrogen, hydroxyl or alkyl, and R" is hydrogen, alkyl or haloalkyl;

or, when the heterocycle of the heterocyclyl and heterocyclylalkyl of R' is selected from heterocyclyl and heterocyclylalkyl, and Y and Y' together is double-bonded oxygen, then $R_7$ and $R_8$ are independently selected from trifluoromethyl and alkoxy.

5. The compound, prodrug, or salt of preferred aspect 4, wherein X is NR'R" where R' is selected from alkyl, trifluoromethyl, alkenyl, alkynyl, hydroxyalkyl, alkylaminoalkyl, dialkylaminoalkyl, heterocyclyl, and heterocyclylalkyl, where the heterocycle is selected from pyrrolyl, thiophenyl, and imidazolyl, and the cyclic structure of heterocyclyl and heterocyclylalkyl is optionally substituted with one or more of halo, alkyl, trifluoromethyl, hydroxyl, alkoxy, amino, alkylamino, dialkylamino, mercapto, alkylmercapto, and carboxamido; R" is selected from hydrogen, cyanoalkyl, and dialkylaminoalkyl, or R' and R" together form a 5-, 6- or 7-membered, saturated or unsaturated, heterocyclic ring containing at least one nitrogen, and optionally oxygen, and the heterocyclic ring is optionally be substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido.

6. The compound, prodrug, or salt of preferred aspect 5, wherein X is NR'R" where R' is selected from alkylaminoalkyl, dialkylaminoalkyl, heterocyclyl, and heterocyclylalkyl where the heterocycle is selected from pyrrolyl, and thiophenyl, and the cyclic structure of heterocyclyl and heterocyclylalkyl is optionally substituted with one or more of halo, alkyl, trifluoromethyl, hydroxyl, alkoxy, amino, alkylamino, and dialkylamino; R" is selected from hydrogen, and dialkylaminoalkyl, or R' and R" together form a 5-, 6- or 7-membered, saturated or unsaturated, heterocyclic ring containing at least one nitrogen, and optionally oxygen, and the heterocyclic ring is optionally be substituted with one or more of halo, alkyl, trifluoromethyl, hydroxyl, alkoxy, amino, alkylamino, dialkylamino, mercapto, alkylmercapto, carboxamido, aldehydo, cyano, oxo, alkylcarbonyloxy, and sulfonamido.

7. The compound, prodrug, or salt of preferred aspect 6, wherein X is NR'R" where R' is selected from dialkylaminoalkyl, heterocyclyl, and heterocyclylalkyl where the heterocycle is pyrrolyl, which is optionally substituted with one or more of halo, alkyl, trifluoromethyl, alkoxy, alkylamino and dialkylamino; and R" is hydrogen or dialkylaminoalkyl.

8. The compound, prodrug, or salt of preferred aspect 7, wherein X is NR'R" where R' is a heterocyclylalkyl selected from 2-pyrrolylmethyl and (1-methyl-1H-pyrrol-2-yl) methyl; and R" is hydrogen.

9. The compound, prodrug, or salt of preferred aspect 8, wherein X is NR'R" where R' is a heterocyclylalkyl selected from (1H-pyrrol-2y1)methyl and (1-methyl-1H-pyrrol-2-yl) methyl; and R" is hydrogen.

10. The compound, prodrug, or salt of preferred aspect 3, wherein R and $R_0$ are independently selected from hydrogen and hydroxyl, and $R_1$, $R_2$, $R_3$ and $R_4$ are independently selected from hydrogen, halogen, alkoxy, alkyl and trifluoromethyl; n is 1; $R_{12}$, $R_{13}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, and sulfonamido, or any two of $R_{12}$, $R_{13}$, $R_{14}$, $R_{15}$ and $R_{16}$ form an alkylenedioxy group.

11. The compound, prodrug, or salt of preferred aspect 10, wherein $R_1$, $R_2$, $R_3$ and $R_4$ are independently selected from halogen, alkoxy, alkyl and trifluoromethyl; three of $R_{12}$, $R_{13}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, and sulfonamido, and $R_{14}$ is selected from hydroxyl, hydroxyalkyl, amino, alkylamino, dialkylamino, and mercapto.

12. The compound, prodrug, or salt of preferred aspect 11, wherein three of $R_{12}$, $R_{13}$, $R_{15}$ and $R_{16}$ are independently selected from halogen, alkyl, trifluoromethyl, alkoxy, amino, alkylamino, aminoalkyl, alkylaminoalkyl, dialkylamino, and mercapto, and $R_{14}$ is selected from hydroxyl, hydroxyalkyl, aldehydo, amino, alkylamino, dialkylamino, and mercapto; and $R_8$ is methyl.

13. The compound, prodrug, or salt of preferred aspect 3, wherein $R_2$ is selected from halogen, alkoxy and alkylmercapto, $R_1$ and $R_3$ are hydrogen; and three of $R_{12}$, $R_{13}$, $R_{15}$ and $R_{16}$ are independently selected from hydrogen, halogen, alkyl, trifluoromethyl, alkoxy, alkylamino, alkylaminoalkyl, and dialkylamino, and $R_{14}$ is selected from hydroxyl, hydroxyalkyl, amino, alkylamino, dialkylamino, and mercapto.

14. The compound, prodrug, or salt of preferred aspect 13, wherein $R_2$ is selected from halogen and alkoxy, and $R_1$ and $R_3$ are hydrogen.

15. The compound, prodrug, or salt of preferred aspect 14, wherein $R_2$ is selected from fluoro and methoxy.

16. The compound, the corresponding E-isomer, prodrug, or salt of preferred aspect 1, wherein the compound is selected from:

(Z)—N-((1H-pyrrol-2-yl)methyl)-2-(5-fluoro-1-(4-hydroxy-3,5-dimethoxybenzylidene)-2-methyl-1H-inden-3-yl)acetamide (018), (Z)-2-(5-fluoro-1-(4-hydroxy-3,5-dimethoxybenzylidene)-2-methyl-1H-inden-3-yl)-N-((1-methyl-1H-pyrrol-2-yl)methyl)acetamide (019), (Z)—N-((1H-pyrrol-2-yl)methyl-2-(1-(4-hydroxy-3,5-dimethoxybenzylidene)-5-methoxy-2-methyl-1H-inden-3-yl)acetamide (022), (Z)-2-(5-methoxy-2-methyl-1-(3,4,5-trimethoxybenzylidene)-1H-inden-3-yl)-N-(1-methylpyrrolidin-3-yl)acetamide (030), (Z)-2-(5-fluoro-2-methyl-1-(3,4,5-trimethoxybenzylidene)-1H-inden-3-yl)-N-(1-methylpyrrolidin-3-yl)acetamide (031), (Z)-2-(5-methoxy-2-methyl-1-(3,4,5-trimethoxybenzylidene)-1H-inden-3-yl)-N-(1-methylpiperidin-3-yl)acetamide (032), (Z)-2-(5-fluoro-2-methyl-1-(3,4,5-trimethoxybenzylidene)-1H-inden-3-yl)-N-(1-methylpiperidin-3-yl)acetamide (033), (Z)-2-(5-methoxy-2-methyl-1-(3,4,5-trimethoxybenzylidene)-1H-inden-3-yl)-N-(5-methylpyridin-3-yl)acetamide (063), (Z)-2-(1-(4-aminocarbonyl-3,5-dimethoxybenzylidene)-5-fluoro-2-methyl-1H-inden-3-yl)-N-((1-methyl-1H-pyrrol-2-yl)methyl)acetamide (065), (Z)-methyl 2,6-dimethoxy-4-((5-methoxy-2-methyl-3-(2-((1-methylpyrrolidin-3-yl)amino)-2-oxoethyl)-1H-inden-1-ylidene)methyl)benzoate (066), (Z)-2-(1-(3,5-dimethoxy-4-sulfamoylbenzylidene)-5-methoxy-2-methyl-1H-inden-3-yl)-N-(1-methylpyrrolidin-3-yl)acetamide (067), (Z)-2-(1-(3,5-dimethoxy-4-ureidobenzylidene)-5-fluoro-2-methyl-1H-inden-3-yl)-N-((4-methylpyridin-3-yl)methyl)acetamide (069), (Z)-2-(5-methoxy-2-methyl-1-(3,4,5-trimethoxybenzylidene)-1H-inden-3-yl)-N-((1-methyl-1H-pyrrol-2-yl)methyl)acetamide (096), (Z)—N-((1H-pyrrol-2-yl)methyl)-2-(5-methoxy-2-methyl-1-(3,4,5-trimethoxybenzylidene)-1H-inden-3-yl)acetamide (097), (Z)-2-(1-(3,5-dimethoxy-4-sulfamoylbenzylidene)-5-fluoro-2-methyl-1H-inden-3-yl)-N-((6-methylpyridin-2-yl)methyl)acetamide (098), (Z)-4-((5-fluoro-3-(2-((furan-2-ylmethyl)amino)-2-oxoethyl)-2-methyl-1H-inden-1-ylidene)methyl)-2,6-dimethoxyphenyl (2-(dimethylamino)ethyl)carbamate (099), and (Z)-2-(5-fluoro-1-(4-mercapto-3,5-dimethoxybenzylidene)-2-methyl-1H-inden-3-yl)-N-((1-methyl-1H-pyrrol-2-yl)methyl)acetamide (100).

17. A pharmaceutical composition comprising a compound of preferred aspect 1, a pharmaceutically acceptable salt or prodrug thereof, and a pharmaceutically acceptable carrier.

18. The pharmaceutical composition of preferred aspect 17, further including at least one therapeutic agent which is not a compound of formula I or II, a pharmaceutically acceptable salt or prodrug thereof.

19. A method of therapeutically or prophylactically treating a human or nonhuman mammalian patient with cancer comprising administering to said patient an anticancer effective amount of at least one compound of preferred aspect 1, a pharmaceutically acceptable salt or prodrug thereof.

20. The method of preferred aspect 19, wherein the cancer is selected from pancreatic cancer, lung cancer, colorectal cancer, melanoma, ovarian cancer, renal cancer, prostate cancer, head and neck cancer, endocrine cancer, uterine cancer, breast cancer, sarcoma cancer, gastric cancer, hepatic cancer, esophageal cancer, central nervous system cancer, brain cancer, hepatic cancer, germline cancer, lymphoma, and leukemia.

21. A method of therapeutically or prophylactically treating a human or nonhuman mammalian patient with a disease or condition treatable by the inhibition of one or more neoplastic or cancerous process, which method comprises administering to a patient in need thereof a therapeutically or prophylactically effective amount of at least one neoplastic or cancerous inhibitory compound of preferred aspect 1, or a compound selected from (001), (002), (006)-(008), (012)-(014), (016)-(022), (026), (029)-(033), (063), (065)-(067), (069), and (095)-(100) or a pharmaceutically acceptable salt or prodrug thereof, either alone or in combination with one other therapeutic agent other than a compound of preferred aspect 1 or a compound selected from (001), (002), (006)-(008), (012)-(014), (016)-(022), (026), (029)-(033), (063), (065)-(067), (069), and (095)-(100) or a pharmaceutically acceptable salt or prodrug thereof.

22. The compound, prodrug, or salt of preferred aspect 3, wherein R and $R_0$ are independently selected from hydrogen and hydroxyl, and $R_1$, $R_2$, $R_3$ and $R_4$ are independently selected from halogen, alkoxy, alkyl and trifluoromethyl; n is 1; $R_{12}$, $R_{13}$, $R_{14}$, $R_{15}$ and $R_{16}$ are independently selected from hydrogen, halogen, alkyl, trifluoromethyl, hydroxyl, alkoxy, formyloxy, alkylcarbonyloxy, hydroxyalkyl, aldehydo, amino, alkylamino, aminoalkyl, alkylaminoalkyl, dialkylamino, mercapto, azido, and substituted or unsubstituted groups selected from alkylsulfinyloxy, alkylsulfonyloxy, carbamate, carbamido, and sulfonamido, or any two of $R_{12}$, $R_{13}$, $R_{14}$, $R_{15}$ and $R_{16}$ form an alkylenedioxy group.

23. A pharmaceutical composition comprising a compound of preferred aspect 16, a pharmaceutically acceptable salt or prodrug thereof, and a pharmaceutically acceptable carrier.

24. A pharmaceutical composition comprising a compound of preferred aspect 3, a pharmaceutically acceptable salt or prodrug thereof, and a pharmaceutically acceptable carrier.

25. The pharmaceutical composition of preferred aspect 24, further including at least one therapeutic agent which is not a compound of formula I or II, a pharmaceutically acceptable salt or prodrug thereof, and a pharmaceutically acceptable carrier.

26. A method of therapeutically or prophylactically treating a human or nonhuman mammalian patient with cancer comprising administering to said patient an anticancer effective amount of at least one compound of preferred aspect 3, a pharmaceutically acceptable salt or prodrug thereof.

27. A method of therapeutically or prophylactically treating a human or nonhuman mammalian patient with a disease or condition treatable by the inhibition of one or more neoplastic or cancerous process, which method comprises administering to a patient in need thereof a therapeutically or prophylactically effective amount of at least one neoplastic or cancerous inhibitory compound of preferred aspect 3 or a pharmaceutically acceptable salt or prodrug thereof, either alone or in combination with at least one therapeutic agent which is not a compound of formula I or II or a pharmaceutically acceptable salt or prodrug thereof.

28. A method of therapeutically or prophylactically treating a human or nonhuman mammalian patient with a disease or condition treatable by the inhibition of one or more neoplastic or cancerous process, which method comprises administering to a patient in need thereof a therapeutically or prophylactically effective amount of at least one neoplastic or cancerous inhibitory compound of preferred aspect 1 or a pharmaceutically acceptable salt or prodrug thereof, either alone or in combination with at least one therapeutic agent which is not a compound of formula I or II, or a pharmaceutically acceptable salt or prodrug thereof.

29. The compound, the corresponding E-isomer, prodrug, or salt of preferred aspect 3, wherein the compound is selected from:

(Z)—N-(furan-2-ylmethyl)-2-(1-(4-hydroxy-3,5-dimethylbenzylidene)-5-methoxy-2-methyl-1H-inden-3-yl)acetamide (001), (Z)-2-(5-fluoro-1-(4-formoxy-3,5-dimethoxybenzylidene)-2-methyl-1H-inden-3-yl)-N-(furan-2-ylmethyl)acetamide (002), (Z)—N-(furan-2-ylmethyl)-2-(1-(4-hydroxy-3,5-dimethoxybenzylidene)-5-methoxy-2-methyl-1H-inden-3-yl)acetamide (006), (Z)-2-(5-fluoro-1-(4-hydroxy-3,5-dimethoxybenzylidene)-2-methyl-1H-inden-3-yl)-N-(furan-2-ylmethyl)acetamide (007), (Z)—N-(furan-2-ylmethyl)-2-(1-(4-hydroxy-3,5-dimethoxybenzylidene)-5,6-dimethoxy-2-methyl-1H-inden-3-yl)acetamide (008), (Z)—N-(furan-2-ylmethyl)-2-(1-(4-hydroxy-3-methoxybenzylidene)-5-methoxy-2-methyl-1H-inden-3-yl)acetamide (012), (Z)-2-(1-(3-bromo-4-hydroxy-5-methoxybenzylidene)-5-methoxy-2-methyl-1H-inden-3-yl)-N-(furan-2-ylmethyl)acetamide (013), (Z)-2-(1-(3-chloro-4-hydroxy-5-methoxybenzylidene)-5-methoxy-2-methyl-1H-inden-3-yl)-N-(furan-2-ylmethyl)acetamide (014), (Z)-2-(1-(3-fluoro-4-hydroxy-5-methoxybenzylidene)-5-methoxy-2-methyl-1H-inden-3-yl)-N-(furan-2-ylmethyl)acetamide (016), (Z)-2-(5-fluoro-1-((7-hydroxybenzo[d][1,3]dioxol-5-yl)methylene)-2-methyl-1H-inden-3-yl)-N-(furan-2-ylmethyl)acetamide (017), (Z)—N-(furan-2-ylmethyl)-2-(1-(3-hydroxy-4-methoxybenzylidene)-5-methoxy-2-methyl-1H-inden-3-yl)acetamide (020), (Z)-2-(5-fluoro-1-(4-(hydroxymethyl)-3,5-dimethoxybenzylidene)-2-methyl-1H-inden-3-yl)-N-(furan-2-ylmethyl)acetamide (021), (Z)—N-(2-(dimethylamino)ethyl)-2-(5-fluoro-1-(furan-2-ylmethylene)-2-methyl-1H-inden-3-yl)acetamide (026), (Z)-2-(5-fluoro-1-(4-mesyloxy-3,5-dimethoxybenzylidene)-2-methyl-1H-inden-3-yl)-N-(furan-2-ylmethyl) acetamide (029), and (Z)—N-(furan-2-ylmethyl)-2-(1-(4-ethoxycarbonyl-3,5-dimethoxybenzylidene)-5-methoxy-2-methyl-1H-inden-3-yl)acetamide (095), 30. A pharmaceutical composition comprising the compound of preferred aspect 29, a pharmaceutically acceptable salt or prodrug thereof, and a pharmaceutically acceptable carrier.

The present invention further provides a pharmaceutical composition comprising a compound as described above, a pharmaceutically acceptable salt or prodrug thereof, and a pharmaceutically acceptable carrier.

In accordance with an embodiment, the pharmaceutical composition may further include at least one therapeutic agent which is not a compound of formula I or II, or salt or prodrug thereof.

In an embodiment, the present invention provides a method of therapeutically or prophylactically treating a human or nonhuman mammalian patient with cancer, which method comprises administering to a patient in need thereof a therapeutically or prophylactically effective amount of at least one compound of formula I or II, either alone or in combination with at least one therapeutic agent which is not a compound of formula I or II, or pharmaceutically acceptable salt or prodrug thereof, for example, an anticancer drug or radiation.

In an embodiment, the cancer is selected from pancreatic cancer, lung cancer, colorectal cancer, melanoma, ovarian cancer, renal cancer, prostate cancer, head and neck cancer, endocrine cancer, uterine cancer, breast cancer, sarcoma cancer, gastric cancer, hepatic cancer, esophageal cancer, central nervous system cancer, brain cancer, hepatic cancer, germline cancer, lymphoma, and leukemia, preferably pancreatic cancer, colorectal cancer, or lung cancer. In an embodiment, the cancer is drug-resistant or radiation-resistant.

In a further embodiment, the invention provides a method of therapeutically or prophylactically treating a human or nonhuman mammalian patient with a disease or condition treatable by the inhibition of one or more neoplastic or cancerous process, which method comprises administering to a patient in need thereof a therapeutically or prophylactically effective amount of at least one neoplastic or cancerous inhibitory compound of formula I or II, or a compound selected from (001), (002), (006)-(008), (012)-(014), (016)-(022), (026), (029)-(033), (063), (065)-(067), (069), (095)-(100), (130)-(135), (138), (139), (141), (143), (144), (145), (151), (152), (154), (155), (214), (300)-(309), (311)-(336), (338)-(353), (355), (202), (203), (401), (404), (410), (412), (413), (415), (416), (420), (423), (425)-(428), (430), (431), (433), (434), and (436), or a pharmaceutically acceptable salt or prodrug thereof, either alone or in combination with at least one therapeutic agent which is not a compound of formula I or II, or salt or prodrug thereof, or a compound selected from (001), (002), (006)-(008), (012)-(014), (016)-(022), (026), (029)-(033), (063), (065)-(067), (069), (095)-(100), (130)-(135), (138), (139), (141), (143), (144), (145), (151), (152), (154), (155), (214), (300)-(309), (311)-(336), (338)-(353), (355), (202), (203), (401), (404), (410), (412), (413), (415), (416), (420), (423), (425)-(428), (430), (431), (433), (434), and (436), or a pharmaceutically acceptable salt or prodrug thereof, for example, an anticancer drug or radiation.

In a preferred embodiment of the above method, the neoplastic or cancerous process is selected from growth, proliferation, survival, metastasis, drug resistance and radiation resistance of a tumor cell.

In an embodiment, the compounds of the invention include Ras-inhibitory compounds. A Ras-inhibitory compound can be identified from one or more compounds of formulas I-II by an assay of Ras inhibition. Some representative assays of selective Ras inhibition are illustrated in the examples that follow herein. As used herein, the terminology selective "Ras inhibition" means selective, preferential or specific inhibition of aberrant Ras-mediated cellular processes, such as, for example, accelerated or aberrant cell growth, proliferation, survival, and invasiveness, relative to these processes in cells or tissues with normal or non-aberrant Ras and Ras-mediated processes. Experimentally, selective Ras inhibition can be shown, for example, by determining the ratio (numerator/denominator) of a given compound's potency (e.g., $IC_{50}$) to inhibit the growth of cells with "normal" or "wild-type" Ras (numerator) relative to that of cells with mutated and/or activated Ras (denominator). The terminology used herein for such an experimentally determined ratio is "selectivity" or "selectivity index", which is further denoted by showing the respective cell types used to determine the numerical ratio (e.g., HT-29/A549; Caco-2/SW-480; HT-29/SW-480; HT-29/CCT-116). For a given compound, a "selectivity" value or "selectivity index" of greater than 1 (one), preferably greater than 10 (ten), more preferably greater than 100 (one hundred) and even more preferably greater than 1000 (one thousand) indicates said compound selectively inhibits hyperactive Ras and/or Ras-mediated cellular functions, such as those which may drive or accelerate cancer cell growth, proliferation, metastasis, resistance to drugs or radiation, and the like.

In another preferred embodiment of the present invention, the aforementioned assay of Ras inhibition employs one or more isogenic cell line pair(s), wherein both of the lines share the same genetic background except that one of the lines ("mutant line") contains one or more mutated or hyperactive ras gene(s), Ras protein(s) and/or aberrant Ras-mediated biological process(es), and the other line ("normal line") lacks such mutation(s) or aberrant function(s).

In a further preferred embodiment of the present invention, the aforementioned assay employing isogenic cell line(s) enables the determination and calculation of a Ras-Inhibitory Specificity Index (RISI). One experimental approach to determination of such a RISI may, for example, comprise determining the ratio of the concentration of a compound producing a specified effect on the normal line, such as, for example, 50% growth inhibition in a specified period of time, divided by the concentration of the same compound producing the same specified effect (e.g., 50% growth inhibition in the same specified period of time) on the mutant line.

Whereas in the aforementioned approach, the 50% growth inhibition values may be obtained by testing the compound against both normal and mutant cell lines at multiple concentrations over a specified concentration range, for example 10 nM-10,000 nM, an alternate, more streamlined approach to determining a RISI value could comprise measuring the ratio of percentage growth inhibition in a given period of time by a specified single concentration of the compound, for example 250 nM, selected from within a range of concentrations, for example from within a range of 10 nM-10,000 nM, against the mutant (numerator) relative to the normal cell line (denominator). This approach may be generally more applicable to larger-scale or preliminary screening of groups of individual compounds or mixtures thereof to obtain a preliminary or screening RISI, whereas a RISI determined using concentration ranges to determine 50% growth inhibition values may be more precise. A RISI value obtained for a given compound by either approach may be less than, equal to or greater than 1 (one), and a RISI value of greater than 1 (one) indicates said compound selectively inhibits Ras or Ras-mediated cellular functions.

In a highly preferred embodiment of the present invention, the employed assay of Ras inhibition enables identification of a compound from one or more compounds of formulas I-II having a RISI of greater than 1, preferably greater than 10, more preferably greater than 100, and even more preferably greater than 1000.

The present invention yet further provides a pharmaceutical composition comprising a therapeutically effective amount of Ras-inhibitory activity from one or more Ras-inhibitory compound(s) of formula I-II, or pharmaceutically acceptable salt(s) or prodrug(s) thereof, alone or in combination with at least one therapeutic agent which is not a compound of formula I or II or salt or prodrug thereof. The therapeutically effective amount can be that amount provided by a Ras-inhibiting and/or a disease-process inhibiting effective amount, such as an anticancer effective amount, of a compound of formula I or II or pharmaceutically acceptable salt or prodrug thereof.

In addition, the present invention provides a method of therapeutically or prophylactically treating a condition treatable by the inhibition of Ras-mediated biological processes including, for example, tumor cell growth, proliferation, survival, invasion and metastasis, as well as resistance to chemotherapy, other molecularly targeted therapeutics, and radiation; and, a method of therapeutically or prophylactically treating cancers harboring hyperactive or mutant Ras. These methods comprise administering a therapeutically or prophylactically effective amount of Ras-inhibiting activity from at least one Ras-inhibitory compound, or pharmaceutically acceptable salt or prodrug thereof, of formula I-II.

For example, the disease or condition treatable by the inhibition of one or more Ras-mediated biological process is cancer, neurofibromatosis, or Costello syndrome. In an embodiment, the Ras-mediated biological process is selected from growth, proliferation, survival, metastasis, drug resistance and radiation resistance of a tumor cell.

In an embodiment of the above method, the patient is pre-selected by utilizing an assay of the patient's tissue, blood or tumor for an abnormal, mutant or hyperactive ras gene or Ras protein, or an aberrant Ras-mediated biological process.

In an embodiment, the patient's tissue, blood or tumor contains an abnormal, mutant or hyperactive ras gene or Ras protein, or aberrant Ras-mediated biological process.

The compounds in the present invention also can be in the form of a pharmaceutically acceptable salt, which may include, for example, the salt of one or more acidic substituents (e.g. a carboxylic salt, a sulfonic acid salt, and the like) and the salt of one or more basic substituents (e.g. the salt of an amine, and the like). Suitable salts of acidic substituents include, for example, metal salts (e.g. sodium salts, potassium salts, magnesium salts, zinc salts, and the like) and ammonium salts (e.g., $NH_4+$ salts, alkylammonium salts, quaternary ammonium salts, and the like). Suitable salts of basic substituents include, for example, acid addition salts (e.g., hydrochloride salts, hydrobromide salts, carboxylate salts (e.g., acetate salts), sulfate salts, sulfonate salts (e.g., mesylate salts), phosphate salts, quaternary ammonium salts, and the like.

A compound of the present invention can also be provided as a prodrug, which is a drug derivative or drug precursor compound that typically is inactive or less than fully active until it is converted in the body through a normal metabolic process such as, for example, hydrolysis of an ester or amide form of the drug, to the active drug. A prodrug may be selected and used instead of the parent drug because, for example, in its prodrug form it is less toxic, and/or may have better absorption, distribution, metabolism and excretion (ADME) characteristics, and the like, than the parent drug. A prodrug might also be used to improve how selectively the drug interacts with cells or processes that are not its intended target. This approach may be employed particularly, for example, to prevent or decrease adverse effects, especially in cancer treatments, which may be especially prone to having severe unintended and undesirable side effects.

The term "prodrug" denotes a derivative of a compound, which derivative, when administered to warm-blooded animals, e.g. humans, is converted into the compound (drug). For example, the enzymatic and/or chemical hydrolytic cleavage of a derivative compound of the present invention occurs in such a manner that the proven drug form is released, and the moiety or moieties split off remain nontoxic or are metabolized so that nontoxic metabolites are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The prodrugs can be prepared in situ during the isolation and purification of the compounds, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched alkyl ester moieties, e.g., ethyl esters, alkenyl esters, di-alkylamino alkyl esters, e.g., dimethylaminoethyl ester, acylamino alkyl esters, acyloxy alkyl esters (e.g., pivaloyloxymethyl ester), aryl esters, e.g., phenyl ester, aryl-alkyl esters, e.g., benzyl ester, optionally substituted, e.g., with methyl, halo, or methoxy substituents aryl and aryl-alkyl esters, amides, alkyl amides, di-alkyl amides, and hydroxy amides. As another example, an alkyloxy group can serve as a prodrug moiety for a hydroxyl group; for instance, an alkoxy group on a phenyl ring can be enzymatically demethylated in vivo to yield a phenolic hydroxyl moiety.

Knowing the disclosures herein, it will be appreciated also that a compound of the present invention can be in the form of a prodrug, and that such prodrugs can be prepared using reagents and synthetic transformations that are well-known to those having ordinary skill in the art. The effectiveness of a particular prodrug can be determined using one or more analytical methods (e.g. pharmacokinetics, bioassays, in vivo efficacy studies, and the like) that are well-known to those of ordinary skill in the art.

More specifically, a prodrug having a formula of I or II may be prepared using routine chemical procedures, such as the exemplary procedures described herein. For instance, any one of $R_1$, $R_2$, $R_3$, $R_4$, R', R" or any substituent on E of formula I can be of the formula Q-U-, for example,

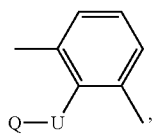

wherein U is selected from the group consisting of oxygen, sulfur, nitrogen, $OCH_2$, $SCH_2$ and $NHCH_2$; and Q is selected from the group consisting of hydrogen, alkyl, PEG-CO, HCO, acetyl, amino acid, substituted benzoic acid and phosphoric acid; or, wherein Q-U- together is selected from phosphonooxy, phosphonoalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy.

Similarly, in a compound of formula II any one of $R_1$, $R_2$, $R_3$, $R_4$, $R_{12}$, $R_{13}$, $R_{14}$, $R_{15}$, $R_{16}$, R', or R" can be of the formula Q-U- wherein U is selected from the group consisting of oxygen, sulfur, nitrogen, $OCH_2$, $SCH_2$ and $NHCH_2$; and Q is selected from the group consisting of hydrogen, alkyl, PEG-CO, HCO, acetyl, amino acid, substituted benzoic acid and phosphoric acid; or, wherein Q-U together is selected from phosphonooxy, phosphonoalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, carbamido, alkoxycarbonyl, alkylaminocarbonyl, aminocarbonyl, arylcarbonyloxy, arylalkylcarbonyloxy, aryloxycarbonyloxy, heterocyclylcarbonyloxy and heterocyclylalkylcarbonyloxy.

Suitable prodrugs may include, but not be limited to, those illustrated below for a compound of formula II, specifically as exemplary prodrug derivatives of compound 018:

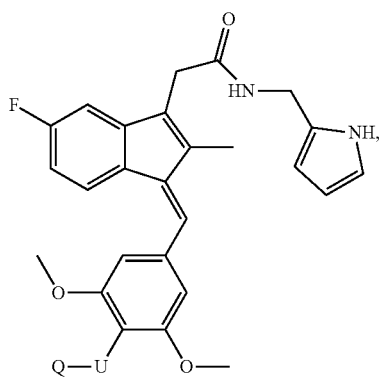

wherein U is selected from the group consisting of oxygen, sulfur, nitrogen, $OCH_2$, $SCH_2$ and $NHCH_2$; and Q, for example, is selected from the group consisting of PEG-CO, HCO, acetyl, amino acid, substituted benzoic acid and phosphoric acid; or, Q-U together, for example, is substituted or unsubstituted phosphonooxy, phosphonooxyalkyloxy, alkyloxy, alkylcarbonyloxy, alkylcarbonyloxyalkyloxy, aminocarbonyloxy, aminocarbonyloxyalkyloxy, dimethylaminocarbonyloxy, dimethylaminocarbonyloxyalkyloxy, piperidinylcarbonyloxy, piperidinylcarbonyloxyalkyloxy, dipiperidinylcarbonyloxy, or dipiperidinylcarbonyloxyalkyloxy.

As used herein, the "alkyl" part of any of the substituents described herein, e.g., but not limited to, alkyl, alkylamino, alkylmercapto, hydroxyalkyl, polyhydroxyalkyl, alkylaminoalkyl, aminoalkyl, arylalkyl, arylcycloalkyl, heterocyclylalkyl, arylalkylenyl, arylcycloalkyl, dialkylamino, alkylcarbonyloxy, dialkylaminoalkyl, cyanoalkyl, haloalkyl, alkylcarbonylalkylcarbonyloxy, dialkylalkylaminoalkyl, alkylsulfonyl, alkylsulfinyl, alkylsulfinyloxy, alkylsulfonyloxy, alkylenedioxy, carbocyclylalkyl, arylalkylcarbonyloxy, heteroarylcarbonyloxy, and phenylalkyl, means a straight-chain or branched-chain saturated alkyl which can contain from 1-20 carbon atoms, for example from 1 to about 10 carbon atoms, or from 1 to about 8 carbon atoms, or, preferably, lower alkyl, i.e., from 1 to 6 carbon atoms. Unless otherwise specified herein, "alkyl" is assumed to mean lower alkyl.

Examples of alkyls include methyl, ethyl, propyl, isopropyl, n-butyl, sec-butyl, isobutyl, tent-butyl, pentyl, isoamyl, hexyl, octyl, dodecanyl, octadecyl, and the like. Alkyl substituents can be unsubstituted or substituted, for example with at least one substituent selected from the group consisting of a halogen, a nitro, an amino, a hydroxyl, a thio, an acyl, a mercapto, and a cyano.

The term "alkenyl" means a straight-chain or branched-chain alkenyl having one or more double bonds. Unless otherwise specified, the alkenyl can contain from 2 to about 10 carbon atoms, for example from 2 to about 8 carbon atoms, or preferably from 2 to about 6 carbon atoms. Examples of alkenyls include vinyl, allyl, 1,4-butadienyl, and isopropenyl substituents, and the like.

The term "alkynyl" means a straight-chain or branched-chain alkynyl having one or more triple bonds. Unless otherwise specified, alkynyls can contain from 2 to about 10 carbon atoms, for example, from 2 to about 8 carbon atoms, or preferably, from 2 to about 6 carbon atoms. Examples of alkynyls include ethynyl, propynyl (propargyl), butynyl, and the like. Alkenyl or alkynyl substituents can be unsubstituted or substituted, for example, with at least one substituent selected from the group consisting of a halogen, a nitro, an amino, a hydroxyl, a thio, an acyl, an alkyl, and a cyano.

The term "aryl" means an aromatic carbocyclic radical, as commonly understood in the art, and includes monocyclic and polycyclic aromatics such as, for example, phenyl and naphthyl rings. Preferably, the aryl comprises one or more six-membered rings including, for example, phenyl, naphthyl, biphenyl, and the like. Typically, the aryl comprises six or more carbon atoms in the ring skeleton thereof (e.g., from 6 to about 10 carbon atoms making up the ring). Unless specified otherwise, "aryl" by itself refers to unsubstituted aryl groups and does not cover substituted aryl groups. Substituted aryl can be an aryl substituted, for example, with at least one substituent selected from the group consisting of a halogen, a nitro, an amino, a hydroxyl, a thio, an acyl, and alkyl, and a cyano. It is to be noted that arylalkyl, benzyl, or heteroaryl groups are not considered "aryl" in accordance with the present invention.

In accordance with the invention, the term "heteroaryl" refers to a cyclic aromatic radical having from five to ten ring atoms of which at least one atom is O, S, or N, and the remaining atoms are carbon. Examples of heteroaryl radicals include pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl. Unless otherwise specified, "heteroaryl" refers to unsubstituted heteroaryl.

In further accordance with the invention, the term "heterocyclyl" refers to a stable, saturated, partially unsaturated or unsaturated monocyclic, bicyclic, or spiro ring system containing 3 to 7 ring members of carbon atoms and other atoms selected from nitrogen, sulfur, and/or oxygen. The term "heterocyclyl" includes "heteroaryl groups. Preferably, a heterocyclyl is a 5, 6, or 7-membered monocyclic ring and contains one, two, or three heteroatoms selected from nitrogen, oxygen, and/or sulfur. The heterocyclyl may be attached alone or via an alkyl linker (thus becoming a "heterocyclylalkyl") to the parent structure through a carbon atom or through any heteroatom of the heterocyclyl that results in a stable structure. Examples of such heterocyclyl rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl.

Further in accordance with the invention, unless otherwise specified, the term "heterocyclyl" refers to a saturated or unsaturated, unsubstituted ring consisting of 3-7 atoms, at least one of which is not a carbon atom, such as an oxygen, nitrogen or sulfur atom.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In light of the disclosures of the present invention, it will be appreciated that the compounds of the present invention can be made by methods well-known to those of ordinary skill in the art, for example, by structurally modifying a given compound or by direct synthesis from available building blocks using routine synthetic transformations that are well-known in the art. See for example, Sperl et al., U.S. Patent Application Publication No. US 2003/0009033 A1, Jan. 9, 2003; Sperl et al., U.S. Pat. No. 6,071,934, Jun. 6, 2000; Sperl et al., International Publication No. WO 97/47303, Dec. 18, 1997; Whitehead et al., U.S. Patent Application Publication No. US 2003/0176316 A1, Sept. 18, 2003; Thompson et al., U.S. Pat. No. 6,538,029 B1, Mar. 25, 2003; Li et al., U.S. Patent Application Publication No. US 2003/0194750 A1, Oct. 16, 2003; and Shen et al., U.S. Pat. No. 3,888,902, Jun. 10, 1975; Alcalde, et al., *Org. Biomol. Chem.*, 6, 3795-3810 (2008); Magar and Lee, *Org. Lett.*, 15, 4288-4291 (2013).

For instance, a compound of formula I can be synthesized according to the general approach depicted in Scheme I:

Scheme I

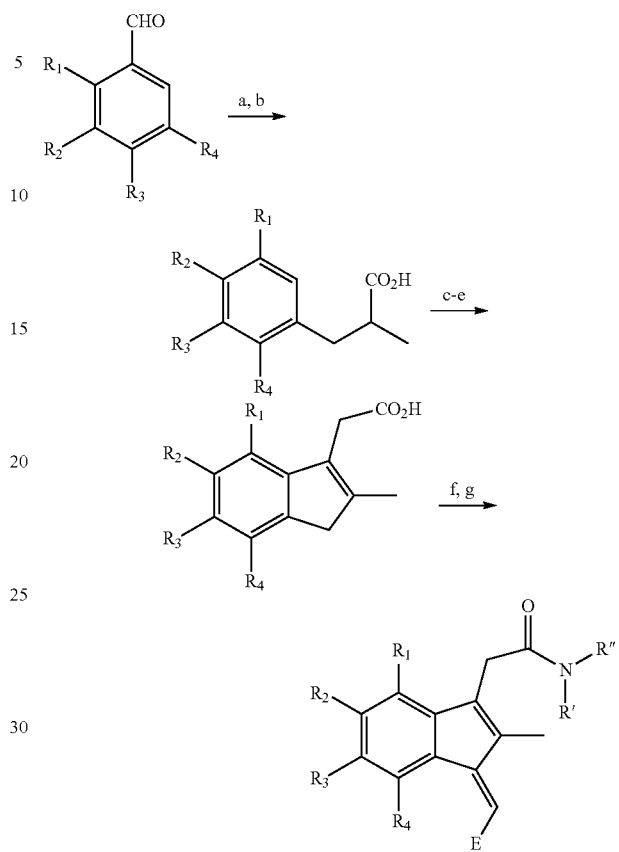

a. (EtCO)$_2$, EtCO$_2$Na, reflux; b. H$_2$, Pd—C; c. PPA, 50-80° C.;
d. NCCH$_2$CO$_2$H, AcOH, AcONH$_4$, toluene, Dean-Stark; e. KOH, H$_2$O;
f. NaOCH$_3$, CH$_3$OH, E-CHO; g. (1) CDI, CH$_2$Cl$_2$, (2) R'R"NH, pyridine, warm Detailed methods to achieve all of the synthesis steps depicted in Scheme I to make a desired substituted or unsubstituted indene derivative, are extensively documented in the published literature (e.g., see Sperl, et. al., 1997, 2000, 2003, supra; Li, et. el., 2003, supra; Thompson, et. al., 2003, supra; Whitehead, et. al., 2003, supra); Alcatel, et al., 2008, supra; Magar and Lee, 2013, supra; Shen et al., 1975, supra. In Scheme I the benzaldehyde building block used for step a, and/or the aldehyde building block (E-CHO) used for step f, and/or the primary or secondary amine (R'R"NH) building block used in step g can independently be unsubstituted, or substituted with any desired substituent(s) required to yield the desired final product of formula I or II of the present invention.

For example, the benzaldehyde building block as shown in Scheme I having the desired substituents at $R_1$, $R_2$, $R_3$ and $R_4$ can be purchased commercially and/or can be prepared routinely by methods well-known to those of ordinary skill in the art. Such optional substituent(s) independently at $R_1$, $R_2$, $R_3$ and $R_4$ in Scheme I for example include but are not limited to hydrogen, halogen, alkyl, cycloalkyl, haloalkyl, hydroxyl, carboxyl, alkoxy, formyloxy, hydroxyalkyl, aldehyde, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, and sulfamido, or any two of $R_1$, $R_2$, $R_3$ and $R_4$ form an alkylenedioxy group.

Likewise, the aldehyde building block (E-CHO) as shown in Scheme I having any desired group at E can be purchased and/or can be prepared by methods well-known to those of ordinary skill in the art. Such optional groups at E in Scheme I for example include but are not limited to any desired substituted or unsubstituted, saturated or unsaturated, 7-membered, 6-membered, 5-membered, 4-membered or 3-membered carbocyclic or heterocyclic ring. Substituents on said ring may include one or more of hydrogen, halogen, alkyl, haloalkyl, hydroxyl, carboxyl, alkoxy, formyloxy, hydroxyalkyl, aldehyde, amino, alkylamino, aminoalkyl, alkylaminoalkyl, dialkylamino, mercapto, alkylmercapto, cyano, cyanoalkyl, nitro, azido, and substituted or unsubstituted groups selected from alkylsulfinyloxy, alkylsulfonyloxy, carbamate, carbamido, alkoxycarbonyl, alkylaminocarbonyl, aminocarbonyl, alkylcarbonyloxy, alkylcarbonyloxyalkyloxy, aminocarbonyloxyalkyloxy, arylcarbonyloxy, arylalkylcarbonyloxy, aryloxycarbonyloxy, heterocyclylcarbonyloxy, heterocyclylalkylcarbonyloxy, phosphonooxy, phosphonoalkyloxy, and sulfonamido, or any two of $R_1$, $R_2$, $R_3$ and $R_4$ form an alkylenedioxy group.

Furthermore, the primary or secondary amine building block (R'R"NH) as shown in Scheme I can be purchased commercially and/or can be prepared routinely by methods well-known to those of ordinary skill in the art. Such optional substituents independently at R' and R" in Scheme I for example include but are not limited to hydrogen, hydroxyl, alkyl, aryloxy, cyanoalkyl, haloalkyl, alkoxy, alkenyl, alkynyl, hydroxyalkyl, polyhydroxyalkyl, alkylaminoalkyl, dialkylaminoalkyl, aminoalkyl, aryl, arylalkyl, arylalkenyl, arylcycloalkyl, arylcycloalkenyl, carbocyclyl, and carbocyclylalkyl where the carbocycle of the carbocyclyl and the carbocyclylalkyl is selected from 7-membered carbocyclic rings containing no double bond, or one, two or three double bonds, 6-membered carbocyclic rings containing no double bond, or one or two double bonds, 5-membered carbocyclic rings containing no double bond, or one or two double bonds, 4-membered carbocyclic rings containing no double bond or one double bond and 3-membered carbocyclic rings containing no double bond, heterocyclyl, and heterocyclylalkyl, where the heterocycle of the heterocyclyl and heterocyclylalkyl is selected from 7-membered heterocyclic rings, 6-membered heterocyclic rings, and 5-membered heterocyclic rings, and the aryl of the aryl, arylalkyl, arylalkylenyl, arylcycloalkyl, or arylcycloalkenyl structure or the carbocyclic or heterocyclic structure is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; and R" is selected from hydrogen, alkyl, hydroxyalkyl, aminoalkyl, dialkylaminoalkyl, cyanoalkyl, haloalkyl, alkylcarbonylalkylcarbonyloxy, pyridyl, and $COR_{11}$ wherein $R_{11}$ is selected from hydrogen, amino, alkyl, haloalkyl, alkoxy, alkylmercapto, and aryl; or R' and R" together form a 5-, 6- or 7-membered, saturated or unsaturated, heterocyclic ring containing at least one nitrogen, and optionally oxygen and/or sulfur, and the heterocyclic ring is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamide.

As a more specific example, a particular compound of formula II can be synthesized according to the general approach depicted in Scheme II, which includes the key intermediate, a substituted indenyl acetic acid:

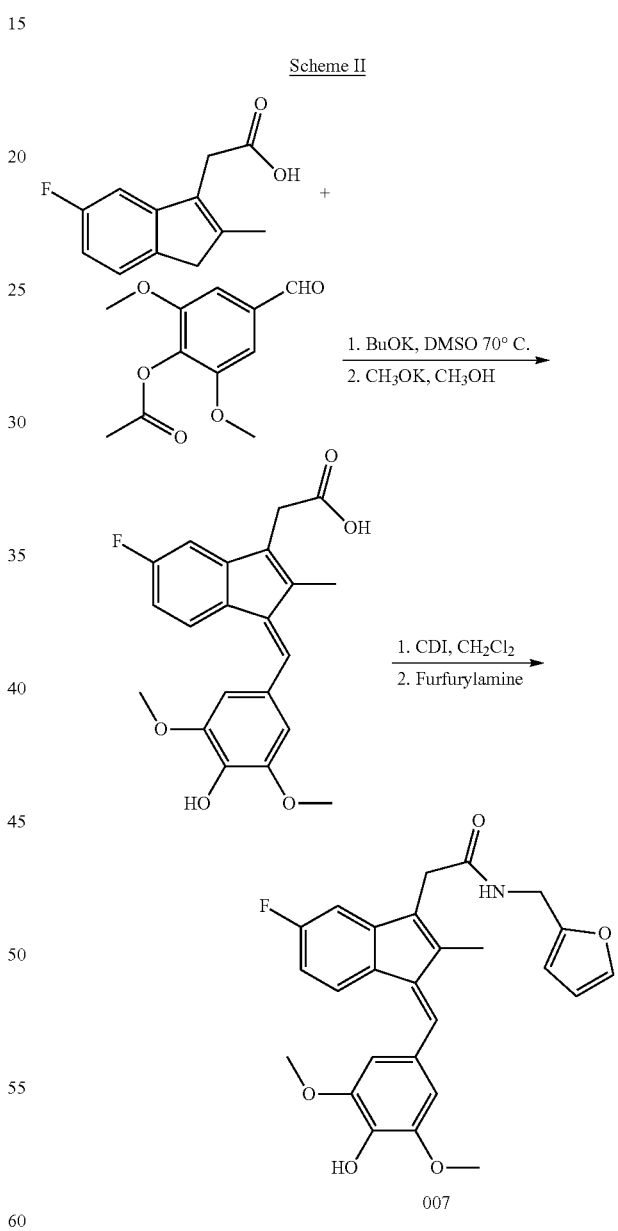

For certain substituents at $R_1$, $R_2$, $R_3$ or $R_4$ (e.g., in Scheme II above, $R_2$ is fluoro), the starting material for preparation of the substituted indenyl acetic acid intermediate, is optionally different than that shown in Schemes I and II, depending upon the nature of the substituent(s) desired on the intermediate and final product, and the optimum reaction conditions sought. For example, attachment of a cyano group at $R_2$ can be accomplished using as starting material a cyano-substituted benzyl halide (e.g., as adapted from Shen, et. al., 1975), as illustrated below in Scheme III:

Scheme III

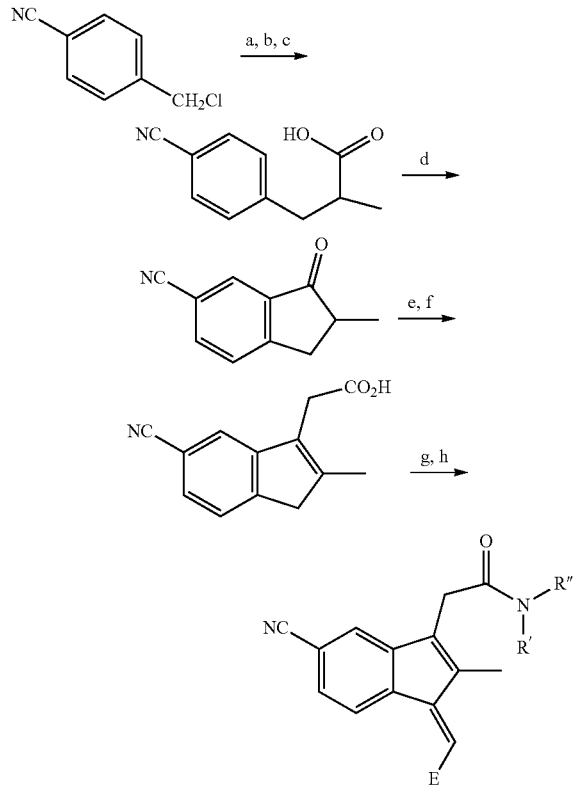

a. $CH_3CH(CO_2Et)_2$, Na, EtOH; b. NaOH, EtOH; c. $H_2SO_4$, aq.; d. PPA, 83-90° C., 2 h; e. $BrCH_2CO_2CH_3$, Zn(HG), $I_2$, benzene; NaOH, Ethanol, warm g. $NaOCH_3$, $CH_3OH$, E-CHO; h. (1) CDI, $CH_2Cl_2$, (2) R'R"NH, pyridine, warm A wide variety of substituents can be introduced at $R_1$, $R_2$, $R_3$ and $R_4$ of a compound of formula I or II in the course of synthesis. In addition to the above-described Schemes I-III, Scheme IV below illustrates yet another approach to making variations in substituents at $R_1$-$R_4$.

Scheme IV

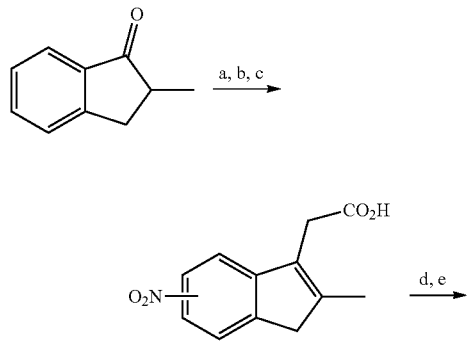

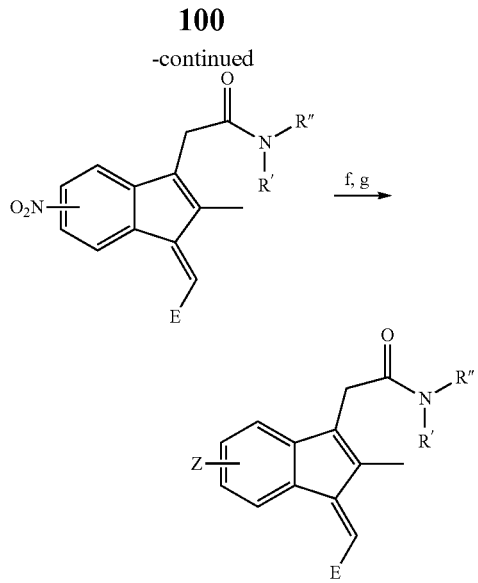

a. $KNO_3$, $H_2SO_4$, 46%; b. $NCCH_2CO_2H$, AcOH, $AcONH_4$, toluene, Dean-Stark; c. (1) KOH, EtOH, $H_2O$, (2) HOAc; d. $NaOCH_3$, $CH_3OH$, E-CHO; e. (1) CDI, $CH_2Cl_2$, (2) R'R"NH, pyridine, warm; f. Zn, HOAc; g. standard procedure Z = NR'R", $NHSO_2R$, isocyanide, NHCOR, azide, urea, carbamate, halogen, OH, Schiff base, etc.

Extensive variations can also be made in R and/or $R_0$ in a medically useful compound of formula I or II of the invention. For example, one skilled in the art can use or adapt as necessary the general synthesis approach illustrated by Scheme V below.

Scheme V

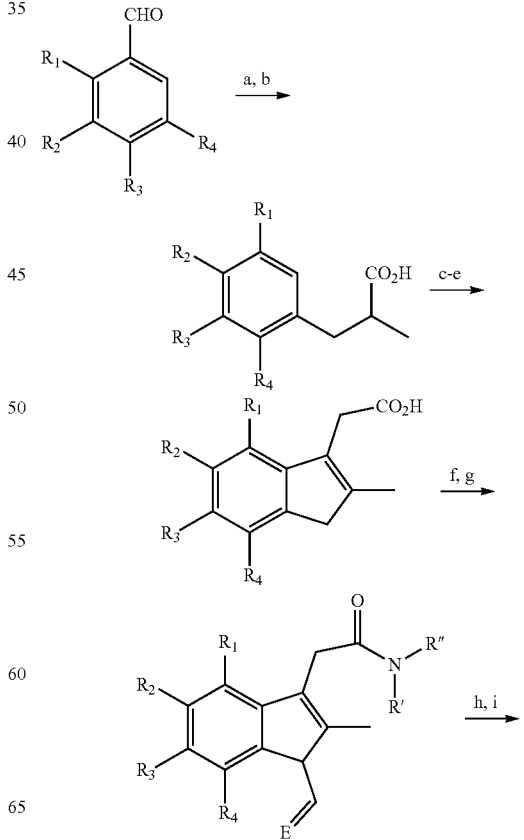

-continued

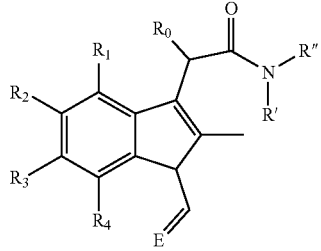

a. (EtCO)₂O, EtCO₂Na, reflux; b. H₂, Pd—C; c. PPA, 50-80° C.; d. NCCH₂CO₂H, AcOH, AcONH₄, toluene, Dean-Stark; e. KOH, H₂O; f. NaOCH₃, CH₃OH, E—CHO; g. (1) CDI, CH₂Cl₂, (2) R'R"NH, pyridine, warm; h. DCM, -15° C., DDQ; i R₀, ethanol, 85° C.

In a more specific example illustrated in Scheme VI below, a compound of the invention, such as compound 007, can serve as the starting point for making other medically useful derivatives thereof which have various different substituents at R and/or $R_0$, such as compounds 202, 203, 404, 410, 430 and 431.

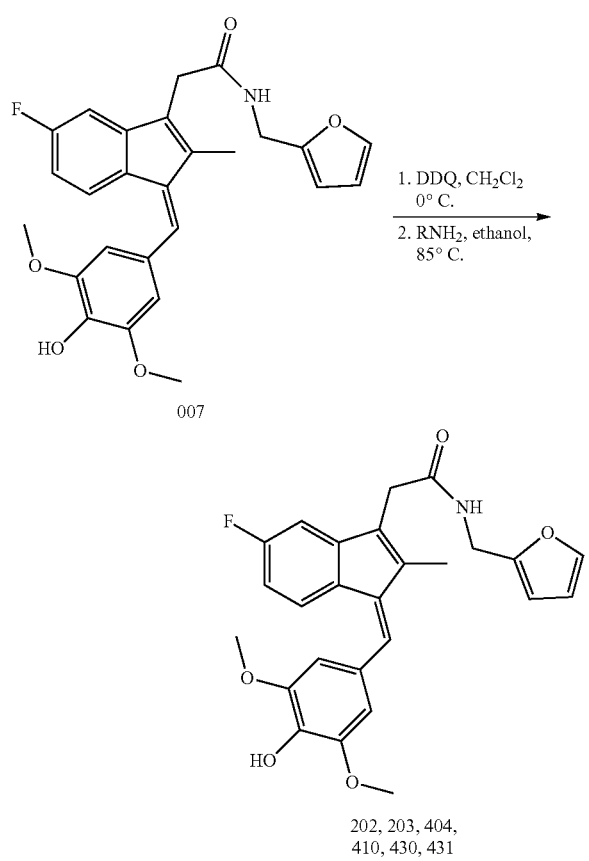

Furthermore, variations in the length of the side-chain linkers in the compounds of formula I or II can be introduced by one of ordinary skill in the art by adapting known methods. For example, adaptations of the methods of Magar and Lee 2013, supra, can be used to produce compounds of formula I and II wherein n=0.

Yet more specific and detailed illustrations using these general synthetic approaches are provided in the particular Examples that follow herein. Furthermore, one skilled in the art and knowing the disclosures of the present invention will appreciate that any of compounds of formula I or II can be modified with different substituents as desired to be in the final products, and/or the final product of a synthesis, for example a synthesis according to Scheme I, II, III, IV, V, or VI can be modified with different substituents as desired. Placement, removal and/or inter-conversion of desired substituents on precursors, building blocks, intermediates or penultimate product compounds of formulas I and II can be accomplished by routine methods well-known to those of ordinary skill in the art, as briefly overviewed in the following:

One or more hydroxyl groups, for example, can be converted to the oxo derivative by direct oxidation, which can be accomplished using any known method such as, for example, a Swern oxidation, or by reaction with a metal oxidant, such as a chromium oxide (e.g., chromium trioxide), a manganese oxide (e.g., manganese dioxide or permanganate) or the like. Primary alcohols can be oxidized to aldehydes, for example, via Swern oxidation, or they can be oxidized to carboxylic acids (e.g., —CO₂H), for example by reaction with a metal oxidant. Similarly, the thiols (e.g., —SR, —SH, and the like) can be converted to oxidized sulfur derivatives (e.g., —SO₂R or the like) by reaction with an appropriate oxidant.

One or more hydroxyl groups can be converted to an ester (e.g., —CO₂R), for example, by reaction with an appropriate esterifying agent such as for example, an anhydride (e.g., (R(CO))₂O) or an acid chloride (e.g., R(CO)Cl), or the like. One or more hydroxyl groups can be converted to a sulfonate (e.g., —SO₂R) by reaction with an appropriate sulfonating agent such as, for example, a sulfonyl chloride (e.g., RSO₂Cl), or the like, wherein R is any suitable substituent including, for example, organic substituents described herein. Ester derivatives also can be obtained, for example, by reacting one or more carboxylic acid substituents (e.g., —CO₂H) with an alkylating agent such as, for example, a diazoalkane (e.g., diazomethane) an alkyl or aryl iodide, or the like. One or more amides can be obtained by reaction of one or more carboxylic acids with an amine under appropriate amide-forming conditions which include, for example, activation of a carboxylic acid (e.g., by conversion to an acid chloride or by reaction with a carbodiimide reagent) followed by coupling of the activated species with a suitable amine.

One or more hydroxyl groups can be converted to a halogen using a halogenating agent such as, for example, an N-halosuccinamide such as N-iodosuccinamide, N-bromosuccinamide, N-chlorosuccinamide, or the like, in the presence of a suitable activating agent (e.g., a phosphine, or the like). One or more hydroxyl groups also can be converted to ether by reacting one or more hydroxyls, for example, with an alkylating agent in the presence of a suitable base. Suitable alkylating agents can include, for example, an alkyl or aryl sulfonate, an alkyl or aryl halide, or the like. One or more suitably activated hydroxyls, for example a sulfonate ester, and/or one or more suitably activated halides, can be converted to the corresponding cyano, halo, or amino derivative by displacement with a nucleophile which can include, for example, a thiol, a cyano, a halide ion, or an amine (e.g., H₂NR, wherein R is a desired substituent), or the like.

Amines can be obtained by a variety of methods known in the art, for example, by hydrolysis of one or more amide groups. Amines also can be obtained by reacting one or more suitable oxo groups (e.g., an aldehyde or ketone) with one or more suitable amines under the appropriate conditions, for example, reductive amination conditions, or the like. One or more amines, in turn, can be converted to a number of other useful derivatives such as, for example, amides, sulfonamides, and the like.

Certain chemical modifications of a compound of formula I or II can be introduced as desired to obtain useful new variants with new or modified biological properties such as: new or improved potency and/or selectivity for inhibiting Ras-mediated biological processes, improved efficacy against a disease process such as, but not limited to, tumor cell growth, proliferation, survival, invasion and metastasis, as well as resistance to chemotherapy, other molecularly targeted therapeutics, and radiation, as well as enhanced oral bioavailability, less toxicity in a particular host mammal, more advantageous pharmacokinetics and/or tissue distribution in a given host mammal, and the like. Therefore, the present invention employs methods for obtaining useful new compounds of formula I-II by applying one or more well-known chemical reactions to a given compound to obtain a derivative wherein, for example, one or more phenolic hydroxyl group(s) may instead be replaced by an ester, sulfonate ester or ether group; one or more methyl ether group(s) may instead be replaced by a phenolic hydroxyl group; one or more phenolic hydroxyl group(s) may instead be replaced by an aromatic hydrocarbon substituent; a secondary amine site may instead be replaced by an amide, sulfonamide, tertiary amine, or alkyl quaternary ammonium salt; a tertiary amine site may instead be replaced by a secondary amine; and one or more aromatic hydrogen substituent(s) may instead be replaced by a halogen, nitro, amino, hydroxyl, thiol or cyano substituent.

Depending upon the stoichiometric amount of the particular reactant, a compound of formula I or II can be substituted at one, some, or all of the respective available positions. For example, when such a compound is reacted with a certain amount of $CH_3COCl$, an acetate substituent can be introduced a one, some, or all of the available positions, which may include, for example ether or amino positions.

Other examples may include, but are not limited to: (1) conversion to ester, sulfonate ester, and ether substituents at one or more phenolic hydroxyl positions in compounds of formula I and II; for instance, for preparation of esters or sulfonate esters a given compound can be reacted with an acid halide (e.g., $RCOX$ or $RSO_2X$, where X is Cl, Br or I, and R is a $C_1$-$C_6$ aliphatic or aromatic radical) in anhydrous pyridine or triethylamine; alternatively, the given compound may be reacted with an acid ($RCO_2H$ or $RSO_3H$) wherein R is an aliphatic or aromatic radical and dicyclohexylcarbodiimide in triethylamine to prepare the ester or sulfonate ester; for preparation of ethers, the given compound is reacted with an organic halide (e.g., RX or $RCH_2X$, where X is Cl, Br or I, and R is a $C_1$-$C_6$ aliphatic or aromatic radical) in anhydrous acetone with anhydrous potassium carbonate; (2) removal of an ether methyl group(s) to provide a phenolic hydroxyl functionality and/or conversion of that moiety to an ester, sulfonate, or other ether in a compound or derivative of formula I or II: for instance, for hydrolytic cleavage of a methyl ether substituent and conversion to a phenolic hydroxyl moiety, the given compound is reacted with $BBr_3$ or $BX_3.(CH_3)_2S$ in $CH_2Cl_2$ (where X is F, Cl or Br); the resulting phenol can be converted to an ester, sulfonate ester or ether as described above; (3) preparation of amide or sulfonamide derivatives at an amine site in a compound of formula I or II: for instance, for preparation of amides or sulfonamide derivatives, the same general procedures described above in (1) apply; in either case (procedure (1) or (3)), an appropriate functional group protection strategy (blocking/deblocking of selected group(s)) may need to be applied; (4) conversion of a secondary amine functionality in a compound of formula I or II to a tertiary amine: for instance, for preparation of a tertiary amine, the given compound is reacted with an aldehyde, and the resulting product is then reduced with $NaBH_4$; alternatively, for preparation of an alkyl ammonium salt, the given compound is reacted with an alkyl halide (RX, where X is Cl, Br or I, and R is a $C_1$-$C_6$ aliphatic radical) in an anhydrous aprotic solvent; (5) conversion of a tertiary amine functionality in a compound of formula I or II to a secondary amine; for instance, for preparation of a secondary amine, the given compound is reacted with cyanogen bromide to give a cyanamide derivative which is then treated with $LiAlH_4$; (6) conversion of one or more phenolic hydroxyl groups in a given compound of formula I or II to an aromatic hydrogen substituent: for instance, the given compound is converted (after suitable protection of any amine substituent(s) if necessary) to the triflate ester to give the corresponding deoxy compound; (7) substitution of one or more hydrogen substituent(s) on the aryl system(s) on a compound of formula I or II by halogen, nitro, amino, hydroxyl, thiol, or cyano groups: for instance, for preparation of a bromine-substituted derivative, the given compound is reacted with $Br_2$ in $H_2O$; for the preparation of other substituted derivatives, the given compound is treated with $HNO_3/HOAc$ to provide a nitro-substituted ($—NO_2$) derivative; in turn, the nitro-derivative can be reduced to an amino derivative, and the amino derivative is the point of origin of the chloro, iodo, cyano, thiol and hydroxyl substitution via well-known and practiced diazonium substitution reactions. More detailed, specific illustrations of synthesis and derivatization procedures that can be employed to access any desired member of the family of compounds represented by formulas I and II and derivatives thereof, are provided in the examples that follow herein.

It will be appreciated that certain compounds of formula I or II can have one or more asymmetric carbon(s) and thus such compounds are capable of existing as enantiomers or diastereomers. Unless otherwise specified, the present invention includes such enantiomers or diastereomers, including any racemates thereof. If desired, the separate enantiomers or diastereomers can be synthesized from appropriate chiral starting materials, or the racemates can be resolved by conventional procedures, which are well-known to those skilled in the art, such as chiral chromatography, fractional crystallization of diastereomers or diastereomeric salts, and the like. Certain compounds can exist as geometrical isomers, such as, for example, compounds with double-bonded substituents with geometrical isomers Z and E, and the present invention includes all such isomers, including certain isomers, for example the Z isomers, which are preferred. Also, certain compounds may contain substituents wherein there is restricted rotation and/or other geometric isomers are possible. For example, certain oxime substituents may exist in syn or anti configurations. The present invention includes all such configurations, including all possible hindered-rotational isomers, and other geometric isomers.

It will be appreciated by one skilled in the art that the proof or confirmation of the chemical structure of a compound provided by or used in the present invention can be demonstrated using at least one or more well-known and established, convergent methods including, but not limited to, for example: proton and/or carbon NMR spectroscopy, mass spectrometry, x-ray crystallography, chemical degradation, and the like.

One or more compound(s) of formula I or II or pharmaceutically acceptable salt(s) or prodrugs(s) thereof can be included in a composition, e.g., a pharmaceutical composition. In that respect, the present invention further provides a composition that includes an effective amount of at least one compound of formula I or II, which may be in the form of pharmaceutically acceptable salt(s) or prodrug(s) thereof and a pharmaceutically acceptable carrier. The composition of the present invention preferably includes a therapeutically or prophylactically effective amount of at least one Ras-inhibitory compound of formula I or II. The therapeutically or prophylactically effective amount can include an amount that produces a therapeutic or prophylactic response in a patient to whom a compound or composition of the present invention is administered. A therapeutically or prophylactically effective amount can include, for example, a Ras-inhibitory and/or an anticancer effective amount.

The composition of the present invention can further include a therapeutically or prophylactically effective amount of at least one additional compound other than a compound of formula I or II, which may or may not be another Ras-inhibitory compound, and may be an anticancer compound. When the additional compound is a Ras-inhibitory compound other than a compound of formula I or II, it is preferably present in the composition in a Ras-inhibiting amount. When the additional compound is an anticancer compound in general, it is preferably present in the composition in an anticancer effective amount.

The composition of the present invention can be produced by combining one or more compound(s) of formula I or II with an appropriate pharmaceutically acceptable carrier, and can be formulated into a suitable preparation, which may include, for example, preparations in solid, semi-solid, liquid or gaseous forms such as tablets, capsules, powers, granules, ointments, solutions, suppositories, injections, inhalants, and aerosols, and other formulations known in the art for their respective routes of administration. In pharmaceutical dosage forms, a compound of formula I or II can be used alone or in appropriate association, as well as in combination, with other pharmacologically active compounds, including other compounds, e.g., other Ras-inhibitory compounds, as described herein.

Any suitable pharmacologically or physiologically acceptable carrier can be utilized. The following methods and carriers are merely exemplary and are in no way limiting. In the case of oral preparations, a compound of formula I or II can be administered alone or in combination with a therapeutically or prophylactically effective amount of at least one other compound. The active ingredient(s) can be combined, if desired, with appropriate additives to make tablets, powders, granules, capsules or the like.

Suitable additives can include, for example, lactose, mannitol, corn starch or potato starch. Suitable additives also can include binders, for example crystalline cellulose, cellulose derivatives, acacia, or gelatins; disintegrants, for example, corn starch, potato starch or sodium carboxymethylcellulose; or lubricants such as talc or magnesium stearate. If desired, other additives such as, for example, diluents, buffering agents, moistening agents, preservatives, and/or flavoring agents, and the like, can be included in the composition.

The Ras-inhibitory compounds used in accordance with the present invention can be formulated into a preparation for injection or infusion by dissolution, suspension, or emulsification in an aqueous or non-aqueous solvent, such as vegetable oil, synthetic aliphatic acid glycerides, esters of higher aliphatic acid or propylene glycol (if desired, with conventional additives such as solubilizers isotonic agents, suspending agents, emulsifying agents, stabilizers, and preservatives).

The compounds of formula I and II also can be made into an aerosol formulation to be administered by inhalation. Such aerosol formulations can be placed into pressurized acceptable propellants such as dichlorodifluoromethane, propane, nitrogen, and the like.

The compounds can be formulated into suppositories by admixture with a variety of bases such as emulsifying bases or water-soluble bases. The suppository formulations can be administered rectally, and can include vehicles such as cocoa butter, carbowaxes, and polyethylene glycols, which melt at body temperature but are solid at room temperature.

Unit dosage forms for oral or rectal administration such as syrups, elixirs, and suspensions can be provided wherein each dosage unit, e.g., teaspoonful, tablet, or suppository contains a predetermined amount of the composition containing the compound of formula I or II. Similarly, unit dosage forms for injection or intravenous administration can comprise a composition as a solution in sterile water, normal saline, or other pharmaceutically acceptable carrier.

The term "unit dosage form" as used herein refers to physically discrete units suitable as unitary dosages for human and animal subjects, each unit containing a predetermined quantity of at least one compound(s) of formula I or II (alone, or if desired, with another therapeutic or prophylactic agent). The unit dosage can be determined by methods known to those of skill in the art, for example, by calculating the amount of active ingredient sufficient to produce the desired effect in association with a pharmaceutically acceptable carrier. The specifications for the unit dosage forms that can be used in accordance with the present invention depend on the particular effect to be achieved and the particular pharmacodynamics associated with the compound(s) in the individual host.

Pharmaceutically acceptable carriers, for example, vehicles, adjuvants, excipients, or diluents, are accessible to those of skill in the art and are typically available commercially. One skilled in the art can easily determine the appropriate method of administration for the exact formulation of the composition being used. Any necessary adjustments in dose can readily be made by an ordinarily skilled practitioner to address the nature or severity of the condition being treated. Adjustments in dose also can be made on the basis of other factors such as, for example, the individual patient's overall physical health, sex age, prior medical history, and the like.

The compounds of formula I and II can be utilized in a variety of therapeutic and prophylactic (disease preventing) applications, and also in certain non-therapeutic or non-prophylactic applications. It will be appreciated that one or more of these compounds can be used, for example, as a control in diagnostic kits, bioassays, or the like. Preferably the method of the present invention is applied therapeutically or prophylactically, for example, toward treatment or prevention of cancer or toward treatment or prevention of a condition (e.g. an abnormal condition or disease) treatable by the inhibition of Ras-mediated biological process(es). The compounds of formula I and II can be administered alone, or in combination with a therapeutically or prophylactically effective amount of at least one additional compound other than a compound of formula I or II.

Accordingly, the present invention further provides a method of therapeutically or prophylactically treating a condition treatable by the inhibition of one or more Ras-mediated biological processes, which method includes administering to a patient a Ras-inhibiting amount of at least one Ras-inhibitory compound of formula I or II. More particularly, the present invention provides a method of therapeutically or prophylactically treating a condition treatable by the inhibition of one or more Ras-mediated biological processes, which includes administering a Ras-inhibiting effective amount of at least one compound of formula I or II.

A number of conditions can be treated in accordance with the method of the present invention. The compounds of formulas I and II, and their compositions can be used medically to regulate biological phenomena, including but not limited to such Ras-modulated processes as tumor cell growth, proliferation, survival, invasion and metastasis, as well as resistance to chemotherapy, other molecularly targeted therapeutics, and radiation. The compounds of formula I and II are therefore useful in the treatment of diseases and conditions that can be controlled by the inhibition of Ras-mediated cellular functions. Such diseases include, for example, diseases wherein hyperactive Ras (e.g., including mutant Ras) is implicated; such diseases prominently include cancer, among others. Compounds of formula I or II can be expected to have efficacious actions in patients with cancer, especially in patients whose cancers have underlying hyperactive, over-expressed or mutant Ras-mediated pathological processes that are inhibited by a compound(s) of formula I or II. Other aberrant Ras-mediated diseases or conditions that are expected to be treatable or preventable by administration of Ras-inhibiting amounts of compound(s) of formula I or II include for example, neurofibromatosis and Costello syndrome. In the instance of cancer particularly, compound(s) of formula I or II may promote broader sensitivity of cancer to other drugs and/or radiation therapy by inhibiting the ability of cancer cells to develop or express resistance to such drugs and/or radiation therapy making possible the effective chemotherapeutic and/or radiotherapeutic treatment of cancer.

In accordance with an embodiment of the method of the present intervention, it is preferred that a Ras-inhibiting effective amount is used. In that regard, it is preferred that the Ras-inhibiting amount is effective to inhibit one or more conditions selected from the group consisting of tumor cell growth, proliferation, survival, invasion and metastasis, as well as resistance to chemotherapy, other molecularly targeted therapeutics, and radiation.

The method of the present invention further includes administering a Ras-inhibiting effective amount of at least one additional compound other than a compound of formula I or II. In some instances, the method of the present invention can be made more effective by administering one or more other Ras-inhibitory compound(s), along with a compound of formula I or II. One or more Ras-inhibitory compound(s) of formula I or II also can be co-administered in combination with an anticancer agent other than a compound of formula I or II, for example, to cause anticancer chemotherapy-resistant and/or radiation-resistant tumor cells to become chemotherapy-sensitive and/or radiation-sensitive and/or to inhibit de novo the development of cancer cell resistance to the anticancer agent and/or to cancer cell resistance to radiation treatment.

In accordance with an embodiment of the method, the patient is pre-selected by utilizing an assay of said patient's tissue, blood or tumor for an abnormal, mutant or hyperactive ras gene or Ras protein, or an aberrant Ras-mediated biological process.

In accordance with the methods of the present invention, one or more compounds of formula I or II can be administered by any suitable route including, for example, oral or parenteral, including intravenous, subcutaneous, intraarterial, intraperitoneal, ophthalmic, intramuscular, buccal, rectal, vaginal, intraorbital, intracerebral, intracranial, intraspinal, intraventricuclar, intrathecal, intracisternal, intracapsular, intrapulmonary, intranasal, transmucosal, transdermal, or via inhalation. For example, one or more compound(s) of formula I or II can be administered as a solution that is suitable for intravenous injection or infusion, or can be administered as a tablet, a capsule, or the like, in any other suitable composition or formulation as described herein. Accordingly, there is a wide variety of suitable formulations of the pharmaceutical composition of the present invention. The formulations may also be applied topically.

The Ras-"inhibiting-effective amount" as utilized in accordance with an embodiment of the composition and method of the present invention, includes the dose necessary to achieve a Ras-"inhibiting effective level" of the active compound in an individual patient. The Ras-inhibiting-effective amount can be defined, for example, as that amount required to be administered to an individual patient to achieve in said patient a Ras-inhibiting-effective blood or tissue level, and/or intracellular target-inhibiting level of a compound of formula I or II to cause the desired medical treatment.

By way of example and not intending to limit the invention, the dose of the pharmaceutically active agent(s) described herein for methods of preventing or treating a disease or disorder can be, in embodiments, about 0.001 to about 1 mg/kg body weight of the subject being treated per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. In certain embodiments, the dose of the pharmaceutically active agent(s) described herein can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

When the effective level is used as the preferred endpoint for dosing, the actual dose and schedule can vary depending, for example, upon inter-individual differences in pharmacokinetics, drug distribution, metabolism, and the like. The effective level also can vary when one or more compound(s) of formula I or II are used in combination with other therapeutic agents, for example, one or more additional anticancer compound(s), or a combination thereof. Moreover, the effective level can vary depending upon the particular disease (e.g., cancer or neurofibromatosis) or biological process (e.g., tumor cell growth, proliferation, survival, invasion and metastasis, as well as resistance to chemotherapy, other molecularly targeted therapeutics, and radiation) for which treatment is desired. Similarly, the effective level can vary depending on whether the treatment is for therapy or prevention of a particular disease such as, for example, cancer.

Compounds of formula I and II can be expected to be broadly efficacious anticancer agents, which will inhibit or destroy human solid tumors, and as well non-solid cancer such as leukemias and certain lymphomas. Solid tumors may include particularly those tumors where ras gene mutations are highly prevalent, such as pancreatic cancer, lung cancer and colon cancer, as well as diverse other solid tumors such as, for example, melanoma, ovarian cancer, renal cancer, prostate cancer, head and neck cancer, endocrine tumors, uterine cancer, breast cancer, sarcomas, gastric cancer, hepatic cancer, esophageal cancer, central nervous system (e.g., brain) cancer, hepatic cancer, germline cancer, and the like.

In a preferred embodiment of the present invention, patients who are most likely to have a favorable response to a Ras-inhibitory compound of formula I or II can be preselected, prior to said treatment with said compound, by assaying said patient's blood, tissues or tumor for the presence ras gene mutations and/or abnormal Ras proteins and/or aberrant Ras-mediated biological function(s), using assay procedures (including use of commercially available assay kits) well-known to those of ordinary skill in the art.

Accordingly, the present invention further provides a method of therapeutically or prophylactically treating cancer, which method comprises administering to a patient in need thereof an anticancer effective amount of at least one Ras-inhibitory compound(s) of formula I or II. The anticancer effective amount can be determined, for example, by determining an amount to be administered effective to produce a Ras-inhibiting-effective blood or tissue level and/or intracellular target-inhibiting "effective level" in the subject patient. The effective level can be chosen, for example, as that blood and/or tissue level (e.g., $10^{-12}$-$10^{-6}$ M from examples that follow) effective to inhibit the proliferation of tumor cells in a screening assay. Similarly, the effective level can be determined, for example, on the basis of the blood, tissue or tumor level in a patient that corresponds to a concentration of a therapeutic agent that effectively inhibits the growth of a human cancer in any assay that is clinically predictive of anticancer activity. Further, the effective level can be determined, for example based on a concentration at which certain markers of cancer in a patient's blood or tumor tissue (e.g., mutant or hyperactive ras gene(s) and/or Ras protein(s) and/or aberrant Ras-mediated biological pathway(s)) are inhibited by a particular compound that inhibits cancer. Alternatively, the effective level can be determined, for example, based on a concentration effective to slow or stop the growth of a patient's cancer, or cause a patient's cancer to regress or disappear, or render a patient asymptomatic to a particular cancer, or improve a cancer patient's subjective sense of condition. The anticancer effective level can then be used to approximate (e.g., by extrapolation) or even to determine precisely, the level which is required clinically to achieve a Ras-inhibiting-effective blood, tissue, tumor and/or intracellular level to cause the desired medical treatment. It will be appreciated that the determination of the therapeutically effective amount clinically required to effectively inhibit Ras-mediated processes also requires consideration of other variables that can influence the effective level, as discussed herein. When a fixed effective amount is used as a preferred endpoint for dosing, the actual dose and dosing schedule for drug administration can vary for each patient depending upon factors that include, for example, inter-individual differences in pharmacokinetics, drug absorption, drug disposition and tissue distribution, drug metabolism, drug excretion, whether other drugs are used in combination, or other factors described herein that influence the effective level.

One skilled in the art and knowing and understanding the disclosures of the present invention can readily determine the appropriate dose, schedule, or method of administering a particular formulation, in order to achieve the desired effective level in an individual patient. Given the disclosures herein, one skilled in the art also can readily determine and use an appropriate indicator of the effective level of the compound(s) of formula I and II. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, if the compound in question has antitumor activity, by direct or indirect observations, such as, for example, observing the shrinkage, slowing or cessation of growth or spreading of a tumor in a cancer patient. There are many references to the art that describe the protocols used in administering and monitoring responses to active compounds in a patient in need thereof. For example, drug-appropriate protocols used in the administration of different types of anticancer agents to patients are described in "*Cancer Chemotherapy and Biotherapy: Principles and Practice*" eds. Chabner and Longo, Lippincott, Williams and Wilkins (2011), and citations therein.

The present inventive method of therapeutically or prophylactically treating cancer further includes administering an anticancer effective amount of at least one additional compound other than a compound of formula I or II. For example, one or more compound(s) of formula I or II can be co-administered with an anticancer agent, and/or can be co-administered with radiation therapy, in which case the effective level is the level needed to inhibit or reverse the ability of the cancer to develop resistance to the anticancer agent and/or to the radiation therapy, respectively.

Examples of anticancer compounds include reversible DNA binders, DNA alkylators, and DNA strand breakers. Examples of suitable reversible DNA binders include topetecan hydrochloride, irinotecan (CPT11-Camptosar), rubitecan, exatecan, nalidixic acid, TAS-103, etoposide, acridines (e.g., amsacrine, aminocrine), actinomycins (e.g., actinomycin D), anthracyclines (e.g., doxorubicin, daunorubicin), benzophenainse, XR 11576/MLN 576, benzopyridoindoles, Mitoxantrone, AQ4, Etopside, Teniposide, (epipodophyllotoxins), and bisintercalating agents such as triostin A and echinomycin.

Examples of suitable DNA alkylators include sulfur mustard, the nitrogen mustards (e.g., mechlorethamine), chlorambucil, melphalan, ethyleneimines (e.g., triethylenemelamine, carboquone, diaziquone), methyl methanesulfonate, busulfan, CC-1065, duocarmycins (e.g., duocarmycin A, duocarmycin SA), metabolically activated alkylating agents such as nitrosoureas (e.g., carmustine, lomustine, (2-chloroethyl)nitrosoureas), triazine antitumor drugs such as triazenoimidazole (e.g., dacarbazine), mitomycin C, leinamycin, and the like.

Examples of suitable DNA strand breakers include doxorubicin and daunorubicin (which are also reversible DNA binders), other anthracyclines, belomycins, tirapazamine, enediyne antitumor antibiotics such as neocarzinostatin, esperamicins, calicheamicins, dynemicin A, hedarcidin, C-1027, N1999A2, esperamicins, zinostatin, and the like.

Examples of anticancer agents include abarelix, aldesleukin, alemtuzumab, altretamine, amifostine, aminoglutethimide, anastrazole, arsenic trioxide, asparaginase, azacitidine, azathioprine, BCG vaccine, bevacizumab, bexarotene, bicalutamide, bleomycin sulfate, bortezomib, bromocriptine, busulfan, capecitabine, carboplatin, carmustine, cetuximab, chlorambucil, chloroquine phosphate, cladribine, cyclophosphamide, cyclosporine, cytarabine, dacarbazine, dactinomycin, daunorubicin hydrochloride, daunorubicin citrate liposomal, dexrazoxane, docetaxel, doxorubicin hydrochloride, doxorubicin hydrochloride liposomal, epirubicin hydrochloride, estramustine phosphate sodium, etoposide, estretinate, exemestane, floxuridine, fludarabine phosphate, fluorouracil, fluoxymesterone, flutamide, fulvestrant, gefitinib, gemcitabine hydrochloride, gemtuzumab ozogamicin, goserelin acetate, hydroxyurea, idarubicin hydrochloride, ifosfamide, imtinib mesylate, interferon alfa-2a, interferon alfa-2b, irinotecan hydrochloride trihydrate, letrozole, leucovorin calcium, leuprolide acetate, levamisole hydrochloride, lomustine, lymphocyte immune anti-thymocyte globulin (equine), mechlorethamine hydrochloride, medoxyprogestone acetate, melphalan, mercaptopurine, mesna, methotrexate, mitomycin, mitotane, mitoxantrone hydrochloride, nilutamide, oxaliplatin, paclitaxel, pegaspargase, pentostatin, plicamycin, porfimer sodium, procarbazine hydrochloride, streptozocin, tamoxifen citrate, temozolomide, teniposide, testolactone, testosterone propionate, thioguaine, thiotepa, topotecan hydrochloride, tretinoin, uracil mustard, valrubicin, vinblastine sulfate, vincristine sulfate, and vinorelbine.

Suitable forms of radiation therapy include, for example, all forms of radiation therapy approved for commercial use in the United States, and those forms that will become approved in the future, for which radiation resistance thereto can be controlled by a Ras-inhibitory compound of formula I or II.

In accordance with an embodiment of the methods of the present invention, prophylaxis includes inhibition as described herein, e.g., inhibition of the growth or proliferation of cancer cells, or inhibition of aberrant Ras-mediated cellular functions. The inhibition can be, but need not be, 100% inhibition in order to be prophylactically effective, and a clinically desirable benefit can be realized with less than 100% inhibition.

The particular Ras-inhibitory compound(s) of formula I or II used in accordance with the present invention can be selected based upon the potency and/or selectivity for inhibiting Ras-mediated cellular processes, as assessed by in vitro or in vivo assays, and/or based on other pharmacological, toxicological, pharmaceutical or other pertinent considerations that are well-known to those skilled in the art. Routine methods for the specific bioassay, quantitation and comparisons of Ras-inhibitory inhibitory and other biological activities and properties of compounds of formula I and II in various tissues, cells, organelles and other preparations, as well as in vivo testing in animals are well-documented in the literature (e.g., see Teicher and Andrews (eds.), Anticancer Drug Development Guide, Humana (2004), and various authors and chapters therein). More specific illustrations of these and other details pertinent to enablement of the present invention are provided in the examples which follow.

The following examples further illustrate the invention but, of course, should not be construed as in any way limiting its scope.

EXAMPLE 1

This example illustrates the synthesis of a compound in accordance with an embodiment of the invention: (Z)-2-(5-fluoro-1-(4-hydroxy-3,5-dimethoxybenzylidene)-2-methyl-1H-inden-3-yl)-N-(furan-2-ylmethyl)acetamide (007).

(A) p-fluoro-α-methylcinnamic acid: p-Fluorobenzaldehyde (200 g, 1.61 mol), propionic anhydride (315 g, 2.42 mol) and sodium propionate (155 g, 1.61 mol) in a 1 L three-necked flask in an atmosphere of argon was stirred in an oil bath to 140° C. for 36 hours. The clear solution was cooled to 100° C. and poured into 8 L of water. The precipitate was collected and dissolved by adding potassium hydroxide to 2 L of ice water to pH 12. The aqueous solution was extracted with ether, and the extracts washed with potassium hydroxide solution (200 mL×2). The combined aqueous solution was acidified with concentrated HCl. The precipitate was collected by filtration, washed with water, ethanol and hexane, dried under air to give p-fluoro-α-methylcinnamic acid, which was used for next step reaction without further purification.

(B) p-Fluoro-α-methylhydrocinnamic acid: A 2 L catalytic hydrogenation flask containing p-fluoro-α-methylcinnamic acid (180 g, 0. 987 mol), 5%-Pd/C (1.2 g) and 1.2 L ethanol was flushed with argon and warmed to 65-70° C. The mixture was treated with hydrogen (40 psi) until the hydrogen uptake ceases (about 30 min). The catalyst was filtered off, and the filtrate was concentrated in vacuum to give p-fluoro-α-methylhydrocinnamic acid as an oil.

(C) 5-fluoro-2-methylindanone: Polyphosphoric acid (PPA 85%, 650 g) was warmed in a 80° C. water bath for 1 h, then transferred to a 1 L 3-necked flask equipped with a mechanical stirrer, a dropping funnel, and a thermometer. The flask was warmed in a 70° C. oil bath and p-fluoro-α-methylhydrocinnamic acid (93.2 g, 0 5 mol) was added in about 5 minutes with stirring. The temperature was gradually raised to 90° C., and kept there for about 30 min. The reaction mixture was poured into 2 L of ice water, the aqueous layer extracted with ether, and the solution washed twice with saturated sodium chloride solution, 5% $Na_2CO_3$ solution, water, dried over $Na_2SO_4$, and then concentrated to give a milky oil. The oil was dissolved in 100 mL of methylene chloride and 200 mL of hexane, and the solution was loaded to a dry-packed silica gel flash column (800 g of TLC grade silica gel tightly packed in a 2 L fritted funnel, vacuum), eluted with 5% ether-hexane to give 5-fluoro-2-methylindanone as a clear oil.

(D) 5-fluoro-2-methylindenyl-3-acetic acid: A mixture of 5-fluoro-2-methylindanone (184 g, 1.12 mol), cyanoacetic acid (105 g, 1.23 mol), acetic acid (130 g), and ammonium acetate (34 g) in dry toluene (about 600 ml) was refluxed for 48 to 72 hours, and the liberated water/acetic acid was collected in a Dean Stark trap. To the cooled reaction mixture was added 600 mL of methylene chloride, the solution washed with water (200 mL×3), the organic layer concentrated, and the residue treated with 150 g of potassium hydroxide in 300 ml of ethanol and 200 ml of water. The mixture was refluxed overnight under nitrogen, the ethanol removed under vacuum, 500 ml water added, the aqueous solution washed well with ether and then boiled with charcoal. The aqueous filtrate was acidified to pH 2 with 50% hydrochloric acid, and extracted with methylene chloride (300 mL×3). The solvent was evaporated, and the residue treated with acetone in a sonicator bath until precipitate formed. The mixture was stored in a −20° C. freezer overnight, and the precipitate collected by filtration. The procedure gave 5-fluoro-2-methylindenyl-3-acetic acid as a colorless solid (mp 164-166° C.).

(E) (Z)-2-(5-fluoro-1-(4-hydroxy-3,5-dimethoxybenzylidene)-2-methyl-1H-inden-3-yl)acetic acid: The 5-fluoro-2-methyl-3-indenylacetic acid (0.54 g, 2.62 mmol), 4-acetoxy-3,5-dimethoxybenzaldehyde (0.60 g, 2.67 mmol) and potassium butoxide (0.69 g, 7.7 mmol) in DMSO (6 ml) were stirred in a microwave synthesizer at 75° C. under argon for 2 h. After cooling, the reaction mixture was poured into 50 ml of ice-water, and was acidified with 2N hydrochloric acid. The mixture was extracted with methylene chloride (25 mL×2), the combined organic layer washed with water (25 mL×2), and concentrated. The residue was purified on a silica gel column three times to produce the titled compound (E, 117 mg) as a yellow/orange solid.

(F) (Z)-2-(5-fluoro-1-(4-hydroxy-3,5-dimethoxybenzylidene)-2-methyl-1H-inden-3-yl)-N-(furan-2-ylmethyl) acetamide (007): The (Z)-2-(5-fluoro-1-(4-hydroxy-3,5-dimethoxybenzylidene)-2-methyl-1H-inden-3-yl)acetic acid (120 mg, 0.324 mmol), 1,1'-Carbonyldiimidazole (100 mg, 0.61 mmol) in 5 mL of anhydrous methylene chloride was stirred for 30 min at room temperature. Furfuryl amine (100 μL, 1.13 mmol) was added, the reaction mixture stirred for 2 h, and quenched with 1 ml of 30% potassium hydroxide solution, which was diluted with 25 mL of methylene chloride, neutralized with 2 mL of acetic acid, washed with water (20 mL×3), dried with sodium sulfate, then concentrated. The residue was purified with silica gel column, eluted with hexane/acetone. The major yellow fraction was collected and after concentration the residue (120 mg) was stored under argon in a freezer, and after 2 weeks crystals formed. The mixture containing the crystals was suspended in 2 mL of ethyl ether and 3 mL of hexane, treated with sonicator for 1 h, then stored in a −20° C. freezer overnight. The precipitate was collected by filtration, and the titled compound (007) was obtained as a yellow solid (41 mg).

EXAMPLE 2

This example illustrates the synthesis of another compound in accordance with an embodiment of the invention: (Z)-2-(5-methoxy-1-(4-hydroxy-3,5-dimethoxybenzylidene)-2-methyl-1H-inden-3-yl)-N-(furan-2-ylmethyl) acetamide (006).

(A) p-methoxy-α-methylcinnamic acid: p-Methoxybenzaldehyde (219 g, 1.61 mol), propionic anhydride (315 g, 2.42 mol) and sodium propionate (155 g, 1.61 mol) in a 1 L three-necked flask in an atmosphere of argon was stirred in an oil bath at 140° C. for 36 hours. The clear solution was cooled to 100° C., poured into 8 L of water, and the precipitate collected and dissolved by adding potassium hydroxide to 2 L of ice water to pH 12. The aqueous solution was extracted with ether, the extracts washed with potassium hydroxide solution (200 mL×2) and the combined aqueous solution acidified with concentrated HCl. The precipitate was collected by filtration, washed with water, ethanol and hexane, then dried over air to give p-methoxy-α-methylcinnamic acid (235 g) which was used for next step reaction without further purification.

(B) p-methoxy-α-methylhydrocinnamic acid: A 2 L catalytic hydrogenation flask containing p-methoxy-α-methylcinnamic acid (192 g, 1.00 mol), 5%-Pd/C (1.2 g) and 1.2 L ethanol was flushed with argon and warmed to 70° C. The mixture was treated with hydrogen (40 psi) until the hydrogen uptake ceased (about 30 min). The catalyst was filtered off, and the filtrate concentrated in vacuum to give p-methoxy-α-methylhydrocinnamic acid as an oil.

(C) 5-methoxy-2-methylindanone: Polyphosphoric acid (PPA 85%, 650 g) was warmed in a 60° C. water bath for 1 h, and transferred to a 1 L 3-necked flask equipped with a mechanical stirrer, a dropping funnel, and a thermometer. The flask was warmed to 50° C. in oil bath and p-methoxy-α-methylhydrocinnamic acid (96 g, 0.50 mol) was added in about 5 minutes with stirring. The temperature was gradually raised to 70° C. for about 15 min, and the solution was poured into 2 L of ice water. The aqueous layer was extracted with ether, and the solution was washed twice with saturated sodium chloride solution, 5% $Na_2CO_3$ solution, water, dried over $Na_2SO_4$, and then concentrated to give a milky oil. The oil was dissolved in 100 mL of methylene chloride and 200 mL of hexane, and applied to a dry-packed silica gel flash column (800 g of TLC grade silica gel tightly packed in a 2 L fritted funnel, vacuum), eluted with 5% ether-petroleum ether to give 6-methoxy-2-methylindanone as a clear oil.

(D) 5-methoxy-2-methylindenyl-3-acetic acid: A mixture of 6-methoxy-2-methylindanone (197 g, 1.12 mol), cyanoacetic acid (105 g, 1.23 mol), acetic acid (130 g), and ammonium acetate (34 g) in dry toluene (about 600 ml) was refluxed for 48 to 72 hours, until the liberated water collected in a Dean Stark trap ceased. To the cooled toluene reaction mixture was added 600 mL of methylene chloride. The solution was washed with water (200 mL×3), the organic layer concentrated, and the residue treated with 150 g of potassium hydroxide in 300 ml of ethanol and 200 ml of water. The mixture was refluxed overnight under nitrogen, the ethanol removed under vacuum, 500 ml water added, the aqueous solution washed well with ether and then boiled with charcoal. The aqueous filtrate was acidified to pH 2 with 50% hydrochloric acid, extracted with methylene chloride (300 mL×3), solvent evaporated, and the residue treated with acetone in a sonicator bath until a precipitate formed. The mixture was stored at −20° C. overnight, and the precipitate collected by filtration. The procedure gave 5-methoxy-2-methylindenyl-3-acetic acid as a colorless solid (mp 164-166° C.).

(E) (Z)-2-(5-methoxy-1-(4-hydroxy-3,5-dimethoxybenzylidene)-2-methyl-1H-inden-3-yl)acetic acid: 5-methoxy-2-methyl-3-indenylacetic acid (0.50 g, 2.29 mmol), 4-acetoxy-3,5-dimethoxybenzaldehyde (0.60 g, 2.67 mmol) and potassium butoxide (1.0 g, 8.9 mmol) in anhydrous DMSO (5 ml) and pyridine (10 mL) were stirred at 95° C. under argon for 1 h. The reaction mixture was cooled to 65° C. 1.0 mL of methanol was added and stirred for 30 min. After cooling, the mixture was poured into 50 ml of ice-water, acidified with 2N hydrochloric acid, and extracted with methylene chloride (25 mL×2), and the combined organic layer washed with water (25 mL×2), and concentrated. The residue was purified on a silica gel column twice, the first eluted with methylene chloride/methanol, followed by washing with hexane, acetone/acetic acid, to produce the title compound (E, 152 mg) as a yellow/orange solid.

(F) (Z)-2-(5-methoxy-1-(4-hydroxy-3,5-dimethoxybenzylidene)-1H-inden-3-yl)-N-(furan-2-ylmethyl) acetamide (006): (Z)-2-(5-methoxy-1-(4-hydroxy-3,5-dimethoxybenzylidene)-2-methyl-1H-inden-3-yl)acetic acid (123 mg, 0.324 mmol), 1,1'-carbonyldiimidazole (100 mg, 0.61 mmol) in 5 mL of anhydrous methylene chloride was stirred for 30 min at room temperature, furfuryl amine (100 µL, 1.13 mmol) was added, and the reaction mixture stirred for 2 h, then quenched with 1 ml of 30% potassium hydroxide solution. The solution was diluted with 25 mL of methylene chloride, neutralized with 2 mL of acetic acid, washed with water (20 mL×3), dried with sodium sulfate, and concentrated. The residue was purified over silica gel, eluted with hexane/acetone, and the major yellow fraction was collected. After concentrating, the residue was stored in a freezer under argon until a crystal seed formed (~2 weeks). The mixture was suspended in 2 mL of ethyl ether and 3 mL of hexane, treated with sonicator for 1 h, then stored in a −20° C. freezer overnight. The precipitate was collected by filtration. The title compound (006) was obtained as a yellow solid (36 mg).

EXAMPLE 3

This example illustrates the synthesis of compound (019): (Z)-2-(5-fluoro-1-(4-hydroxy-3,5-dimethoxybenzylidene)-2-methyl-1H-inden-3-yl)-N-((1-methyl-1H-pyrrol-2-yl)methyl)acetamide (019).

(Z)-2-(5-fluoro-1-(4-hydroxy-3,5-dimethoxybenzylidene)-2-methyl-1H-inden-3-yl)acetic acid (120 mg, 0.324 mmol) (see (E) under Example 1 above), and 1,1'-carbonyldiimidazole (100 mg, 0.61 mmol) in 5 mL of anhydrous methylene chloride was stirred for 30 min at room temperature. To the reaction mixture (1-methyl-1H-pyrrol-2-yl)methanamine (110 µL, 1.0 mmol) and 0.5 mL of pyridine were added. The mixture was stirred for 2 h, quenched with 1 ml of 30% potassium hydroxide solution, diluted with 25 mL of methylene chloride, neutralized with 2 mL of acetic acid, washed with water (20 mL×3) and dried with sodium sulfate. The organic layer was concentrated and the residue was purified with silica gel column eluted with hexane/acetone. The major yellow fraction was collected, and after concentration the residue was treated with acetone/hexane, sonicated for 1 h, and stored in a −20° C. freezer for 2 h. The precipitate was collected by filtration, and the titled compound (019) was obtained as a yellow solid (75 mg).

EXAMPLE 4

This example illustrates the synthesis of various other exemplary compounds of formula I. When the same synthetic approach (e.g., Scheme I) is used as illustrated in Examples 1-2, except in the acetamide-forming step (F) using the appropriate precursor acetic acid derivative reacted with one of the following amines to produce the corresponding amides (designated in parentheses): furfuryl amine (001, 008, 012, 013, 014, 016, 017, 020, 021); (1H-pyrrol-2-yl)methanamine (018, 022); and (1-methyl-1H-pyrrol-2-yl)methanamine (019).

EXAMPLE 5

This example illustrates synthesis of compound (029): (Z)-2-(5-fluoro-1-(4-mesyloxy-3,5-dimethoxybenzylidene)-2-methyl-1H-inden-3-yl)-N-(furan-2-ylmethyl)acetamide (029).

(Z)-2-(5-fluoro-1-(4-hydroxy-3,5-dimethoxybenzylidene)-2-methyl-1H-inden-3-yl)-N-(furan-2-ylmethyl)acetamide (007) (139 mg, 0.31 mmol), methanesulfonic anhydride (80 mg, 0.46 mmol) in 3 mL of anhydrous pyridine were stirred at 50° C. for 3 h. The reaction mixture was quenched with water, diluted with 20 mL of methylene chloride, the organic solution washed with 10 mL water three times, and concentrated. The residue was purified on a silica gel column, eluted with hexane/acetone. The major yellow fraction was collected and recrystallized from dichloromethane and hexane to give the titled compound (029) as a yellow solid (78 mg).

EXAMPLE 6

This example illustrates the synthesis of another exemplary compound of formula I, specifically (Z)—N-(2-(dimethylamino)ethyl)-2-(5-fluoro-1-(furan-2-ylmethylene)-2-methyl-1H-inden-3-yl)acetamide (026).

(A) (Z)-2-(5-fluoro-1-(furan-2-ylmethylene)-2-methyl-1H-inden-3-yl)acetic acid: 5-Fluoro-2-methyl-3-indenylacetic acid (0.50 g, 2.29 mmol), 2-furaldehyde (256 mg, 2.67 mmol) and sodium methoxide (0.40 g) in 5 mL of anhydrous methanol were treated with microwave synthesizer at 85° C. under argon for 1 h. The reaction mixture was cooled to room temperature, concentrated, and acidified with acetic acid. The mixture was dissolved in methylene chloride (35 mL), washed with water (25 mL×2), and concentrated. The residue was purified on a silica gel column eluted with hexane and acetone/acetic acid. The titled compound (A, 463 mg) was obtained as a yellow solid after crystallization from ethyl acetate/hexane.

(B) (Z)—N-(2-(dimethylamino)ethyl)-2-(5-fluoro-1-(furan-2-ylmethylene)-2-methyl-1H-inden-3-yl)acetamide (026). (Z)-2-(5-fluoro-1-(furan-2-ylmethylene)-2-methyl-1H-inden-3-yl)acetic acid (142 mg, 0.500 mmol) and 1,1'-carbonyldiimidazole (100 mg, 0.61 mmol) in 5 mL of anhydrous methylene chloride was stirred for 30 min at room temperature. To the solution was added 2-N,N-dimethylaminoethylamine (100 µL, 1.13 mmol), followed by stirring for 45 min. The reaction mixture was quenched with 1 ml of 30% potassium hydroxide solution, diluted with 25 mL of methylene chloride, washed with water (20 mL×3), dried over sodium sulfate, and concentrated. The residue was purified over silica gel eluted with methylene chloride/methanol. The major yellow fraction was collected and recrystallized from acetone/ethyl ether. The title compound (026) was obtained as a yellow solid (152 mg).

EXAMPLE 7

This example illustrates the synthesis of an exemplary prodrug of a compound of the invention, specifically (Z)-2-(5-fluoro-1-(4-formoxy-3,5-dimethoxybenzylidene)-2-methyl-1H-inden-3-yl)-N-(furan-2-ylmethyl)acetamide (002, which is a prodrug of 007).

In a sealed 25 mL round-bottom flask (Z)-2-(5-fluoro-1-(4-hydroxy-3,5-dimethoxybenzylidene)-2-methyl-1H-inden-3-yl)-N-(furan-2-ylmethyl)acetamide (007) (90 mg, 0.2 mmol) was dissolved in 4 mL of pyridine. Acetic anhydride (0.2 mL) was added. The solution was stirred at 50° C. for 2 h. The reaction mixture was quenched with ethanol, concentrated, and the residue purified on a silica gel column eluted with hexane/acetone. The major yellow fraction was collected, and recrystallized from acetone/hexane to give the title compound (002) as a yellow solid.

EXAMPLE 8

This example illustrates the synthesis of compound 030 in accordance with an embodiment of the invention: (S) and (R) (Z)-2-(5-methoxy-2-methyl-1-(3,4,5-trimethoxybenzylidene)-1H-inden-3-yl)-N-(1-methylpyrrolidin-3-yl)acetamide .

(A) (Z)-2-(5-methoxy-1-(3,4,5-trimethoxybenzylidene)-2-methyl-1H-inden-3-yl)acetic acid. To a 500 mL round-bottom flask containing 5-methoxy-2-methylindenyl-3-acetic acid (Example 2D) (18.0 g, 0.083 mmol), 3,4,5-trimethoxybenzaldehyde (22 g, 0.112 mole), sodium methoxide (14 g, 0.259 mole), 300 mL of anhydrous methanol was added. The flask was securely sealed with a septum, and the reaction mixture was stirred in an oil bath at 80-85° C. for 5 h. The reaction mixture was cooled in a freezer for 2 h, the precipitate collected by filtration, and washed with acetone to give a yellow solid, which was then suspended in 500 mL of dichloromethane, neutralized with hydrochloric acid and washed with water (200 mL×3). The organic layer was concentrated, and the residue dissolved in 100 mL of acetone, followed by addition of 300 mL of hexane. The suspension was treated with sonication until a precipitate formed, then stored in freezer for 2 h, and the precipitate collected by filtration, washed with hexane, dried in vacuum to obtain the titled compound as a bright yellow solid (22.5 g). Repeating the recrystallization procedure gave a second crop (2.2 g).

(B) (S)—(Z)-2-(5-methoxy-2-methyl-1-(3,4,5-trimethoxybenzylidene)-1H-inden-3-yl)-N-(1-methylpyrrolidin-3-yl)acetamide (S-030). (Z)-2-(5-methoxy-1-(3,4,5-trimethoxybenzylidene)-2-methyl-1H-inden-3-yl)acetic acid (20.90 g, 50 mmole), 1,1'-carbonyldiimidazole (10.0 g, 61 mmole) in 150 mL of anhydrous methylene chloride was stirred for 30 min at room temperature, (S)-1-methylpyrrolidin-3-amine (5.0 mL, 50 mmol) was added with 60 mL of anhydrous pyridine. The reaction mixture was stirred for 1 h at rt, then the temperature was brought up to 45° C., and stirred for 5 h. The reaction was quenched with 15 ml of 30% potassium hydroxide solution, the mixture diluted with 200 mL of methylene chloride, neutralized with acetic acid to pH 5, washed with water (150 mL×3), dried with sodium sulfate, and concentrated. The residue was purified over silica gel eluted with hexane/acetone/methanol, and the major yellow fraction was collected, treated with 1.1 eq. of hydrogen chloride (4M in dioxane), then concentrated. A 5 mg sample was diluted in the acetone/ethanol and left in the air until crystals formed on the glass wall. The crystal seed was added to the concentrated solution of acetone/ethanol at −20° C., stored for 48 h, and the precipitate was collected by filtration to give the titled compound as a yellow solid. Repeating the procedure give second and third crops (14.5 g).

(C) (R)—(Z)-2-(5-methoxy-2-methyl-1-(3,4,5-trimethoxybenzylidene)-1H-inden-3-yl)-N-(1-methylpyrrolidin-3-yl)acetamide (R-030). (Z)-2-(5-methoxy-1-(3,4,5-trimethoxybenzylidene)-2-methyl-1H-inden-3-yl)acetic acid (418 mg, 1.00 mmol), 1,1'-carbonyldiimidazole (100 mg, 1.21 mmol) in 8 mL of anhydrous methylene chloride was stirred for 30 min at room temperature, (R)-1-methylpyrrolidin-3-amine (0.11 mL, 1.1 mmol) was added with 1 mL of anhydrous pyridine. The reaction mixture was stirred for 1 h at rt, then the temperature was brought up to 45° C., and stirred for 3 h. The reaction was quenched with 1.5 ml of 30% potassium hydroxide solution, diluted with 20 mL of methylene chloride, neutralized with acetic acid to pH 5, washed with water (15 mL×3), dried with sodium sulfate, and concentrated. The residue was purified over silica gel eluted with hexane/acetone/methanol, and the major yellow fraction was collected. The major faction was treated with 1.1 eq. of hydrogen chloride (4M in dioxane), then concentrated. The residue was crystallized from acetone/ethanol stored at −20° C. for 48 h. The precipitate was collected by filtration to give the titled compound as a yellow solid (65 mg).

EXAMPLE 9

This example illustrates the synthesis of compound 031 in accordance with an embodiment of the invention: (RS)—(Z)-2-(5-fluoro-2-methyl-1-(3,4,5-trimethoxybenzylidene)-1H-inden-3-yl)-N-(1-methylpyrrolidin-3-yl)acetamide.

(A) (Z)-2-(5-fluoro-1-(3,4,5-trimethoxybenzylidene)-2-methyl-1H-inden-3-yl)acetic acid. To a 500 mL round-bottom flask containing 5-fluoro-2-methylindenyl-3-acetic acid (Example 1D) (18.0 g, 0.087 mmol), was added 3, 4,5-trimethoxybenzaldehyde (22 g, 0.112 mole), sodium methoxide (14 g, 0.259 mole) and 300 mL of anhydrous methanol. The flask was securely sealed with a septum, and the reaction mixture was stirred in an oil bath at 80-85° C. for 5 h, and cooled in a freezer for 2 h. The precipitate was collected by filtration, washed with acetone to give a yellow solid, which was then suspended in 500 mL of dichloromethane, neutralized with hydrochloric acid and washed with water (200 mL×3). The organic layer was concentrated, and the residue dissolved in 100 mL of acetone, followed by addition of 300 mL of hexane. The suspension was treated with sonication to initiate precipitate formation, stored in freezer for 2 h, the precipitate was collected by filtration, washed with hexane, and dried under vacuum to obtain the titled compound as a bright yellow solid (21.5 g).

(B) (RS)—(Z)-2-(5-fluoro-2-methyl-1-(3,4,5-trimethoxybenzylidene)-1H-inden-3-yl)-N-(1-methylpyrrolidin-3-yl)acetamide (031). (Z)-2-(5-fluoro -1-(3,4,5-trimethoxybenzylidene)-2-methyl-1H-inden-3-yl)acetic acid (20.40 g, 50 mmole), 1,1'-carbonyldiimidazole (10.0 g, 61 mmole) in 150 mL of anhydrous methylene chloride was stirred for 30 min at room temperature, then 1-methylpyrrolidin-3-amine (5.0 mL, 50 mmol) was added with 60 mL of anhydrous pyridine. The reaction mixture was stirred for 1 h at r, then the temperature was brought up to 45° C., and the mixture stirred for 5 h. The reaction was quenched with 15 ml of 30% potassium hydroxide solution, and then the solution was diluted with 200 mL of methylene chloride, neutralized with acetic acid to pH 5, washed with water (150 mL×3), dried with sodium sulfate, and concentrated. The residue was purified over silica gel eluted with hexane/acetone/methanol, and the major yellow fraction was collected, treated with 1.1 eq. of hydrogen chloride (4M in dioxane), and concentrated. The residue was recrystallized from acetone/ethanol to give the titled compound as a yellow solid (13.6 g).

EXAMPLE 10

This example illustrates the synthesis of compound 032 in accordance with an embodiment of the invention: (RS)—(Z)-2-(5-methoxy-2-methyl-1-(3,4,5-trimethoxybenzylidene)-1H-inden-3-yl)-N-(1-methylpiperidin-3-yl)acetamide.

(Z)-2-(5-methoxy-1-(3,4,5-trimethoxybenzylidene)-2-methyl-1H-inden-3-yl)acetic acid (see (A) under synthesis of 030, above) (209 mg, 0.50 mmole), and 1,1'-carbonyldiimidazole (100 mg, 0.61 mmole) in 10 mL of anhydrous methylene chloride was stirred for 30 min at room temperature, then 1-methylpiperidin-3-amine (0.6 mmol) was added with 1.0 mL of anhydrous pyridine. The reaction mixture was stirred for 1 h at rt, then the temperature was brought up to 45° C., and the mixture stirred for 2 h. The reaction was quenched with 1 ml of 30% potassium hydroxide solution, the solution diluted with 20 mL of methylene chloride, neutralized with acetic acid to pH 5, washed with water (10 mL×3), dried on sodium sulfate, and concentrated. The residue was purified over silica gel eluted with hexane/acetone/methanol, and the major yellow fraction was collected, treated with 0.2 mL of hydrogen chloride (4M in dioxane), and concentrated. The residue was recrystallized from acetone/ethanol to give the titled compound as a yellow solid (101 mg).

EXAMPLE 11

This example illustrates synthesis of compound 033 in accordance with an embodiment of the invention: (RS)—(Z)-2-(5-fluoro-2-methyl-1-(3,4,5-trimethoxybenzylidene)-1H-inden-3-yl)-N-(1-methylpiperidin-3-yl)acetamide.

(Z)-2-(5-fluoro-1-(3,4,5-trimethoxybenzylidene)-2-methyl-1H-inden-3-yl)acetic acid (see (A) under synthesis of 031, above) (204 mg, 0.50 mmol), and 1,1'-carbonyldiimidazole (100 mg, 0.61 mmole) in 10 mL of anhydrous methylene chloride was stirred for 30 min at room temperature, then 1-methylpiperidin-3-amine (0.6 mmol) was added with 1.0 mL of anhydrous pyridine. The reaction mixture was stirred for 1 h at rt, then the temperature was brought up to 45° C., and the mixture stirred for 2 h. The reaction was quenched with 1 ml of 30% potassium hydroxide solution, and the solution was diluted with 20 mL of methylene chloride, neutralized with acetic acid to pH 5, washed with water (10 mL×3), dried on sodium sulfate, and concentrated. The residue was purified over silica gel eluted with hexane/acetone/methanol, and the major yellow fraction was collected, treated with 0.2 mL of hydrogen chloride (4M in dioxane), and concentrated. The residue was recrystallized from acetone/ethanol to give the titled compound as a yellow solid (86 mg).

EXAMPLE 12

This example illustrates synthesis of additional exemplary compounds of the present invention, particularly compounds 130, 131, 132, 133, 134, 135, 138, 139, 141, 143, 144, 145, 151, 152 and 155 (the synthesis of 154 was illustrated previously herein, under Scheme III). These compounds were chosen to further illustrate and reinforce that extensive variations in substituents on the aryl and heteroaryl rings, and variations of E, R' and R" can be achieved readily using methods well known to those of ordinary skill in the art. The synthesis schemes below all start with the key intermediate, the desired substituted or unsubstituted indenyl acetic acid, synthesis of which is illustrated in detail in previous examples herein.

Synthesis of compound 130:

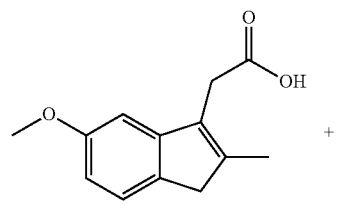

+

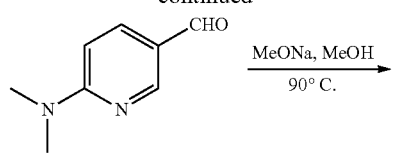

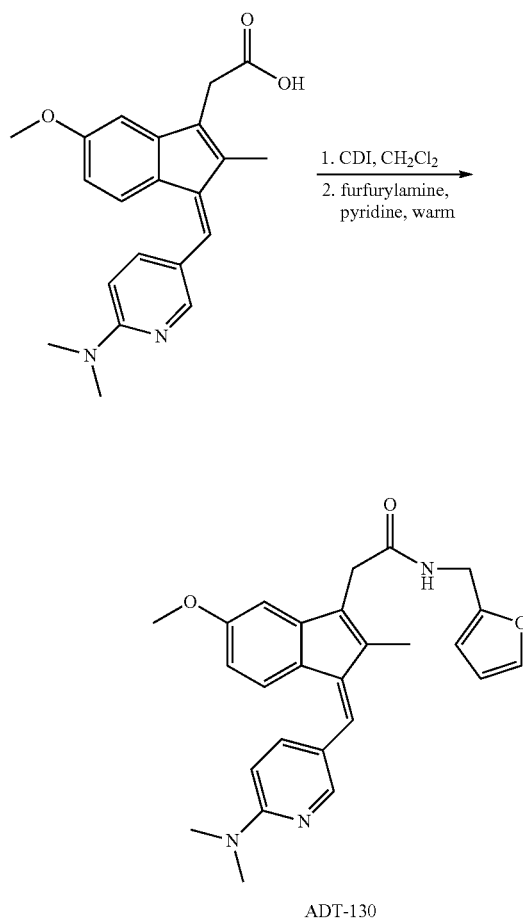

Synthesis of compound 131:

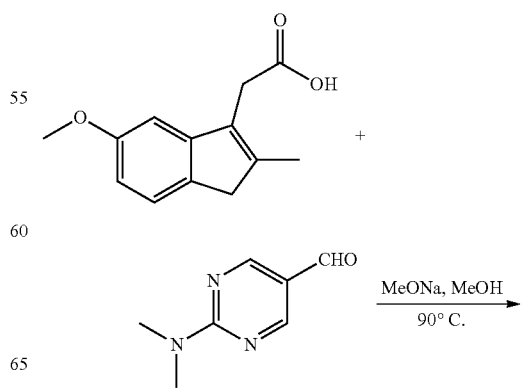

121
-continued
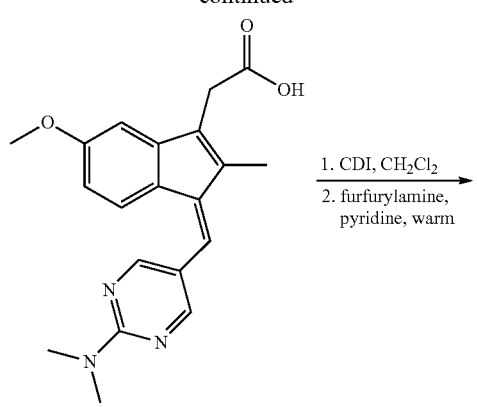
1. CDI, CH$_2$Cl$_2$
2. furfurylamine, pyridine, warm
122
-continued
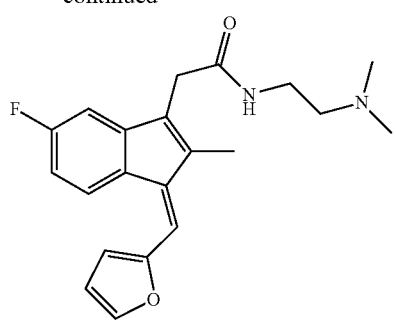
ADT-132
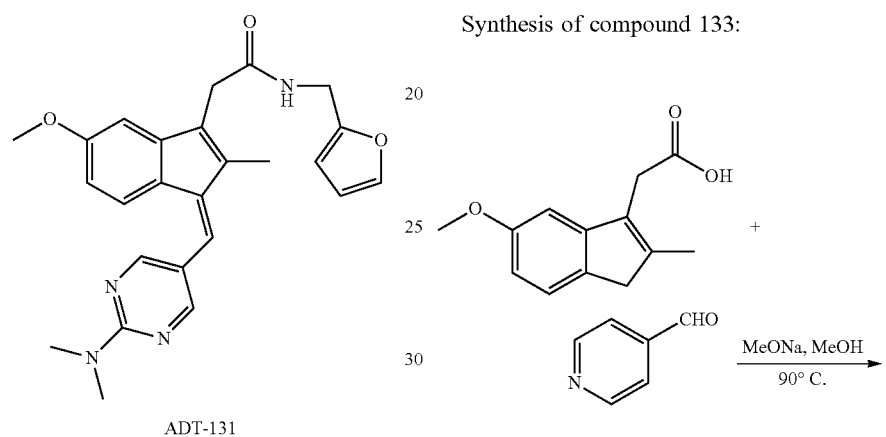
ADT-131
Synthesis of compound 133:
Synthesis of compound 132:
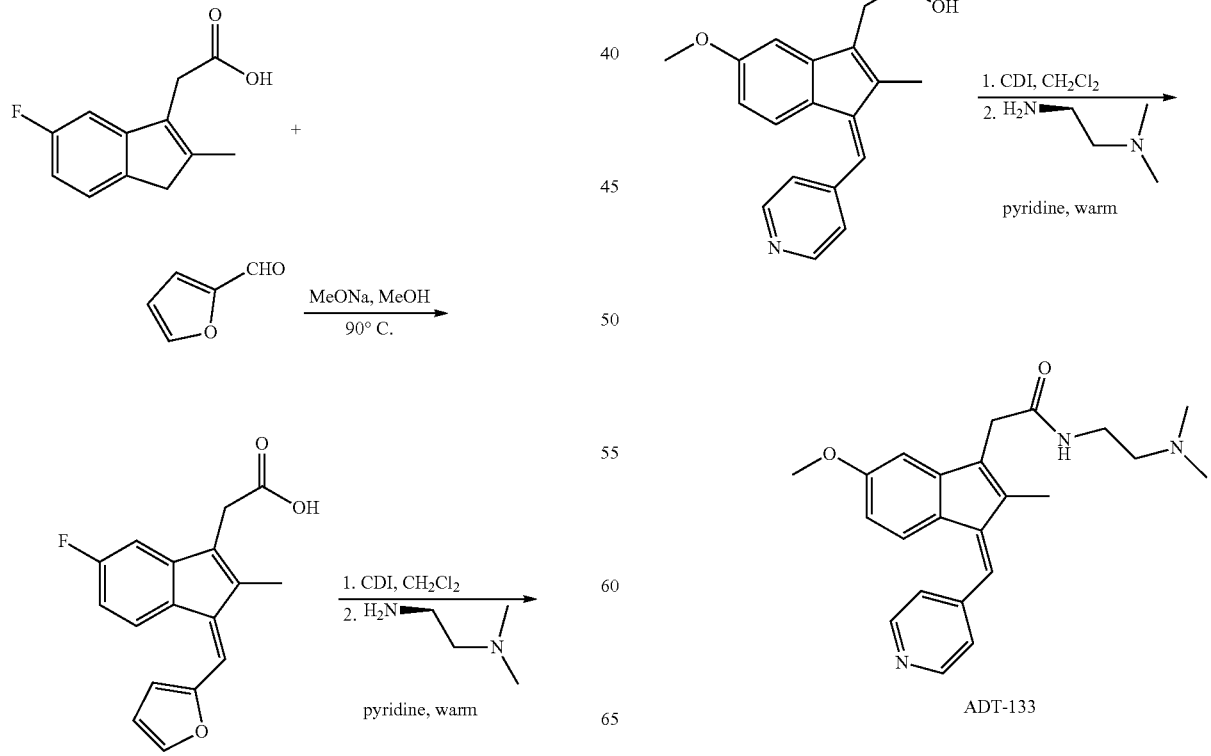
1. CDI, CH$_2$Cl$_2$
2. H$_2$N⌇⌇N⌇
pyridine, warm
MeONa, MeOH
90° C.
1. CDI, CH$_2$Cl$_2$
2. H$_2$N⌇⌇N⌇
pyridine, warm
ADT-133

Synthesis of compound 134:
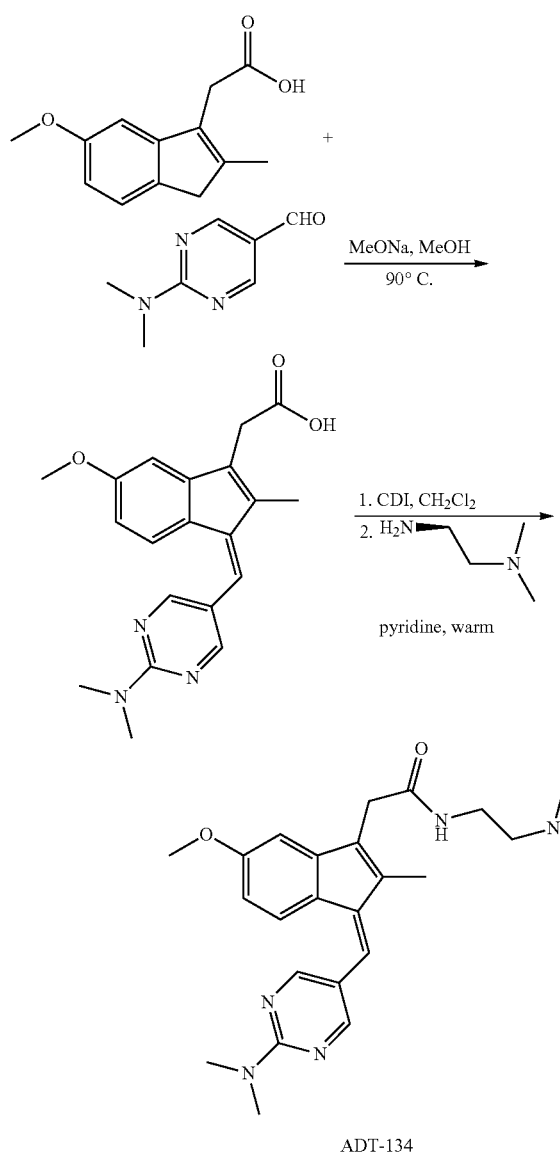
ADT-134
Synthesis of compound 135:
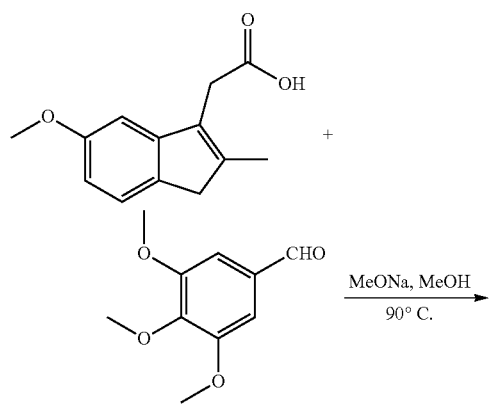
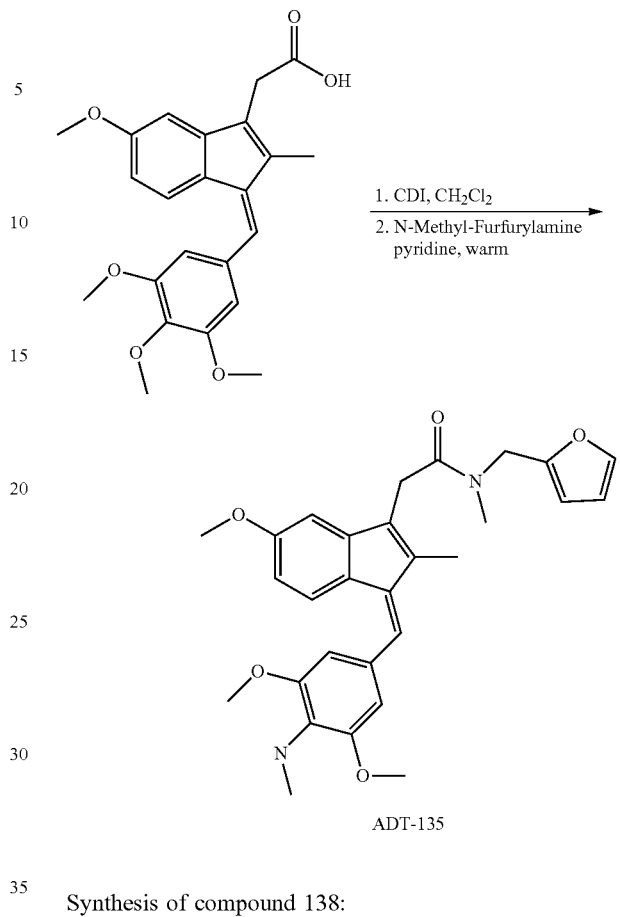
ADT-135
Synthesis of compound 138:
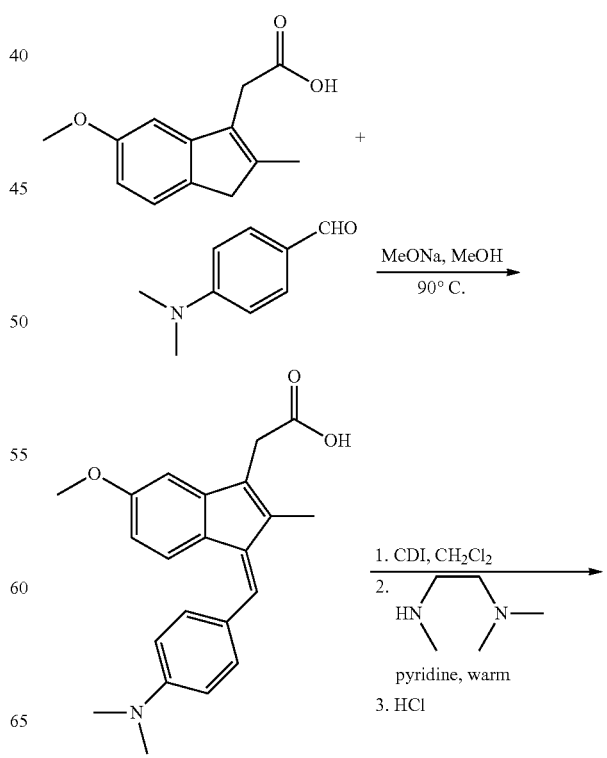

125
-continued
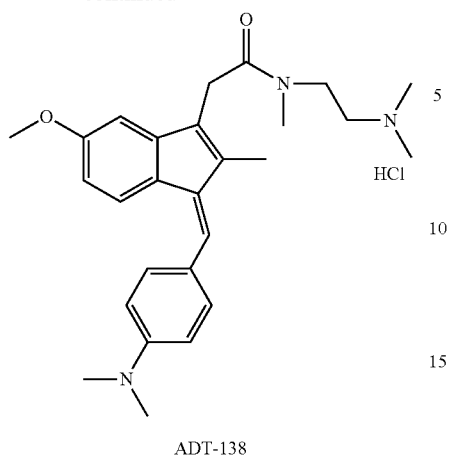
ADT-138
Synthesis of compound 139:
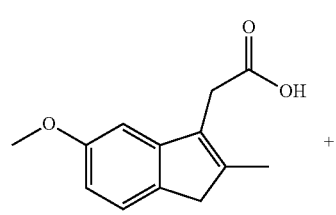
+
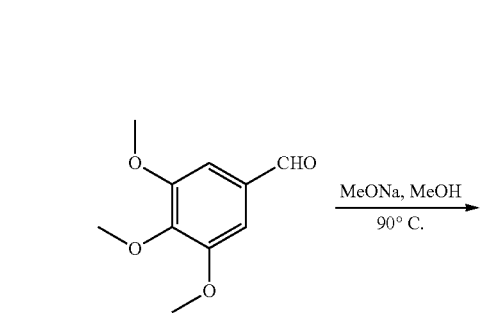
126
-continued
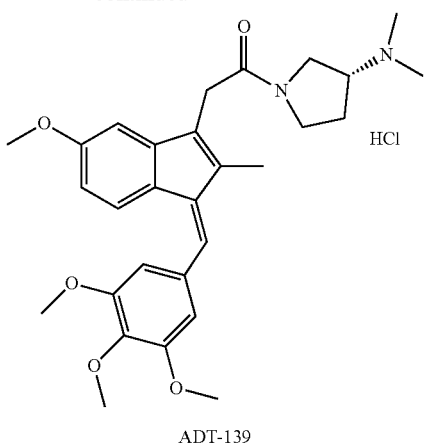
ADT-139
Synthesis of compound 141:
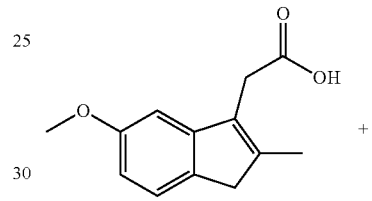
+
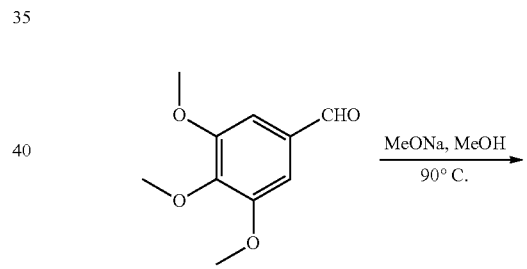
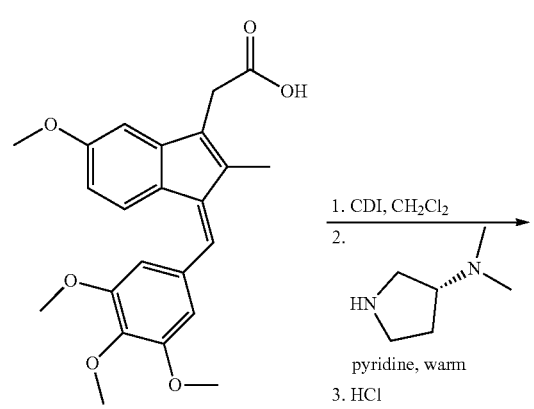
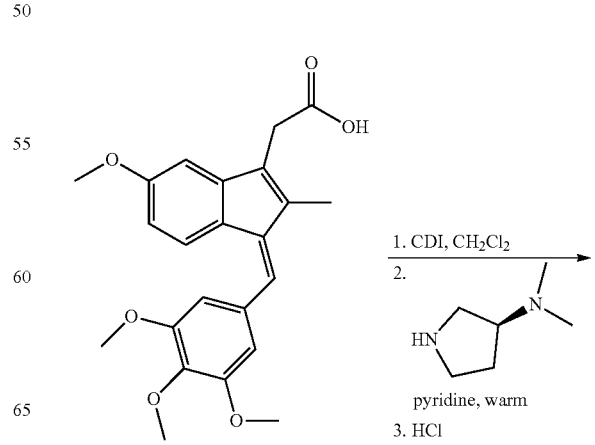

127
-continued
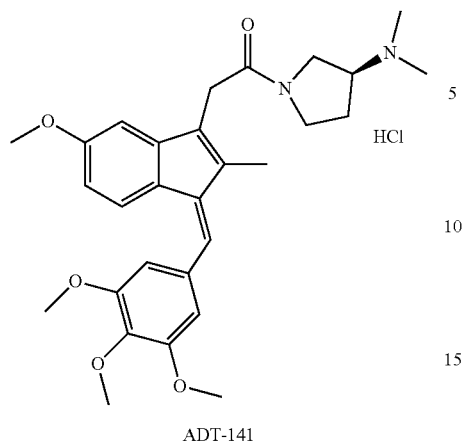
ADT-141
Synthesis of compound 143:
128
-continued
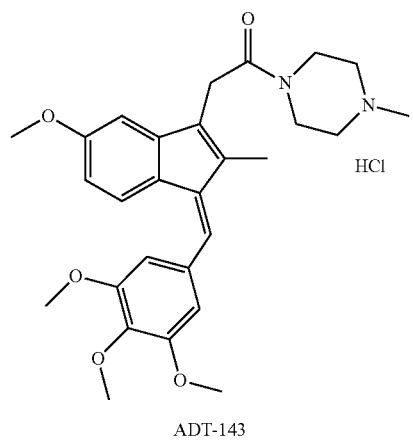
ADT-143
Synthesis of compound 144:
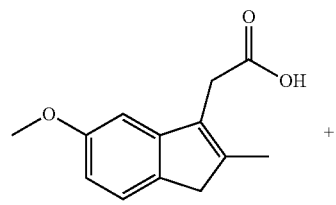
+
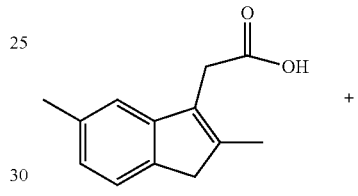
+
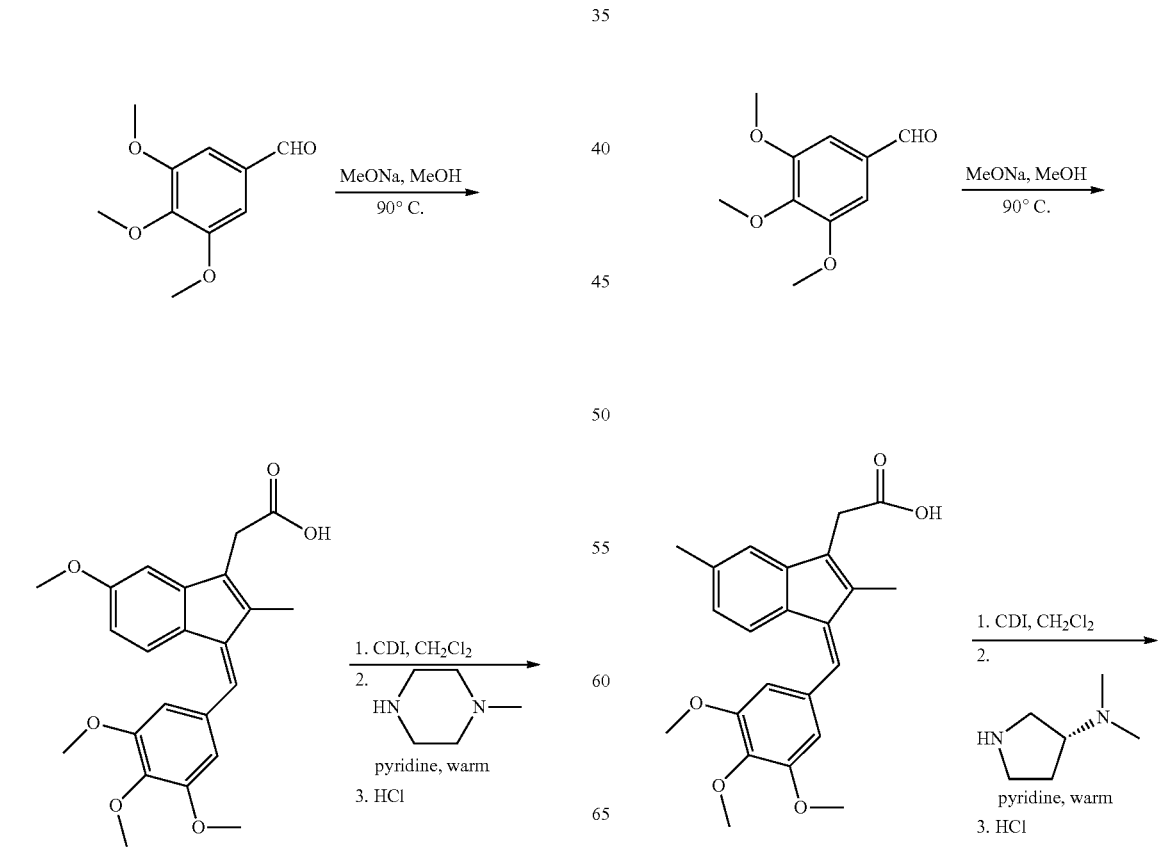

129
-continued
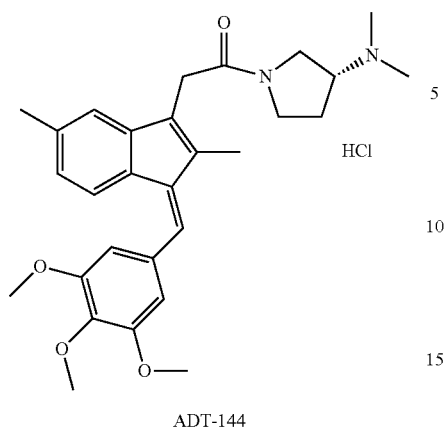
ADT-144
Synthesis of compound 145:
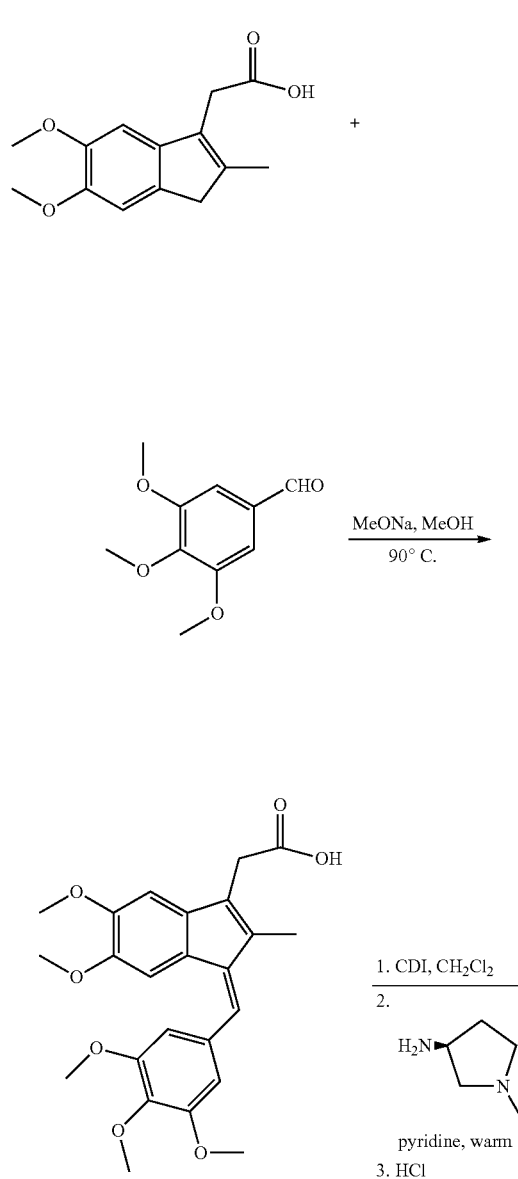
130
-continued
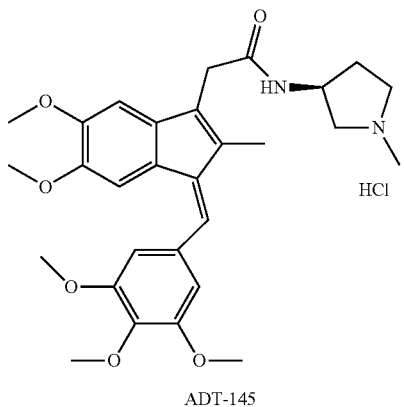
ADT-145
Synthesis of compound 151:
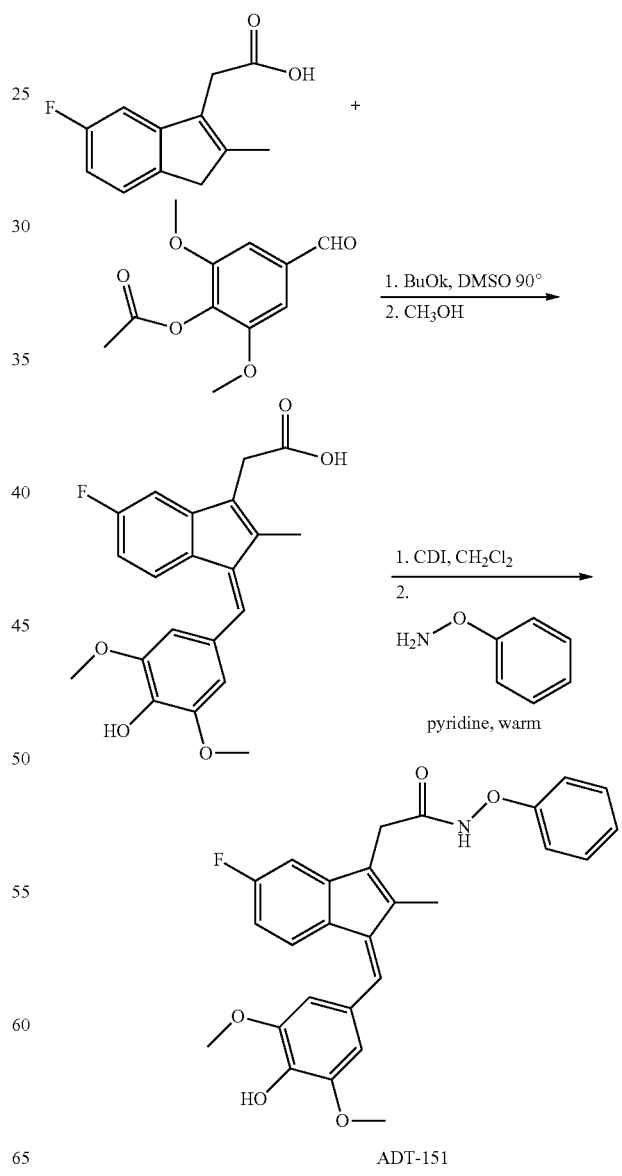
ADT-151

Synthesis of compound 152:

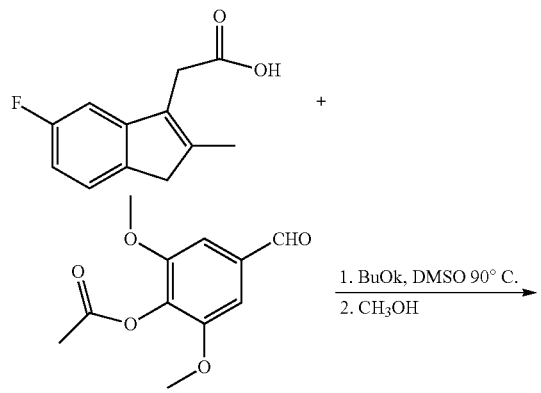

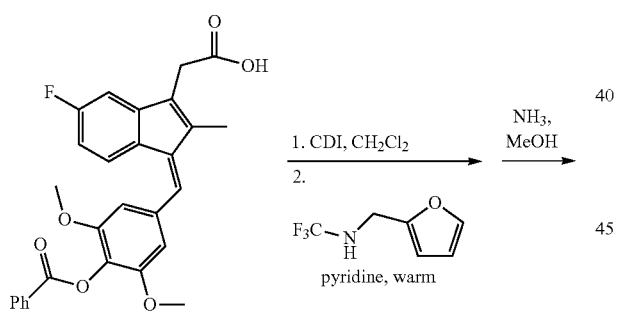

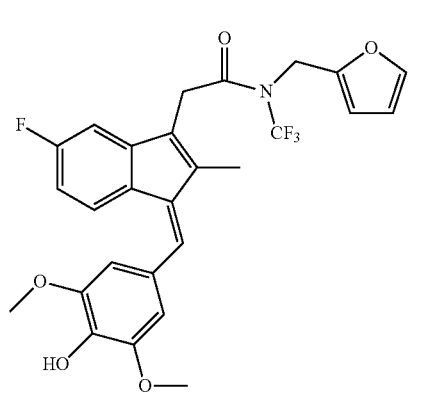

ADT-152

Synthesis of compound 155:

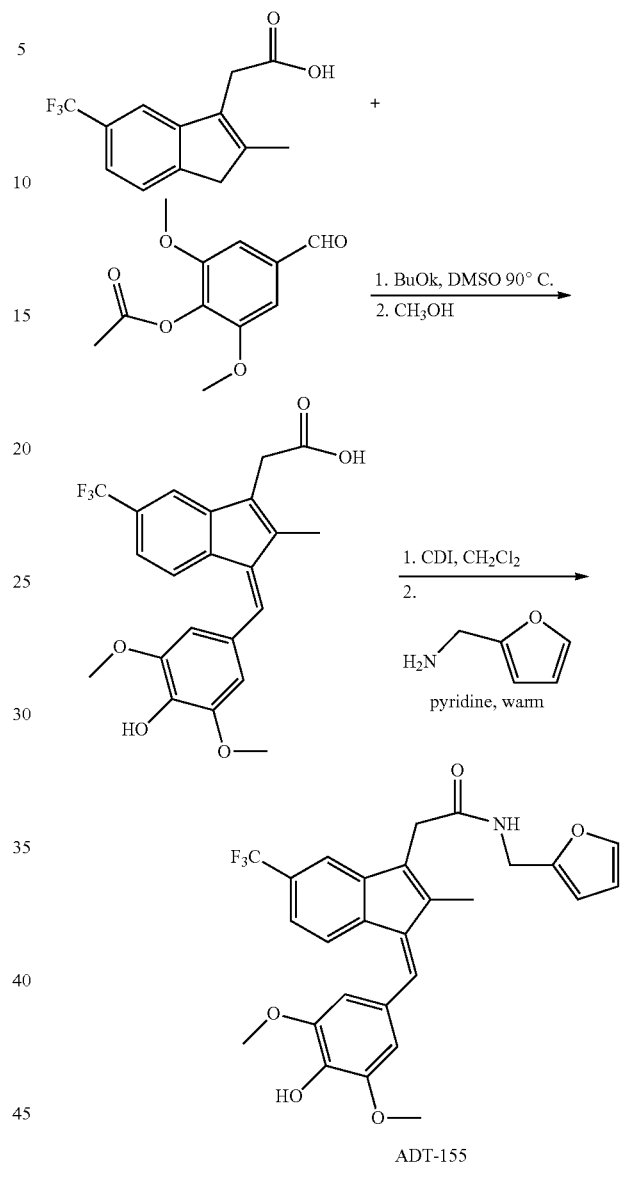

ADT-155

EXAMPLE 13

This example illustrates a synthesis of a representative compound (210) of formula I or II having no hydrogen substituent on the amide nitrogen; and, this also illustrates a benzoyl ester derivative compound (209) which is an example of a prodrug of 210.

(A) To a stirred mixture of (Z)-2-(5-fluoro-1-(4-hydroxy-3,5-dimethoxybenzylidene)-2-methyl-1H-indene-3-yl)acetic acid (370 mg, 1 mmol), sodium hydroxide (160 mg, 4 mmol), and H₂O (10 mL), benzoyl chloride (1 mmol) was added dropwise at 0° C. The reaction mixture was stirred for 2 hrs, acidified, filtered, the precipitate extracted with 20 ml hot water and the insoluble part was recrystallized from ethylacetate-hexane to give (Z)-2-(1-(4-(benzoyloxy)-3,5-dimethoxybenzylidene)-5-fluoro-2-methyl-1H-inden-3-yl) acetic acid in 70% yield.

(B) To a stirred solution of (Z)-2-(1-(4-(benzoyloxy)-3,5-dimethoxybenzylidene)-5-fluoro-2-methyl-1H-inden-3-yl)acetic acid (100 mg, 0.21 mmol) in dichloromethane (5 ml), 1,1'-carbonyl diimidazol (38 mg, 0.23 mmol) was added in one portion resulting in the evolution of $CO_2$ gas. The solution was stirred for 20 minutes, then N-methyl furfurylamine (28 mg, 0.25 mmol) and pyridine (3 ml) was added, and the reaction mixture was heated to 45° C. for 3 hrs. Solvent was removed under vacuum and the residue was extracted with dichloromethane, then the organic layer was washed with water, brine and dried (anhydrous MgSO4). The filtered organic layer was evaporated under vacuum and the residue was purified by silica column chromatography eluting with hexane-acetone (1:1). The product (209) was recrystallized from EtOAc-hexane in 65% yield as a yellow solid.

(C) Compound 209 (35 mg) was dissolved in methanolic ammonia (12 mL, 7N) and was stirred overnight. Solvent was evaporated under vacuum and the residue was purified by silica column chromatography by eluting with hexane-acetone (1:1). The product compound (210) was recrystallized from ethyl acetate-hexane as a yellow solid (55% yield).

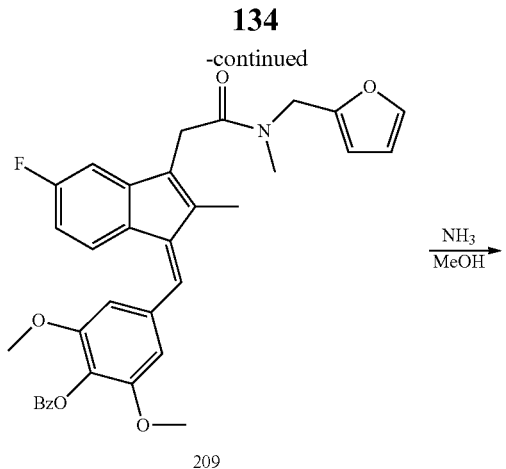

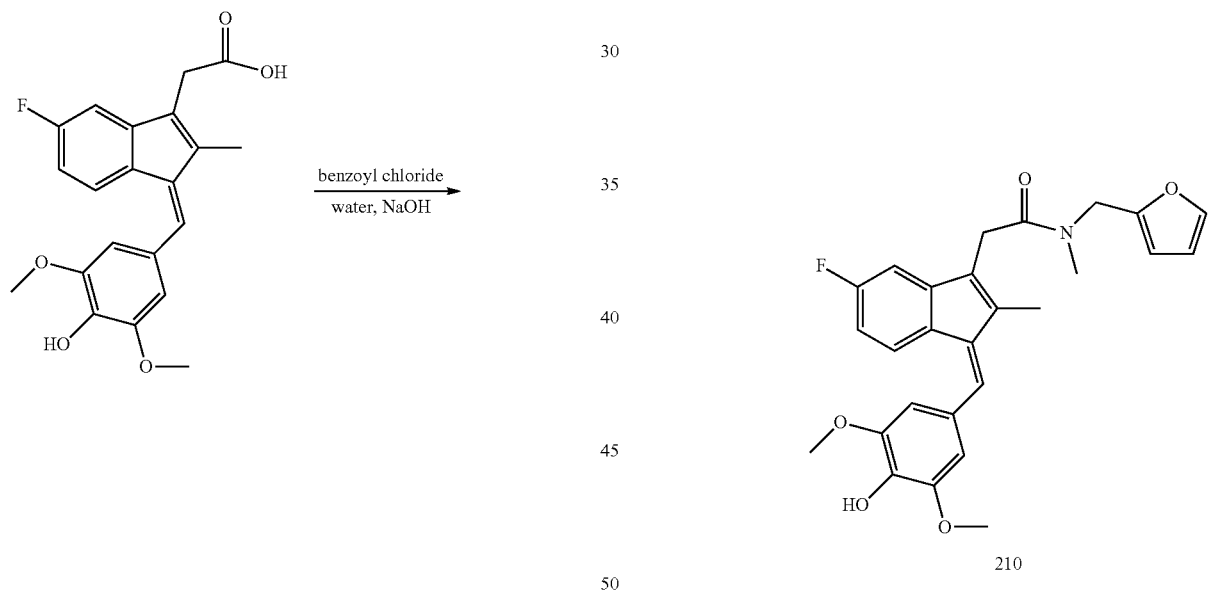

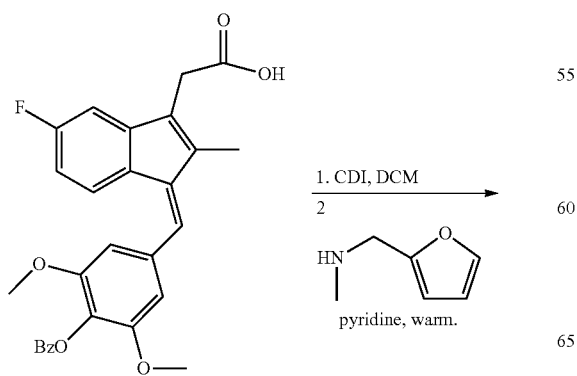

EXAMPLE 14

This example illustrates typical synthesis schemes for making various exemplary prodrug compounds having formula I or II. Given the disclosures of the invention, one of ordinary skill in the art can use or adapt as necessary such schemes as shown below to make certain desired prodrugs or other derivative compounds having formula I or II of the invention.

Synthesis of compound 320:
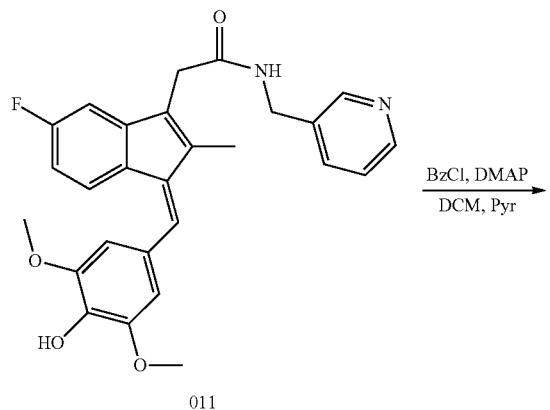
Synthesis of compound 321:
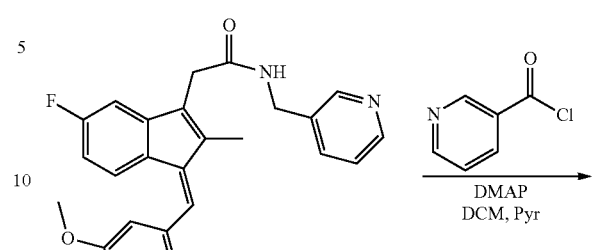
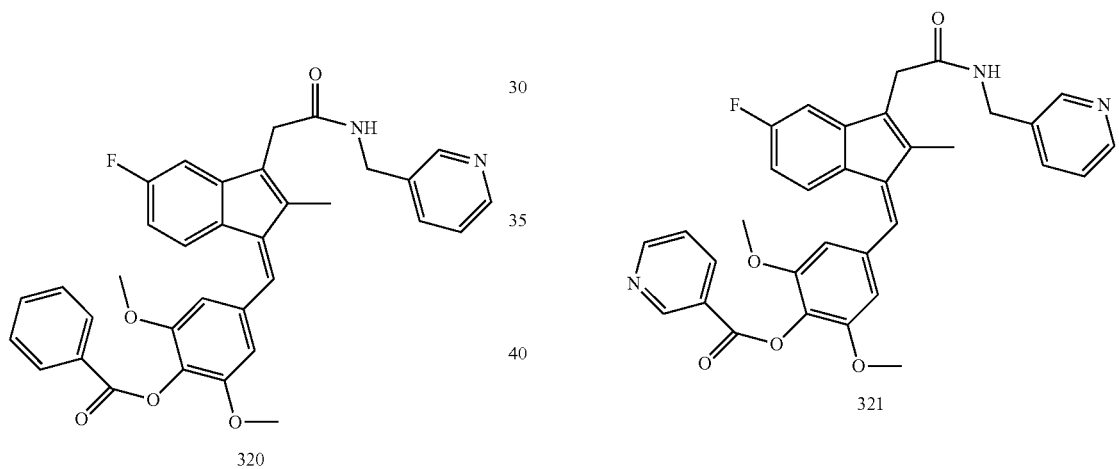
Such a scheme as used for compound 320 can be adapted to make other exemplary compounds having formula I or II, such as 214, 301, 330 and 340.
Such a scheme as used for compound 321 can be adapted to make other exemplary compounds having formula I or II, such as 302, 311, 331 and 341.
Synthesis of compound 323:
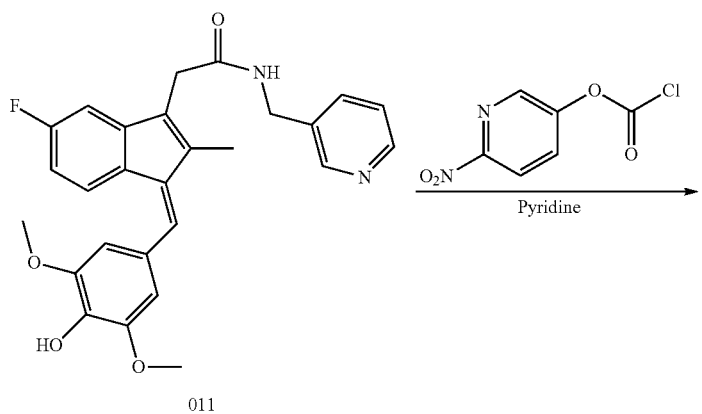

-continued
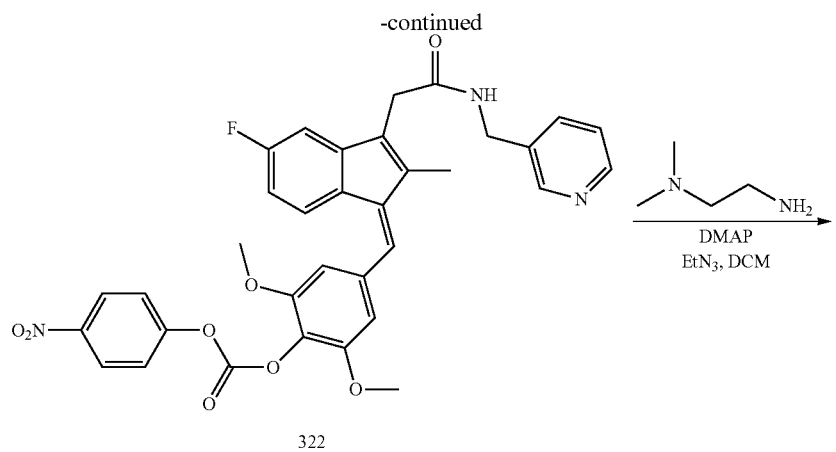
322
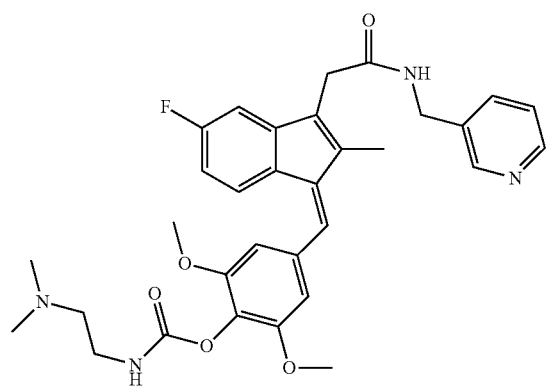
323
Such a scheme as used for compound 323 can be adapted to make other exemplary compounds having formula I or II, such as 300, 312, 332, 342, 350, 352, 303, 313, 333 and 343.
Synthesis of compound 324:
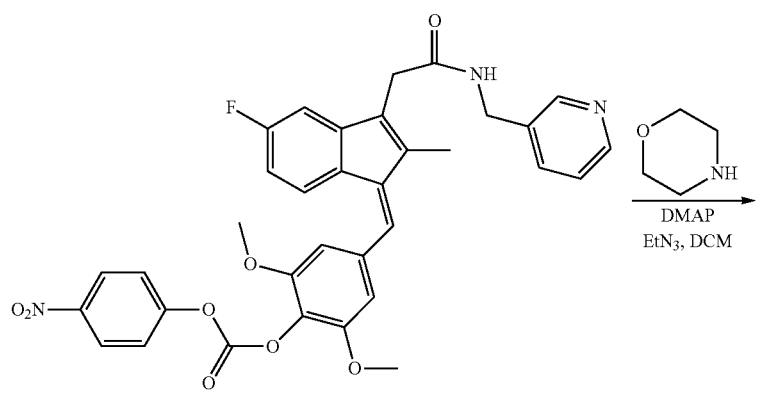
322

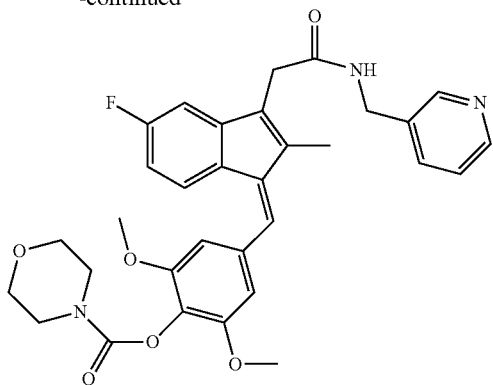
324
Such a scheme as used for compound 324 can be adapted to make other exemplary compounds having formula I or II, such as 304, 314, 334 and 344.
Synthesis of compound 325:
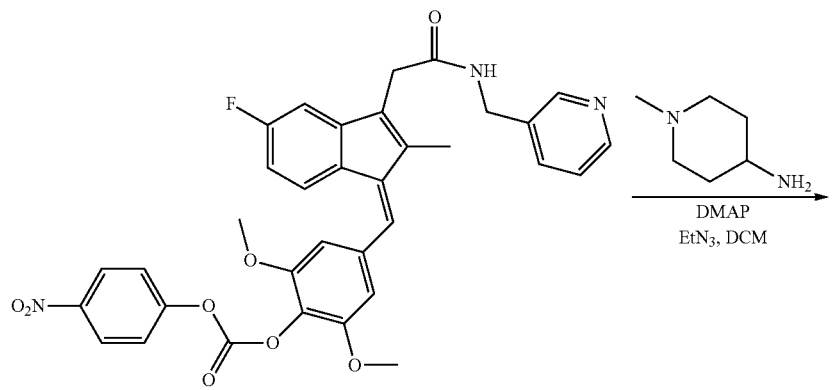
322
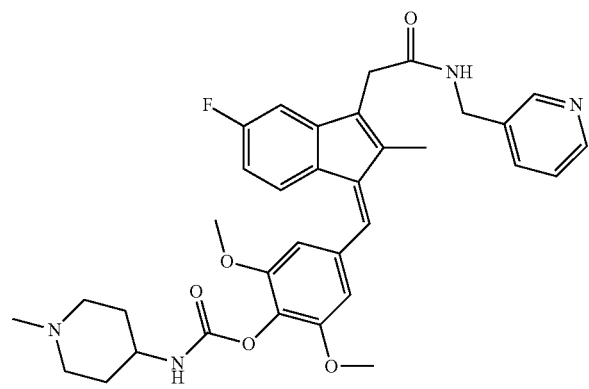
325

Such a scheme as used for compound 325 can be adapted to make other exemplary compounds having formula I or II, such as 305, 315, 335 and 345.
Synthesis of compound 326:
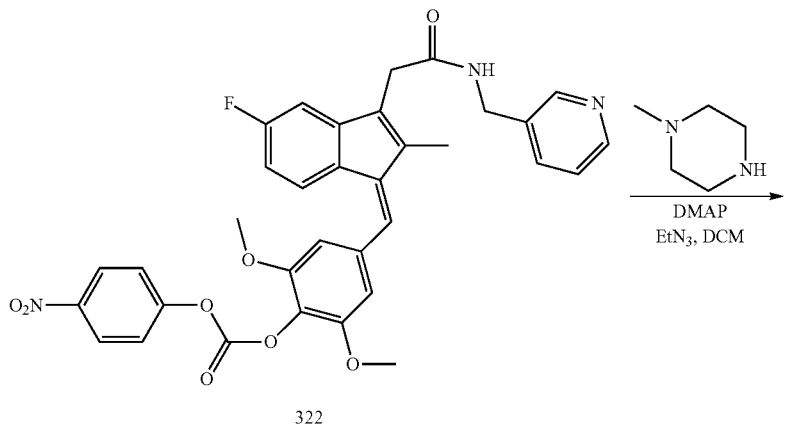
322
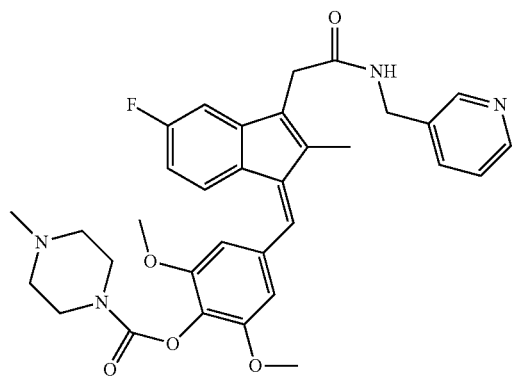
326
Such a scheme as used for compound 326 can be adapted to make other exemplary compounds having formula I or II, such as 306, 316, 336, 346, 351, 353 and 355. Synthesis of compound 327:
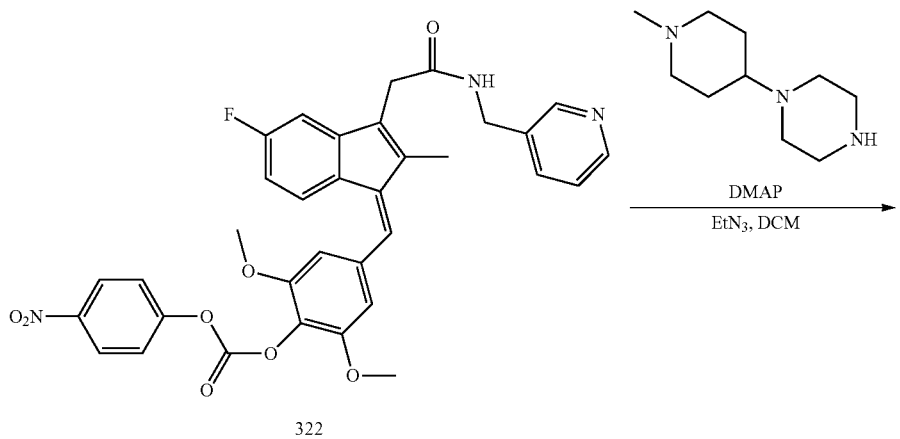
322

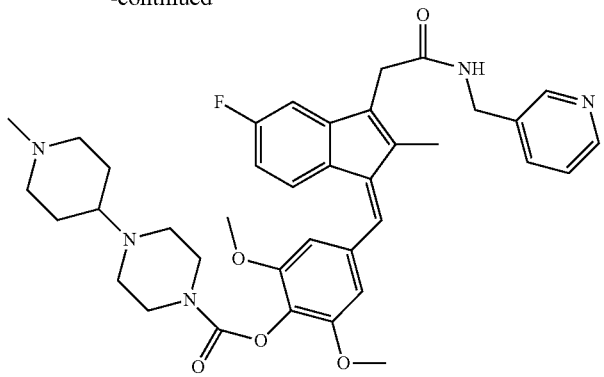

327

Such a scheme as used for compound 327 can be adapted to make other exemplary compounds having formula I or II, such as 307, 317 and 347.

Synthesis of compound 328:

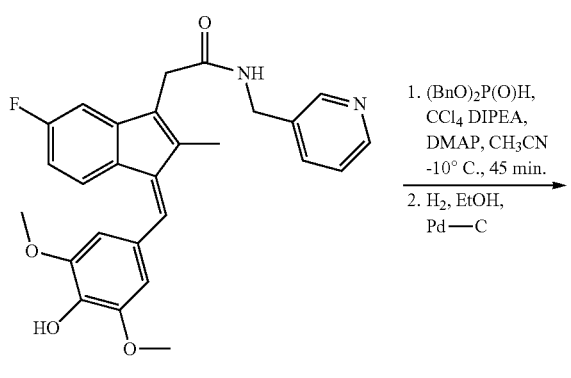

Synthesis of compound 329:

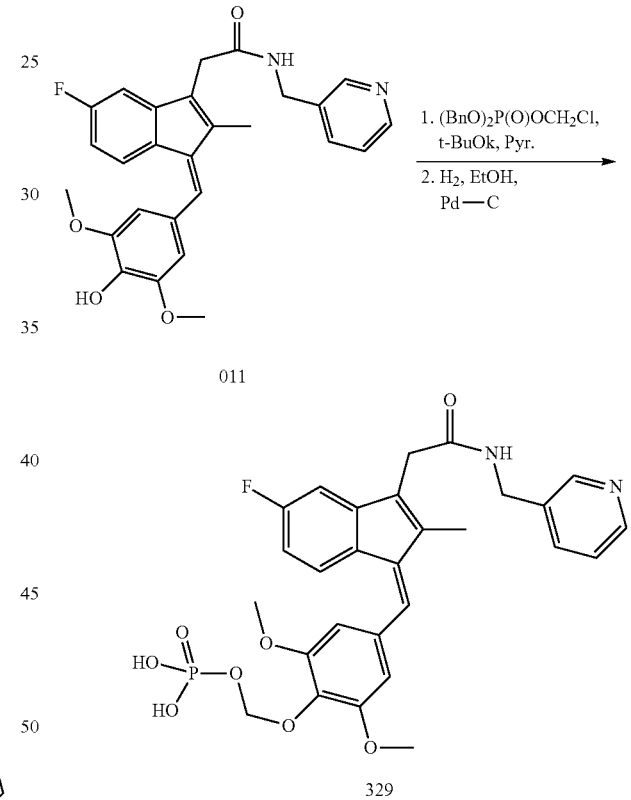

Such a scheme as used for compound 328 can be adapted to make other exemplary compounds having formula I or II, such as 308, 318, 338 and 348.

Such a scheme as used for compound 329 can be adapted to make other exemplary compounds having formula I or II, such as 309, 319, 339 and 349.

EXAMPLE 15

This example illustrates the synthesis of additional exemplary compounds of the present invention, in particular compounds 095, 096 and 097.

The synthesis of (Z)—N-(furan-2-ylmethyl)-2-(1-(4-ethoxycarbonyl-3,5-dimethoxybenzylidene)-5-methoxy-2-fluruo-1H-inden-3-yl)acetamide (095) is as follows. A solution of 3,4,5-trimethoxybenzaldehyde dimethyl ketal (4 mmol) in anhydrous THF (5 mL) was added dropwise to a suspension of freshly cut sodium (0.0012 g-atom) in anhydrous THF (30mL) under dry Ar). The mixture was stirred at room temperature for 24 h, then chilled to −40° C. Ethyl chloroformate (4.2 mmol) in 3 mL of THF was added dropwise and stirred for 5 h, followed by quenching by slow addition of 1 mL water. The mixture was neutralized with 2 mL of acetic acid, concentrated, and the residue dissolved in methylene chloride (100 mL), washed with water (50 mL×2), and concentrated. The residue was purified over silica gel eluted with acetone/hexane, recrystallized from acetone/hexane to give 3,5-dimethoxyl-4-methoxycarbonyl-benzaldehyde dimethyl ketal as colorless crystals, and treated with 6M HCl to afford 3,5-dimethoxyl-4-methoxy-carbonyl-benzaldehyde as a colorless solid. This aldehyde (0.60 g), along with 5-fluoro-2-methylindenyl-3-acetic acid (0.54 g), and sodium methoxide (0.42 g) in 8 mL of anhydrous methanol was treated in a microwave synthesizer at 85° C. for 2 h. The mixture was transferred to a beaker containing 15 mL acetone and 15 ml of ethyl ether, and the precipitate was collected, neutralized with acetic acid, purified over silica gel eluted with hexane and acetone, and recrystallized from acetone/hexane to give the (Z)-2-(5-fluoro-1-(3,4,5-trimethoxybenzylidene)-2-methyl-1H-inden-3-yl)acetic acid as a yellow solid (0.62 g). A solution of this acid (120 mg) and carbonyldiimidazole (100 mg) in 6 mL of anhydrous methylene chloride was stirred for 30 min, then furfuryl amine (150 μL) was added, and stirred for 2 h at room temperature. Following recrystallization, 126 mg of 095 was obtained as a yellow solid.

The synthesis of (Z)-2-(5-methoxy-2-methyl-1-(3,4,5-trimethoxybenzylidene)-1H-inden-3-yl)-N-((1-methyl-1H-pyrrol-2-yl)methyl)acetamide (096) is as follows. A solution of (Z)-2-(5-methoxy-1-(3,4,5-trimethoxybenzylidene)-2-methyl-1H-inden-3-yl)acetic acid (120 mg) and carbonyl-diimidazole (100 mg) in 6 mL of anhydrous methylene chloride was stirred for 30 min, followed by addition of 1-methyl-1H-pyrrol-2-yl)methylamine (50 μL) and 2 mL of anhydrous pyridine. The reaction solution was stirred for at 50° C. for 2 h, quenched with water, diluted with 50 mL of methylene chloride, washed with water (20 mL×3), and concentrated. The residue was purified on a silica gel column, recrystallized from acetone/ethyl ether to afford 47 mg of 096 as a yellow solid.

The synthesis of (Z)—N-((1H-pyrrol-2-yl)methyl)-2-(5-methoxy-2-methyl-1-(3,4,5-trimethoxybenzylidene)-1H-inden-3-yl)acetamide (097) is as follows. A solution of (Z)-2-(5-methoxy-1-(3, 4, 5-trimethoxybenzylidene)-2-methyl-1H-inden-3-yl)acetic acid (120 mg) and carbonyldiimidazole (100 mg) in 6 mL of anhydrous methylene chloride was stirred for 30 min, followed by addition of (1H-pyrrol-2-yl) methylamine (50 μL) and 2 mL of anhydrous pyridine. The reaction solution was stirred for at 50° C. for 2 h, quenched with water, diluted with 50 mL of methylene chloride, washed with water (20 mL×3), and concentrated. The residue was purified the on a silica gel column, and recrystallized from acetone/ethyl ether to afford 47 mg of 097 as a yellow solid.

EXAMPLE 16

This example illustrates synthesis of a medically useful compound of formula I or II wherein a substitution is made at R and/or $R_0$ of an existing compound of formula I or II. Here, for example, a new substituent is introduced at R or $R_0$ of compound 007. To a solution of 007 (120 mg, 0.27 mmol) in dichloromethane (20 ml) at −15° C., a dichloromethane solution of DDQ (30 mg, 0.14 mmol, 12 ml) was slowly added under argon. The reaction mixture was stirred at 0-4° C. for 10 min, then diluted with hexane, followed by silica column chromatography eluted with hexane-acetone (1:1). The major fraction was recrystallized as an orange solid from acetone-hexane, and 50 mg of this material was dissolved in ethanol (2 ml), followed by addition of benzylamine (18 mg, 0.16 mmol) and acetic acid (0.01 mL). The reaction was stirred at 85° C. for 6 hrs. and the solvent removed under vacuum. The residue was purified by silica column chromatography eluting with hexane-acetone (1:1) and methylene chloride-methanol to afford 202 as a yellow solid in overall 40% yield.

In another illustration, to a solution of 007 (120 mg, 0.27 mmol) in dichloromethane (20 ml) at 15° C., a dichloromethane solution of DDQ (30 mg, 0.14 mmol, 12 ml) was slowly added under argon. The reaction mixture was stirred at 0-4° C. for 10 min, then diluted with hexane, followed by silica column chromatography eluted with hexane-acetone (1:1). An orange solid was recrystallized from acetone-hexane, and 50 mg of this material was dissolved in ethanol (2 ml), followed by addition of pyridine-4-ylmethanamine (21 mg, 0.2 mmol) along with a catalytic quantity of acetic acid (0.01 mL). The reaction was heated at 85-90° C. overnight, and the solvent was removed under vacuum. The residue was purified by silica column chromatography eluting with hexane-acetone (1:1.5) and further purified by eluting with dichloromethane-methanol and recrystallized from dichloromethane and hexane to give 203 as a yellow in overall 35% yield.

EXAMPLE 17

Table 1 provides the $^1$H-NMR data confirming structures of exemplary compounds of the invention. All spectra were recorded using DMSO-$d^6$ as solvent, except for compound 030 (unstable in DMSO) for which CHCl$_3$ was used, at 400 MHz for all compounds, except for compounds 030 and 032 for which 500 MHz was used.

TABLE 1

$^1$H-NVIR data of exemplary compounds of the invention

| Cpd. No. | NMR (δ ppm) |
|---|---|
| 002 | 8.603 (t br, 1H, J = 5.62 Hz, CONH), 8.521 (s, 1H, HCO), 7.550 (d, 1H, 7.57 Hz, furanH), 7.549 (s, 1H, IndH), 7.383 (dd, 1H, J1 = 8.30 Hz, J2 = 5.37 Hz, indH), 7.285 (s, 1H, furanH), 7.099 (dd, 1H, J1 = 9.68 Hz, J2 = 2.20 Hz, indH), 6.945 (s, 2H, PhH), 6.910 (s, 1H, =CH), 6.763 (m, 1H, furanH), 4.267 (d, 1H, J = 5.61 Hz, NCH$_2$), 3.767 (s, 6H, OCH$_3$), 3.460 (s, 2H, CH$_2$), 2.182 (s, 3H, CH$_3$) |

TABLE 1-continued

¹H-NVIR data of exemplary compounds of the invention

| Cpd. No. | NMR (δ ppm) |
|---|---|
| 006 | 8.714 (s br, 1H, OH), 8.549 (t, 1H, NH), 7.480 (d, 1H, J = 8.54 Hz, FuranH), 7.071 (s, 1H, indH), 6.857 (d, 1H, J = 7.08 Hz, indH), 6.833 (s, 2H, PhH), 6.48 (d, 1H, indH), 6.371 (m, 1H, furanH), 6.122 (m, 1H, furanH), 6.175 (d, 1H, J = 2.93 Hz, =CH), 4.261 (d, 2H, J = 5.37 Hz, NCH₂), 3.745 (s, 6H, CH₃O), 3.707 (s, 3H, CH₃O), 3.429 (s, 2H, CH₂), 2.162 (s, 3H, CH₃) |
| 007 | 8.792 (s br, 1H, OH), 8.574 (t, 1H, J = 5.62 Hz, NH), 7.559 (d, 1H, J = 4.88 Hz, furanH), 7.233 (s, 1H, indH), 7.084 (dd, 1H, J1 = 9.22 Hz, J2 = 2.20 Hz, indH), 6.841 (s, 2H, PhH), 6.752 (1H, m, indH), 6.481 (m, 1H, furanH), 6.322 (m, 1H, furanH), 6.205 (d, 1H, J = 2.93 Hz, =CH), 4.264 (d, 2H, J = 6.17 Hz, NCH₂), 3.747 (s, 6H, MeO), 3.448 (s, 2H, COCH₂), 2.16 (s, 3H, CH₃) |
| 008 | 8.68 (s br, 1H, OH), 8.556 (t, 1H, J = 5.37 Hz, NH), 7.539 (d, 1H, J = 4.88 Hz, furanH), 7.196 (s, 1H, indH), 7.088 (s, 1H, indH), 6.915 (s, 1H, =CH), 6.846 (s, 2H, PhH), 6.37 (m, 1H, furanH), 6.198 (d, 1H, J = 2.93 Hz, furanH), 4.264 (d, 2H, J = 5.38 Hz, NCH₂), 3.752 (s, 6H, OCH₃), 3.713 (s, 3H, OCH₃), 3.493 (s, 3H, OCH₃), 3.414 (s, 2H, COCH₂), 2.16 (s, 3H, CH₃) |
| 012 | 9.335 (s br, 1H, OH), 8.541 (t br, 1H, J = 5.61 Hz, CONH), 7.552 (d, 1H, J = 0.97 Hz), 7.423 (d, 1H, J = 8.55 Hz, PhH), 7.106 (d, 1H, J = 1.72 Hz), 7.064 (s, 1H), 6.986 (dd, 1H, J1 = 8.30 Hz, J2 = 1.47 Hz,), 6.851 (s, 1H, PhH), 6.841 (d, 1H, J = 8.02 Hz), 6.480 (d, 1H, J1 = 8.58 Hz, J2 = 2.44 Hz), 6.372 (dd, 1H, J1 = 2.93 Hz, J2 = 1.83 Hz), 6.197 (d, 1H, J = 2.69 Hz), 4.254 (d, 2H, J = 5.62 Hz, NCH₂), 3.748 (s, 3H, CH₃O), 3.703 (s, 3H, CH₃O), 3.424 (s, 2H, CH₂), 2.162 (s, 3H, CH₃) |
| 018 | 10.575 (s br, 1H, NH), 9.740 (s br, 1H, OH), 8.342 (t br, 1H, J = 5.37 Hz, CONH), 7.332 (d, 1H, J = 8.30 Hz, indH), 7.108 (s, 2H, PhH), 7.029 (s, 1H, IndH), 6.874 (d, 1H, J = 2.27 Hz, =CH)), 6.616 (m, 1H, PyrroH), 6.496 (dd, 1H, J1 = 8.30 Hz, J2 = 2.20 Hz, IndH), 5.906 (dd, 1H, PyrroH), 5.871 (s, 1H, PyrroH), 4.188 (d, 1H, J = 5.12 Hz, CONH), 3.805 (s, 3H, OCH3), 3.703 (s, 3H, OCH3), 3.418 (s, 2H, CH2), 2.18 (s, 3H, CH3) |
| 022 | 10.582 (s br, 1H, NH), 8.520 (s br, 1H, OH), 8.342 (t br, 1H, CONH), 7.820 (s, 1H, indH), 7.276 (d, 1H, J = 8.30 Hz, IndH), 6.995 (s, 2H, PhH), 6.889 (d, 1H, PyrroH), 6.620 (s, 1H, =CH), 6.519 (d, 1H, J = 8.30 Hz, IndH), 5.911 (d, 1H, PyrroH), 5.878 (d, 1H, PyrroH), 4.197 (d, 1H, J = 4.87 Hz, CONH), 3.795 (s, 6H, OCH3), 3.706 (s, 3H, OCH3), 3.438 (s, 2H, CH2), 2.18 (s, 3H, CH3) |
| 030 | (CDCl₃, 500 MHz) 7.4603 (d, 1H, J = 8.6 Hz, IndH), 7.0755 (s, 1H, IndH). 6.7990 (s, 2H, PhH), 6.7051 (d, 1H, J = 2.3 Hz, =CH), 6.57 (dd, 1H, IndH), 5.97 (d, br, CONH), 4.51 (m, 1H, PyrrolinH), 3.9337 (s, 3H, MeO), 3.8667 (s, 6H, MeO), 3.7963 (s, 3H, MeO), 3.5066 (s, 2H, CH₂CO), 2.765 (m, 1H,, PyrrolinH), 2.4844 (m, 1H, PyrrolinH), 2.479 (m, 1H, PyrrolinH), 2.2686 (s, 3H, NCH3), 2.260 (m, 1H, PyrrolinH), 2.1770 (s, 3H, CH3), 2.131 (m, 1H, PyrrolinH), 1.461 (m, 1H, PyrrolinH) |
| 032 | (500 Hz), 9.89 (br, 1H, NH + Cl—), 8.189 (d, br, 1H, J = 7.45 Hz, CONH), 7.3759 (d, 1H, J = 8.6 Hz, IndH), 7.0682 (s, 1H, IndH). 6.8174 (s, 2H, PhH), 6.8170 (s, 1H, =CH), 6.57 (dd, 1H, J1 = 8.0 Hz, J2 = 2.3 Hz, IndH), 3.853 (m, 1H, CH), 3.7346 (s, 3H, MeO), 3.7048 (s, 6H, MeO), 3.6936 (s, 3H, MeO), 3.344 (m, 1H, CH), 3.3693 (s, 2H, CH₂CO), 2.80 (m, 1H, CH) , 2.7314 (s, 3H, NCH₃), 2.61 (m, 1H, CH), 2.1187 (s, 3H, CH₃), 1.8-1.9 (m, 2H, CH₂), 1.67 (m, 1H, CH) 1.35 (m, 1H, CH) |
| 095 | 8.86 (br t, 1H, CONH), 7.56 (d, 1H, furanH), 7.32 (dd, 1H, indH), 7.28 (s, 1H, =CH), 7.10 (dd, 1H, indH), 6.86 (s, 2H, PhH), 6.78 (td, 1H, indH), 6.38 (dd, 1H, furanH), 6.21 (d, 1H, furan), 4.26 (q, 2H, CH₂Me), 4.23 (d, 2H, CH₂N), 3.77 (s, 6H, CH₃O) 2.15 (s, 3H, CH₃), 1.26 (s, 3H, CH₃) |
| 202 | 2.06 (s, 3H), 3.68 (s, 2H), 3.76 (s, 6H), 4.25 (s, 1H), 4.37 (d, 2H), 6.14 (d, 1H, J = 3.0), 6.36 (m, 1H), 6.74 (s, 1H), 6.78 (m, 1H), 6.86 (s, 2H), 7.18-7.36 (m, 7H), 7.55 (1H), 8.53 (1H) |
| 203 | 2.06 (s, 3H), 3.68 (s, 2H), 3.76 (s, 6H), 4.25 (s, 1H), 4.37 (d, 2H), 6.14 (d, 1H, J = 3.0), 6.36 (m, 1H), 6.74 (s, 1H), 6.78 (m, 1H), 6.86 (s, 2H), 7.18-7.36 (m, 7H), 7.55 (1H), 8.53 (1H) |

EXAMPLE 18

This example illustrates cell growth assays employed in the present invention. Cells used in such assays included A-549, HT-29, MDA-MB-231, Colo-205, Caco2, HCT-116, SW-480, and DLD-1 human cancer cells obtained from the American Type Culture Collection (ATCC). Human tumor cells were cultured using standard methods in RPMI-1640 growth medium supplemented with 5% fetal bovine serum (FBS). Normal rat kidney (NRK) and Ki-Ras transformed NRK cells (K-NRK) were obtained from ATCC, and were cultured according to supplier recommendations. CellTiter-Glo ATP cell growth assay reagents were obtained from Promega and used according to the manufacturer's protocol. Inhibitors of EGFR, Raf, and MEK were obtained from Selleck Chemicals. Cells were plated at a density of 5,000 cells per well in 96-well microplates or 1,250 cells per well in 384-well plates, and allowed to attach for at least 4 h. Test compounds were dissolved in dimethyl sulfoxide (DMSO), and this working stock was further diluted in growth medium for addition to cell cultures. Serial dilutions of the test compound were prepared in growth medium containing an equal amount of DMSO not exceeding 0.2% final concentration. Each compound concentration was tested in at least 3 separate samples per cell line. At the end of a 3-day treatment period, growth inhibition was analyzed using a bioluminescent assay of ATP concentration (Promega Cell-Titer-Glo) according to the manufacturer's protocol. Resulting luminescence was measured using the luminescence cartridge of the Molecular Devices Spectramax Paradigm microplate reader. Relative growth inhibition for each sample was determined by comparison with the values obtained for vehicle treated control samples. Growth inhibition values were plotted with the GraphPad Prism5 software using the 4-parameter logistic fit to obtain $IC_{50}$ values, which corresponds to the growth inhibitory potency of the compound.

EXAMPLE 19

Selected compounds of formula I and II were screened initially for tumor cell growth inhibition using the methods described in Example 15. The measured HT-29 tumor cell growth inhibitory $IC_{50}$ values (micromolar) for compounds 130, 131, 132, 133, 134, 135, 138, 139, 141, 143, 144 and 145 were 4.3, 2.7, 4.1, 9.3, 8.2, 0.26, 3.0, 0.49, 2.2, 1.3, 7.4 and 17.6, respectively.

EXAMPLE 20

This example illustrates a Ras binding domain assay used in an embodiment of the present invention to measure Ras activation status. The activation state of Ras in cell lines was assayed using the Active Ras Pull-Down and Detection Kit (Thermo Scientific). Cell lines were cultured as described above. Cells were disrupted with non-ionic detergent, and the active (GTP-bound) Ras was isolated by its high affinity for Raf via precipitate with sepharose-bound GST-Raf fusion protein. The precipitated active Ras was then subjected to polyacrylamide gel electrophoresis (PAGE) and transferred to nitrocellulose membrane (western blot). Detection was achieved using the anti-Ras mouse primary antibody and anti-mouse-horseradish peroxidase conjugated secondary antibody. Paired samples of whole cell lysate were analyzed by western blot for expression level of total Ras protein as well as a gel loading control, glyceraldehyde 3-phosphate dehydrogenase (GAPDH). Digital enhanced chemiluminescence imaging of the resulting western blots was performed using a Syngene G:Box. The intensity of Ras bands from each cell line and the corresponding GAPDH bands were quantitated using NIH ImageJ, and expressed as "relative Ras activation."

EXAMPLE 21

This example illustrates effects of exemplary compounds of the present invention on cancer cells having activated or mutated Ras compared to wild-type (WT) Ras. Compounds were tested for their ability to inhibit the growth of cells expressing constitutively active K-Ras oncogene compared with cells with inactive Ras. A549 lung cancer cells, which harbor a mutation in the K-Ras oncogene were treated for three days with the compounds. As indicated in Table 2, the $IC_{50}$ values of the compounds ranged from <1 nM to over 5900 nM in cells with mutated Ras. In contrast, when these compounds were tested for their ability to inhibit the growth of colon cancer cells having the wild-type Ras protein (HT29), these compounds were significantly less potent, with $IC_{50}$ values ranging from 280 nM to over 8000 nM. The ratio of a given compound's potency ($IC_{50}$) to inhibit the growth of cells lacking activated Ras (HT-29) relative to that of cells with mutated or activated Ras (A549) demonstrates selectivity for the Ras-mutant-containing cells.

TABLE 2

Growth inhibition of cells with mutant Ras.

| Cpd # | A549 (Ras-activated) $IC_{50}$ (nM) | HT-29 (WT Ras) $IC_{50}$ (nM) | Selectivity HT-29/A549 |
|---|---|---|---|
| 001 | 716 | 6,280 | 9 |
| 006 | 11 | 8,130 | 739 |
| 007 | 0.86 | 280 | 326 |
| 008 | 167 | 1,540 | 9 |
| 012 | 170 | 900 | 5 |
| 013 | 300 | 730 | 2 |
| 014 | 110 | 500 | 5 |

EXAMPLE 22

Figure 1:
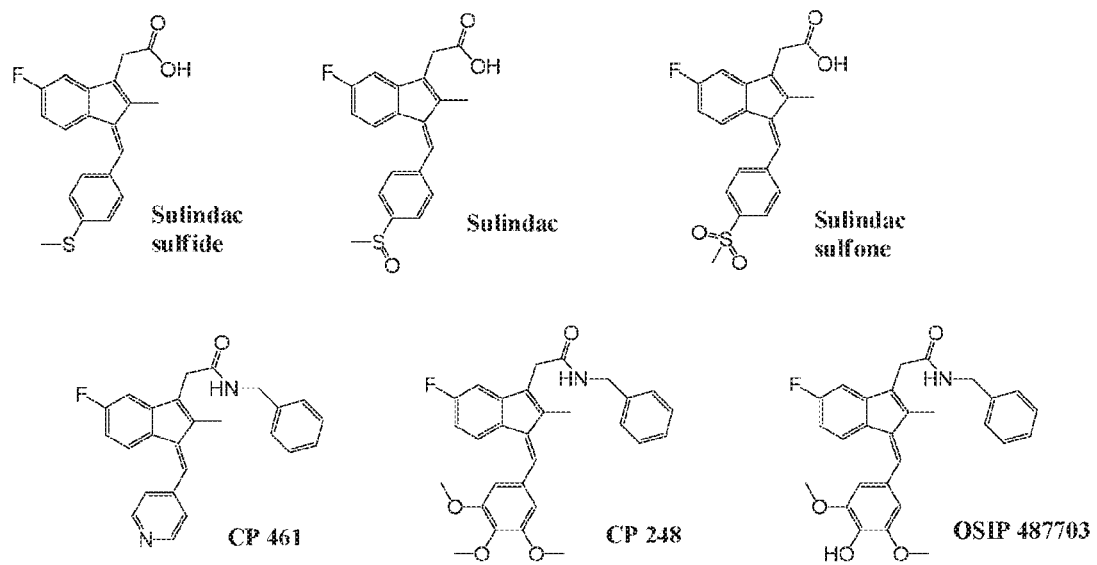
FIG. 1 depicts the chemical structures of sulindac and certain derivatives thereof reportedly having anticancer activity.
Figure 2:
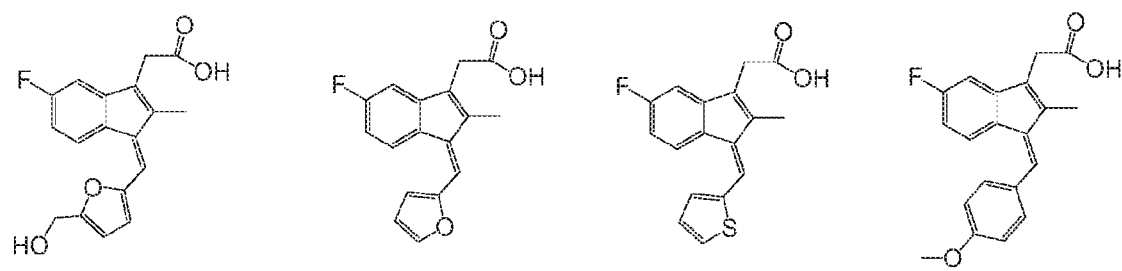
FIG. 2 depicts the chemical structures of certain other sulindac derivatives reported to inhibit Ras.
Figure 3:
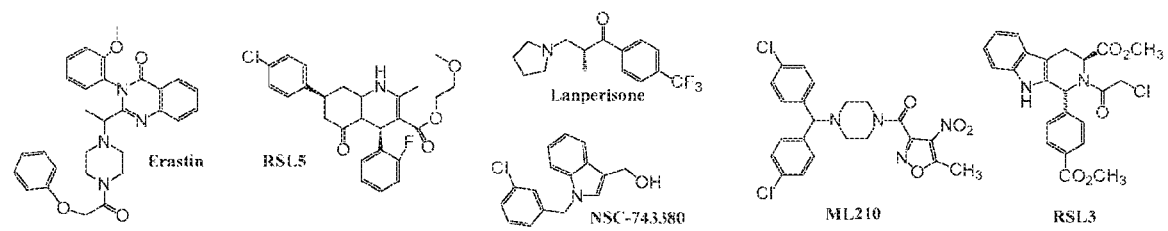
FIG. 3 shows chemical structures of selective Ras-inhibitory compounds identified by synthetic lethal screening.
Figure 4:
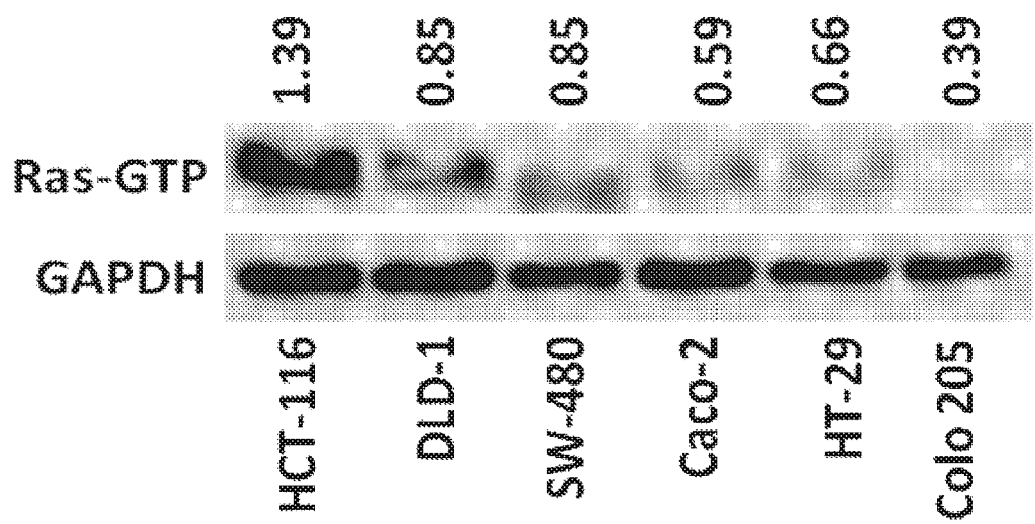
FIG. 4 depicts the results of a Ras Binding Domain (RBD) pulldown assay paired with Western blot showing the relative levels of Ras activation in a panel of colorectal cancer cell lines.

This example illustrates the levels of Ras activation in different colorectal cancer cells. In particular, a panel of human colorectal cancer cell lines was selected to further describe the selectivity of the compounds for cells with activated Ras. Three of the cell lines in the panel have been reported to harbor ras mutations: HCT-116, DLD-1, and SW-480 (Stoneman and Morris, *Clin Mol Pathol.*, 48, M326-332(1995)). Three of the cell lines were reported to express wild type Ras: HT-29, Caco-2, and Colo-205(Stoneman and Morris, supra; Shirasawa et al., *Science*, 260, 85-88 (1993)). The activation state of Ras in the cell lines was assayed using the Active Ras Pull-Down and Detection Kit. The ratio of the intensity of the Ras to GAPDH bands was expressed as relative Ras activation, which is presented above each lane in FIG. 4. This experiment demonstrated that the level of Ras activation in HCT-116 >DLD-1≈SW-480>Caco2>HT-29>Colo205.

EXAMPLE 23

This example illustrates selective growth inhibition in colorectal cell lines constitutively containing activated Ras or wild-type Ras. The growth inhibitory activity of the compounds was tested using the CellTiter-Glo assay. Cells were seeded in 384-well plates and allowed to attach, then ten-fold serial dilutions of compounds were tested. Each concentration was tested in at least 3 separate samples per cell line. As indicated in Table 3, the potency of the compounds ranged from <1 nM in cells with Ras activation, to greater than 1300 nM in cells with WT Ras. The ratio of a given compound's potency (($IC_{50}$) to inhibit the growth of cells having wild-type Ras (Caco-2) relative to that of cells having activated Ras (SW-480) demonstrates selectivity for the Ras-mutant-containing cells.

TABLE 3

Selective growth inhibition for active Ras in a panel of colorectal cancer cell lines.

| Cpd # | SW-480 (Ras Activated) $IC_{50}$ (nM) | Caco-2 (WT Ras) $IC_{50}$ (nM) | Selectivity Caco-2/SW-480 |
|---|---|---|---|
| 001 | 435 | 1,100 | 3 |
| 006 | 2.85 | 428 | 150 |
| 007 | 0.37 | 1.97 | 5 |
| 008 | 139 | 1,330 | 10 |

EXAMPLE 24

This example illustrates the correlation between the sensitivity to these compounds and Ras activation status. The log of the $IC_{50}$ values of four highly active compounds were plotted on the y-axis of the graphs and the log of the relative levels of Ras activation (e.g., as described in Example 8) was plotted on the x-axis. Linear regression analysis of the resulting coordinates demonstrates a statistically significant inverse correlation between Ras activation and sensitivity of the cell lines as shown in FIG. 6A-6F, in which HCT-116, DLD-1, and SW-480 cells harbor Ras mutations, while: HT-29, Caco-2, and Colo-205 express wild-type Ras. Correlation coefficients ($r^2$) are presented in each of the plots.

EXAMPLE 25

This example illustrates use of well-established human colon tumor cell lines with widely divergent Ras activation status to determine selectivity values for exemplary compounds of the present invention. Cell lines thus employed in this example were HCT-116, a highly Ras-driven line expressing mutant Ras, and HT-29, a non-Ras-driven line expressing wild-type, non-mutated Ras. Cells were plated at 5000 cells/well in 96-well plates, and viable cell numbers were measured using the Cell Titer Glo ATP luminescence assay (Promega). FIGS. 6A-6F show the results of these studies for exemplary compounds 006, 007, 019, 029, 002, and 022, respectively. The calculated HT-29/HCT-116 selectivity values for the aforementioned compounds were 142, 290, 185, 35, 116, and 117, respectively. These selectivity values are the ratios of each compound's potency ($IC_{50}$) to inhibit the growth of cells lacking activated Ras (HCT-29) relative to that of cells with activated Ras (HCT-116), demonstrating selectivity for the Ras-mutant-containing cells. Similar results were found for compounds 202 and 203, as illustrated in FIGS. 6G-6J.

This example furthermore shows that prior art studies (e.g., U.S. Pat. Nos. 6,063,818 and 6,121,321) employing individual cell lines such as HT-29 or SW-480 could not have revealed compounds with Ras-selective activity useful for Ras-directed medical treatments or preventions. Employment of a cell line having normal, non-mutant Ras (e.g., HT-29) concurrently with at least one or more cell line(s) having hyperactive or mutant Ras (e.g., HCT-116 and/or SW-480) in comparative assays of tumor cell growth inhibition are required to demonstrate Ras-selectivity, and to enable selection of a Ras-inhibitory compound necessary for the novel methods disclosed in the present invention.

EXAMPLE 26

This example illustrates non-selective growth inhibition with known Ras pathway inhibitors which are not compounds of the present invention. In particular, the growth inhibitory activity of commercially available compounds which are active in the Ras signal transduction pathway were tested in the same panel of cell lines using the CellTiter-Glo assay. Cells were seeded in 384-well plates and allowed to attach. Ten-fold serial dilutions of compounds were tested. Each compound concentration was tested in at least 3 separate samples per cell line. As indicated in Table 4 below, the potency of the EGF receptor inhibitor compounds ranged from 4 µM to >20 µM, with no pattern of selectivity with regard to Ras activation. Likewise, the C-Raf inhibitor, GW5074, did not show selectivity for cell lines expressing activated Ras. The B-Raf inhibitors tested were generally active in the low micromolar range, but were significantly more potent in Colo-205 cells, which have the lowest level of active Ras. The MEK inhibitor, Selumetinib was also most potent against COLO-205 and HT-29 cell lines showing, if anything, a "reverse" selectivity toward inactive Ras compared with the compounds of this invention.

TABLE 4

Non Ras-selective growth inhibition with known Ras pathway inhibitors.

| Compound | Target | HCT-116 $IC_{50}$ (nM) | DLD-1 $IC_{50}$ (nM) | SW-480 $IC_{50}$ (nM) | Caco-2 $IC_{50}$ (nM) | HT-29 $IC_{50}$ (nM) | COLO-205 $IC_{50}$ (nM) |
|---|---|---|---|---|---|---|---|
| Gefitinib | EGFR | 12,600 | 7,550 | 8,630 | 8,920 | 6,370 | 8,200 |
| GW5074 | C-Raf | 15,800 | 7,750 | 8,070 | >20,000 | 19,100 | 7,100 |
| GDC0879 | B-Raf | 8,140 | 7,640 | >20,000 | >20,000 | 23,600 | 75.8 |
| Vemurafenib | B-Raf | 5,990 | 5,620 | 6,860 | 5,200 | 5,100 | 151 |
| Selumetinib | MEK | 4,110 | 20,400 | >20,000 | >20,000 | 854 | 4.60 |

Together, these data demonstrate the activated Ras selective growth inhibitory activity of the compounds of this invention. This is in contrast to the current clinically used inhibitors of proteins within the Ras signaling cascade that exhibit no selectivity or selectivity for cells lacking activated Ras.

EXAMPLE 27

This example illustrates the treatment of a mammalian patient with a compound of the present invention. The antitumor activity of compound 030 (specifically the S-enantiomer thereof) was evaluated in an orthotopic mouse model of lung cancer utilizing human A549 lung adenocarcinoma cells. Toxicity and efficacy were assessed by determining treatment effects on weight gain and by necropsy observations. Treatment effects on tumor growth in live mice were also measured with human A549 lung adenocarcinoma cells that were engineered to contain a luciferase expression vector using an In Vivo Imaging System (IVIS). In brief, female athymic nude-Foxn1$^{nu}$ mice, 6-7 weeks old were randomly divided into two groups that were treated with either vehicle (Maalox®) or compound 030 (100 mg/kg). Each group contained 15 mice in which 10 were implanted with non-luciferase A549 cells and 5 were implanted with luciferase A549 cells. Treatment was initiated 5 days before implanting tumor cells and was administrated to both groups by gastric gavage twice a day. For tumor cell implantation, cultured luciferase or non-luciferase human A549 lung tumor cells were collected and mixed with equal volume of Matrigel at a final concentration of 0.250 mg/mL. The mice were weighed and anesthetized and a mark placed on the skin at the lateral dorsal line, approximately 1.5 cm above the lower rib line just below the inferior border of the scapula. A pre-cooled 0.5 mL insulin syringe with a permanently attached 28G needle was loaded with 75 microliters of a cell suspension containing one million cells and inserted at the mark to a depth of approximately 5 mm. Body weight was measured twice a week and IVIS imaging one done once a week. All of the mice treated with compound 030 survived for the duration of the experiment, while one mouse in the vehicle group died.

FIG. 7A shows the effect of treatment on body weight for the duration of the experiment. Relative to the mice treated with vehicle group, the mice treated with compound 030 showed increased weight gain, demonstrating that the compound was not overtly toxic and that mice treated with 030 were in better health compared with mice treated with vehicle only. FIG. 7B shows the results from grading at necropsy in which 2 of 10 mice treated with 030 showed no tumors on the lung or chest cavity, 7 of 10 showed no tumors on the lung but having tumors in the chest cavity, and 1 with tumors on the lung and in the chest cavity. By comparison, 9 of 10 mice treated with vehicle showed tumors on the lung and chest cavity including 2 having lung effusions as well. FIG. 7C shows the effect of treatment with compound 030 on tumor growth in live mice over the duration of the experiment as measured by luminescence.

EXAMPLE 28

This example, which describes an investigation employing genetically engineered isogenic tumor cell lines, shows confirmation of Ras selectivity of an exemplary compound of the present invention. In one study, human colon HT29 tumor cells were transfected with retroviral mutant H-Ras-G12V (H-Ras$^m$) or retroviral control (Retro) and stable clones were selected by puromycin. The cell lines, including parental lines (Par) were treated with compound 007 (ADT-007) for 72 hours and viable cell numbers were measured using the Cell Titer Glo assay. Ras pull-downs were performed with GST-RBD-C-Raf kits (ThermoSci) following cell extraction and detected by Ras antibody on Western-blots for the amount of active GTP-Ras. Total Ras levels among these cell extractions were detected by the same Ras antibody. Results shown in FIG. 8A demonstrate that the cells transfected with activated Ras were hypersensitive to the test drug (007) relative to the respective control cells. In another study human lung H322 tumor cells were stably transfected with retroviral mutant H-Ras-G12V (H-Ras$^m$) or retroviral control (Retro). Cell lines, including parental lines (Par) were treated with compound 007 (ADT-007) for 72 hours and viable cell number measured using the Cell Titer Glo assay. Ras pull-downs were performed with GST-RBD-C-Raf kits (ThermoSci) following cell extraction and detected by Ras antibody on Western-blots for the amount of active GTP-Ras. Total Ras levels among these cell extractions were detected by the same Ras antibody. Results shown in FIG. 8B demonstrate that the cells transfected with activated Ras were hypersensitive to the test drug (007) relative to the respective control cells.

EXAMPLE 29

This example illustrates that representative Ras-inhibitory compounds of the present invention interact with high affinity directly with activated Ras to disrupt Ras interactions with a normal binding partner. In particular, this study shows (FIG. 9) disruption of Ras-Raf binding by compound 007 (ADT-007) and compound 006 (ADT-006). Inhibition studies of Ras binding to Raf by treatment with Ras inhibitors using a Raf pull-down assay was conducted in vitro in cell lysates (FIG. 9, top panel) or in intact cells (FIG. 9, bottom panel). For in vitro experiments, whole cell lysates from human H322 lung tumor cells transfected with activated (mutant) H-Ras were incubated for 30 minutes at room temperature with 007 or 006 at the designated concentrations. GTP-bound (active) Ras was precipitated with GST-Raf1-RBD/GSH Sepharose (Thermo Scientific) and detected by western blotting. Numerical values below the blots show the quantification of Ras protein by densitometry. As a positive control, lysates were incubated with 5 mM GDP to deactivate Ras. For experiments involving intact cells, the same method as described above was used except intact H322 lung tumor cells were incubated with 007 for 1 hour at 37° C. prior to the Raf pull-down assay.

EXAMPLE 30

This example illustrates that administration of therapeutic or preventive doses of representative compounds used in the present invention produced no evidence of in vivo animal toxicity as assessed by animal weight gains over time. Female athymic Nude-Foxn1$^{nu}$ mice, 6-7 weeks old were purchased from Harlan and acclimated for 1 week. Mice had access to water and food ad libitum for the duration of the experiment. HCT-116 cells were cultured under optimal conditions (RPMI media, 5% fetal bovine serum, antibiotics, glutamate at 5% $CO_2$ and 36° C.). On the day of inoculation, cells were collected from flasks 70-80% confluent. Mice were inoculated with $5 \times 10^6$ cells/100 µL in the right flank and $10 \times 10^6$ cells/100 µL in the left flank. Compounds 006, 011 and 019 (identified in FIG. 10 as ADT-006, ADT-011, and ADT-019, respectively) were administered twice daily by ip injection for 14 days at a dosage of 5 mg/kg. Compound 007 (identified as ADT-007 in FIG. 10) was administered in a similar manner except at a dosage 2.5 mg/kg. The vehicle for all compounds contained ethanol, polyethylene glycol-300, and water at a ratio of 5:75:20. Percent body weight change of mice treated with vehicle alone or with vehicle with test compounds relative to the body weight of the mice prior to treatment is shown. No change in body weight is shown as 100%. Error bars represent standard errors of the means. While there were some minor differences in animal weights early in the experiment, the drug-treated animal weights were statistically indistinguishable from controls for the duration of the experiment, indicating little if any toxic effects of any of the test drugs that would otherwise be manifest as significant body weight change.

EXAMPLE 31

This example illustrates efficacious therapeutic antitumor treatments (FIGS. 11A-D) of a representative Ras-driven tumor in vivo with exemplary Ras-inhibitory compounds of the present invention. Female athymic Nude-Foxn1$^{nu}$ mice, 6-7 weeks old were purchased from Harlan and acclimated for 1 week. Mice had access to water and food ad libitum for the duration of the experiment. HCT-116 cells were cultured in optimal conditions (RPMI media, 5% fetal bovine serum, antibiotics, glutamate at 5% $CO_2$ and 36° C.). On the day of inoculation, cells were collected from flasks 70-80% confluent. Mice were inoculated with $5 \times 10^6$ cells/100 µL on the right flank. Treatment was initiated once tumors reached an average size of 50 mm$^3$. Compounds 006, 011 and 019 (identified in FIGS. 11A, 11C and 11D as ADT-006, ADT-011, and ADT-019, respectively) were administered twice daily by ip injection for 14 days at a dosage of 5 mg/kg. Compound 007 (identified in FIG. 11B as ADT-007) was administered in a similar manner except at a dosage 2.5 mg/kg. The vehicle for all compounds contained ethanol, polyethylene glycol-300, and water at a ratio of 5:75:20. Error bars represent standard errors of the means at each point, and analysis of variance showed that the growth curves of drug-treated animals versus vehicle-only control animals were highly statistically different. Namely, the results shown in FIGS. 11A-D demonstrate that all four compounds profoundly suppressed tumor growth; in fact, in this study there were multiple "cures" in each drug-treated group (i.e., animals were completely free of macroscopically visible tumor at the end of the experiment). Another study, results of which are illustrated in FIGS. 11E-H, employed a "prevention" protocol rather than a "therapeutic" protocol. Female athymic Nude-Foxn1$^{nu}$ mice, 6-7 weeks old were purchased from Harlan and acclimated for 1 week. Mice had access to water and food ad libitum for the duration of the experiment. HCT-116 cells were cultured in optimal conditions (RPMI media, 5% fetal bovine serum, antibiotics, glutamate at 5% $CO_2$ and 36° C.). On the day of inoculation, cells were collected from flasks 70-80% confluent. Mice were inoculated with $10 \times 10^6$ cells/100 µL on the left flank, and treatment was initiated one day following tumor implantation. Compounds 006, 011 and 019 (identified in FIGS. 11E, 11G and 11H as ADT-006, ADT-011, and ADT-019, respectively) were administered twice daily by ip injection for 14 days at a dosage of 5 mg/kg. Compound 007 (identified in FIG. 11F as ADT-007) was administered in a similar manner except at a dosage 2.5 mg/kg. The vehicle for all compounds contained ethanol, polyethylene glycol-300, and water at a ratio of 5:75:20. Treatment was initiated one day following tumor implantation. Error bars represent standard errors of the means at each point, and P-values are derived from analysis of variance which showed that the growth curves of drug-treated animals versus vehicle-only control animals were highly statistically different. Namely, the results shown in FIGS. 11E-H demonstrate that all four compounds profoundly prevented tumor growth.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound, (Z)- or (E)-isomer thereof, of formula IIa:

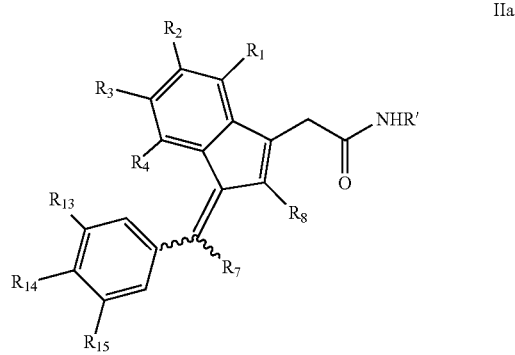

wherein:
$R_1$, $R_3$, $R_4$, $R_{13}$ and $R_{15}$ are independently selected from hydrogen, halogen, alkyl, cycloalkyl, haloalkyl, and alkoxy;
$R_2$ is alkoxy;
$R_7$ and $R_8$ are independently selected from hydrogen and alkyl;
$R_{14}$ is a cleavable alcohol prodrug moiety; and
R' is selected from the group consisting of heterocyclyl and heterocyclylalkyl, wherein the heterocyclyl of the heterocyclyl and heterocyclylalkyl is selected from the group consisting of azepanyl, oxazepanyl, thiazepanyl, azepinyl, oxepinyl, thiepanyl, homopiperazinyl, diazepinyl, thiazepinyl, oxanyl, thianyl, pyranyl, thiopyranyl, thiomorpholinyl, dioxanyl, dithianyl, diazinyl, oxazinyl, thiazinyl, dioxinyl, dithiinyl, trioxanyl, trithianyl, triazinyl, tetrazinyl, tetrahydrofuranyl, tetrahydrothiophenyl, thiophenyl, imidazolidinyl, pyrazolidinyl, oxazolidinyl, isoxazolidinyl, thiazolidinyl, isothiazolidinyl, dioxolanyl, dithiolanyl, imidazolyl, pyrazolyl, oxazolyl, isoxazolyl, thiazolyl, isothiazolyl, triazolyl, furazanyl, oxadiazolyl, thiadiazolyl, dithiazolyl and tetrazolyl, wherein the heterocyclyl of the heterocyclyl and heterocyclylalkyl of the R' is optionally substituted with one or more of halo, alkyl, haloalkyl, hydroxyl, alkoxy, amino, alkylamino, dialkylamino, mercapto, alkylmercapto, carboxamido, aldehydo, cyano, oxo, alkylcarbonyloxy, and sulfonamido; or
a pharmaceutically acceptable salt thereof.

2. The compound, (Z)- or (E)-isomer thereof, or a pharmaceutically acceptable salt thereof, of claim 1, wherein $R_{14}$ is a substituted or unsubstituted group selected from phosphonooxy, phosphonooxyalkyloxy, formyloxy, alkyloxy, alkylcarbonyloxy, alkylcarbonyloxyalkyloxy, aminocarbonyloxyalkyloxy, alkylsulfinyloxy, alkylsulfonyloxy, carbamate, arylcarbonyloxy, arylalkylcarbonyloxy, aryloxycarbonyloxy, heterocyclylcarbonyloxy, and heterocyclylalkylcarbonyloxy.

3. The compound, (Z)- or (E)-isomer thereof, or a pharmaceutically acceptable salt thereof, of claim 1, wherein the heterocyclyl of the heterocyclyl and heterocyclylalkyl of the R' is selected from the group consisting of diazinyl, oxazinyl, thiazinyl, dioxinyl, dithiinyl, thiophenyl, imidazolidinyl, pyrazolidinyl, oxazolidinyl, isoxazolidinyl, dioxolanyl, dithiolanyl, imidazolyl, pyrazolyl, oxazolyl, isoxazolyl, thiazolyl, isothiazolyl, furazanyl, and oxadiazolyl.

4. The compound, (Z)- or (E)-isomer thereof, or a pharmaceutically acceptable salt thereof, of claim 1, wherein the heterocyclyl of the heterocyclyl and heterocyclylalkyl of the R' is selected from diazinyl, thiophenyl, oxazolyl, isoxazolyl, thiazolyl, isothiazolyl, dioxolanyl, pyrazolyl and imidazolyl, wherein the heterocyclyl is optionally substituted with one or more of halo, alkyl, haloalkyl, hydroxyl, alkoxy, amino, alkylamino, dialkylamino, mercapto, alkylmercapto, and carboxamido.

5. The compound, (Z)- or (E)-isomer thereof, or a pharmaceutically acceptable salt thereof, of claim 4, wherein the heterocyclyl of the heterocyclyl and heterocyclylalkyl of the R' is selected from diazinyl, oxazolyl, isoxazolyl, and dioxolanyl, wherein the heterocyclyl is optionally substituted with one or more of halo, alkyl, haloalkyl, hydroxyl, and alkoxy.

6. The compound, (Z)- or (E)-isomer thereof, or a pharmaceutically acceptable salt thereof, of claim 1, wherein R' is a diazinyl selected from pyridizinyl, pyrimidinyl and pyrazinyl.

7. The compound, (Z)- or (E)-isomer thereof, or a pharmaceutically acceptable salt thereof, of claim 1, wherein $R_1$, $R_3$ and $R_4$ are independently selected from hydrogen, halogen, alkoxy, alkyl, and haloalkyl.

8. The compound, (Z)- or (E)-isomer thereof, or a pharmaceutically acceptable salt thereof, of claim 7, wherein $R_1$, $R_3$ and $R_4$ are each hydrogen.

9. The compound, (Z)- or (E)-isomer thereof, or a pharmaceutically acceptable salt thereof, of claim 8, wherein $R_7$ is hydrogen.

10. The compound, (Z)- or (E)-isomer thereof, or a pharmaceutically acceptable salt thereof, of claim 1, wherein $R_7$ is hydrogen and $R_8$ is alkyl.

11. The compound, (Z)- or (E)-isomer thereof, or a pharmaceutically acceptable salt thereof, of claim 1, wherein $R_{13}$ and $R_{15}$ are each alkoxy.

12. The compound, (Z)- or (E)-isomer thereof, or a pharmaceutically acceptable salt thereof, of claim 5, wherein $R_1$, $R_3$ and $R_4$ are hydrogens; $R_7$ is hydrogen; $R_8$ is alkyl; the heterocyclyl of the heterocyclyl and heterocyclylalkyl of the R' is unsubstituted; and $R_{13}$, $R_{14}$ and $R_{15}$ are each alkoxy.

13. The compound of claim 1, which is selected from:
(Z)-2-(5-methoxy-2-methyl-1-(3,4,5-trimethoxybenzylidene)-1H-inden-3-yl)-N-(pyrazin-2-yl)acetamide,
(Z)-2-(5-methoxy-2-methyl-1-(3,4,5-trimethoxybenzylidene)-1H-inden-3-yl)-N-(1H-1,2,4-triazol-3-yl)acetamide,
(Z)-2-(5-methoxy-2-methyl-1-(3,4,5-trimethoxybenzylidene)-1H-inden-3-yl)-N-(pyrimidin-2-yl)acetamide,
(Z)-2-(5-methoxy-2-methyl-1-(3,4,5-trimethoxybenzylidene)-1H-inden-3-yl)-N-(thiazol-2-yl)acetamide,
(Z)-2-(5-methoxy-2-methyl-1-(3,4,5-trimethoxybenzylidene)-1H-inden-3-yl)-N-(oxazol-2-yl)acetamide,
(Z)-2-(5-methoxy-2-methyl-1-(3,4,5-trimethoxybenzylidene)-1H-inden-3-yl)-N-(pyridazin-3-yl)acetamide,
(Z)-2-(5-methoxy-2-methyl-1-(3,4,5-trimethoxybenzylidene)-1H-inden-3-yl)-N-(pyrazin-2-ylmethyl)acetamide,
(Z)-2-(5-methoxy-2-methyl-1-(3,4,5-trimethoxybenzylidene)-1H-inden-3-yl)-N-(pyrimidin-5-yl)acetamide,
(Z)-2-(5-methoxy-2-methyl-1-(3,4,5-trimethoxybenzylidene)-1H-inden-3-yl)-N-(pyridazin-4-yl)acetamide,
(Z)-2-(5-methoxy-2-methyl-1-(3,4,5-trimethoxybenzylidene)-1H-inden-3-yl)-N-(thiazol-2-ylmethyl)acetamide, and
(Z)—N-((1,3-dioxolan-2-yl)methyl)-2-(5-methoxy-2-methyl-1-(3,4,5-trimethoxybenzylidene)-1H-inden-3-yl)acetamide, or
(E)-isomer thereof, or pharmaceutically acceptable salt thereof.

14. A pharmaceutical composition comprising a compound, (Z)- or (E)-isomer thereof, or a pharmaceutically acceptable salt thereof, of claim 1, and a pharmaceutically acceptable carrier.

15. A method of therapeutically treating a human or nonhuman mammalian patient with cancer, wherein the cancer is selected from pancreatic cancer, lung cancer, colorectal cancer, melanoma, ovarian cancer, renal cancer, prostate cancer, head and neck cancer, endocrine cancer, uterine cancer, breast cancer, sarcoma cancer, gastric cancer, hepatic cancer, esophageal cancer, central nervous system cancer, brain cancer, hepatic cancer, germline cancer, lymphoma, and leukemia, comprising administering to said patient an anticancer effective amount of at least one compound, (Z)- or (E)-isomer thereof, or a pharmaceutically acceptable salt thereof, of claim 1, wherein said at least one compound, (Z)- or (E)-isomer thereof, or a pharmaceutically acceptable salt thereof is administered alone or in combination with an antitumor drug or radiation, wherein said antitumor drug is not a compound, (Z)- or (E)-isomer thereof, or a pharmaceutically acceptable salt thereof, of claim 1.

* * * * *